(12) United States Patent
Verdine et al.

(10) Patent No.: US 10,039,839 B2
(45) Date of Patent: Aug. 7, 2018

(54) COMPOUNDS THAT PARTICIPATE IN COOPERATIVE BINDING AND USES THEREOF

(71) Applicant: Warp Drive Bio, Inc., Cambridge, MA (US)

(72) Inventors: Gregory Lawrence Verdine, Bedford, MA (US); Matthew James Nichols, Charlestown, MA (US); Dylan Talbot Stiles, Cambridge, MA (US); Neville John Anthony, Northborough, MA (US); Brian Roger Bowman, New Rochelle, NY (US); Mathew Edward Sowa, Watertown, MA (US); Sharon Ann Townson, Cambridge, MA (US)

(73) Assignee: Warp Drive Bio, Inc., Cambridge, MA (US)

( * ) Notice: Subject to any disclaimer, the term of this patent is extended or adjusted under 35 U.S.C. 154(b) by 0 days.

(21) Appl. No.: 14/991,403

(22) Filed: Jan. 8, 2016

(65) Prior Publication Data
US 2016/0199506 A1  Jul. 14, 2016

Related U.S. Application Data

(60) Provisional application No. 62/101,925, filed on Jan. 9, 2015.

(51) Int. Cl.
| | |
|---|---|
| *C12N 5/00* | (2006.01) |
| *A61K 47/48* | (2006.01) |
| *C07D 498/18* | (2006.01) |
| *C07K 7/64* | (2006.01) |
| *C07K 7/56* | (2006.01) |
| *C07D 405/06* | (2006.01) |
| *C07D 498/22* | (2006.01) |

(52) U.S. Cl.
CPC ...... *A61K 47/48346* (2013.01); *C07D 405/06* (2013.01); *C07D 498/18* (2013.01); *C07D 498/22* (2013.01); *C07K 7/56* (2013.01); *C07K 7/64* (2013.01); *C07K 7/645* (2013.01)

(58) Field of Classification Search
None
See application file for complete search history.

(56) References Cited

U.S. PATENT DOCUMENTS

| | | | |
|---|---|---|---|
| 6,183,965 | B1 | 2/2001 | Verdine et al. |
| 6,372,712 | B1 | 4/2002 | Briesewitz et al. |
| 6,713,607 | B2 | 3/2004 | Caggiano et al. |
| 8,664,186 | B2 | 3/2014 | Aigle et al. |
| 9,428,845 | B1 | 8/2016 | Verdine et al. |
| 2002/0110874 | A1 | 8/2002 | Khosla et al. |
| 2002/0147133 | A1 | 10/2002 | Briesewitz et al. |
| 2005/0233431 | A1 | 10/2005 | Ashley et al. |
| 2007/0203168 | A1* | 8/2007 | Zhao ............. C07D 498/18 514/291 |
| 2012/0208720 | A1 | 8/2012 | Kashiwagi et al. |
| 2012/0270800 | A1 | 10/2012 | Verdine et al. |
| 2013/0072439 | A1 | 3/2013 | Nash et al. |
| 2014/0073581 | A1 | 3/2014 | Liu et al. |
| 2016/0341719 | A1 | 11/2016 | Verdine et al. |

FOREIGN PATENT DOCUMENTS

| | | |
|---|---|---|
| EP | 0562853 A1 | 9/1993 |
| EP | 1079859 B1 | 7/2010 |
| WO | WO-95/32294 A1 | 11/1995 |
| WO | WO-1996/020216 A1 | 7/1996 |
| WO | WO-01/36460 A2 | 5/2001 |
| WO | WO-2010/031185 A1 | 3/2010 |
| WO | WO-2010/034243 A1 | 4/2010 |
| WO | WO-2010/088573 A1 | 8/2010 |
| WO | WO-2012/075048 A2 | 6/2012 |
| WO | WO-2012/174489 A2 | 12/2012 |
| WO | WO-2014/187959 A2 | 11/2014 |
| WO | WO-2015/132784 A1 | 9/2015 |

OTHER PUBLICATIONS

Andrei et al. Expert Opinion on Drug Discovery (2017), pp. 1-16, at the website dx.doi.org/1080/17460441.2017.1346608.*
Chaurasia et al. Chem. Phys. Lett. (2013) 587: 68-74.*
Bruce et al. Proteomics (2012) 12: 1565-1575.*
Luengo et al. Chemistry and Biology (1995) 2: 471-481 (Year: 1995).*
Wu et al. ACS Combinatorial Sci. (2011) 13: 486-495 (Year: 2011).*
International Search Report and Written Opinion for International Application No. PCT/US16/12631, dated Mar. 16, 2016 (13 pages).
"A simple and efficient route to the FKBP-binding domain from rapamycin," available in PMC Sep. 28, 2012, published in final edited form as: Tetrahedron Lett. 52(39):5070-2 (2011) (7 pages).
Wright et al., "Multivalent binding in the design of bioactive compounds," Curr Org Chem. 5(11):1107-31 (2001).
Wilson et al., "Immune system applications of structure-aided drug design," Acta Cryst. D51:511-21 (1995).

(Continued)

*Primary Examiner* — Susan M Hanley
(74) *Attorney, Agent, or Firm* — Clark & Elbing LLP

(57) ABSTRACT

The invention relates to macrocyclic compounds capable of modulating biological processes through binding to a presenter protein and a target protein. These compounds bind endogenous intracellular presenter proteins, such as the FKBPs or cyclophilins, and the resulting binary complexes selectively bind and modulate the activity of intracellular target proteins. Formation of a tripartite complex among the presenter protein, the compound, and the target protein is driven by both protein-compound and protein-protein interactions, and both are required for modulation of the targeted protein's activity. In some embodiment, the compounds of the invention "re-program" the binding of the presenter proteins to protein targets that either do not normally bind to the presenter protein.

3 Claims, 44 Drawing Sheets

(56) References Cited

OTHER PUBLICATIONS

Banaszynski et al., "Characterization of the FKBP.rapamycin.FRB ternary complex," J Am Chem Soc. 127(13):4715-21 (2005).
Vignot et al., "mTOR-targeted therapy of cancer with rapamycin derivatives," Ann Oncol. 16(4):525-37 (2005).
Findlay et al., "The structure of demethoxyrapamycin," Can J Chem. 60:2046-7 (1982).
Briesewitz et al., "Affinity modulation of small-molecule ligands by borrowing endogenous protein surfaces," Proc Natl Acad Sci U.S.A. 96(5):1953-8 (1999).
Sieber et al., "Novel inhibitors of the calcineurin/NFATc hub—alternatives to CsA and FK506?," Cell Commun Signal. 7:25 (2009).
Schwecke et al., "The biosynthetic gene cluster for the polyketide immunosuppressant rapamycin," Proc Natl Acad Sci USA. 92(17):7839-43 (1995).
Sweeney et al., "From chemical tools to clinical medicines: non-immunosuppressive cyclophilin inhibitors derived from the cyclosporin and sanglifehrin scaffolds," J Med Chem. 57(17):1-62 (2014).
Papageorgiou et al., "Improved binding affinity for cyclophilin A by a cyclosporin derivative singly modified at its effector domain," J Med Chem. 37:3674-6 (1994).
Hubler et al., "Synthetic routes routes to NEtXaa4-cyclosporin a derivatives as potential anti-HIV I drugs," Tetrahedron Lett. 41:7193-6 (2000).
Kawakami et al., "In vitro selection of multiple libraries created by genetic code reprogramming to discover macrocyclic peptides that antagonize VEGFR2 activity in living cells," ACS Chem Biol. 8(6):1205-14 (2013).
Ishizawa et al., "TRAP display: a high-speed selection method for the generation of functional polypeptides," J Am Chem. 135:5433-40 (2013).
"Creating diverse target-binding surfaces on FKBP12: synthesis and evaluation of a rapamycin analogue library," available in PMC Sep. 12, 2012, published in final edited form as: ACS Comb Sci. 13(5):486-95 (2011) (22 pages).
Leskiw et al., "TTA codons in some genes prevent their expression in a class of developmental, antibiotic-negative, Streptomyces mutants," Proc Natl Acad Sci USA. 88:2461-5 (1991).
Blodgett et al., "Unusual transformations in the biosynthesis of the antibiotic phosphinothricin tripeptide," Nat Chem Biol. 3(8):480-5 (2007).
Hosted et al., "Use of rpsL for dominance selection and gene replacement in Streptomyces roseosporus," J Bacteriol. 179(1):180-6 (1997).
Horton et al., "Engineering hybrid genes without the use of restriction enzymes: gene splicing by overlap extension," Gene. 77:61-8 (1989).
Ochi et al., "New strategies for drug discovery: activation of silent or weakly expressed microbial gene clusters," Appl Microbiol Biotechnol. 97:87-98 (2013).
Laureti et al., "Identification of a bioactive 51-membered macrolide complex by activation of a silent polyketide synthase in Streptomyces ambofaciens," Proc Natl Acad Sci USA. 108(15):6258-63 (2011).
Huang et al., "Enhanced rapamycin production in Streptomyces hygroscopicus by integrative expression of aveR, a LAL family transcriptional regulator," World J Microbiol Biotechnol. 27:2103-9 (2011).
Meyer et al., "Selective palladation of a large (32 ring atom) macrocyclic ligand at a bis(N-heterocyclic carbene) coordination pocket through transmetallation of the corresponding mercury(II) derivative," Dalton Trans. 41(46):14059-67 (2012).
Burgess et al., "Controlled translocation of palladium(II) within a 22 ring atom macrocyclic ligand," Dalton Trans. 43(45):17006-16 (2014).
Substructure Search Report on Specifically Substituted Macrocycles—Substances Only, prepared by Science IP, dated Dec. 17, 2014 (6177 pages).
Wagner et al., "New naturally occurring amino acids," Angew Chem Int Ed Engl. 22:816-28 (1983).
Antunes et al., "A mutational analysis defines Vibrio fischeri LuxR binding sites," J Bacteriol. 190(13):4392-7 (2008).
Guerra et al., "LAL regulators SCO0877 and SCO7173 as pleiotropic modulators of phosphate starvation response and actinorhodin biosynthesis in Streptomyces coelicolor," PLoS One. 7(2):e31475 (2012) (11 pages).
Pfeifer et al., "Biosynthesis of complex polyketides in a metabolically engineered strain of E. coli," Science 291(5509):1790-2 (2001).
Bayle et al., "Rapamycin analogs with differential binding specificity permit orthogonal control of protein activity," Chem Biol. 13(1):99-107 (2006).
Che et al., "Inducing protein-protein interactions with molecular glues," Bioorganic & Medicinal Chemistry Letters (2018).
Extended European Search Report for European Application No. 16735470.3, dated May 3, 2018 (13 pages).
Wu et al., "Inhibition of ras-effector interactions by cyclic peptides," Med Chem Commun. 4(2):378-82 (2013).

* cited by examiner

| Structure | # | Molecular Weight | Chemical Formula | cLogP | Found LC-MS [M+Na]+ |
|---|---|---|---|---|---|
| 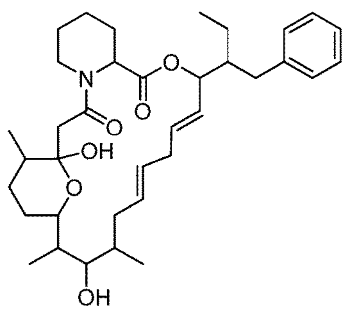 | F1 | 595.82 | $C_{36}H_{53}NO_6$ | 6.7 | 618.4 |
| 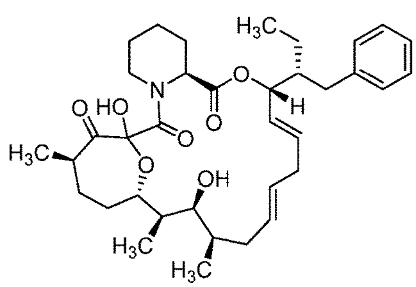 | F2 | 609.80 | $C_{36}H_{51}NO_7$ | 6.3 | 632.4 |
| 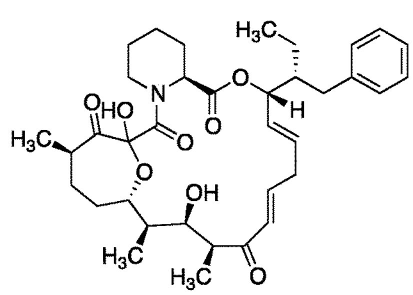 | F3 | 623.79 | $C_{36}H_{49}NO_8$ | 5.2 | 646.3 |

| Structure | # | Molecular Weight | Chemical Formula | cLogP | Found LC-MS [M+Na]+ |
|---|---|---|---|---|---|
| 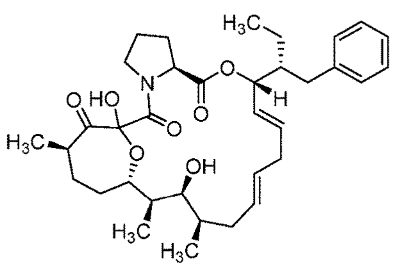 | F4 | 595.78 | $C_{35}H_{49}NO_7$ | 5.9 | 618.3 |
| 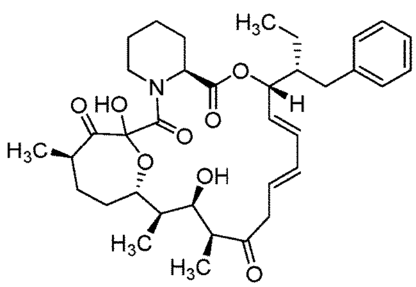 | F5 | 623.79 | $C_{36}H_{49}NO_8$ | 4.9 | 646.3 |
| 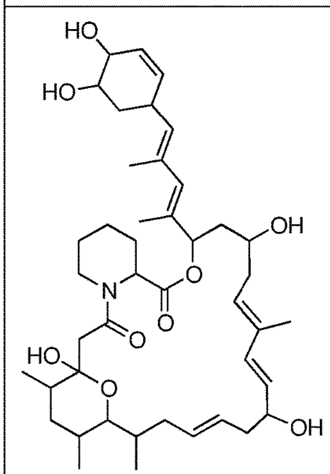 | F6 | 739.99 | $C_{43}H_{65}NO_9$ | | 762.4 |

| Structure | # | Molecular Weight | Chemical Formula | cLogP | Found LC-MS [M+Na]+ |
|---|---|---|---|---|---|
| 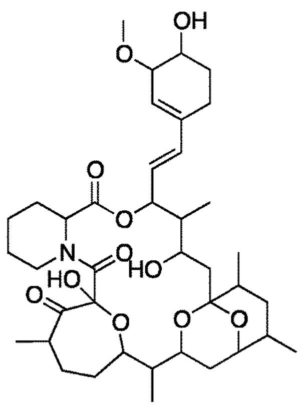 | F7 | 717.90 | $C_{39}H_{59}NO_{11}$ | | 740.4 |
| 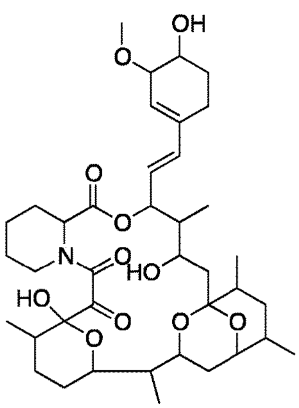 | F8 | 717.90 | $C_{39}H_{59}NO_{11}$ | | 740.4 |
| 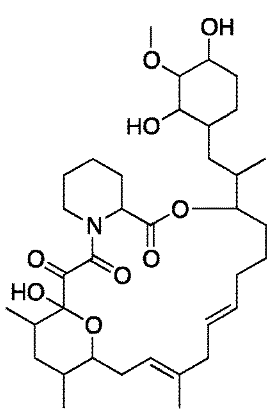 | F9 | 647.85 | $C_{36}H_{57}NO_{9}$ | | 670.4 |

FIG. 1 (continued)

| Structure | # | Molecular Weight | Chemical Formula | cLogP | Found LC-MS [M+Na]+ |
|---|---|---|---|---|---|
| 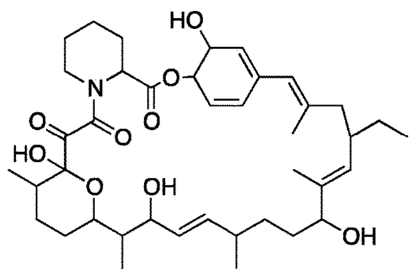 | F10 | 697.91 | $C_{40}H_{59}NO_9$ | | 720.3 |
| 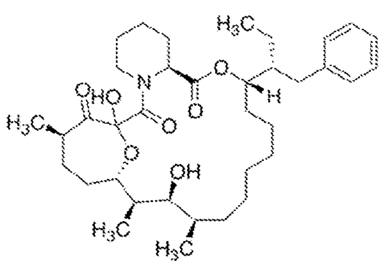 | F11 | 613.82 | $C_{36}H_{55}NO_7$ | | 636.4 |
| 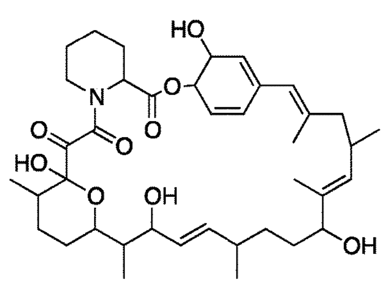 | F12 | 683.88 | $C_{39}H_{57}NO_9$ | | 706.3 |

| Structure | # | Molecular Weight | Chemical Formula | cLogP | Found LC-MS [M+Na]+ |
|---|---|---|---|---|---|
| 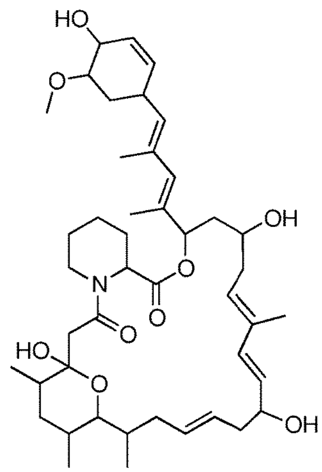 | F13 | 754.02 | $C_{44}H_{67}NO_9$ | | 776.4 |
| 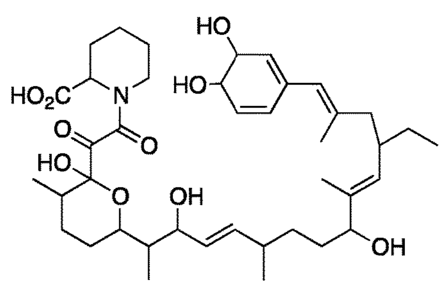 | F14 | 715.92 | $C_{40}H_{61}NO_{10}$ | | 738.4 |
| 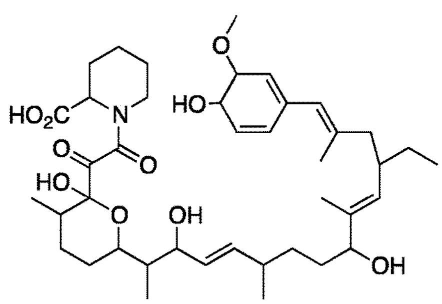 | F15 | 729.95 | $C_{41}H_{63}NO_{10}$ | | 752.4 |

FIG. 1 (continued)

| Structure | # | Molecular Weight | Chemical Formula | cLogP | Found LC-MS [M+Na]+ |
|---|---|---|---|---|---|
| 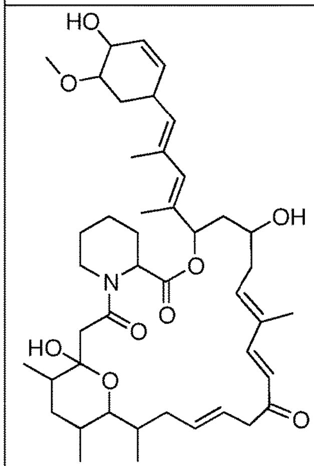 | F16 | 752.00 | C$_{44}$H$_{65}$NO$_9$ | | 774.3 |
| 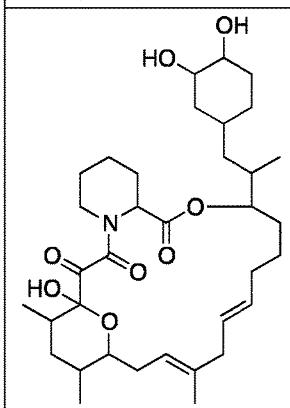 | F17 | 617.82 | C$_{35}$H$_{55}$NO$_8$ | | 640.4 |
| 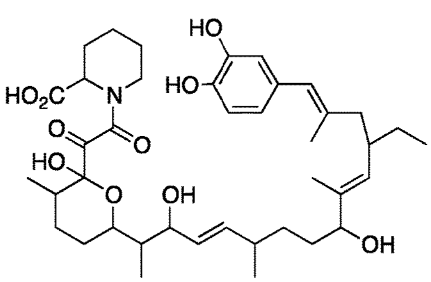 | F18 | 713.91 | C$_{40}$H$_{59}$NO$_{10}$ | | 736.3 |

| Structure | # | Molecular Weight | Chemical Formula | cLogP | Found LC-MS [M+Na]+ |
|---|---|---|---|---|---|
| 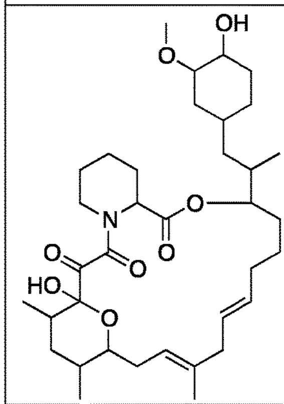 | F19 | 631.85 | C36H57NO8 | | 654.4 |
| 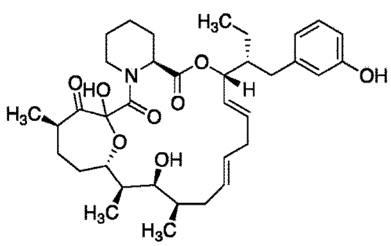 | F20 | 625.80 | C36H51NO8 | | 648.4 |
| 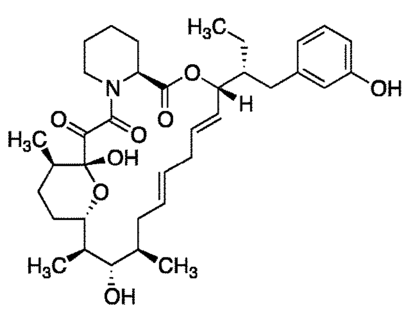 | F21 | 625.80 | C36H51NO8 | | 648.4 |

FIG. 1 (continued)

| Structure | # | Molecular Weight | Chemical Formula | cLogP | Found LC-MS [M+Na]+ |
|---|---|---|---|---|---|
| 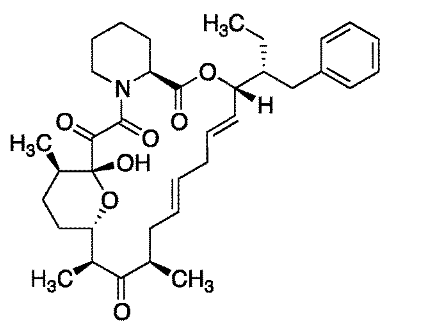 | F22 | 607.79 | C36H49NO7 | | 630.3 |
| 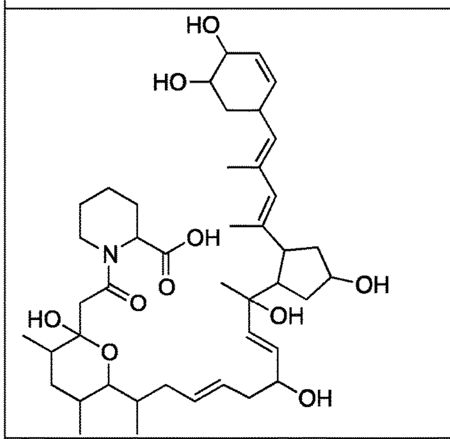 | F23 | 758.01 | C43H67NO10 | | 781.5 |
| 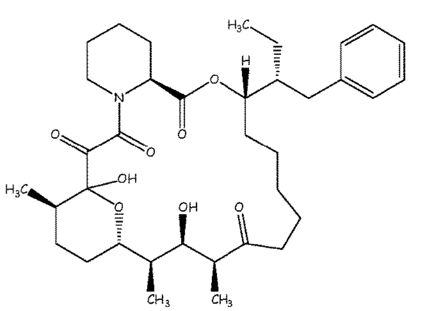 | F24 | 627.82 | C36H53NO8 | | 650.4 |

FIG. 1 (continued)

| Structure | # | Molecular Weight | Chemical Formula | cLogP | Found LC-MS [M+Na]+ |
|---|---|---|---|---|---|
| 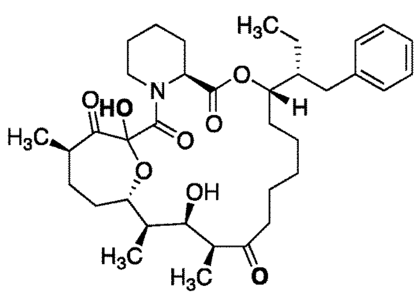 | F25 | 628.37 | $C_{36}H_{53}NO_8$ | | 650.3 |

FIG. 2

Table 2.

| Entry | AA1 | AA2 | AA3 | AA4 | Structure |
|---|---|---|---|---|---|
| C1 | Ala | MeAla | Val | MeIle | 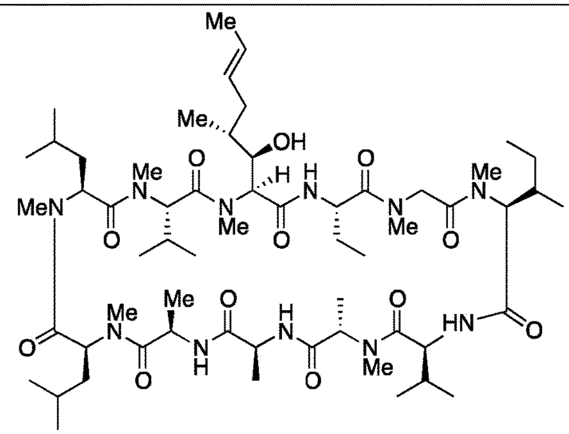 |
| C2 | Ala | MeAla | Val | MeAla | 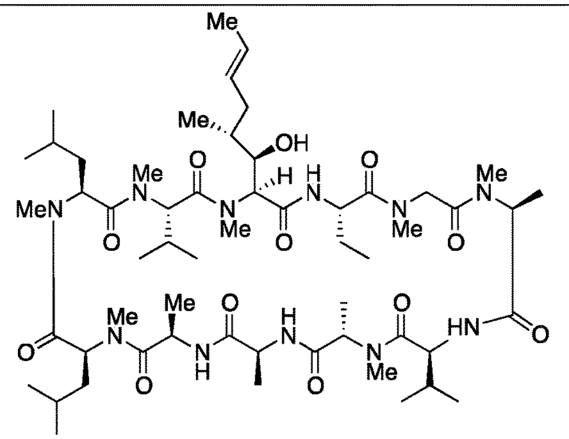 |

| Entry | AA1 | AA2 | AA3 | AA4 | Structure |
|---|---|---|---|---|---|
| C3 | Ala | MeAla | Val | D-MeAla | 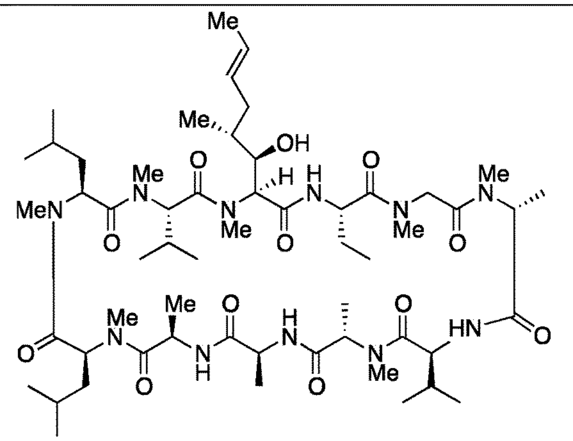 |
| C4 | Ala | MeAla | Val | MePhe | 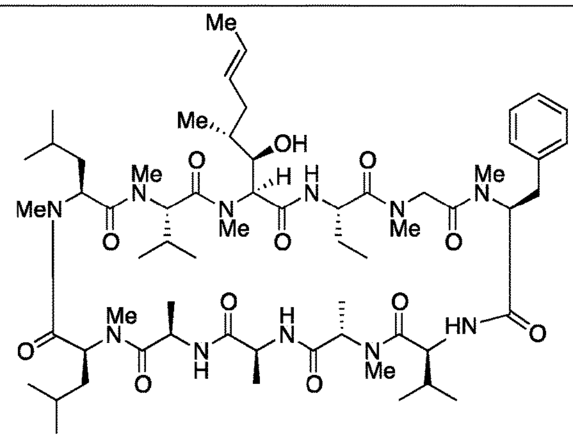 |
| C5 | Ala | MeAla | Val | Sar | 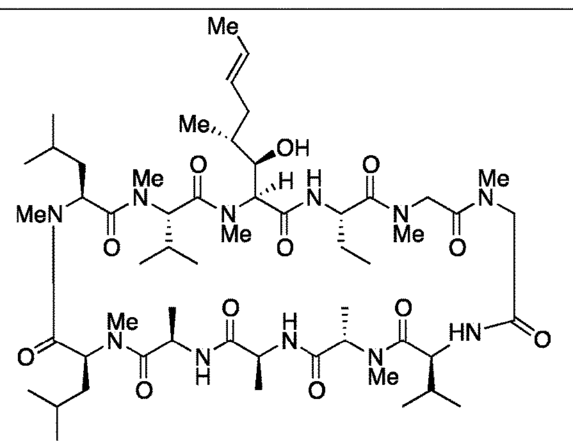 |

FIG. 2 (continued)

| Entry | AA1 | AA2 | AA3 | AA4 | Structure |
|---|---|---|---|---|---|
| C6 | Ala | MeAla | Val | MeLeu | 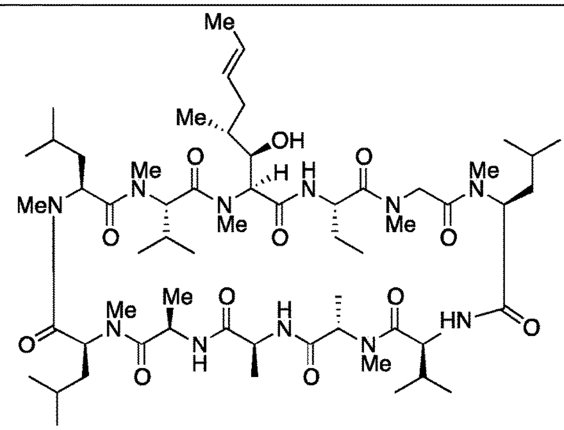 |
| C7 | Ala | MeAla | Val | MeThr | 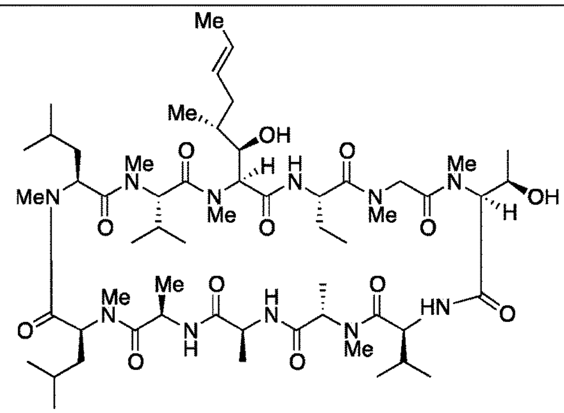 |
| C8 | Ala | MeAla | Val | MeTyr | 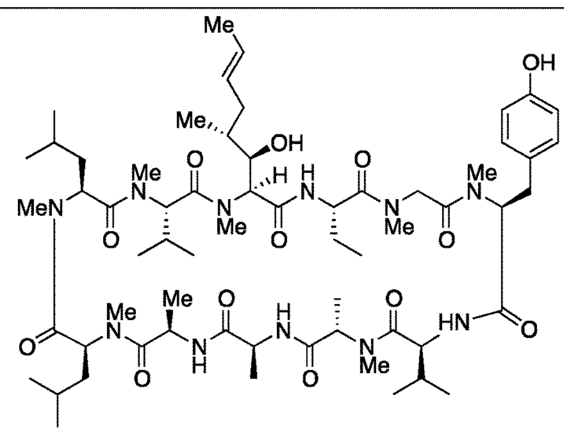 |

FIG. 2 (continued)

| Entry | AA1 | AA2 | AA3 | AA4 | Structure |
|---|---|---|---|---|---|
| C9 | Ala | MeAla | Leu | MeIle | 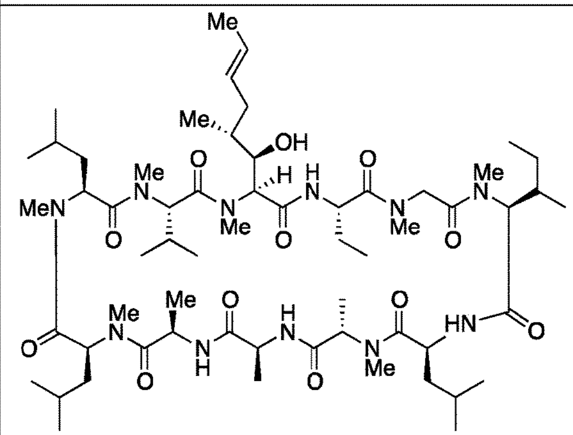 |
| C10 | Ala | MeAla | Leu | MeAla | 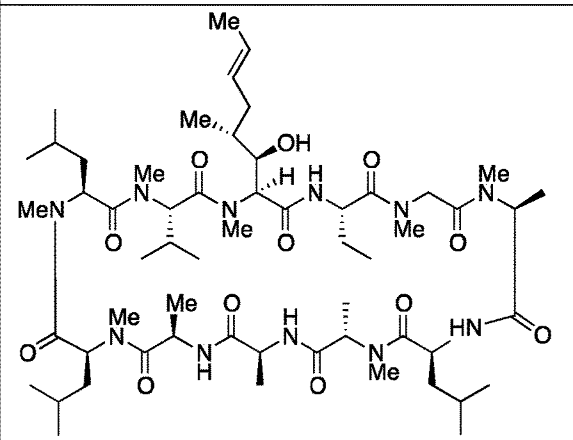 |
| C11 | Ala | MeAla | Leu | D-MeAla | 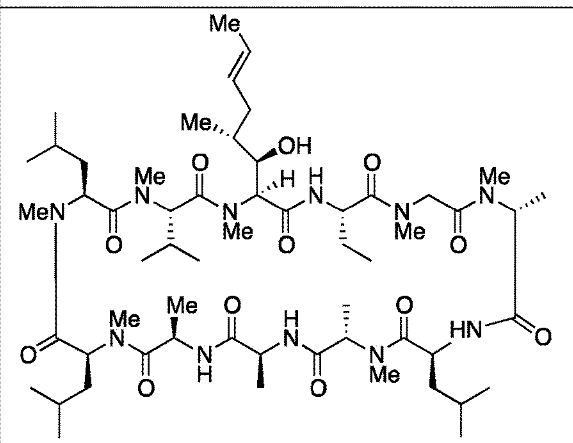 |

FIG. 2 (continued)

| Entry | AA1 | AA2 | AA3 | AA4 | Structure |
|---|---|---|---|---|---|
| C12 | Ala | MeAla | Leu | MePhe | 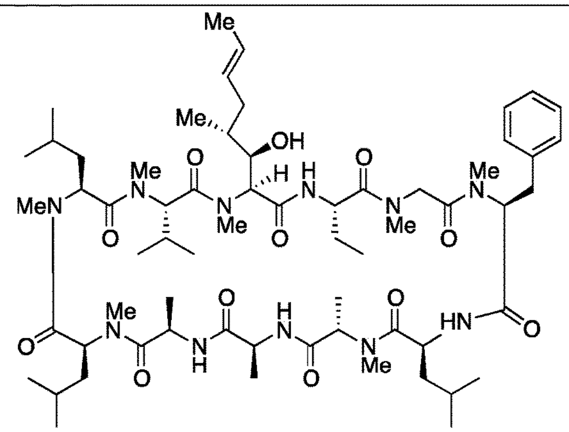 |
| C13 | Ala | MeAla | Leu | Sar | 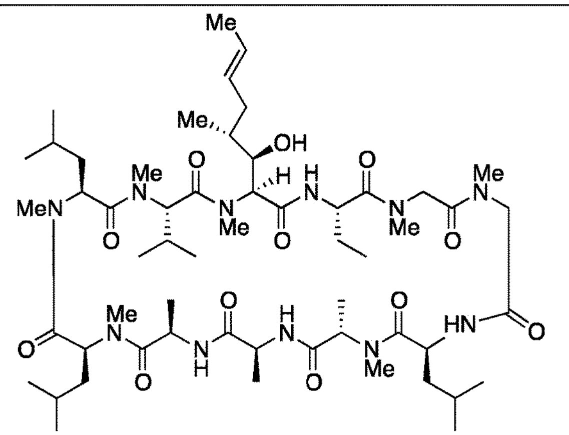 |
| C14 | Ala | MeAla | Leu | MeLeu | 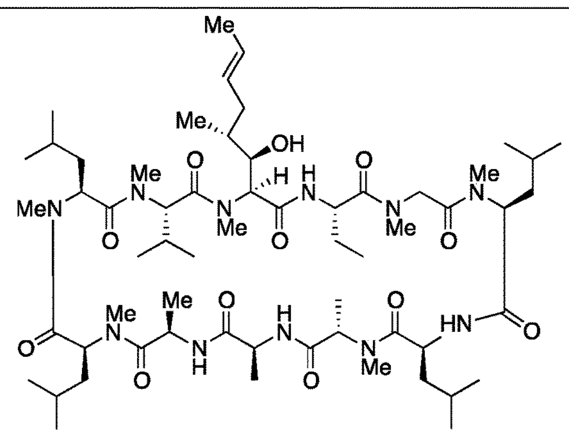 |

FIG. 2 (continued)

| Entry | AA1 | AA2 | AA3 | AA4 | Structure |
|---|---|---|---|---|---|
| C15 | Ala | MeAla | Leu | MeThr | 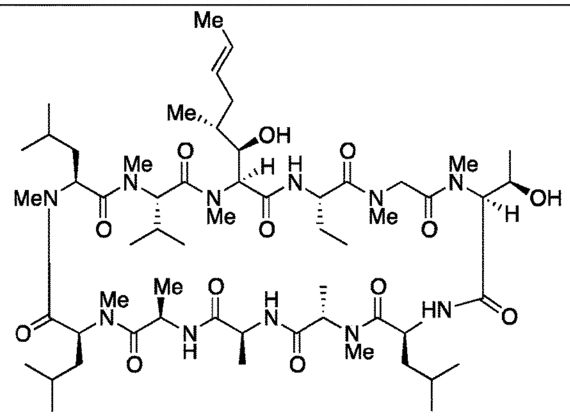 |
| C16 | Ala | MeAla | Leu | MeTyr | 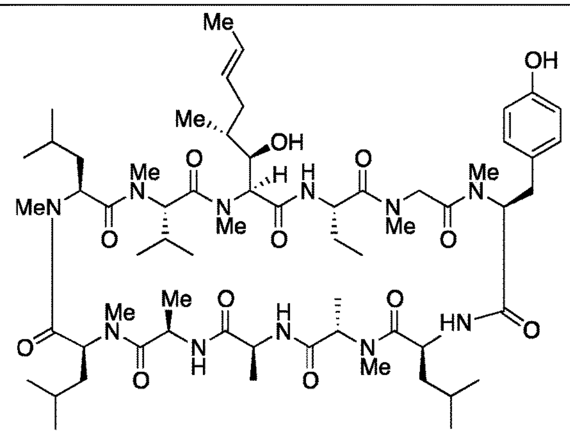 |
| C17 | Ala | Sar | Ala | MeIle | 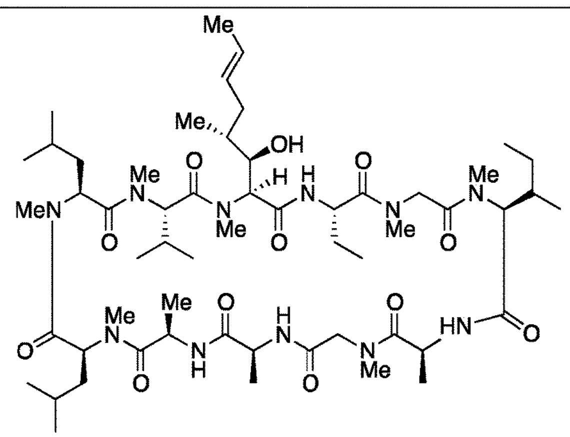 |

FIG. 2 (continued)

| Entry | AA1 | AA2 | AA3 | AA4 | Structure |
|---|---|---|---|---|---|
| C18 | Ala | Sar | Ala | MeAla | 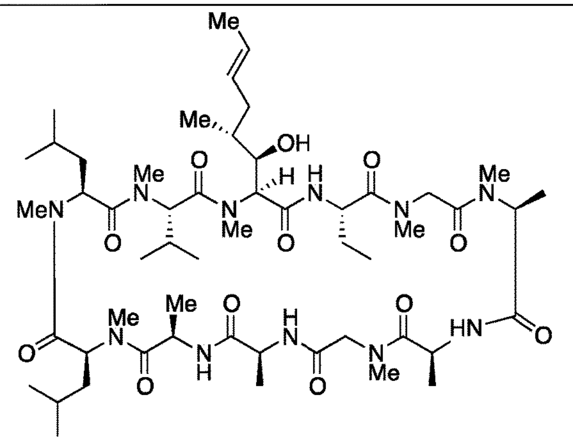 |
| C19 | Ala | Sar | Ala | D-MeAla | 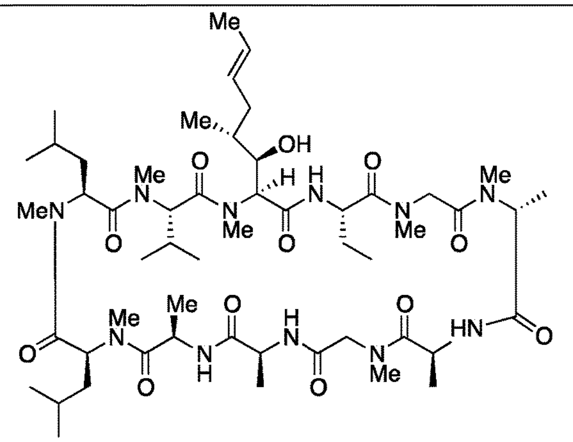 |
| C20 | Ala | Sar | Ala | MePhe | 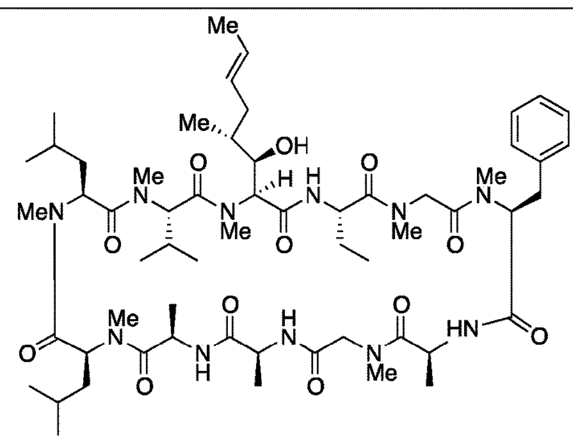 |

FIG. 2 (continued)

| Entry | AA1 | AA2 | AA3 | AA4 | Structure |
|---|---|---|---|---|---|
| C21 | Ala | Sar | Ala | Sar | 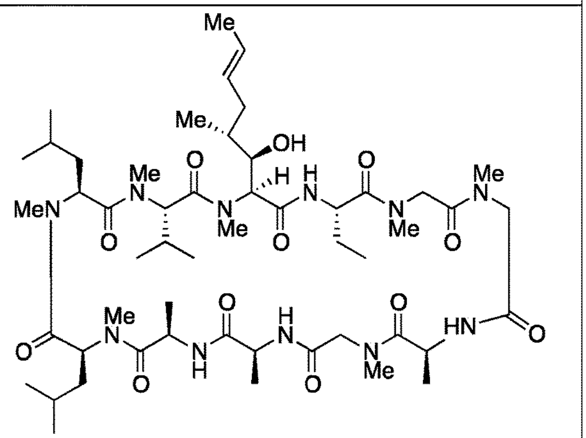 |
| C22 | Ala | Sar | Ala | MeLeu | 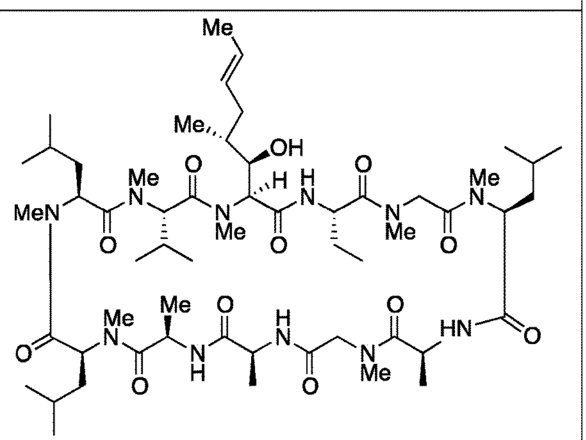 |
| C23 | Ala | Sar | Ala | MeThr | 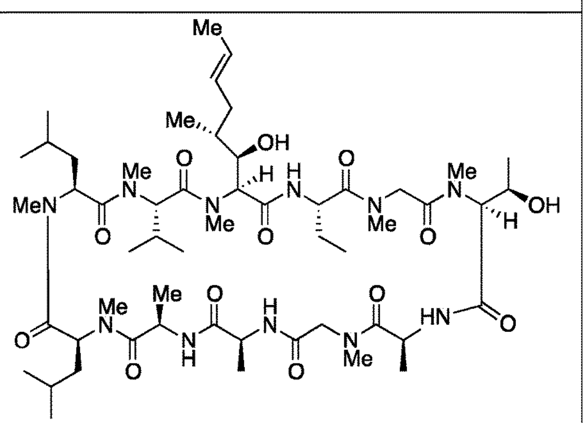 |

| Entry | AA1 | AA2 | AA3 | AA4 | Structure |
|---|---|---|---|---|---|
| C24 | Ala | Sar | Ala | MeTyr | 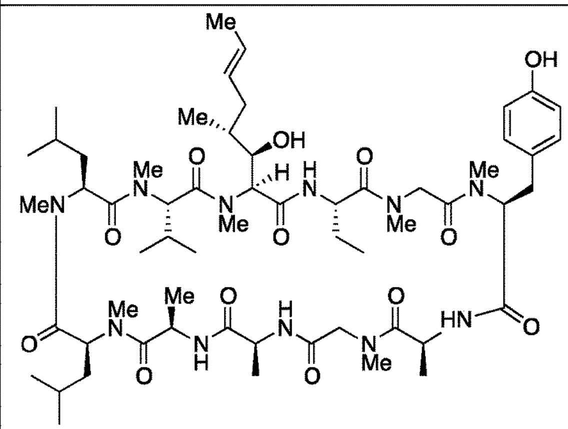 |
| C25 | Ala | Sar | Val | MeIle | 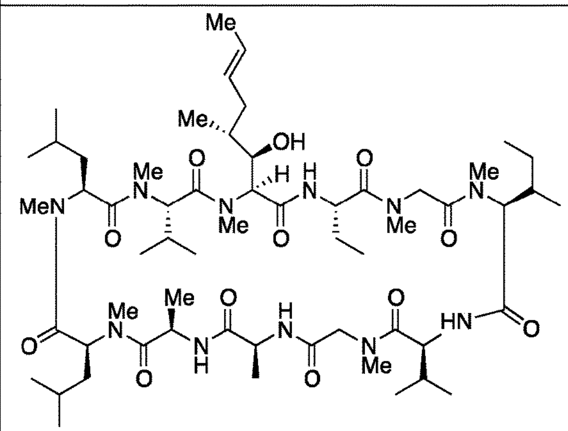 |
| C26 | Ala | Sar | Val | MeAla | 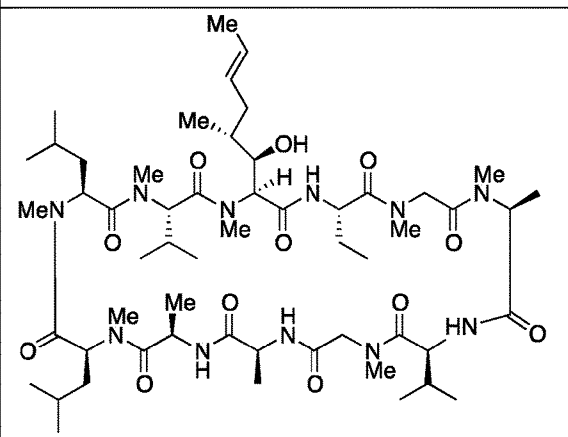 |

FIG. 2 (continued)

| Entry | AA1 | AA2 | AA3 | AA4 | Structure |
|---|---|---|---|---|---|
| C26 | Ala | Sar | Val | D-MeAla | 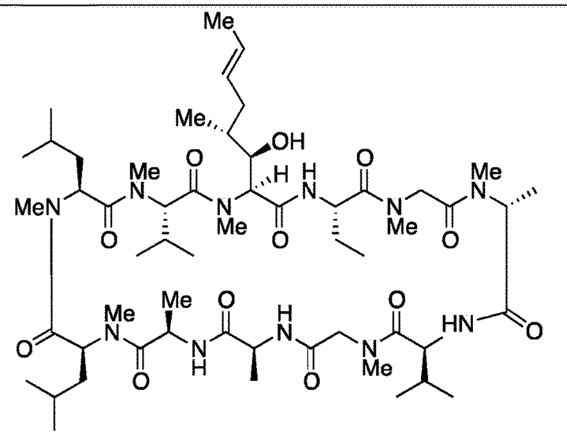 |
| C27 | Ala | Sar | Val | MePhe | 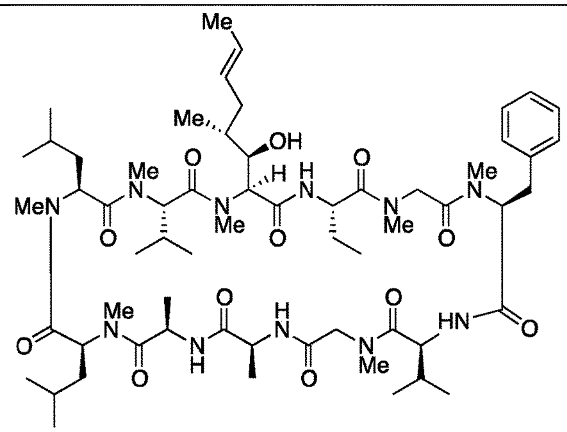 |
| C28 | Ala | Sar | Val | Sar | 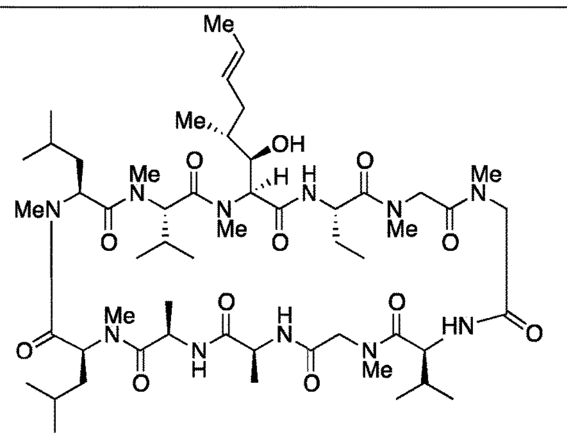 |

| Entry | AA1 | AA2 | AA3 | AA4 | Structure |
|---|---|---|---|---|---|
| C30 | Ala | Sar | Val | MeLeu | 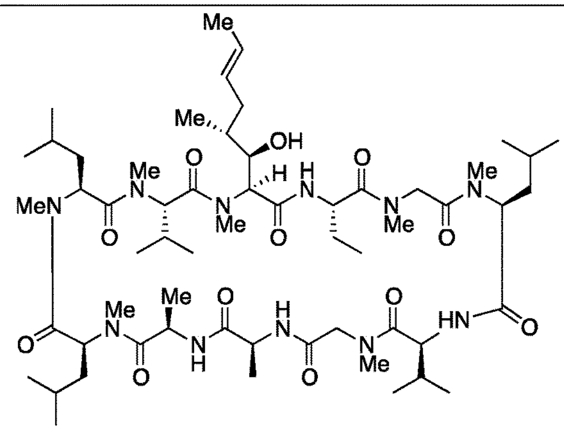 |
| C31 | Ala | Sar | Val | MeThr | 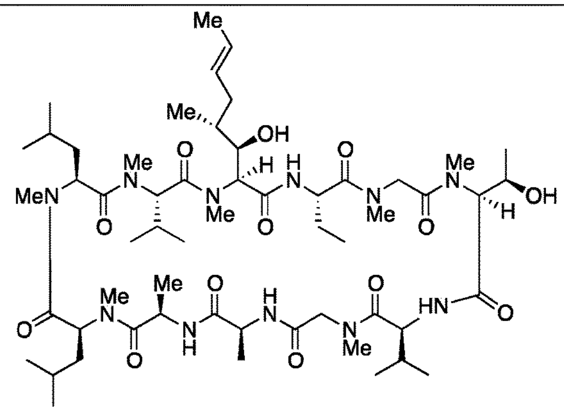 |
| C32 | Ala | Sar | Val | MeTyr | 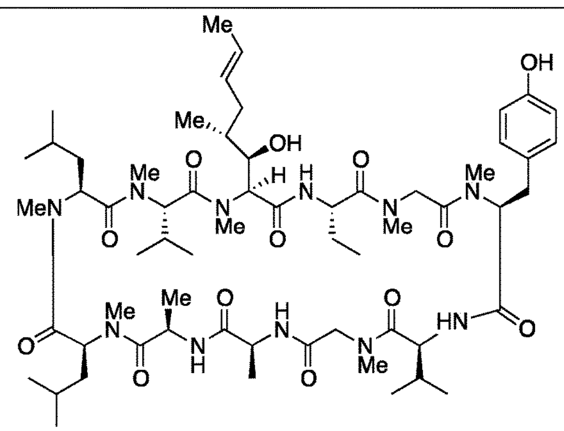 |

| Entry | AA1 | AA2 | AA3 | AA4 | Structure |
|---|---|---|---|---|---|
| C33 | Ala | MeLeu | Val | MeIle | 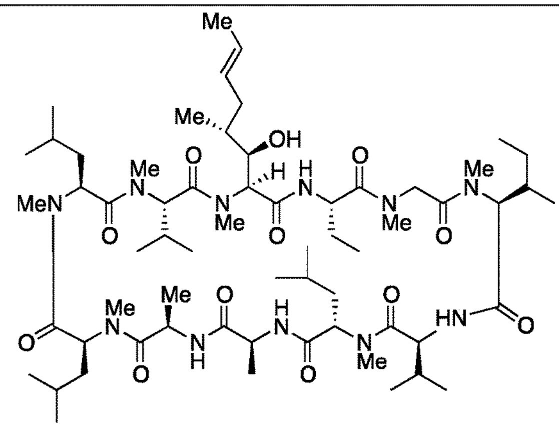 |
| C34 | Ala | MeLeu | Val | MeAla | 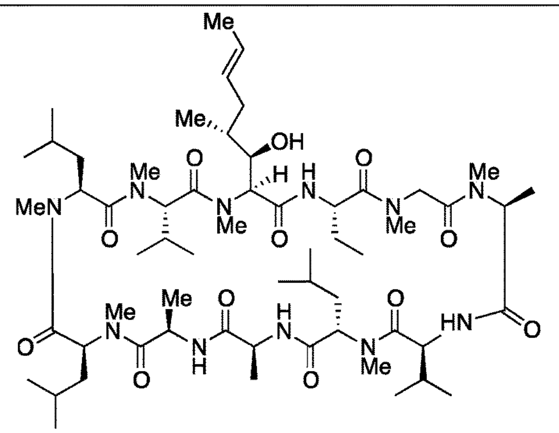 |
| C35 | Ala | MeLeu | Val | D-MeAla | 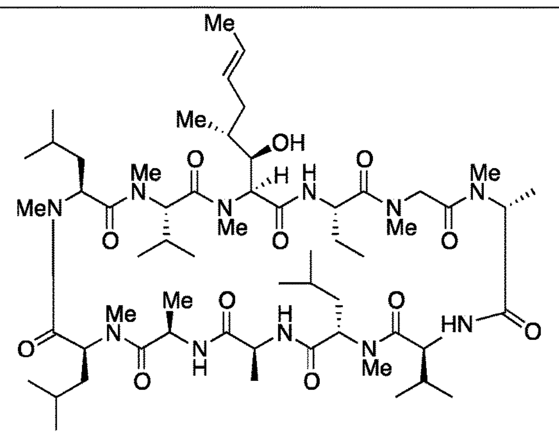 |

| Entry | AA1 | AA2 | AA3 | AA4 | Structure |
|---|---|---|---|---|---|
| C36 | Ala | MeLeu | Val | MePhe | 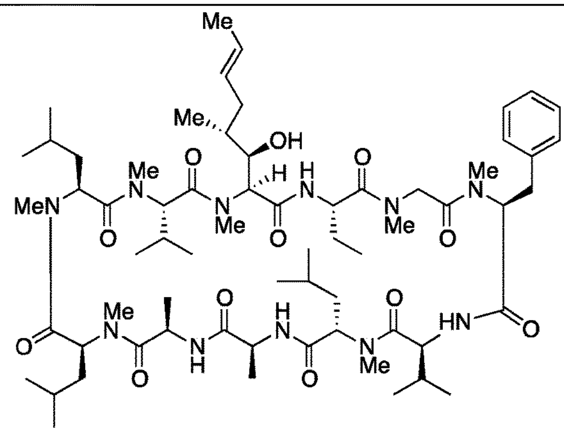 |
| C37 | Ala | MeLeu | Val | Sar | 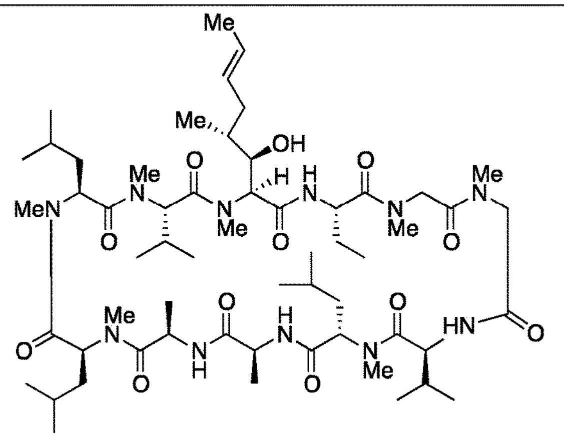 |
| C38 | Ala | MeLeu | Val | MeThr | 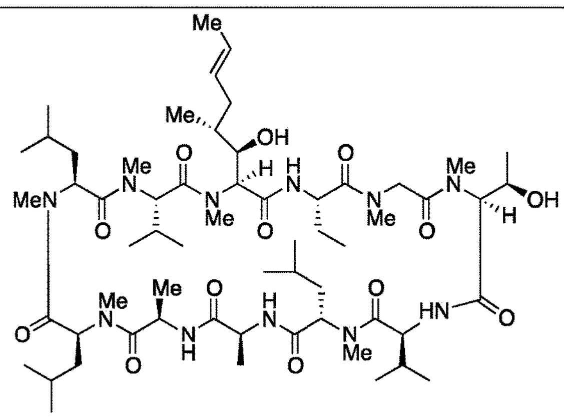 |

| Entry | AA1 | AA2 | AA3 | AA4 | Structure |
|---|---|---|---|---|---|
| C39 | Ala | MeLeu | Val | MeTyr | 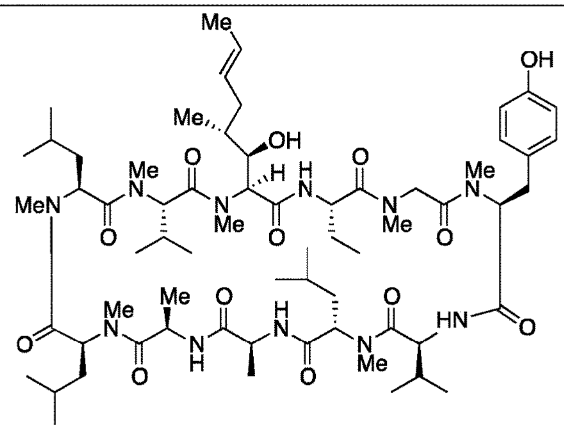 |
| C40 | Ala | MeLeu | Val | MeVal | 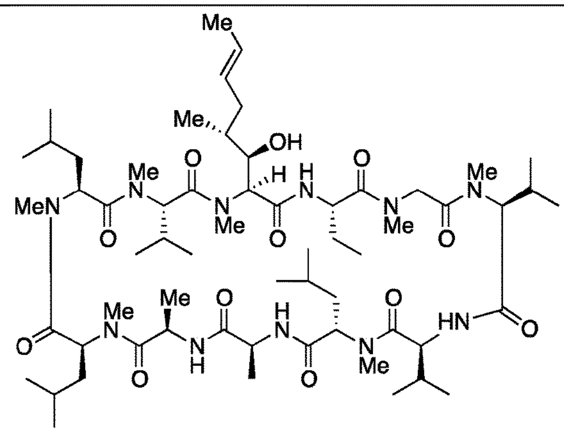 |
| C41 | Ala | MeLeu | Val | MeTyr(PO3H2) | 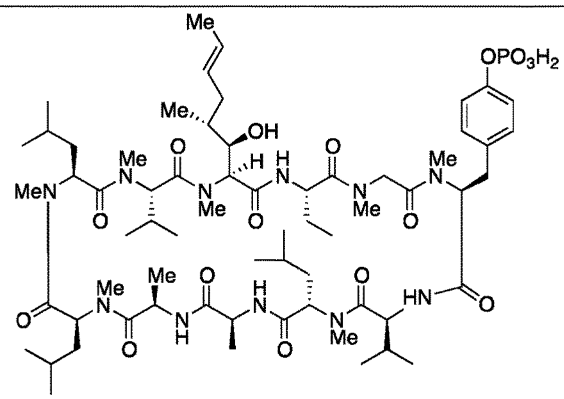 |

| Entry | AA1 | AA2 | AA3 | AA4 | Structure |
|---|---|---|---|---|---|
| C42 | Ala | MeLeu | Val | D-MeVal | 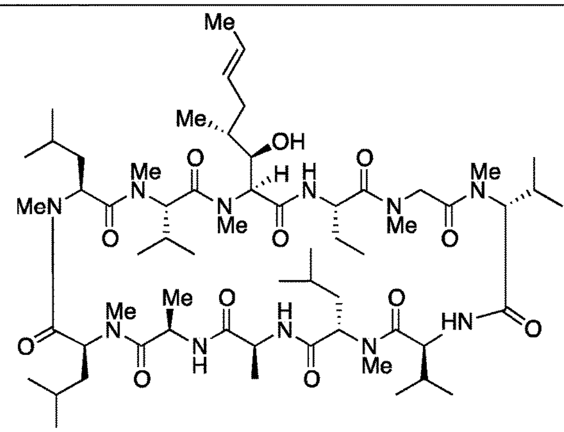 |
| C43 | Ala | MeLeu | Val | MeNle | 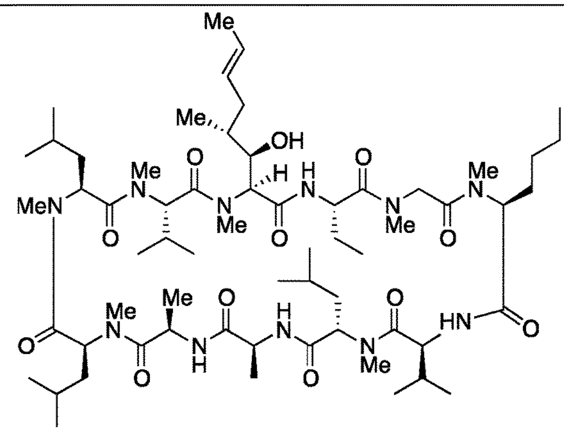 |
| C44 | Ala | MeLeu | Val | MeNva | 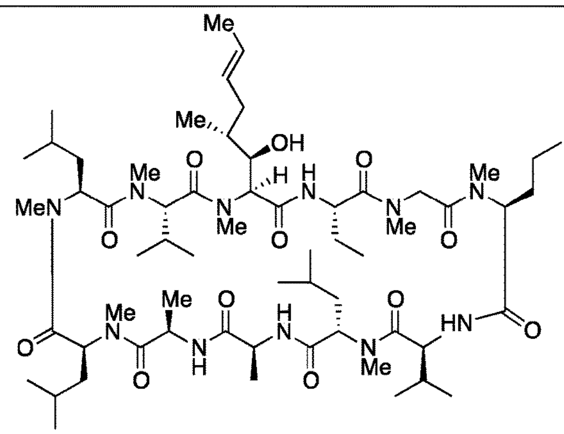 |

FIG. 2 (continued)

| Entry | AA1 | AA2 | AA3 | AA4 | Structure |
|---|---|---|---|---|---|
| C45 | Leu | MeLeu | Val | MeIle | 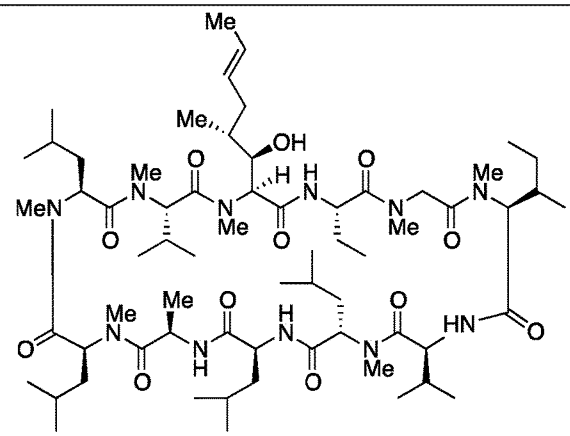 |
| C46 | Leu | MeLeu | Val | MeAla | 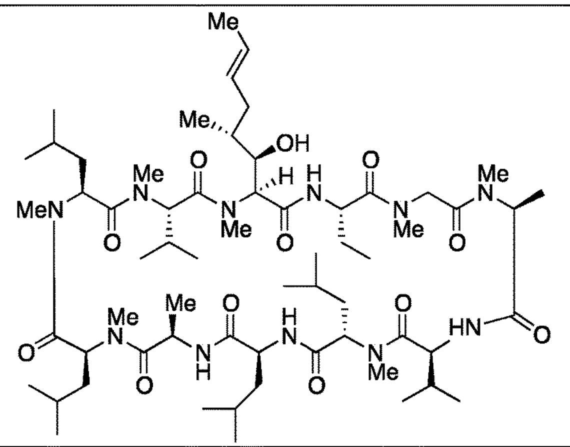 |
| C47 | Leu | MeLeu | Val | D-MeAla | 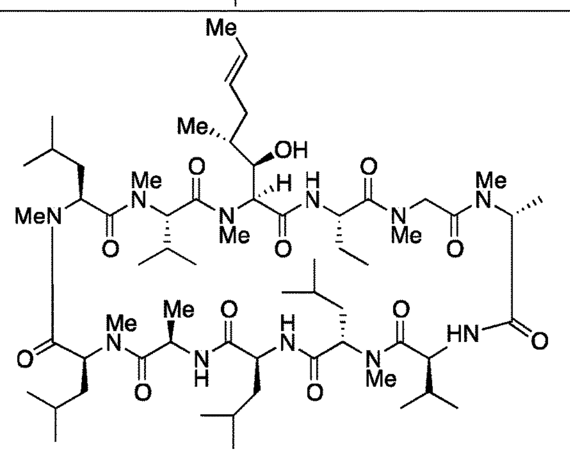 |

FIG. 2 (continued)

| Entry | AA1 | AA2 | AA3 | AA4 | Structure |
|---|---|---|---|---|---|
| C48 | Leu | MeLeu | Val | MePhe | 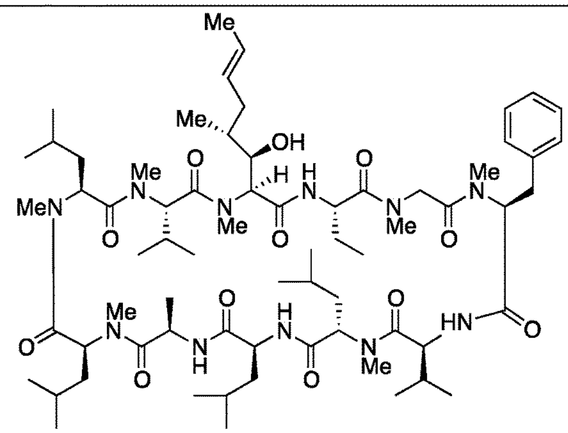 |
| C49 | Leu | MeLeu | Val | Sar | 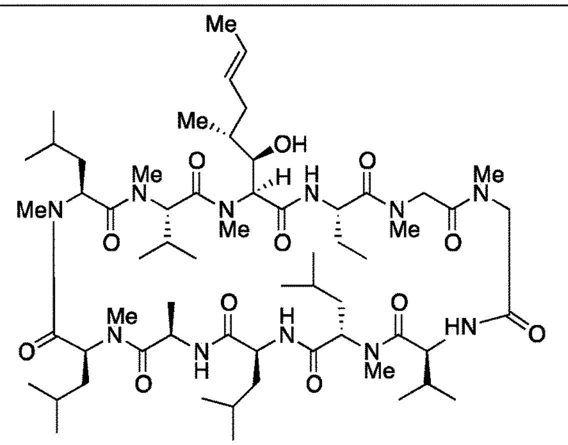 |
| C50 | Leu | MeLeu | Val | MeLeu | 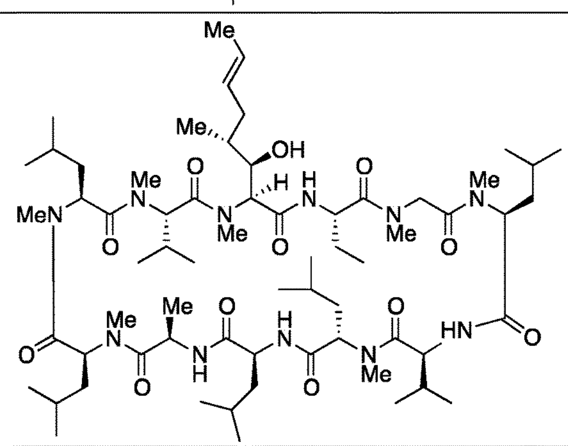 |

| Entry | AA1 | AA2 | AA3 | AA4 | Structure |
|---|---|---|---|---|---|
| C51 | Leu | MeLeu | Val | MeThr | 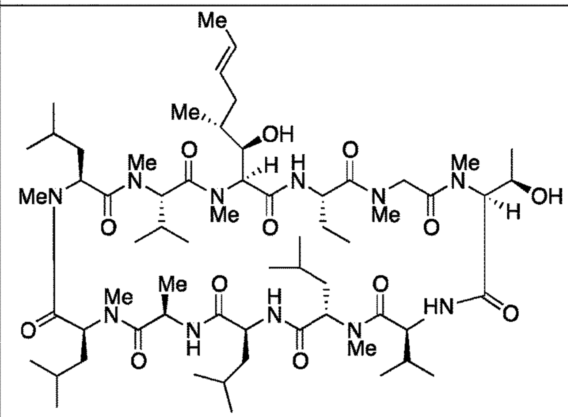 |
| C52 | Leu | MeLeu | Val | MeTyr | 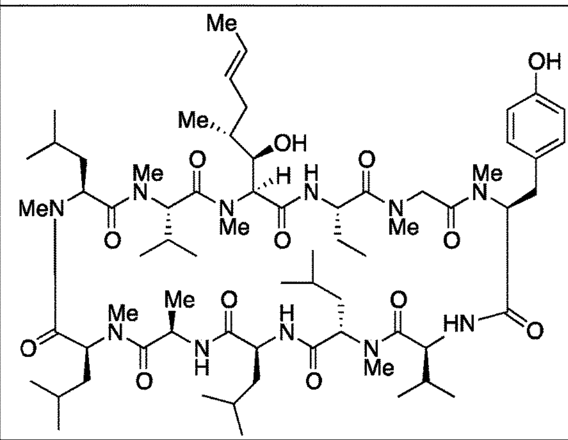 |
| C53 | Leu | MeLeu | Val | MeVal | 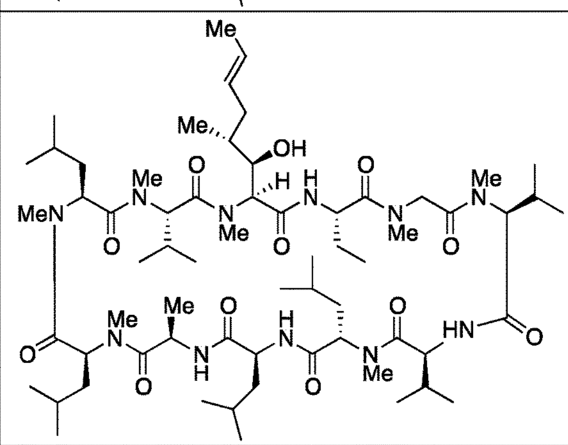 |

| Entry | AA1 | AA2 | AA3 | AA4 | Structure |
|---|---|---|---|---|---|
| C54 | Leu | MeLeu | Val | MeNva | 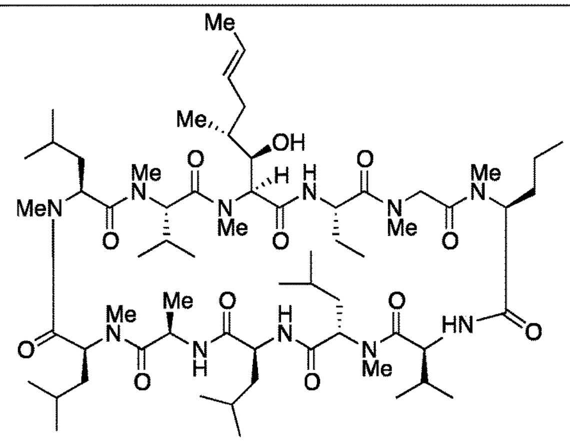 |
| C55 | Leu | MeLeu | Val | D-MeVal | 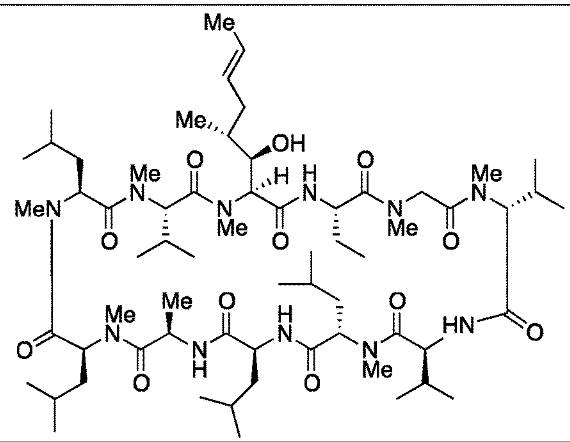 |
| C56 | Leu | MeLeu | Val | MeNle | 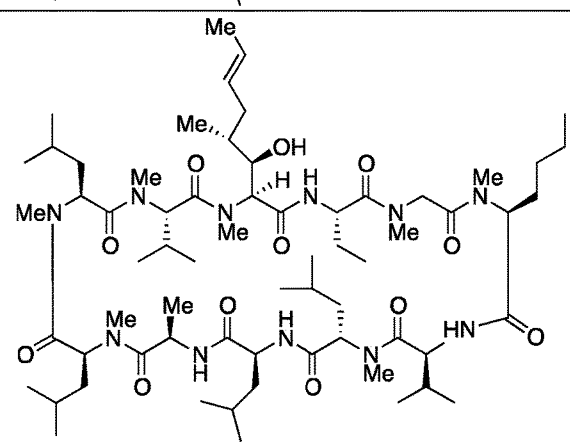 |

| Entry | AA1 | AA2 | AA3 | AA4 | Structure |
|---|---|---|---|---|---|
| C57 | Leu | MeLeu | Leu | MeIle | 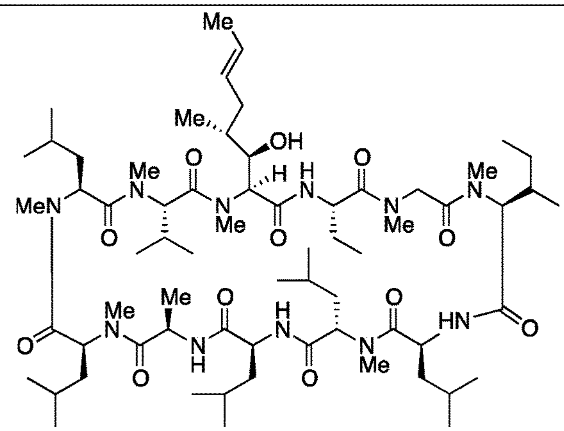 |
| C58 | Leu | MeLeu | Leu | MeAla | 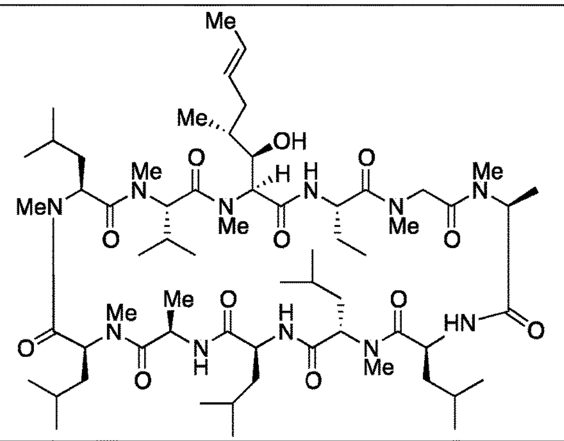 |
| C59 | Leu | MeLeu | Leu | D-MeAla | 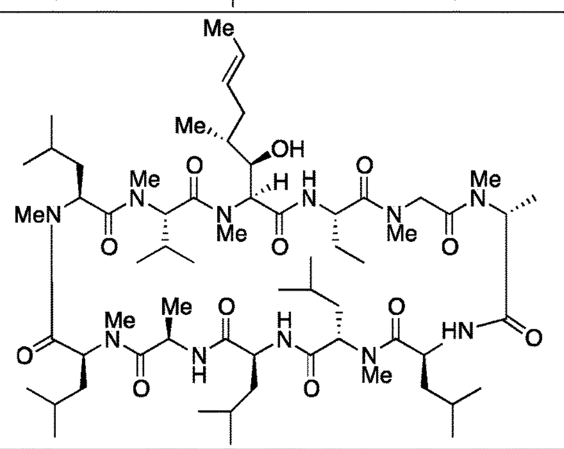 |

FIG. 2 (continued)

| Entry | AA1 | AA2 | AA3 | AA4 | Structure |
|-------|-----|-----|-----|-----|-----------|
| C60 | Leu | MeLeu | Leu | MePhe | 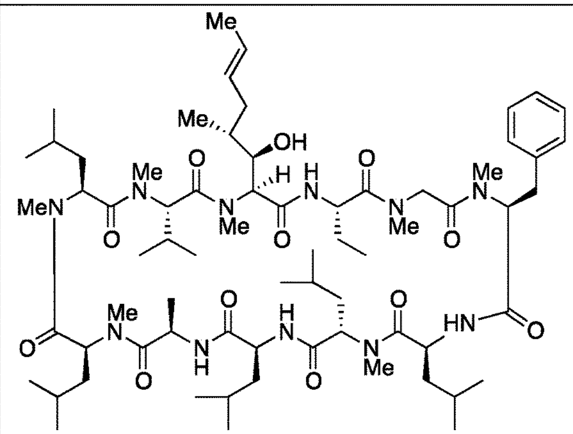 |
| C61 | Leu | MeLeu | Leu | Sar | 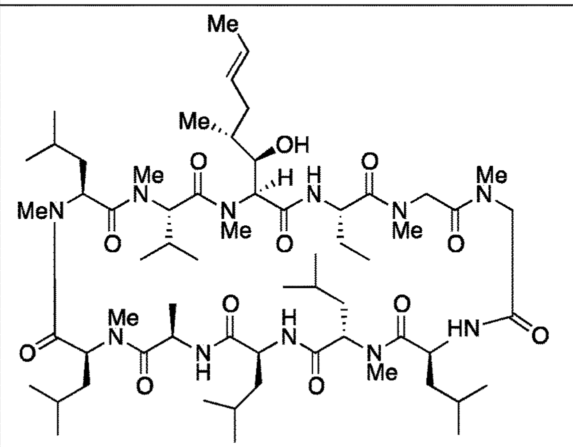 |
| C62 | Leu | MeLeu | Leu | MeLeu | 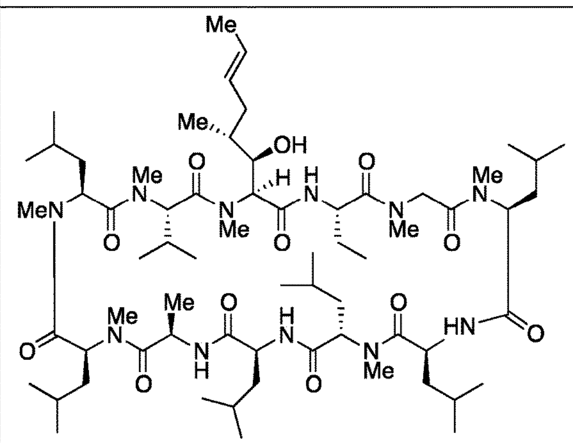 |

FIG. 2 (continued)

| Entry | AA1 | AA2 | AA3 | AA4 | Structure |
|---|---|---|---|---|---|
| C63 | Leu | MeLeu | Leu | MeThr | 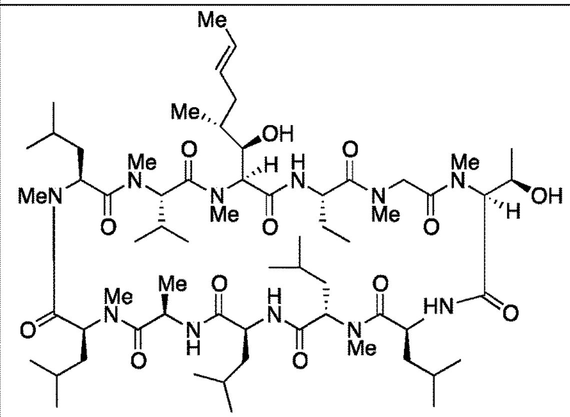 |
| C64 | Leu | MeLeu | Leu | MeTyr | 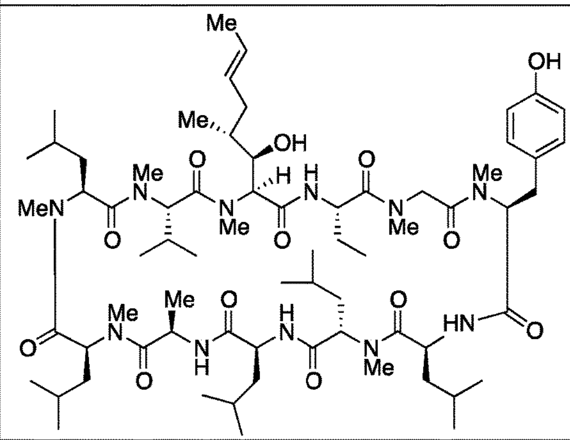 |
| C65 | Leu | MeLeu | Leu | MeVal | 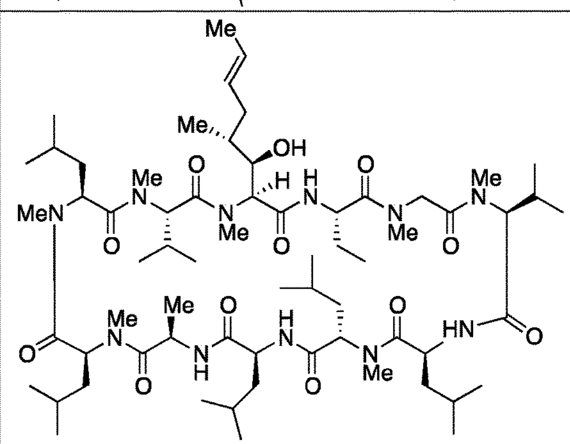 |

| Entry | AA1 | AA2 | AA3 | AA4 | Structure |
|---|---|---|---|---|---|
| C66 | Leu | MeLeu | Leu | MeNva | 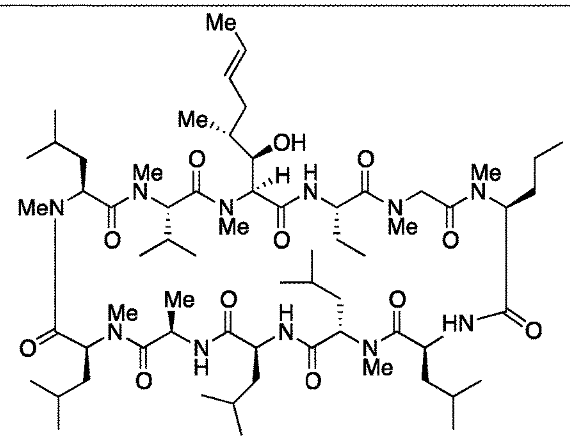 |
| C67 | Leu | MeLeu | Leu | D-MeVal | 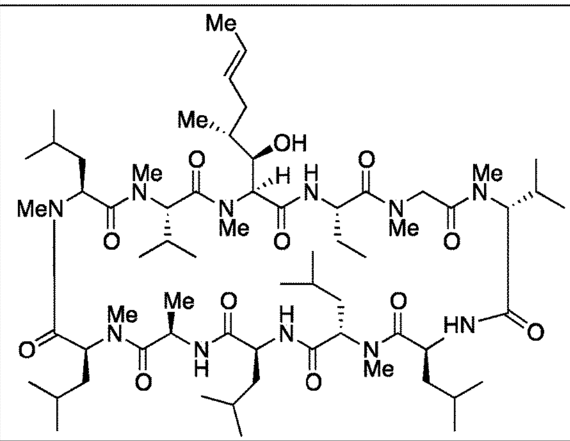 |
| C68 | Leu | MeLeu | Leu | MeNle | 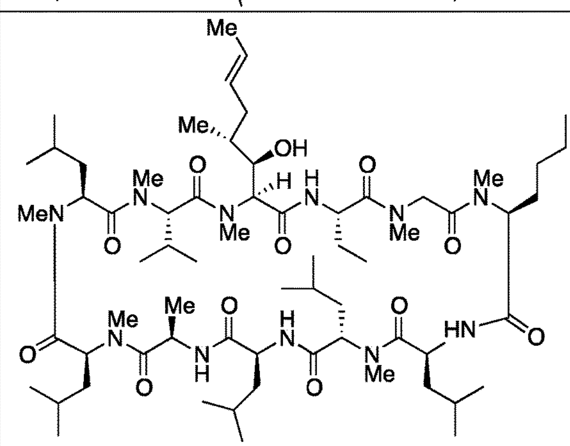 |

| Entry | AA1 | AA2 | AA3 | AA4 | Structure |
|---|---|---|---|---|---|
| C69 | Leu | MeAla | α-tBu-Gly | MeIle | 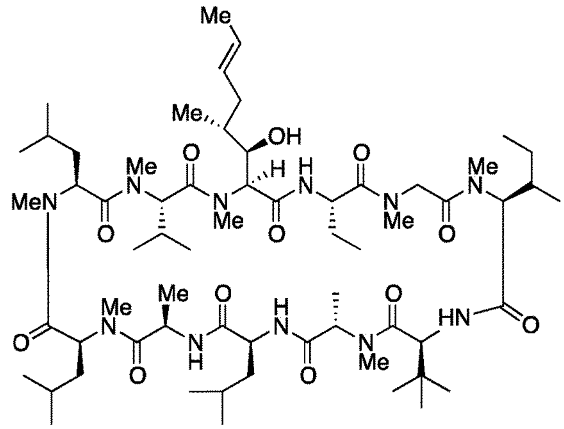 |
| C70 | Leu | MeAla | α-tBu-Gly | MeAla | 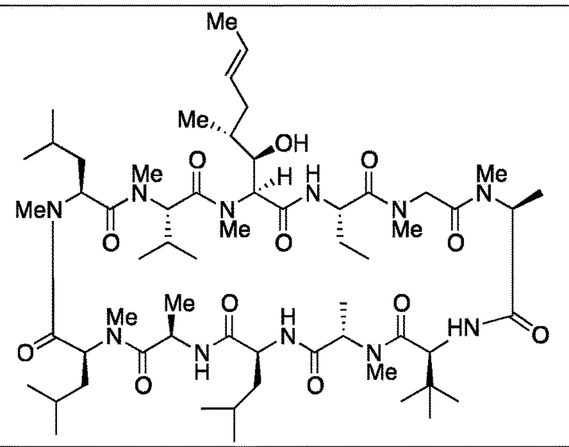 |
| C71 | Leu | MeAla | α-tBu-Gly | D-MeAla | 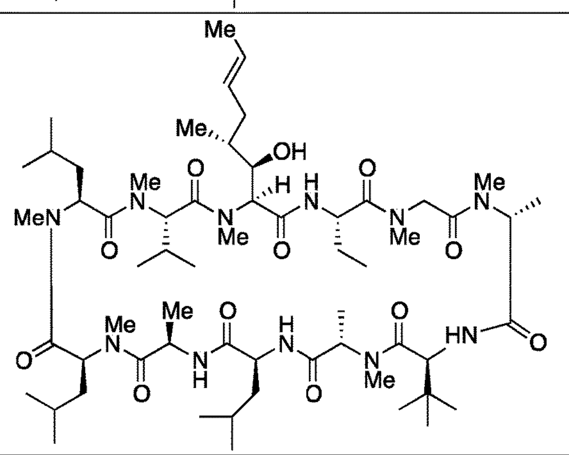 |

FIG. 2 (continued)

| Entry | AA1 | AA2 | AA3 | AA4 | Structure |
|---|---|---|---|---|---|
| C72 | Leu | MeAla | α-tBu-Gly | MePhe | 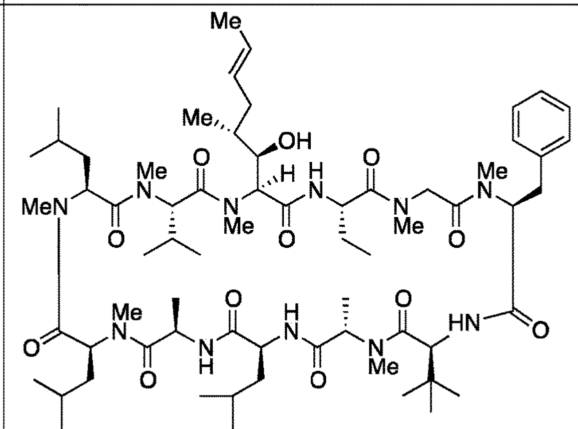 |
| C73 | Leu | MeAla | α-tBu-Gly | Sar | 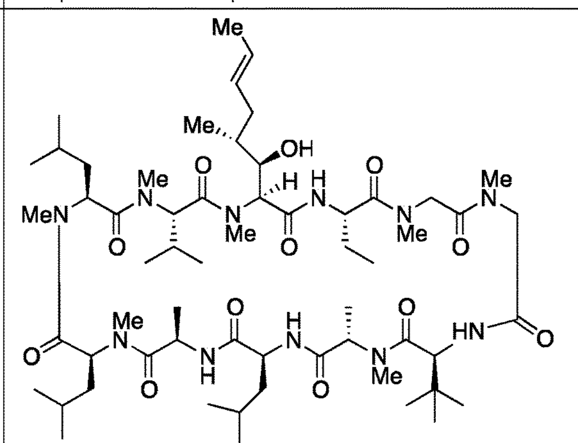 |
| C74 | Leu | MeAla | α-tBu-Gly | MeLeu | 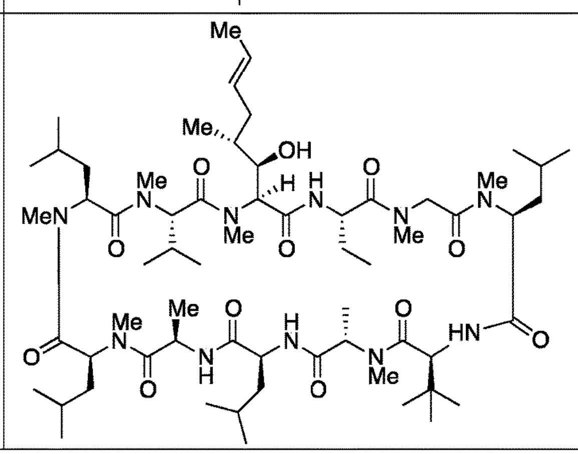 |

FIG. 2 (continued)

| Entry | AA1 | AA2 | AA3 | AA4 | Structure |
|---|---|---|---|---|---|
| C75 | Leu | MeAla | α-tBu-Gly | MeThr | 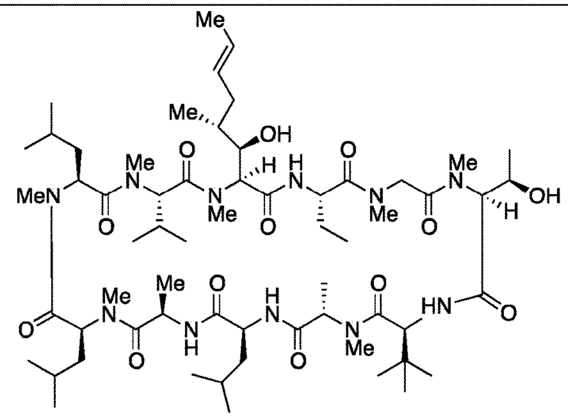 |
| C76 | Leu | MeAla | α-tBu-Gly | MeTyr | 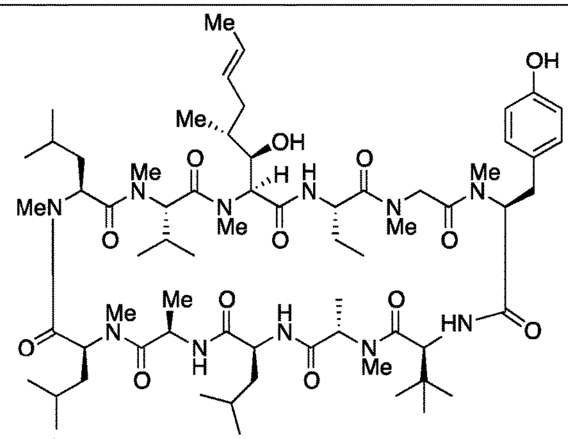 |
| C77 | Leu | MeAla | α-tBu-Gly | MeVal | 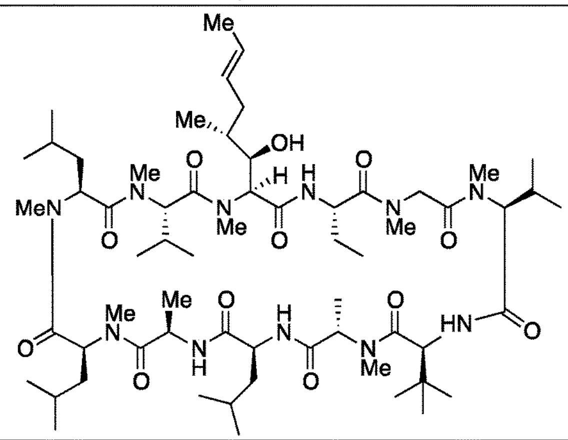 |

FIG. 2 (continued)

| Entry | AA1 | AA2 | AA3 | AA4 | Structure |
|---|---|---|---|---|---|
| C78 | Leu | MeAla | α-tBu-Gly | MeNva | 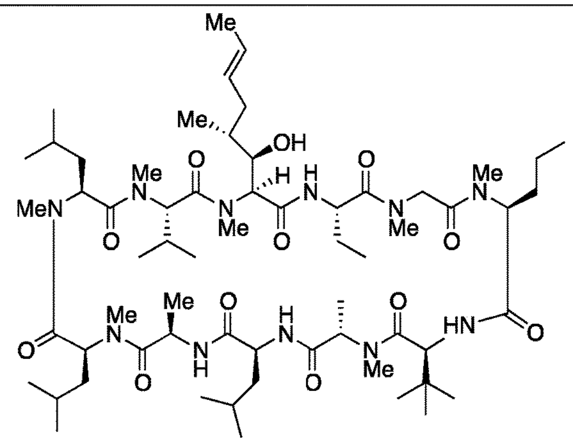 |
| C79 | Leu | MeAla | α-tBu-Gly | D-MeVal | 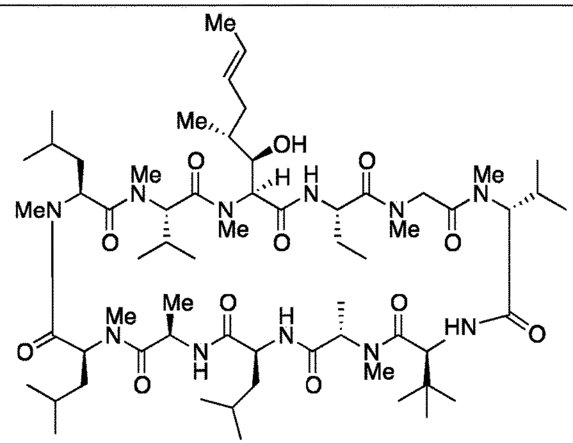 |
| C80 | Leu | MeAla | α-tBu-Gly | MeNle | 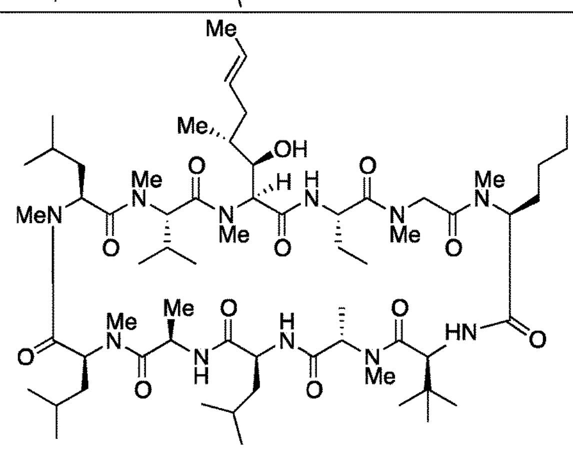 |

| Entry | AA1 | AA2 | AA3 | AA4 | Structure |
|---|---|---|---|---|---|
| C81 | Leu | MeAla | Val | MeIle | 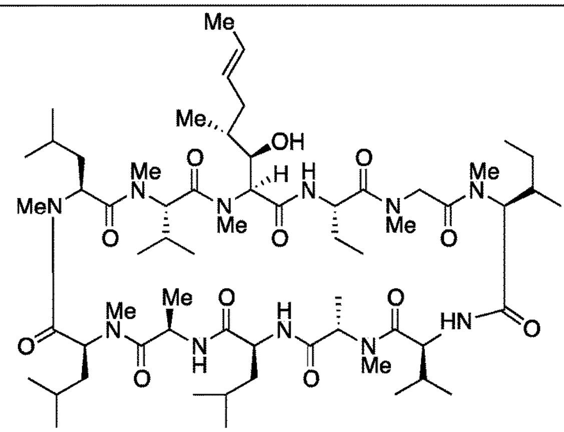 |
| C82 | Leu | MeAla | Val | MeAla | 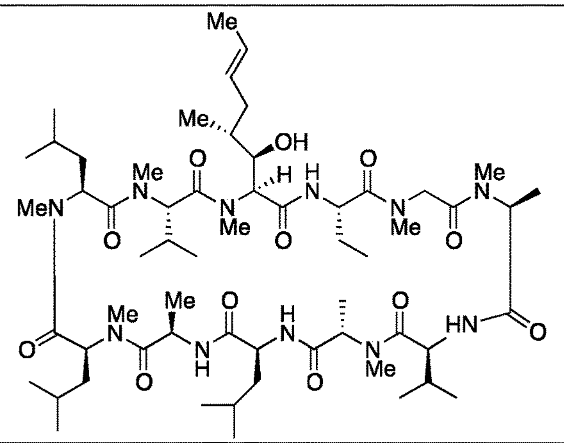 |
| C83 | Leu | MeAla | Val | D-MeAla | 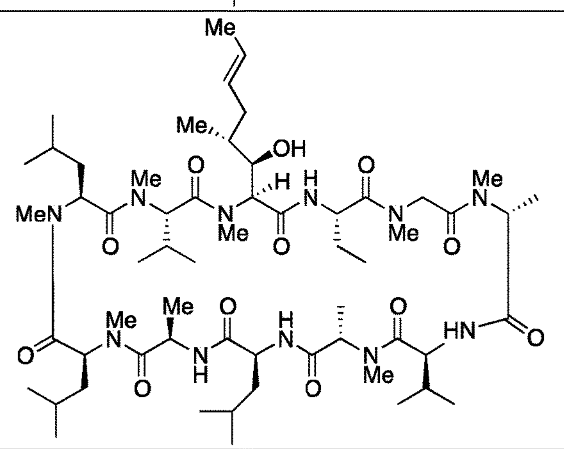 |

FIG. 2 (continued)

| Entry | AA1 | AA2 | AA3 | AA4 | Structure |
|---|---|---|---|---|---|
| C84 | Leu | MeAla | Val | MePhe | 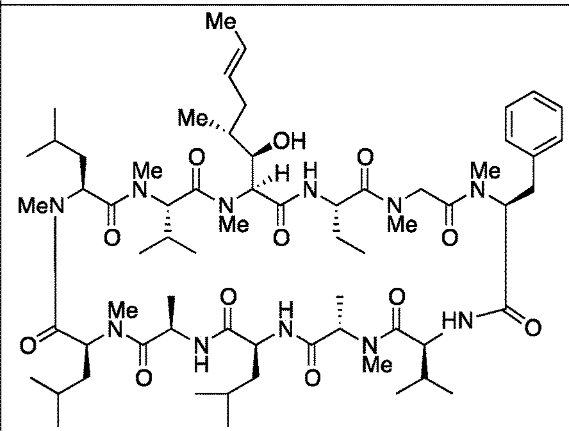 |
| C85 | Leu | MeAla | Val | Sar | 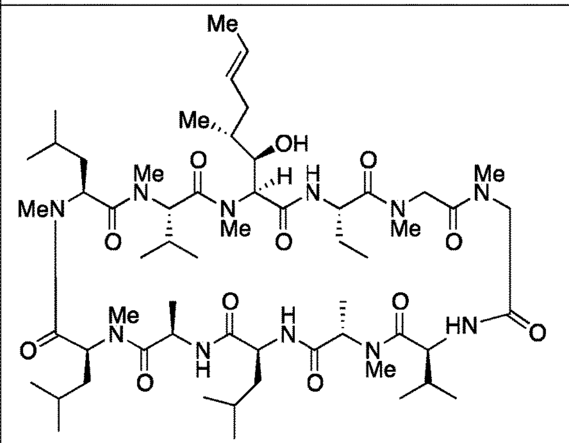 |
| C86 | Leu | MeAla | Val | MeLeu | 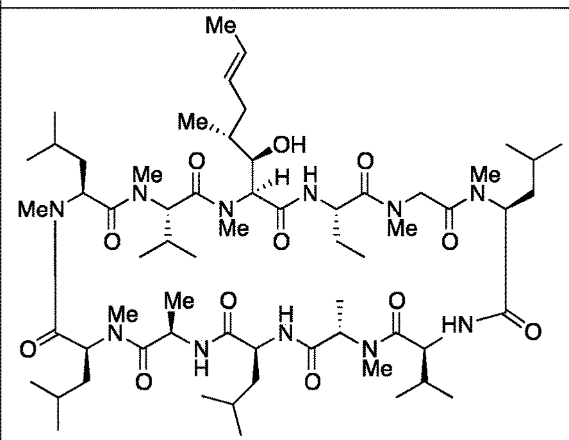 |

| Entry | AA1 | AA2 | AA3 | AA4 | Structure |
|---|---|---|---|---|---|
| C87 | Leu | MeAla | Val | MeThr | 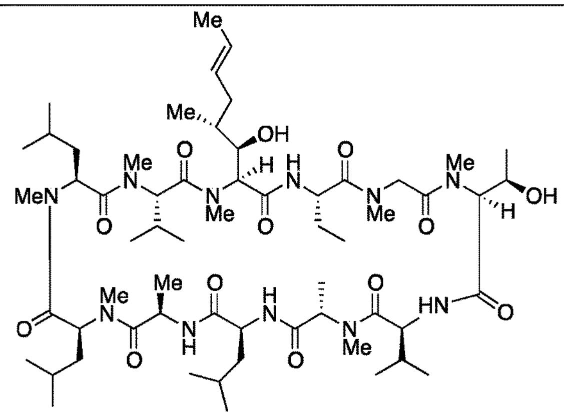 |
| C88 | Leu | MeAla | Val | MeTyr | 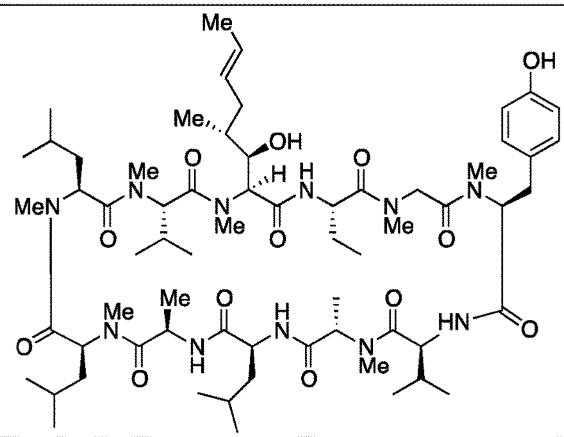 |
| C89 | Leu | MeAla | Val | MeVal | 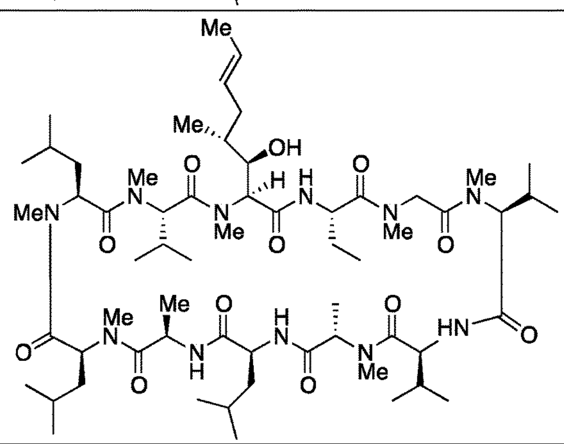 |

FIG. 2 (continued)

| Entry | AA1 | AA2 | AA3 | AA4 | Structure |
|---|---|---|---|---|---|
| C90 | Leu | MeAla | Val | MeNva | 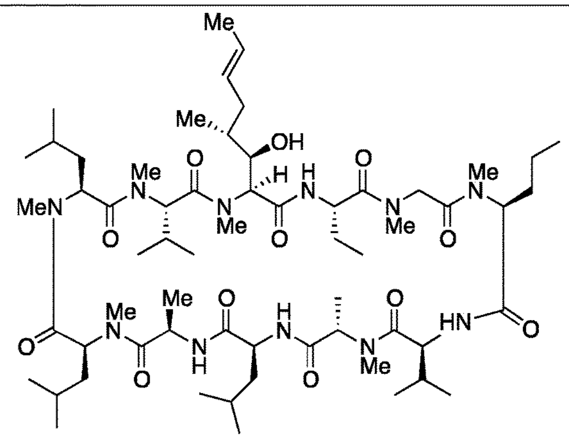 |
| C91 | Leu | MeAla | Val | D-MeVal | 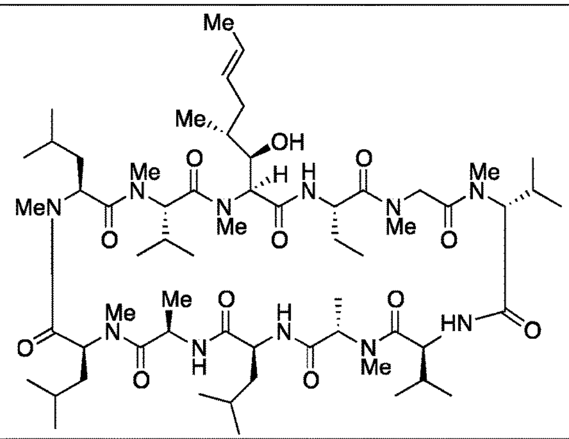 |
| C92 | Leu | MeAla | Val | MeNle | 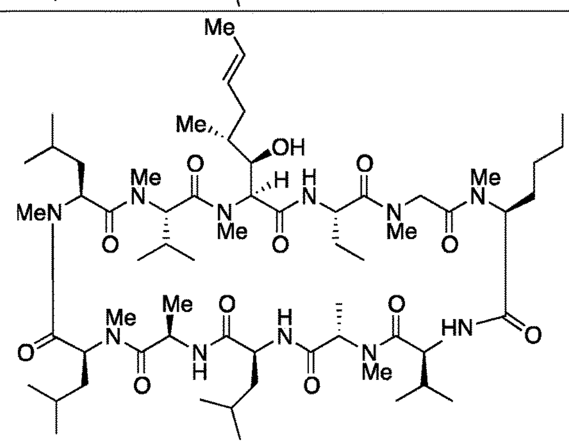 |

FIG. 2 (continued)

| Entry | AA1 | AA2 | AA3 | AA4 | Structure |
|---|---|---|---|---|---|
| C93 | Abu | MeLeu | Val | MeIle | 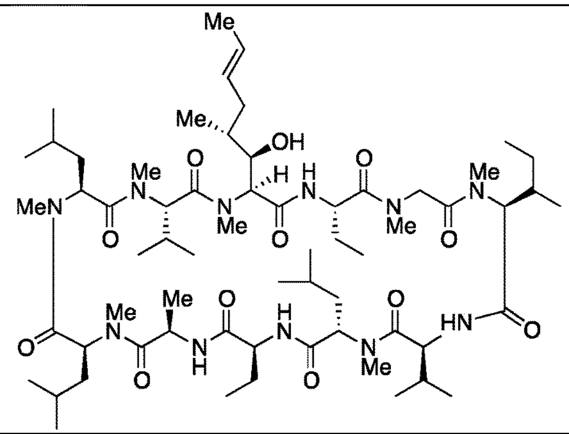 |
| C94 | Abu | MeLeu | Val | MeAla | 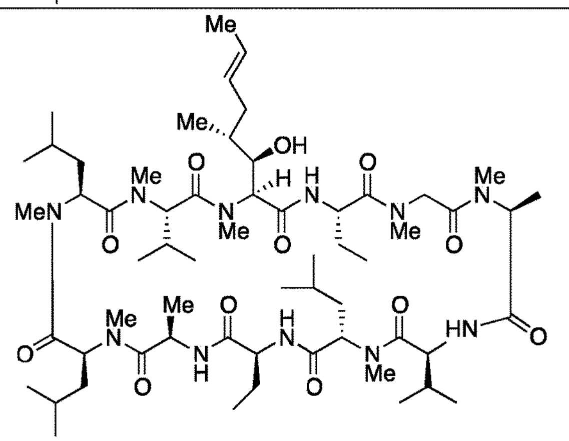 |
| C95 | Abu | MeLeu | Val | D-MeAla | 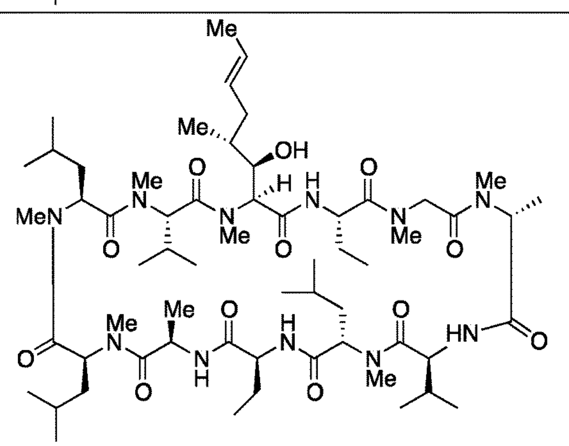 |

| Entry | AA1 | AA2 | AA3 | AA4 | Structure |
|---|---|---|---|---|---|
| C96 | Abu | MeLeu | Val | MePhe | 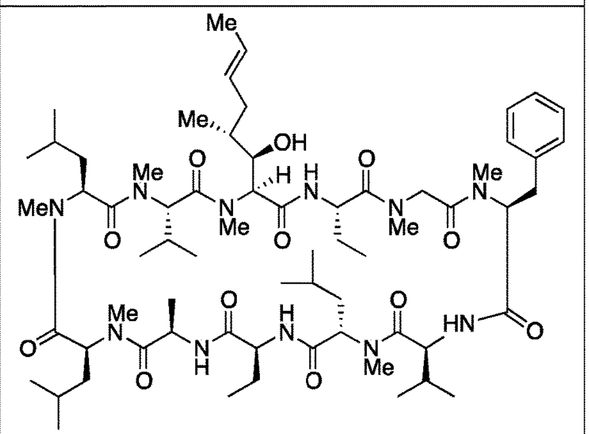 |
| C97 | Abu | MeLeu | Val | Sar | 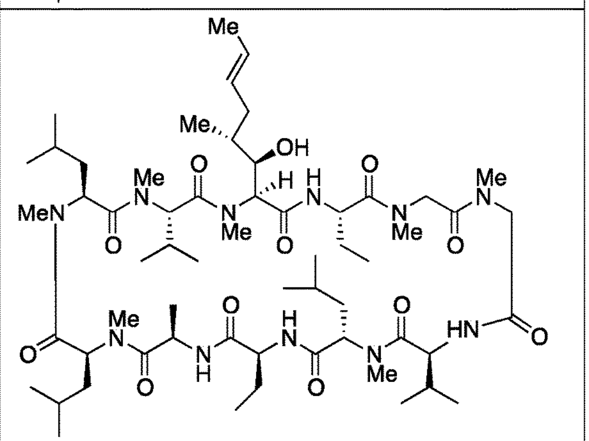 |
| C98 | Abu | MeLeu | Val | MeLeu | 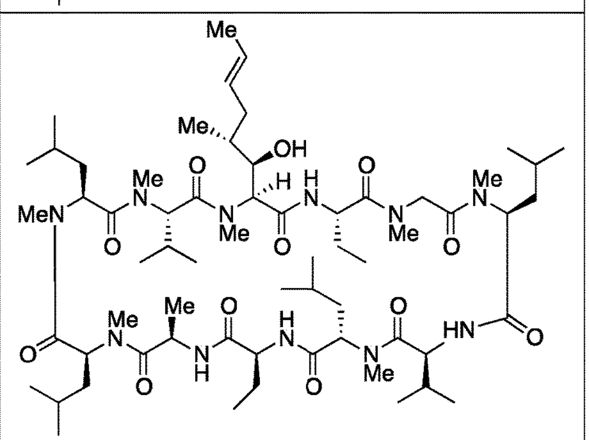 |

FIG. 2 (continued)

| Entry | AA1 | AA2 | AA3 | AA4 | Structure |
|---|---|---|---|---|---|
| C99 | Abu | MeLeu | Val | MeThr | 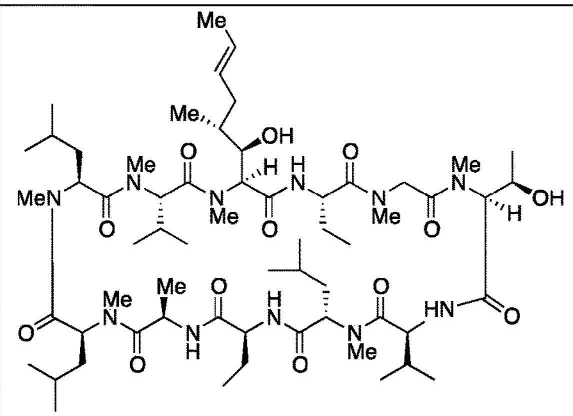 |
| C100 | Abu | MeLeu | Val | MeTyr | 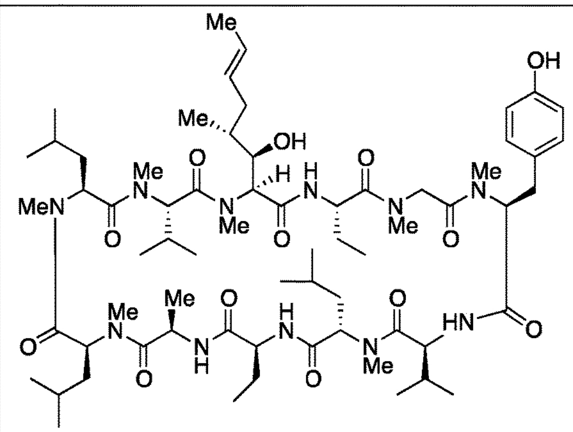 |
| C101 | Abu | MeLeu | Val | MeVal | 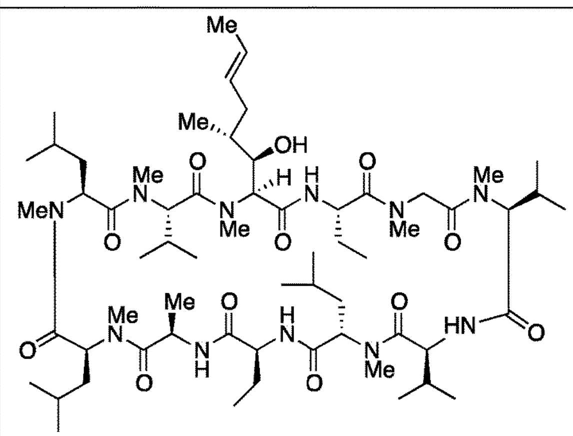 |

FIG. 2 (continued)

| Entry | AA1 | AA2 | AA3 | AA4 | Structure |
|---|---|---|---|---|---|
| C102 | Abu | MeLeu | Val | MeNva | 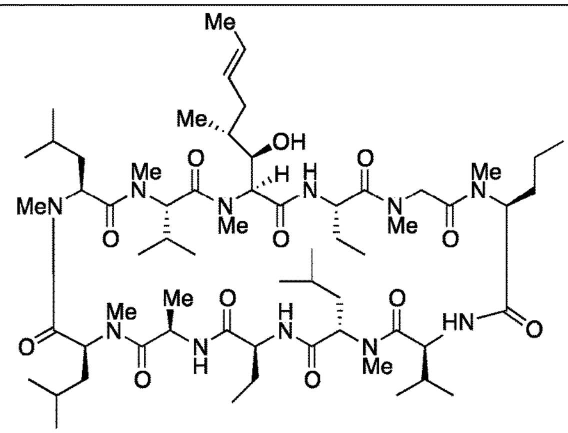 |
| C103 | Abu | MeLeu | Val | D-MeVal | 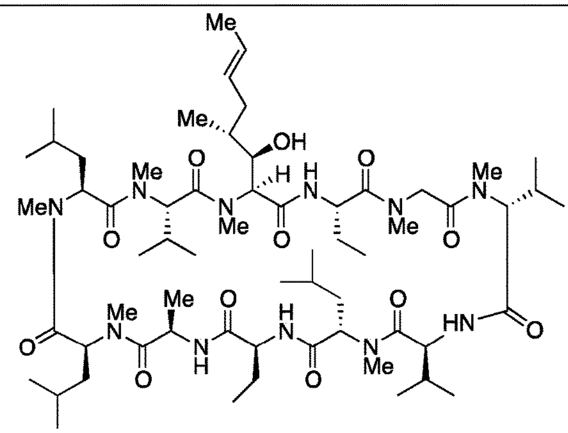 |
| C104 | Abu | MeLeu | Val | MeNle | 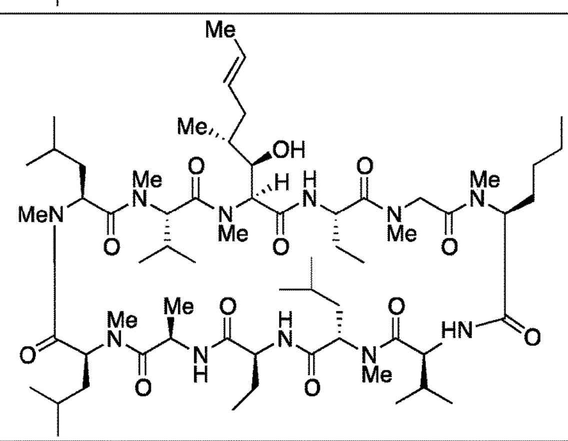 |

COMPOUNDS THAT PARTICIPATE IN COOPERATIVE BINDING AND USES THEREOF

BACKGROUND

The vast majority of small molecule drugs act by binding a functionally important pocket on a target protein, thereby modulating the activity of that protein. For example, the cholesterol-lowering drugs statins bind the enzyme active site of HMG-CoA reductase, thus preventing the enzyme from engaging with its substrates. The fact that many such drug/target interacting pairs are known may have misled some into believing that a small molecule modulator could be discovered for most, if not all, proteins provided a reasonable amount of time, effort, and resources. This is far from the case. Current estimates hold that only about 10% of all human proteins are targetable by small molecules. The other 90% are currently considered refractory or intractable toward small molecule drug discovery. Such targets are commonly referred to as "undruggable." These undruggable targets include a vast and largely untapped reservoir of medically important human proteins. Thus, there exists a great deal of interest in discovering new molecular modalities capable of modulating the function of such undruggable targets.

SUMMARY

The present invention features compounds (e.g., macrocyclic compounds) capable of modulating biological processes, for example through binding to a presenter protein (e.g., a member of the FKBP family, a member of the cyclophilin family, or PIN1) and a target protein. In some embodiments, the target and/or presenter proteins are intracellular proteins. In some embodiments, the target and/or presenter proteins are mammalian proteins. In some embodiments, provided compounds participate in tripartite presenter protein/compound/target protein complexes inside cells, e.g., mammalian cells. In some embodiments, provided compounds may be useful in the treatment of diseases and disorders such as cancer, inflammation, or infections.

In one aspect, the invention features a compound (e.g., a macrocyclic compound comprising 14 to 40 ring atoms). The compound includes: (a) a target protein interacting moiety (e.g., a eukaryotic target protein interacting moiety such as a mammalian target protein interacting moiety or a fungal target protein interacting moiety or a prokaryotic target protein interacting moiety such as a bacterial target protein interacting moiety); and (b) a presenter protein binding moiety; wherein the compound and a presenter protein form a complex that specifically binds to a target protein, and each of the compound and the presenter protein do not substantially bind to the target protein in the absence of forming the complex; or the compound and a presenter protein form a complex that binds to a target protein with at least 5-fold greater affinity than the affinity of each of the compound and the presenter protein to the target protein in the absence of forming said complex; or a pharmaceutically acceptable salt thereof.

In some embodiments, the compound is a macrocyclic compound. In certain embodiments, the compound is an acyclic compound.

In some embodiments, a provided compound includes one or more linker moieties. In some embodiments, a linker moiety connects the presenter protein binding moiety (or portion thereof) and the target protein interacting moiety (or portion thereof).

In some embodiments, the compound has the structure:

wherein A includes a mammalian target protein interacting moiety;
B includes a presenter protein binding moiety; and
$L^1$ and $L^2$ are independently selected from a bond and a linear chain of up to 10 atoms, independently selected from carbon, nitrogen, oxygen, sulfur or phosphorous atoms, wherein each atom in the chain is optionally substituted with one or more substituents independently selected from alkyl, alkenyl, alkynyl, aryl, heteroaryl, chloro, iodo, bromo, fluoro, hydroxyl, alkoxy, aryloxy, carboxy, amino, alkylamino, dialkylamino, acylamino, carboxamido, cyano, oxo, thio, alkylthio, arylthio, acylthio, alkylsulfonate, arylsulfonate, phosphoryl, and sulfonyl, and wherein any two atoms in the chain may be taken together with the substituents bound thereto to form a ring, wherein the ring may be further substituted and/or fused to one or more optionally substituted carbocyclic, heterocyclic, aryl, or heteroaryl rings.

In some embodiments, the compound has the structure:

wherein each of $Z^1$ and $Z^2$ are, independently, hydrogen or hydroxyl.

In other embodiments, at least one atom of $L^1$, $L^2$, $Z^1$, and/or $Z^2$ participates in binding to the presenter protein and the target protein. In certain embodiments, at least one atom of $L^1$, $L^2$, $Z^1$, and/or $Z^2$ does not participate in binding to the presenter protein or the target protein.

In some embodiments, $L^1$, $L^2$, $Z^1$, and/or $Z^2$ includes one or more atoms that participates in binding to the presenter protein and/or to the target protein. In some embodiments, at least one atom of the one or more of $L^1$, $L^2$, $Z^1$, and/or $Z^2$ participates in binding to the presenter protein and/or the target protein. In certain embodiments, at least one atom of the one or more of $L^1$, $L^2$, $Z^1$, and/or $Z^2$ does not participate in binding to the presenter protein and/or the target protein.

In some embodiments, the presenter protein binding moiety includes 5 to 20 ring atoms (e.g., 5 to 10, 7 to 12, 10 to 15, 12 to 17, or 15 to 20 ring atoms).

In some embodiments, the compound consists of 14 to 20 ring atoms (e.g., 14 to 16, 14 to 17, 15 to 18, 16 to 19, or 17 to 20 ring atoms or 14, 15, 16, 17, 18, 19, or 20 ring atoms). In certain embodiments, the compound consists of 21 to 26 ring atoms (e.g., 21 to 23, 22 to 24, 23 to 25, or 24 to 26 ring atoms or 21, 22, 23, 24, 25, 26 ring atoms). In some embodiments, the compound consists of 27 to 40 ring atoms (e.g., 27 to 30, 29 to 34, 33 to 38, 37 to 40 ring atoms or 27, 28, 29, 30, 31, 32, 33, 34, 35, 36, 37, 38, 39, or 40 ring atoms).

In some embodiments, the presenter protein binding moiety includes the structure of Formula I:

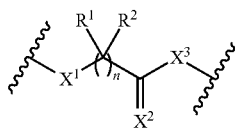

Formula I wherein n is 0 or 1;

$X^1$ and $X^3$ are each independently O, S, $CR^3R^4$, or $NR^5$;

$X^2$ is O, S, or $NR^5$;

$R^1$, $R^2$, $R^3$, and $R^4$ are each independently hydrogen, hydroxyl, optionally substituted amino, halogen, thiol, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ carbocyclyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl, or any two of $R^1$ $R^2$, $R^3$, or $R^4$ are taken together with the atom or atoms to which they are bound to form an optionally substituted carbocyclyl, optionally substituted heterocyclyl, optionally substituted aryl, or optionally substituted heteroaryl; and each $R^5$ is, independently, hydrogen, hydroxyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ carbocyclyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl, or $R^5$ and one of $R^1$, $R^2$, $R^3$, or $R^4$ are taken together with the atom or atoms to which they are bound to form an optionally substituted heterocyclyl or optionally substituted heteroaryl.

In some embodiments, $X^1$ is connected to $L^1$ and $X^3$ is connected to $L^2$. In some embodiments, $X^1$ is connected to $L^2$ and $X^3$ is connected to $L^1$.

In some embodiments, the presenter protein binding moiety includes the structure of Formula Ia:

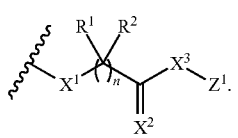

Formula Ia

In some embodiments, the presenter protein binding moiety is or includes the structure of any one of Formulae II-IV:

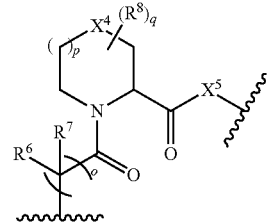

Formula II

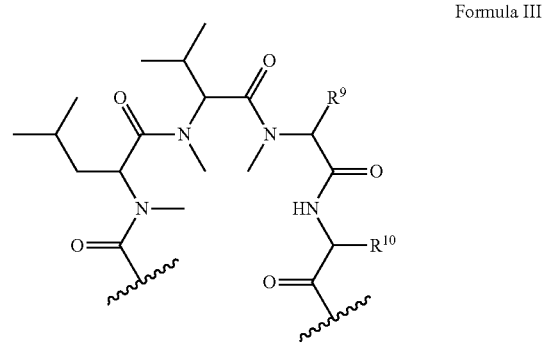

Formula III

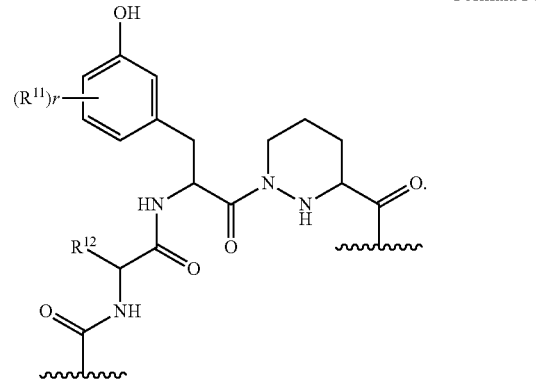

Formula IV wherein o, and p are independently 0, 1, or 2;

q is an integer between 0 and 7;

r is an integer between 0 and 4;

$X^4$ and $X^5$ are each, independently, absent, $CH_2$, O, S, SO, $SO_2$, or $NR^{13}$;

each $R^6$ and $R^7$ are independently hydrogen, hydroxyl, optionally substituted amino, halogen, thiol, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ carbocyclyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, optionally substituted $C_2$-$C_9$ heterocyclyl $C_1$-$C_6$ alkyl, or $R^6$ and $R^7$ combine with the carbon atom to which they are bound to form C=O or $R^6$ and $R^7$ combine to form an optionally substituted $C_3$-$C_{10}$ carbocyclyl or optionally substituted $C_2$-$C_9$ heterocyclyl;

each $R^8$ is, independently, hydroxyl, optionally substituted amino, halogen, thiol, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ carbocyclyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl or two $R^8$ combine to form an optionally substituted $C_3$-$C_{10}$ carbocyclyl, optionally substituted $C_6$-$C_{10}$ aryl, or optionally substituted $C_2$-$C_9$ heteroaryl;

$R^9$ is optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ carbocyclyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl;

$R^{10}$ is optionally substituted $C_1$-$C_6$ alkyl;

each $R^{11}$ is, independently, hydroxyl, cyano, optionally substituted amino, halogen, thiol, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ carbocyclyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl or two $R^{11}$ combine to form an optionally substituted $C_3$-$C_{10}$ carbocyclyl, optionally substituted $C_6$-$C_{10}$ aryl, or optionally substituted $C_2$-$C_9$ heteroaryl; and $R^{12}$ and $R^{13}$ are each, independently, hydrogen, optionally substituted $C_1$-$C_6$ alkyl, optionally substituted $C_2$-$C_6$ alkenyl, optionally substituted $C_2$-$C_6$ alkynyl, optionally substituted aryl, $C_3$-$C_7$ carbocyclyl, optionally substituted $C_6$-$C_{10}$ aryl $C_1$-$C_6$ alkyl, and optionally substituted $C_3$-$C_7$ carbocyclyl $C_1$-$C_6$ alkyl.

In some embodiments, $L^1$ is connected to the left of the presenter protein binding moiety and $L^2$ is connected to the right of the presenter protein binding moiety. In some embodiments, $L^1$ is connected to the right of the presenter protein binding moiety and $L^2$ is connected to the left of the presenter protein binding moiety.

In some embodiments, the presenter protein binding moiety is or includes the structure of any one of Formulae IIa-IVa:

Formula IIa

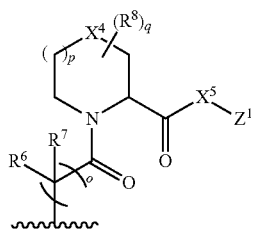

Formula IIIa

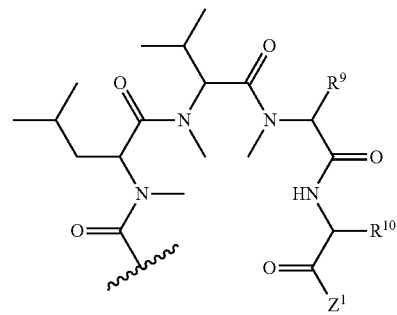

Formula IVa

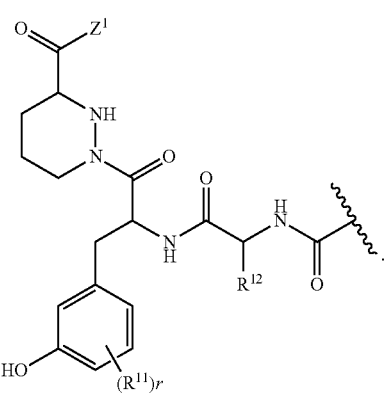

In some embodiments, the presenter protein binding moiety is or includes the structure of Formula V:

Formula V

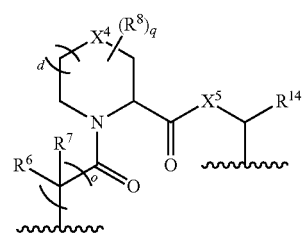

wherein $R^{14}$ is hydrogen, hydroxyl, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ carbocyclyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, optionally substituted $C_2$-$C_9$ heterocyclyl $C_1$-$C_6$ alkyl.

In certain embodiments, the presenter protein binding moiety is or includes the structure of Formula VI, VII, or VIII:

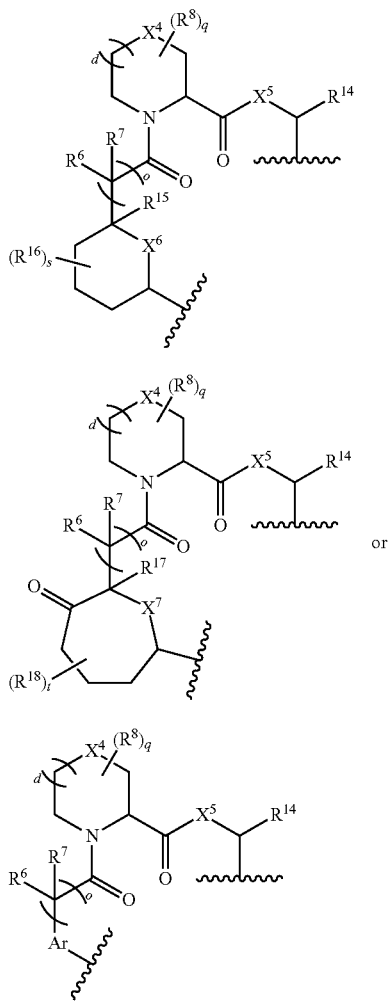

Formula VI

Formula VII

Formula VIII wherein s and t are each, independently, an integer from 0 to 7;

$X^6$ and $X^7$ are each, independently, O, S, SO, $SO_2$, or $NR^{19}$;

$R^{15}$ and $R^{17}$ are each, independently, hydrogen hydroxyl, or optionally substituted $C_1$-$C_6$ alkyl;

$R^{16}$ and $R^{18}$ are each, independently, hydroxyl, optionally substituted amino, halogen, thiol, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_2$-$C_6$ heteroalkenyl, optionally substituted $C_2$-$C_6$ heteroalkynyl, optionally substituted $C_3$-$C_{10}$ carbocyclyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl;

$R^{19}$ is optionally substituted $C_1$-$C_6$ alkyl, optionally substituted $C_2$-$C_6$ alkenyl, optionally substituted $C_2$-$C_6$ alkynyl, optionally substituted aryl, $C_3$-$C_7$ carbocyclyl, optionally substituted $C_6$-$C_{10}$ aryl $C_1$-$C_6$ alkyl, and optionally substituted $C_3$-$C_7$ carbocyclyl $C_1$-$C_6$ alkyl; and Ar is optionally substituted $C_6$-$C_{10}$ aryl or optionally substituted $C_2$-$C_9$ heteroaryl.

In certain embodiments, the presenter protein binding moiety is or includes the structure:

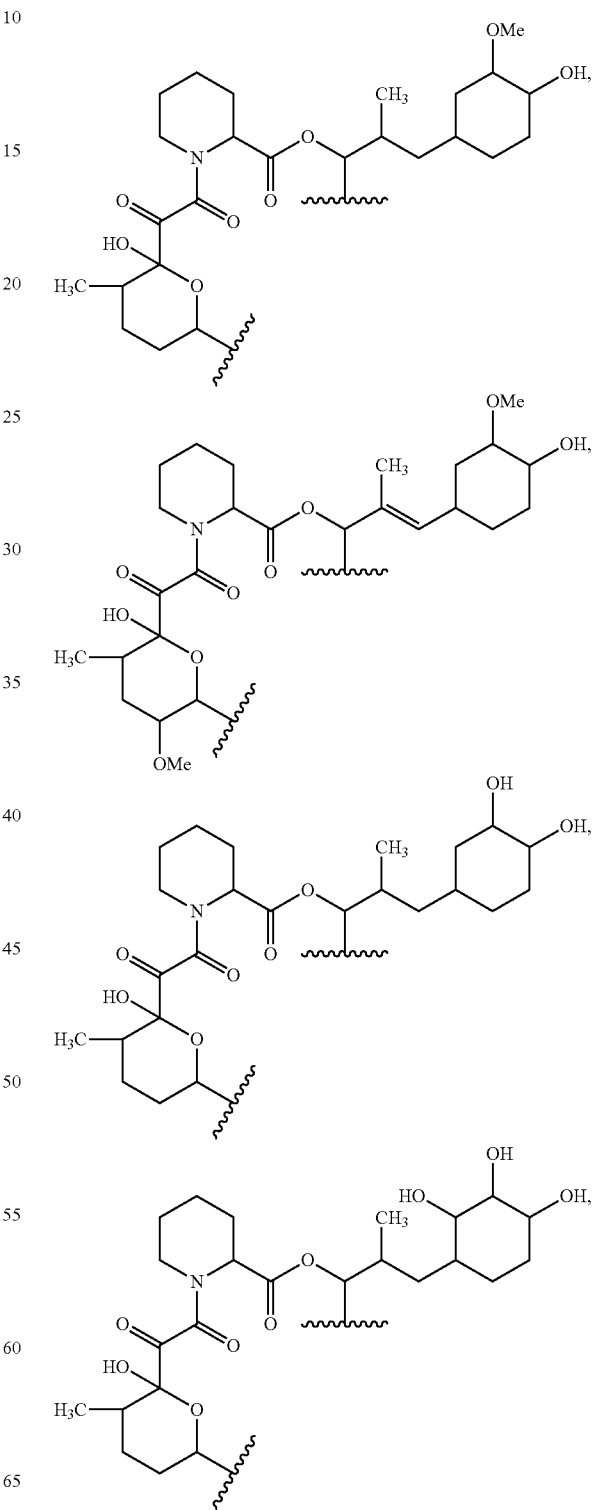

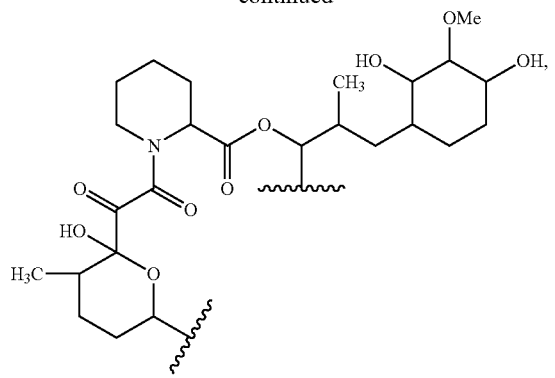
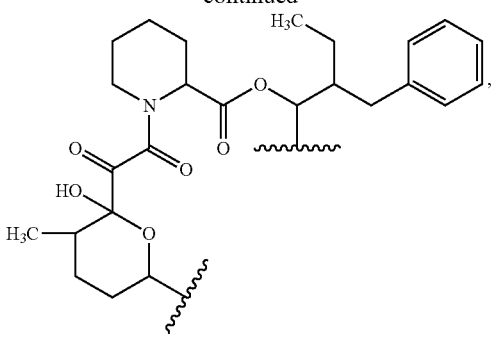
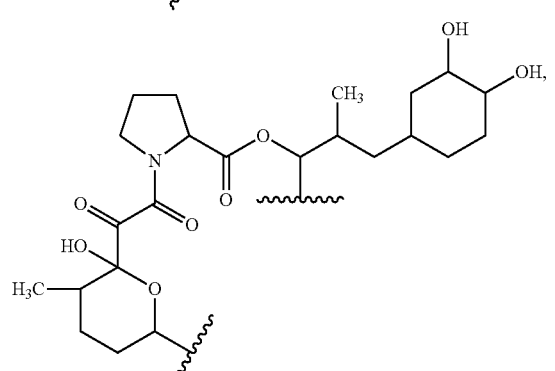
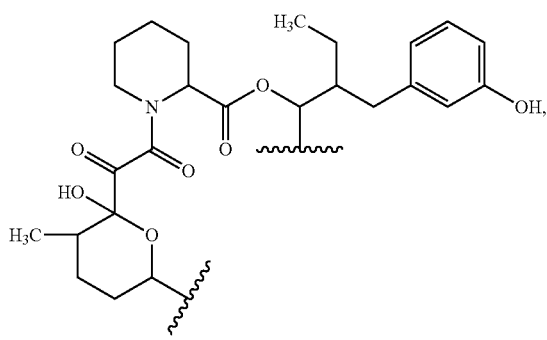
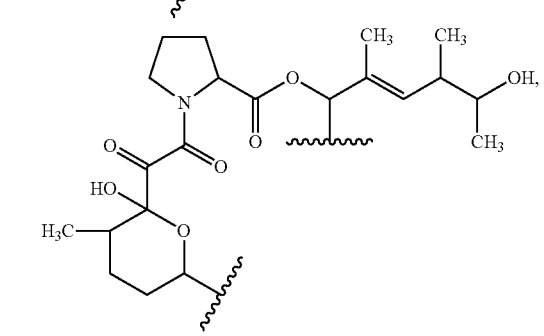
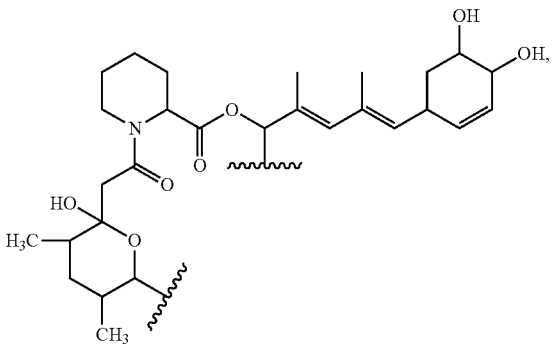
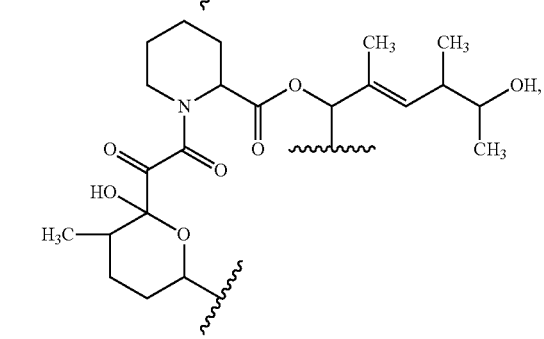
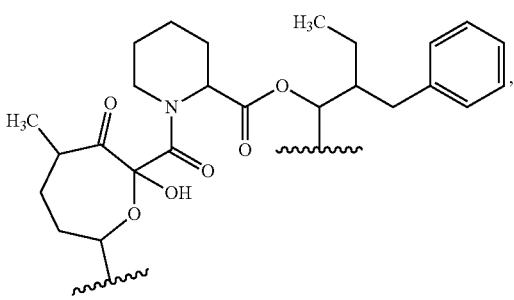
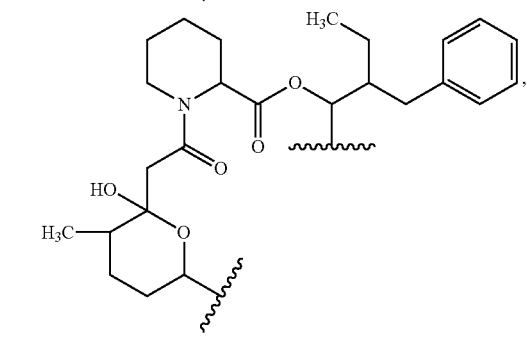
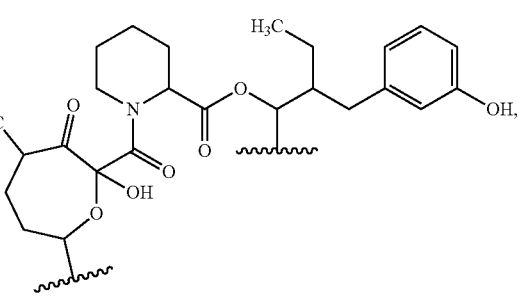

11
-continued
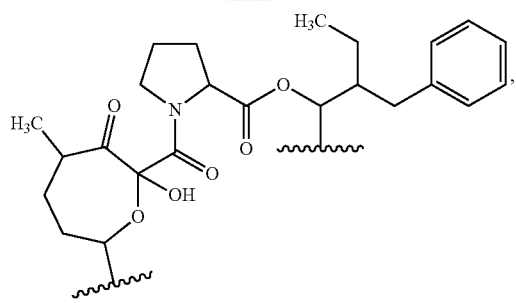
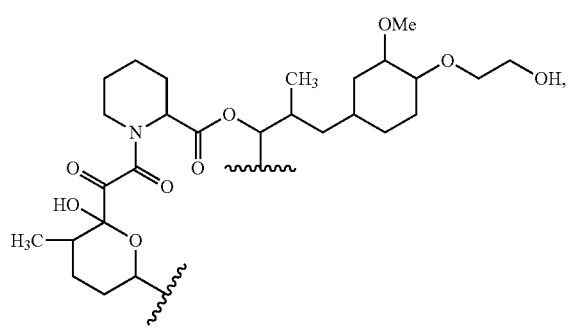
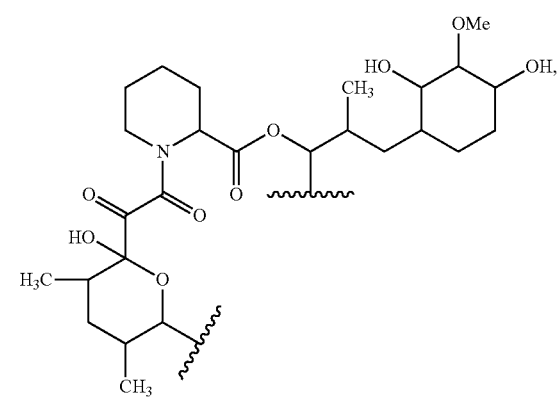
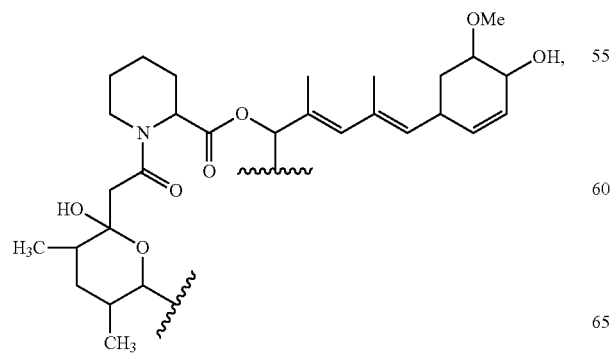
12
-continued
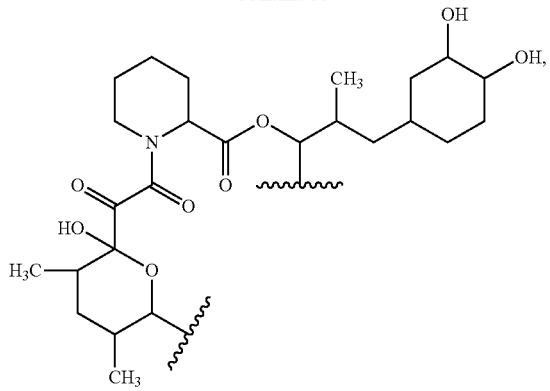
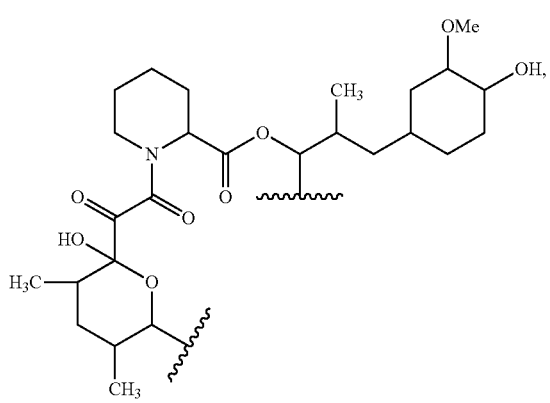
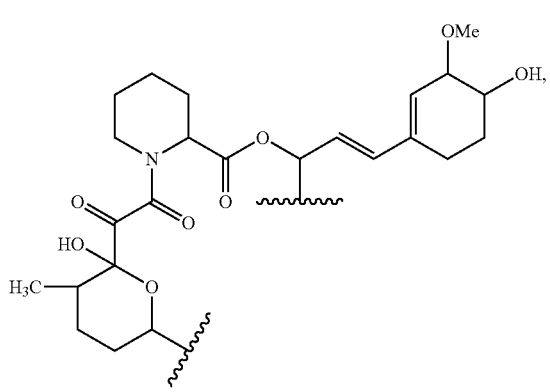
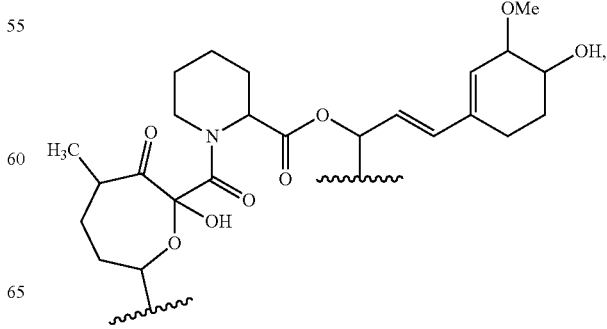

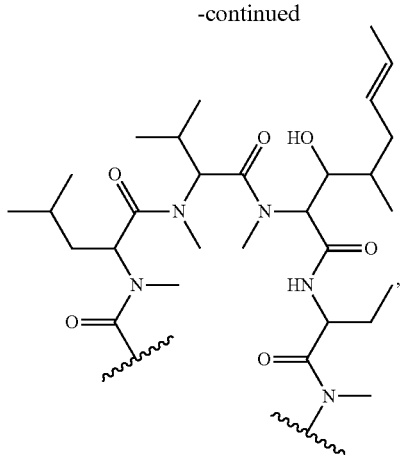
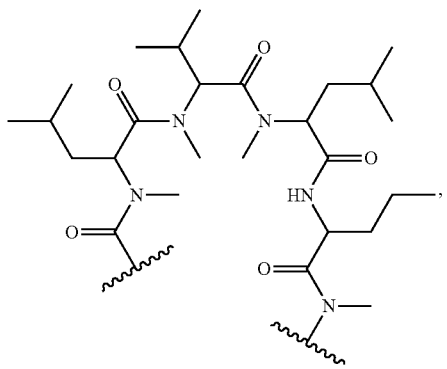
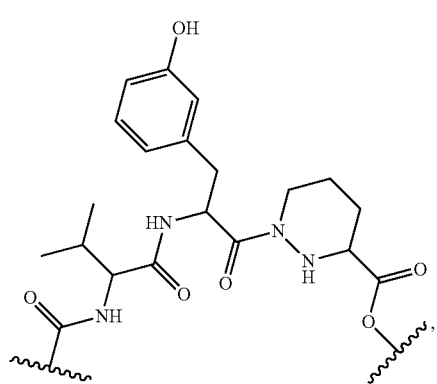
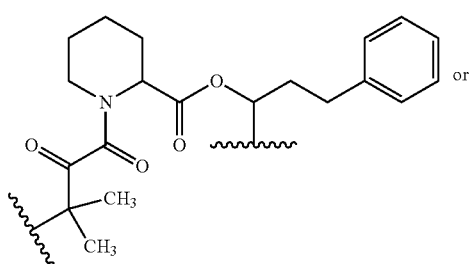
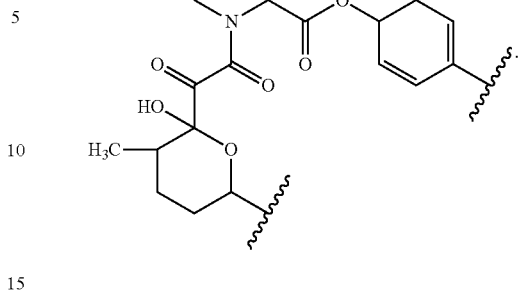
In certain embodiments, the presenter protein binding moiety is or includes the structure:
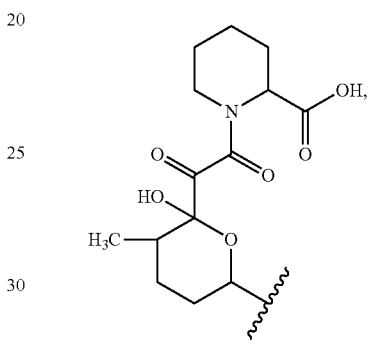
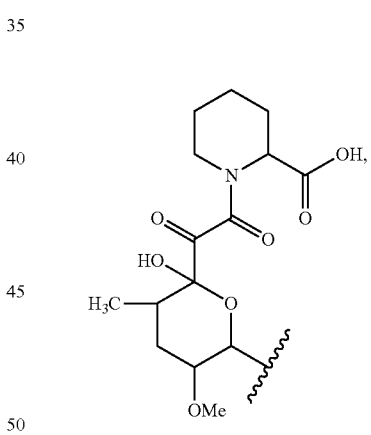
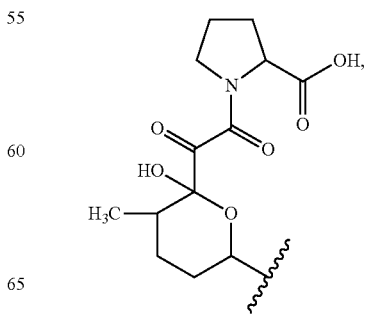

-continued
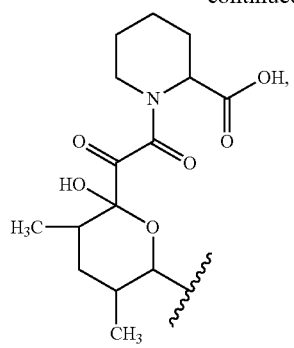
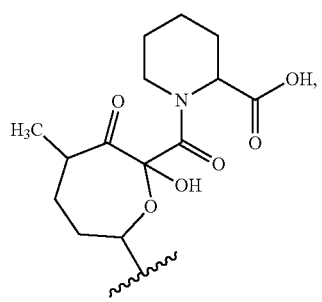
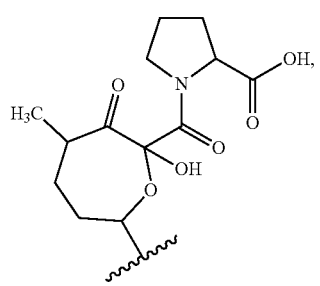
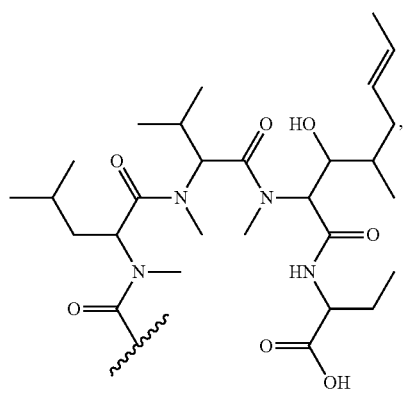
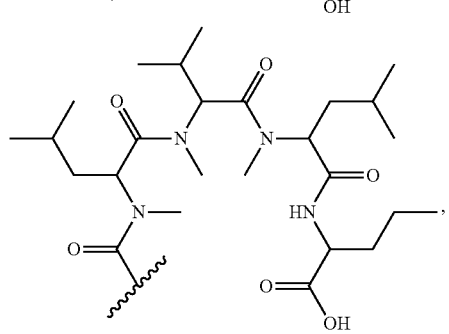
-continued
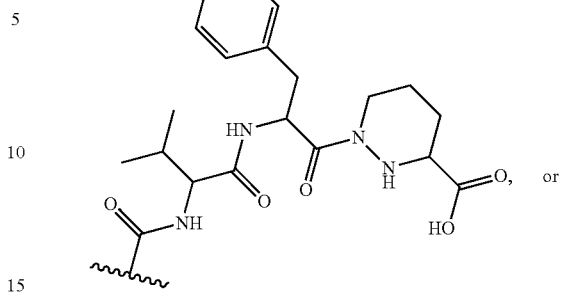
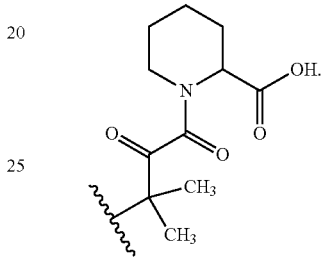
In some embodiments, presenter protein binding moiety is or includes the structure:
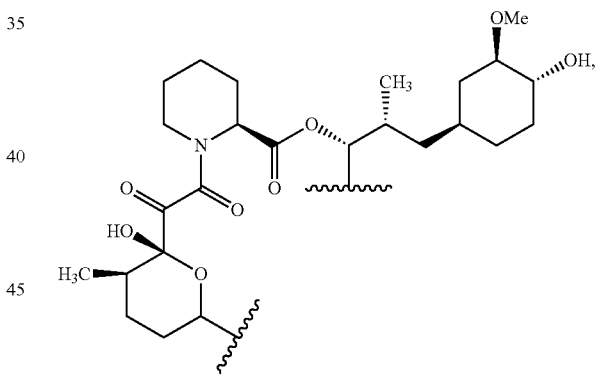
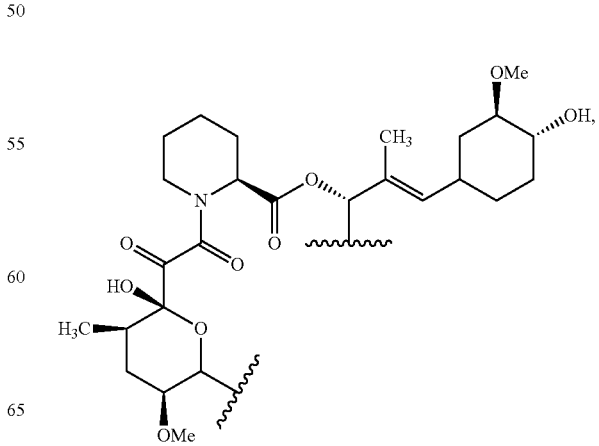

-continued
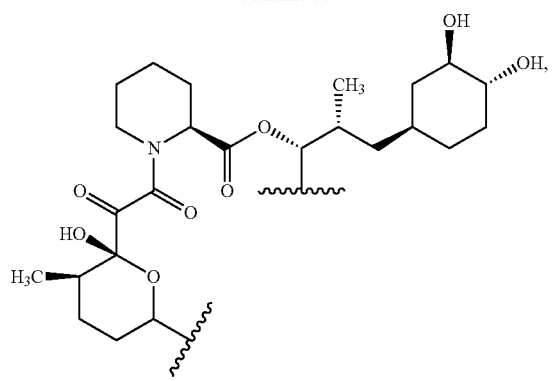
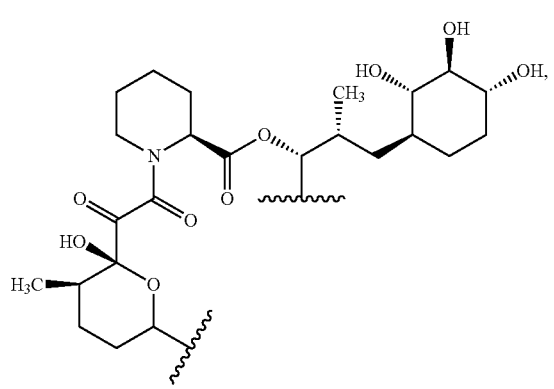
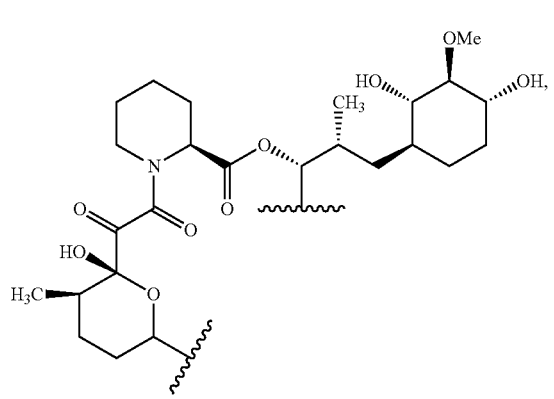
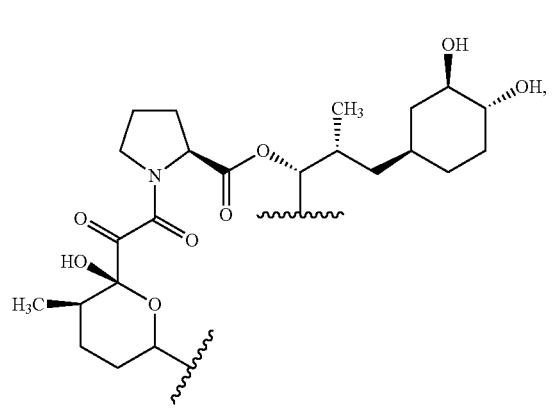
-continued
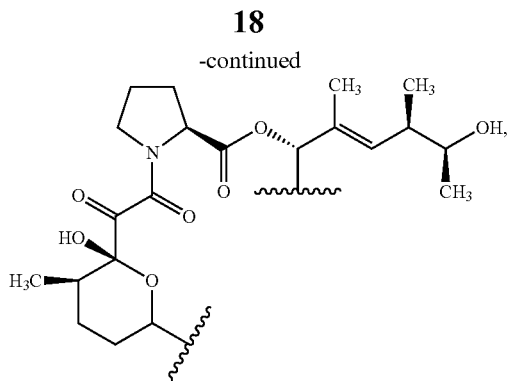
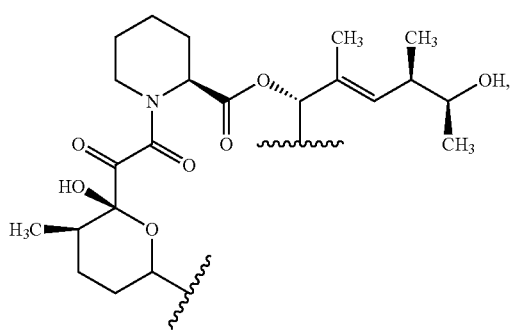
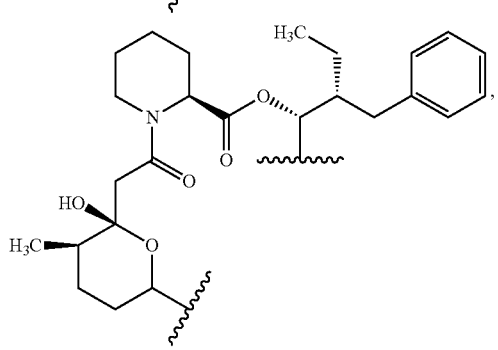
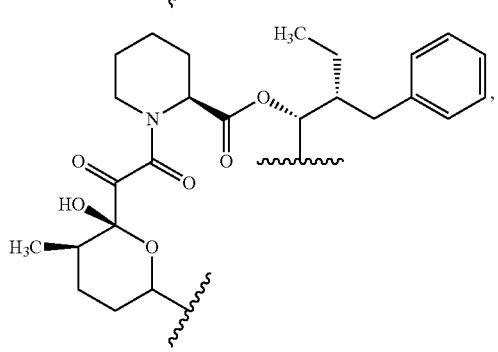
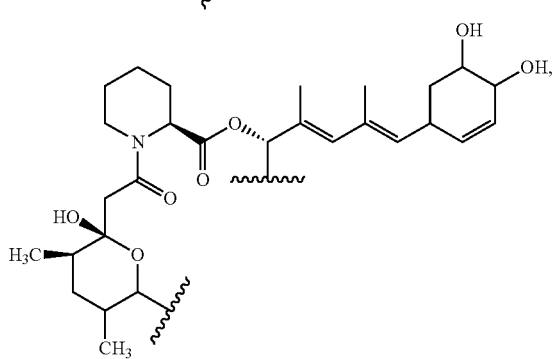

US 10,039,839 B2
19
-continued
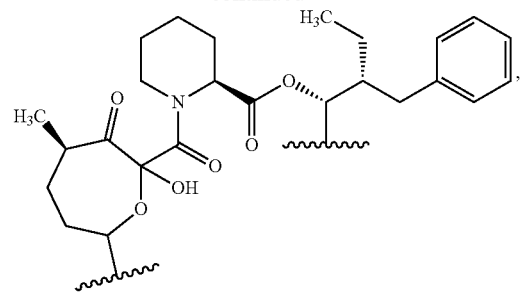
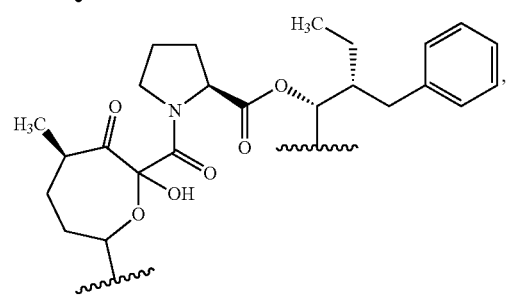
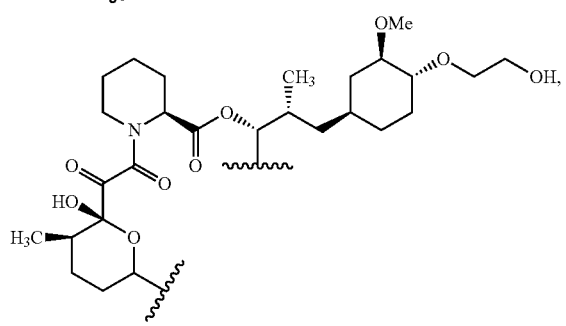
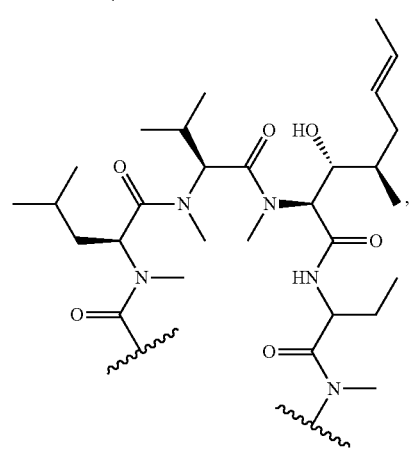
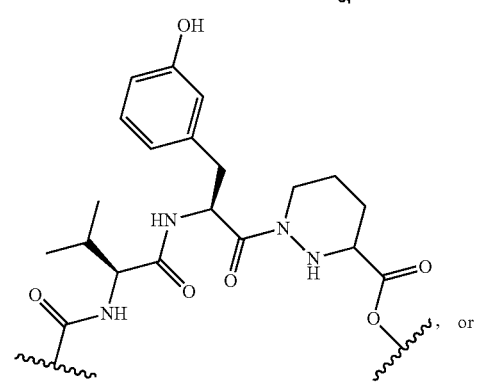, or
20
-continued
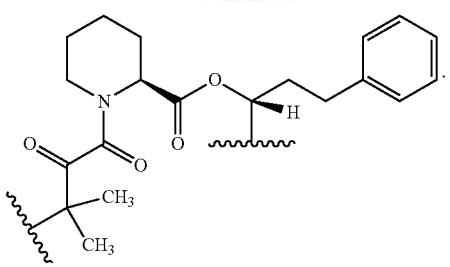
In some embodiments, presenter protein binding moiety is or includes the structure:
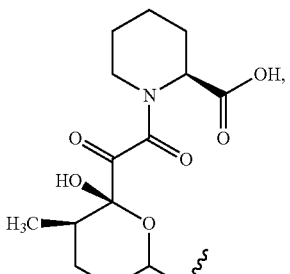
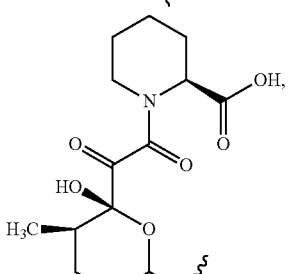
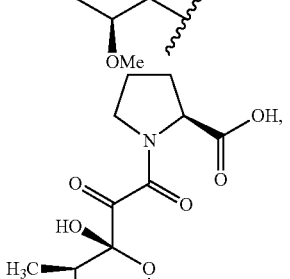

-continued

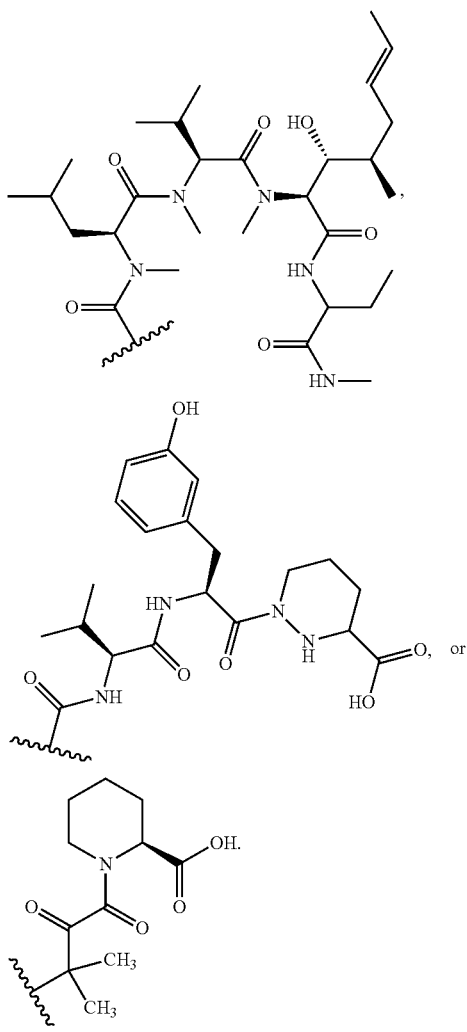

In certain embodiments, the target interacting moiety is or includes the structure of Formula IX:

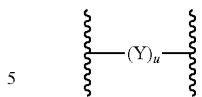
Formula IX wherein u is an integer from 1 to 20; and
each Y is, independently, any amino acid, O, $NR^{20}$, S, S(O), $SO_2$, or has the structure of any one of Formulae X-XIII:

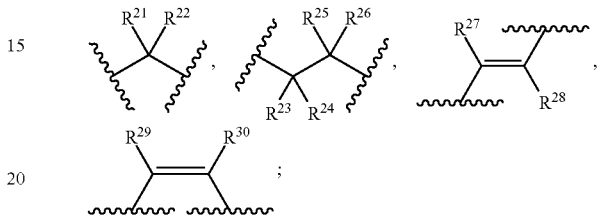

Formula X Formula XI Formula XII Formula XIII wherein each $R^{20}$ is, independently, hydrogen, optionally substituted $C_1$-$C_6$ alkyl, optionally substituted $C_2$-$C_6$ alkenyl, optionally substituted $C_2$-$C_6$ alkynyl, optionally substituted aryl, $C_3$-$C_7$ carbocyclyl, optionally substituted $C_6$-$C_{10}$ aryl $C_1$-$C_6$ alkyl, and optionally substituted $C_3$-$C_7$ carbocyclyl $C_1$-$C_6$ alkyl or $R^{20}$ combines with any $R^{20}$, $R^{21}$, $R^{22}$, $R^{23}$, $R^{24}$, $R^{25}$, $R^{26}$, $R^{27}$, $R^{28}$, $R^{29}$, or $R^{30}$ to form an optionally substituted $C_3$-$C_{10}$ carbocyclyl, optionally substituted $C_6$-$C_{10}$ aryl, or optionally substituted $C_2$-$C_9$ heteroaryl;

each $R^{21}$ and $R^{22}$ is, independently, hydrogen, halogen, optionally substituted hydroxyl, optionally substituted amino, or $R^{21}$ and $R^{22}$ combine to form =O, optionally substituted $C_1$-$C_6$ alkyl, optionally substituted $C_2$-$C_6$ alkenyl, optionally substituted $C_2$-$C_6$ alkynyl, optionally substituted $C_3$-$C_{10}$ carbocyclyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl, or $R^{21}$ or $R^{22}$ combines with any $R^{20}$, $R^{21}$, $R^{22}$, $R^{23}$, $R^{24}$, $R^{25}$, $R^{26}$, $R^{27}$, $R^{28}$, $R^{29}$, or $R^{30}$ to form an optionally substituted $C_3$-$C_{10}$ carbocyclyl, optionally substituted $C_6$-$C_{10}$ aryl, or optionally substituted $C_2$-$C_9$ heteroaryl;

each $R^{23}$, $R^{24}$, $R^{25}$, or $R^{26}$ is, independently, hydrogen, hydroxyl, or $R^{23}$ and $R^{24}$ combine to form =O, or $R^{23}$, $R^{24}$, $R^{25}$, or $R^{26}$ combines with any $R^{20}$, $R^{21}$, $R^{22}$, $R^{23}$, $R^{24}$, $R^{25}$, $R^{26}$, $R^{27}$, $R^{28}$, $R^{29}$, or $R^{30}$ to form an optionally substituted $C_3$-$C_{10}$ carbocyclyl, optionally substituted $C_6$-$C_{10}$ aryl, or optionally substituted $C_2$-$C_9$ heteroaryl; and each $R^{27}$, $R^{28}$, $R^{29}$, and $R^{30}$ is, independently, hydrogen, halogen, optionally substituted hydroxyl, optionally substituted amino, optionally substituted $C_1$-$C_6$ alkyl, optionally substituted $C_2$-$C_6$ alkenyl, optionally substituted $C_2$-$C_6$ alkynyl, optionally substituted $C_3$-$C_{10}$ carbocyclyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl, or $R^{26}$, $R^{27}$, $R^{28}$, $R^{29}$, or $R^{30}$ combines with any $R^{20}$, $R^{21}$, $R^{22}$, $R^{23}$, $R^{24}$, $R^{25}$, $R^{26}$, $R^{27}$, $R^{28}$, $R^{29}$, or $R^{30}$ to form an optionally substituted $C_3$-$C_{10}$ carbocyclyl, optionally substituted $C_6$-$C_{10}$ aryl, or optionally substituted $C_2$-$C_9$ heteroaryl.

In certain embodiments, the target interacting moiety is or includes the structure of Formula IX:
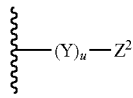
Formula IXa
In some embodiments, the compound has the structure of any one of Formulae XIV-XVIII:
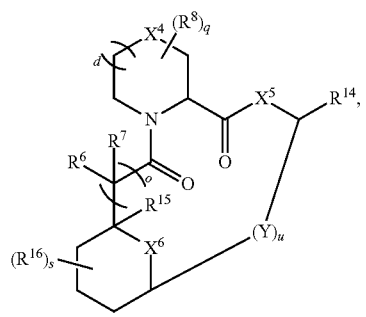
Formula XIV
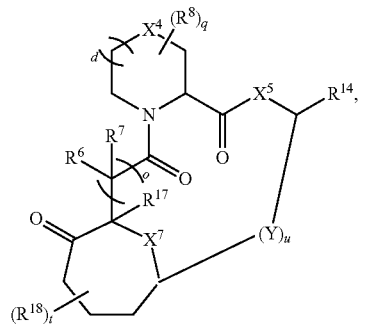
Formula XV
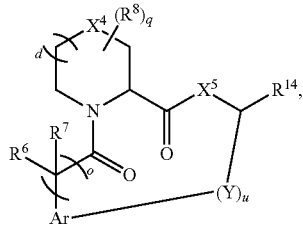
Formula XVI
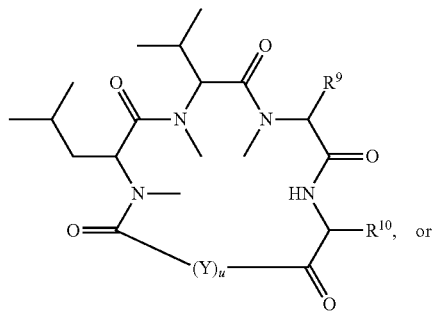
Formula XVII
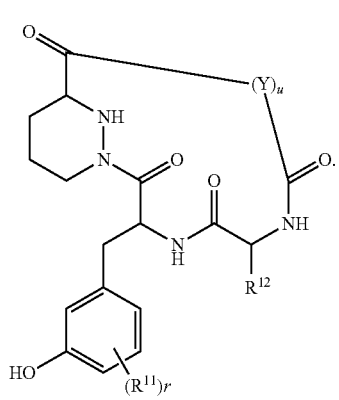
Formula XVIII
In some embodiments, the compound does not comprise the structure:
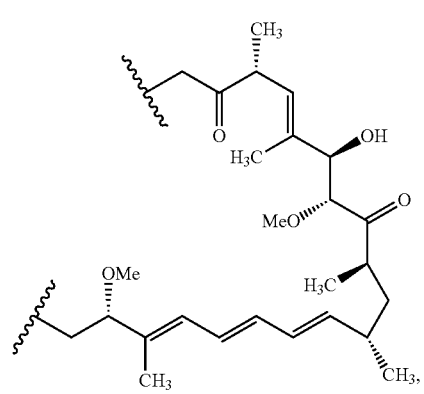
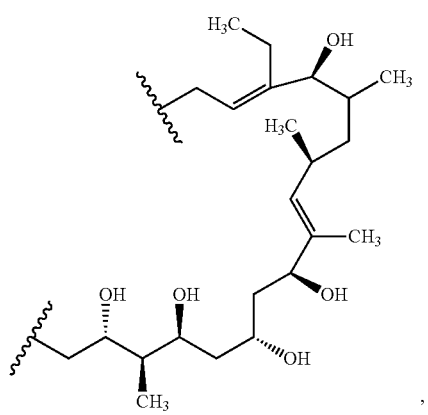

25
-continued
26
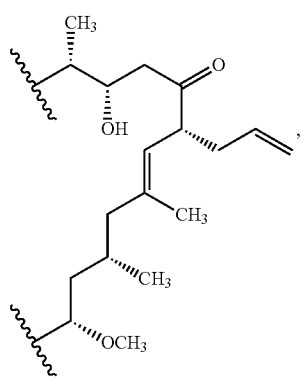
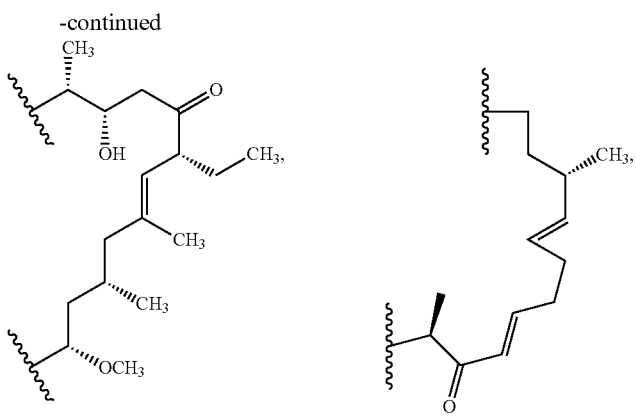
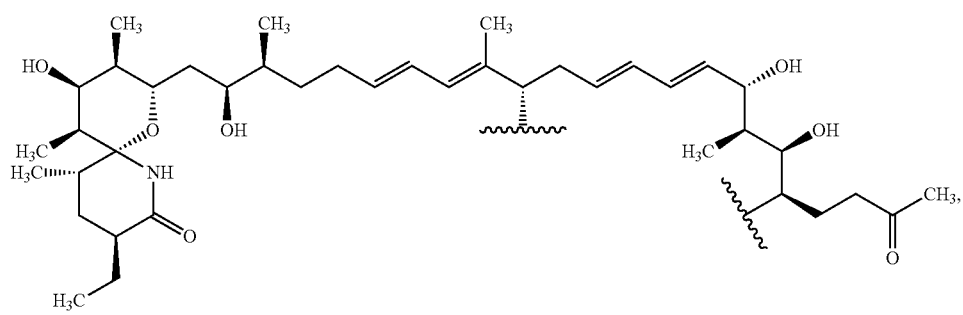
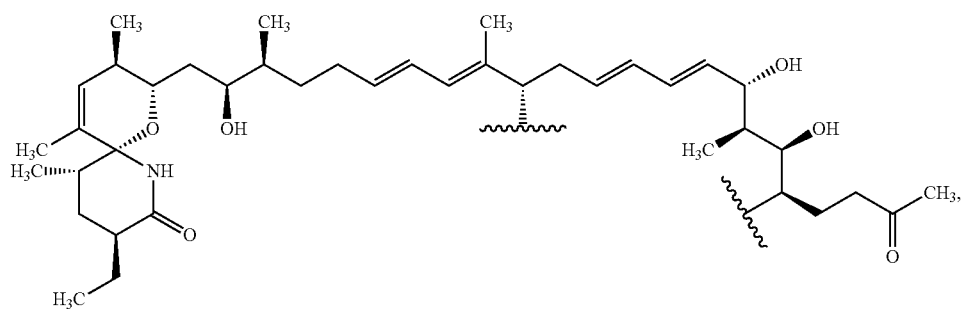
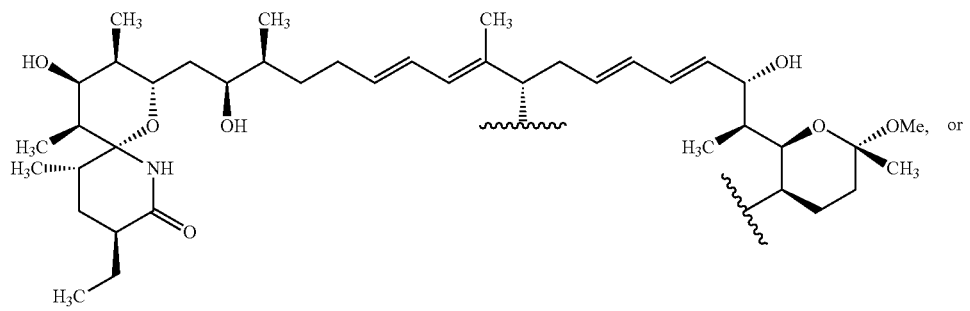
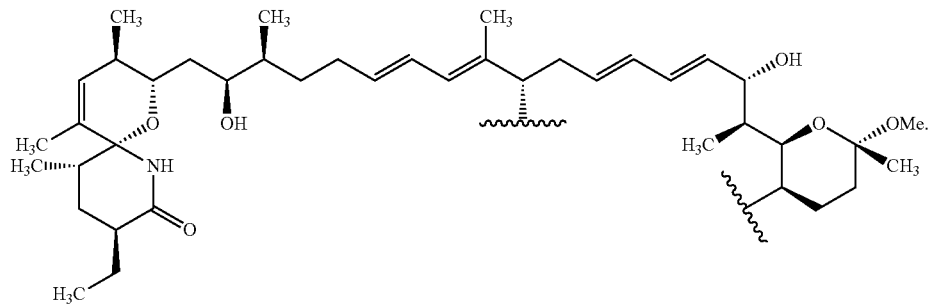 [SMILES: *[C@@H]1CC[C@@](C)(OC)O[C@@H]1[C@@H](C)[C@@H](O)/C=C/C=C/C[C@H](*)/C(C)=C/C=C/CC[C@H](C)[C@@H](O)C[C@@H]1O[C@@]2(NC(=O)[C@@H](CC)C[C@@H]2C)C(C)=C[C@H]1C]

In some embodiments, the target interacting moiety is or includes the structure:
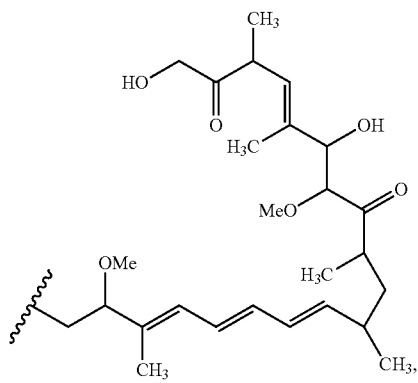
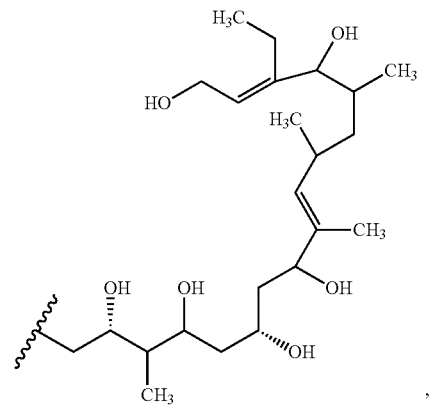
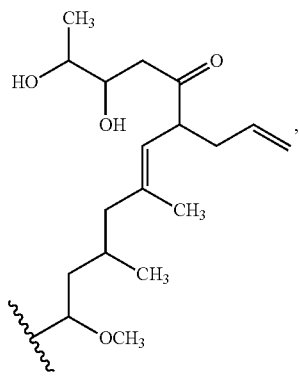
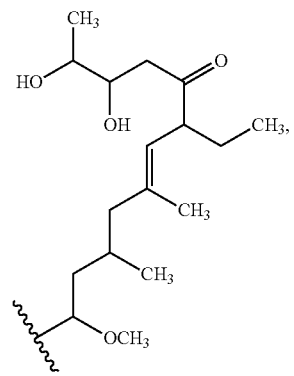
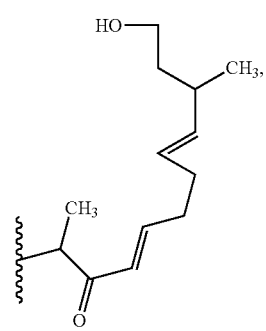
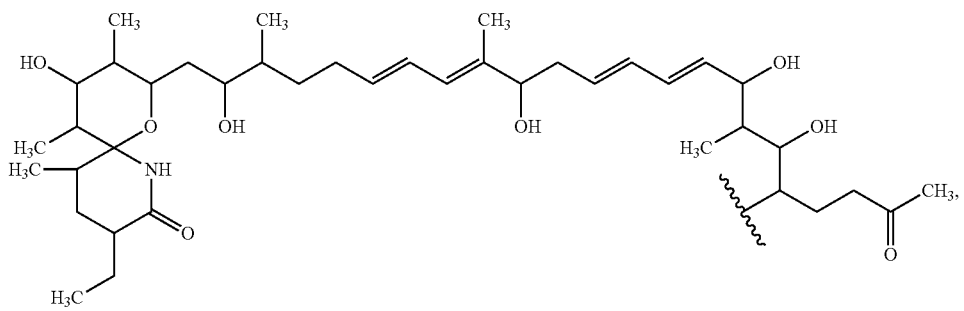
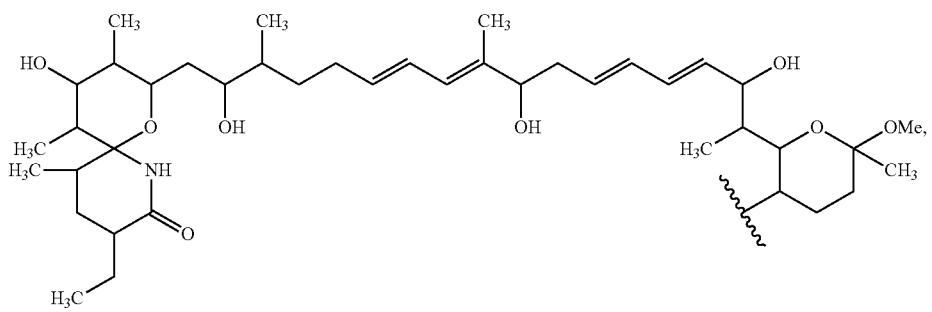 [SMILES: *C1CCC(C)(OC)OC1C(C)C(O)/C=C/C=C/CC(O)/C(C)=C/C=C/CCC(C)C(O)CC1OC2(NC(=O)C(CC)CC2C)C(C)=CC1C]

-continued

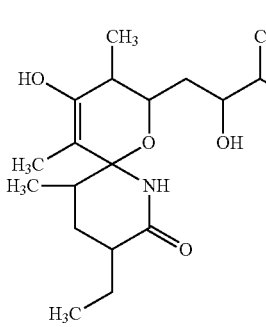 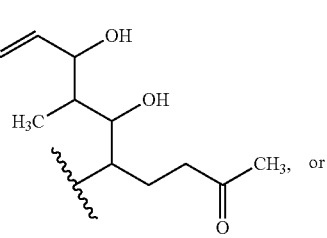

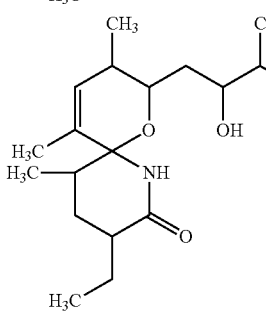 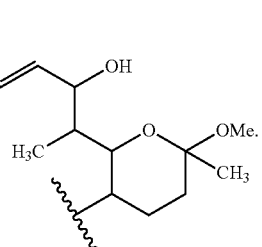

In some embodiments, at least one Y is an N-alkylated amino acid (e.g., an N-methyl amino acid). In some embodiments, at least one Y is a D-amino acid. In some embodiments, at least one Y is a non-natural amino acid. In certain embodiments, at least one Y includes a depsi-linkage.

In some embodiments, the compound does not include the structure:

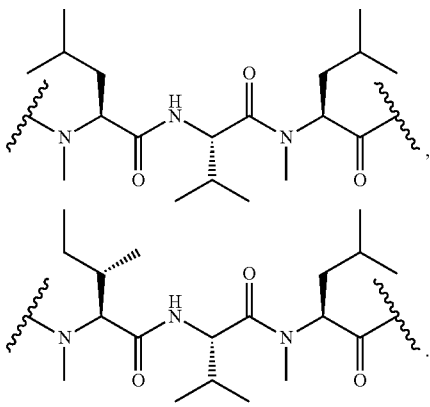

In some embodiments, the portion of the molecule that comprises each ring atom that participates in binding to the target protein has a cLogP greater than 2 (e.g., greater than 3, greater than 4, greater than 5, greater than 6). In certain embodiments, the portion of the molecule that comprises each ring atom that participates in binding to the target protein has a polar surface area less than 350 Å$^2$ (e.g., less than 300 Å$^2$, less than 250 Å$^2$, less than 200 Å$^2$, less than 150 Å$^2$, less than 125 Å$^2$). In some embodiments, the portion of the molecule that comprises each ring atom that participates in binding to the target protein includes at least one atom of a linker.

In some embodiments, the compound has a molecular weight between 400 and 2000 Daltons (e.g., 400 to 600, 500 to 700, 600 to 800, 700 to 900, 800 to 1000, 900 to 1100, 1000 to 1200, 1100 to 1300, 1200 to 1400, 1300 to 1500, 1400 to 1600, 1500 to 1700, 1600 to 1800, 1700 to 1900, or 1800 to 2000 Daltons). In certain embodiments, the compound has an even number of ring atoms (e.g., 14, 16, 18, 20, 22, 24, 26, 28, 30, 32, 34, 36, 38, or 40 ring atoms). In some embodiments, the compound is cell penetrant. In some embodiments, the compound is substantially pure (e.g., compound is provided in a preparation that is substantially free of contaminants such as other compounds and/or components of a cell lysate. In certain embodiments, the compound is isolated. In some embodiments, the compound is an engineered compound. In some embodiments, the compound is non-naturally occurring.

In certain embodiments, the complex binds to a target protein (e.g., (e.g., a eukaryotic target protein such as a mammalian target protein or a fungal target proteins or a prokaryotic target protein such as a bacterial target protein) with at least 5-fold greater (e.g., at least 10-fold greater, at least 20-fold greater, at least 50-fold greater, at least 100-fold greater) affinity than the complex binds to mTOR and/or calcineurin. In some embodiments, the complex binds to the target protein with at least 5-fold greater (e.g., at least 10-fold greater, at least 20-fold greater, at least 50-fold greater, at least 100-fold greater) affinity than the affinity of the compound to the target protein when the compound is not bound in a complex with the presenter protein. In some embodiments, the complex binds to the target protein with at least 5-fold greater (e.g., at least 10-fold greater, at least 20-fold greater, at least 50-fold greater, at least 100-fold greater) affinity than the affinity of the presenter protein to the target protein when the presenter protein is not bound in a complex with the compound. In certain embodiments, the complex inhibits the naturally occurring interaction between the target protein and a ligand that specifically binds the target protein.

In some embodiments, the presenter protein is a prolyl isomerase (e.g., a member of the FKBP family such as FKBP12, FKBP12.6, FKBP25, or FKBP52, a member of the cyclophilin family such as PP1A, CYPB, CYPC, CYP40, CYPE, CYPD, NKTR, SRCyp, CYPH, CWC27, CYPL1, CYP60, CYPJ, PPIL4, PPIL6, RANBP2, PPWD1, or PIN1).

In certain embodiments, the target protein is a eukaryotic target protein. In some embodiments, the eukaryotic target protein is a mammalian target protein such as a GTPase, GTPase activating protein, Guanine nucleotide-exchange factor, a heat shock protein, an ion channel, a coiled-coil protein, a kinase, a phosphatase, a ubiquitin ligase, a transcription factor, a chromatin modifier/remodeler, proteins with classical protein-protein interaction domains and motifs, or any other protein that participates in a biological pathway associated with a disease, disorder or condition. In some embodiments, the eukaryotic target protein is a fungal target protein. In certain embodiments, the target protein is a prokaryotic target protein such as a bacterial target protein.

In some embodiments, the compound is any one of the compounds of FIG. 1, or a stereoisomer, or pharmaceutically acceptable salt thereof:

In certain embodiments, the compound is any one of the compounds of FIG. 2, or a stereoisomer, or pharmaceutically acceptable salt thereof:

In some aspects, the invention features a presenter protein/compound complex including any of the compounds of the invention and a presenter protein.

In some embodiments of the presenter protein/compound complex, the presenter protein is a protein encoded by any one of the genes or a homolog thereof of Table 1. In some embodiments of the presenter protein/compound complex the presenter protein is a prolyl isomerase (e.g., a member of the FKBP family such as FKBP12, FKBP12.6, FKBP25, or FKBP52, a member of the cyclophilin family such as PP1A, CYPB, CYPC, CYP40, CYPE, CYPD, NKTR, SRCyp, CYPH, CWC27, CYPL1, CYP60, CYPJ, PPIL4, PPIL6, RANBP2, PPWD1, or PIN1).

In some aspects, the invention features a pharmaceutical composition including any of the compounds or complexes of the invention and a pharmaceutically acceptable excipient. In some embodiments, the pharmaceutical composition is in unit dosage form.

In some aspects, the invention features a method of modulating a target protein (e.g., a eukaryotic target protein such as a mammalian target protein or a fungal target proteins or a prokaryotic target protein such as a bacterial target protein). In some embodiments, such a method includes steps of contacting the target protein with a modulating (e.g., positive or negative modulation) amount of any of the compounds (e.g., in the presence of a presenter protein), presenter protein/compound complexes, or compositions of the invention.

In some aspects, the invention features a method of modulating (e.g., positively or negatively modulating) a target protein (e.g., a eukaryotic target protein such as a mammalian target protein or a fungal target proteins or a prokaryotic target protein such as a bacterial target protein). In some embodiments, such a method includes steps of contacting a cell expressing the target protein and a presenter protein with an effective amount of a compound or composition of the invention under conditions wherein the compound can form a complex with the presenter protein and the resulting complex can bind to the target protein, thereby modulating (e.g., positively or negatively modulating) the target protein.

In some aspects, the invention features a method of modulating (e.g., positively or negatively modulating) a target protein (e.g., a eukaryotic target protein such as a mammalian target protein or a fungal target proteins or a prokaryotic target protein such as a bacterial target protein).

In some embodiments, such a method includes steps of contacting the target protein with a presenter protein/compound complex of the invention, thereby modulating the target protein.

In some aspects, the invention features a method of inhibiting prolyl isomerase activity. In some embodiments, such a method includes contacting a cell expressing the prolyl isomerase with a compound or composition of the invention under conditions that permit the formation of a complex between the compound and the prolyl isomerase, thereby inhibiting the prolyl isomerase activity.

In some aspects, the invention features a method of forming a presenter protein/compound complex in a cell. In some embodiments, such a method includes steps of contacting a cell expressing the presenter protein with a compound or composition of the invention under conditions that permit the formation of a complex between the compound and the presenter protein.

In some aspects, the invention features a method for the preparation of a compound of the invention. In some embodiments, such a method includes steps of culturing a bacterial strain of the genus *Streptomyces* and isolating the compound from the fermentation broth. In some embodiments, the bacterial strain is an engineered strain. In some embodiments, the bacterial strain is engineered in that it has been modified to produce the compound and/or to secrete the compound into the broth.

In some embodiments, the present disclosure provides methods for preparing a compound as described herein, the method comprising steps of culturing a bacterial strain of the genus *Streptomyces* under conditions in which the strain produces the compound and releases it into the and isolating the compound from the fermentation broth.

In some embodiments, a provided method comprises isolating a compound as described herein from fermentation broth.

In some aspects, the invention features a tripartite complex including (i) a target protein (e.g., a eukaryotic target protein such as a mammalian target protein or a fungal target proteins or a prokaryotic target protein such as a bacterial target protein) and (ii) a presenter protein/compound complex, the presenter protein/compound complex including a presenter protein and any of the compounds of the invention.

In some embodiments of the tripartite complex, the target protein (e.g., a eukaryotic target protein such as a mammalian target protein or a fungal target proteins or a prokaryotic target protein such as a bacterial target protein) does not have a traditional binding pocket. In some embodiments of the tripartite complex, the presenter protein/compound complex binds at a flat surface site on the target protein. In certain embodiments of the tripartite complex, the compound (e.g., macrocyclic compound) in the presenter protein/compound complex binds at a hydrophobic surface site (e.g., a hydrophobic surface site on the target protein including at least 30%, such as at least 40%, at least 50%, at least 60%, at least 70%, at least 80%, at least 90%, or at least 95%, hydrophobic residues) on the target protein. In some embodiments of the tripartite complex, the presenter protein/compound complex binds to the target protein at a site of a naturally occurring protein-protein interaction between the target protein and a protein that specifically binds said target protein. In some embodiments of the tripartite complex, presenter protein/compound complex does not bind at an active site of the target protein. In certain embodiments of the tripartite complex, presenter protein/compound complex binds at an active site of the target protein. In some embodiments of the tripartite complex, target protein is an undruggable target.

In some embodiments of the tripartite complex, the structural organization of the compound (e.g., macrocyclic compound) is substantially unchanged in the tripartite complex compared to the compound (e.g., macrocyclic compound) in the presenter protein/compound complex but not in the tripartite complex.

In certain embodiments of the tripartite complex, at least 10% (e.g., at least 20%, at least 30%, at least 40%, at least 50%, at least 60%, at least 70%, at least 80%, at least 90%) of the total buried surface area of the target protein in the tripartite complex includes one or more atoms that participate in binding to the compound (e.g., macrocyclic compound). In some embodiments of the tripartite complex, at least 10% (e.g., at least 20%, at least 30%, at least 40%, at least 50%, at least 60%, at least 70%, at least 80%, at least 90%) of the total buried surface area of the target protein in the tripartite complex includes one or more atoms that participate in binding to the presenter protein.

In some embodiments of the tripartite complex, the compound (e.g., macrocyclic compound) contributes at least 10% (e.g., at least 20%, at least 30%, at least 40%, at least 50%, at least 60%, at least 70%, at least 80%, at least 90%) of the total binding free energy of the tripartite complex. In certain embodiments of the tripartite complex, the presenter protein contributes at least 10% (e.g., at least 20%, at least 30%, at least 40%, at least 50%, at least 60%, at least 70%, at least 80%, at least 90%) of the total binding free energy of the tripartite complex.

In some embodiments of the tripartite complex, at least 70% (e.g., at least 80%, at least 90%, at least 95%) of binding interactions between one or more atoms of the compound (e.g., macrocyclic compound) and one or more atoms of the target protein (e.g., a eukaryotic target protein such as a mammalian target protein or a fungal target proteins or a prokaryotic target protein such as a bacterial target protein) are van der Waals interactions and/or π-effect interactions.

In another aspect, the invention features a compound collection comprising a plurality of compounds (e.g., of macrocyclic compounds as described herein). In some embodiments, compound collections include a plurality of compounds that are variants of one another.

Chemical Terms

Those skilled in the art will appreciate that certain compounds described herein can exist in one or more different isomeric (e.g., stereoisomers, geometric isomers, tautomers) and/or isotopic (e.g., in which one or more atoms has been substituted with a different isotope of the atom, such as hydrogen substituted for deuterium) forms. Unless otherwise indicated or clear from context, a depicted structure can be understood to represent any such isomeric or isotopic form, individually or in combination.

Compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present disclosure. Cis and trans geometric isomers of the compounds of the present disclosure are described and may be isolated as a mixture of isomers or as separated isomeric forms.

In some embodiments, one or more compounds depicted herein may exist in different tautomeric forms. As will be clear from context, unless explicitly excluded, references to such compounds encompass all such tautomeric forms. In some embodiments, tautomeric forms result from the swapping of a single bond with an adjacent double bond and the concomitant migration of a proton. In certain embodiments, a tautomeric form may be a prototropic tautomer, which is an isomeric protonation states having the same empirical formula and total charge as a reference form. Examples of moieties with prototropic tautomeric forms are ketone-enol pairs, amide-imidic acid pairs, lactam-lactim pairs, amide-imidic acid pairs, enamine-imine pairs, and annular forms where a proton can occupy two or more positions of a heterocyclic system, such as, 1H- and 3H-imidazole, 1H-, 2H- and 4H-1,2,4-triazole, 1H- and 2H-isoindole, and 1H- and 2H-pyrazole. In some embodiments, tautomeric forms can be in equilibrium or sterically locked into one form by appropriate substitution. In certain embodiments, tautomeric forms result from acetal interconversion, e.g., the interconversion illustrated in the scheme below:

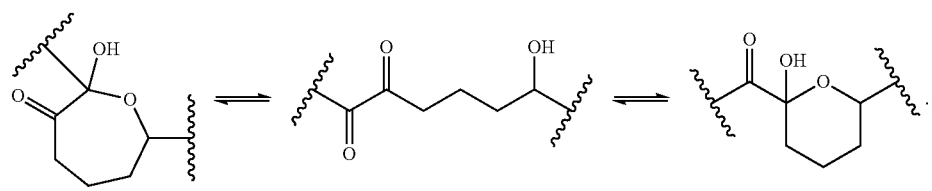 [SMILES: *C1CCCC(=O)C(*)(O)O1 ; *C(=O)C(=O)CCCC(*)O ; *C(=O)C1(O)CCCC(*)O1]

Those skilled in the art will appreciate that, in some embodiments, isotopes of compounds described herein may be prepared and/or utilized in accordance with the present invention. "Isotopes" refers to atoms having the same atomic number but different mass numbers resulting from a different number of neutrons in the nuclei. For example, isotopes of hydrogen include tritium and deuterium. In some embodiments, an isotopic substitution (e.g., substitution of hydrogen with deuterium) may alter the physiciochemical properties of the molecules, such as metabolism and/or the rate of racemization of a chiral center.

As is known in the art, many chemical entities (in particular many organic molecules and/or many small molecules) can adopt a variety of different solid forms such as, for example, amorphous forms and/or crystalline forms (e.g., polymorphs, hydrates, solvates, etc). In some embodiments, such entities may be utilized in any form, including in any solid form. In some embodiments, such entities are utilized in a particular form, for example in a particular solid form.

In some embodiments, compounds described and/or depicted herein may be provided and/or utilized in salt form.

In certain embodiments, compounds described and/or depicted herein may be provided and/or utilized in hydrate or solvate form.

At various places in the present specification, substituents of compounds of the present disclosure are disclosed in groups or in ranges. It is specifically intended that the present disclosure include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl. Furthermore, where a compound includes a plurality of positions at which substitutes are disclosed in groups or in ranges, unless otherwise indicated, the present disclosure is intended to cover individual compounds and groups of compounds (e.g., genera and subgenera) containing each and every individual subcombination of members at each position.

Herein a phrase of the form "optionally substituted X" (e.g., optionally substituted alkyl) is intended to be equivalent to "X, wherein X is optionally substituted" (e.g., "alkyl, wherein said alkyl is optionally substituted"). It is not intended to mean that the feature "X" (e.g. alkyl) per se is optional.

The term "alkyl," as used herein, refers to saturated hydrocarbon groups containing from 1 to 20 (e.g., from 1 to 10 or from 1 to 6) carbons. In some embodiments, an alkyl group is unbranched (i.e., is linear); in some embodiments, an alkyl group is branched. Alkyl groups are exemplified by methyl, ethyl, n- and iso-propyl, n-, sec-, iso- and tert-butyl, neopentyl, and the like, and may be optionally substituted with one, two, three, or, in the case of alkyl groups of two carbons or more, four substituents independently selected from the group consisting of: (1) $C_{1-6}$ alkoxy; (2) $C_{1-6}$ alkylsulfinyl; (3) amino, as defined herein (e.g., unsubstituted amino (i.e., —$NH_2$) or a substituted amino (i.e., —$N(R^{N1})_2$, where $R^{N1}$ is as defined for amino); (4) $C_{6-10}$ aryl-$C_{1-6}$ alkoxy; (5) azido; (6) halo; (7) ($C_{2-9}$ heterocyclyl) oxy; (8) hydroxyl, optionally substituted with an O-protecting group; (9) nitro; (10) oxo (e.g., carboxyaldehyde or acyl); (11) $C_{1-7}$ spirocyclyl; (12) thioalkoxy; (13) thiol; (14) —$CO_2R^{A'}$, optionally substituted with an O-protecting group and where $R^{A'}$ is selected from the group consisting of (a) $C_{1-20}$ alkyl (e.g., $C_{1-6}$ alkyl), (b) $C_{2-20}$ alkenyl (e.g., $C_{2-6}$ alkenyl), (c) $C_{6-10}$ aryl, (d) hydrogen, (e) $C_{1-6}$ alk-$C_{6-10}$ aryl, (f) amino-$C_{1-20}$ alkyl, (g) polyethylene glycol of —$(CH_2)_{s2}$ $(OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h) amino-polyethylene glycol of —$NR^{N1}(CH_2)_{s2}(CH_2CH_2O)_{s1}(CH_2)_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (15) —$C(O)NR^{B'}R^{C'}$, where each of $R^{B'}$ and $R^{C'}$ is, independently, selected from the group consisting of (a) hydrogen, (b) $C_{1-6}$ alkyl, (c) $C_{6-10}$ aryl, and (d) $C_{1-6}$ alk-$C_{6-10}$ aryl; (16) —$SO_2R^{D'}$, where $R^{D'}$ is selected from the group consisting of (a) $C_{1-6}$ alkyl, (b) $C_{6-10}$ aryl, (c) $C_{1-6}$ alk-$C_{6-10}$ aryl, and (d) hydroxyl; (17) —$SO_2NR^{E'}R^{F'}$, where each of $R^{E'}$ and $R^{F'}$ is, independently, selected from the group consisting of (a) hydrogen, (b) $C_{1-6}$ alkyl, (c) $C_{6-10}$ aryl and (d) $C_{1-6}$ alk-$C_{6-10}$ aryl; (18) —$C(O)R^{G'}$, where $R^{G'}$ is selected from the group consisting of (a) $C_{1-20}$ alkyl (e.g., $C_{1-6}$ alkyl), (b) $C_{2-20}$ alkenyl (e.g., $C_{2-6}$ alkenyl), (c) $C_{6-10}$ aryl, (d) hydrogen, (e) $C_{1-6}$ alk-$C_{6-10}$ aryl, (f) amino-$C_{1-20}$ alkyl, (g) polyethylene glycol of —$(CH_2)_{s2}$ $(OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h) amino-polyethylene glycol of —$NR^{N1}(CH_2)_{s2}(CH_2CH_2O)_{s1}(CH_2)_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (19) —$NR^{H'}C(O)R^{I'}$, wherein $R^{H'}$ is selected from the group consisting of (a1) hydrogen and (b1) $C_{1-6}$ alkyl, and $R^{I'}$ is selected from the group consisting of (a2) $C_{1-20}$ alkyl (e.g., $C_{1-6}$ alkyl), (b2) $C_{2-20}$ alkenyl (e.g., $C_{2-6}$ alkenyl), (c2) $C_{6-10}$ aryl, (d2) hydrogen, (e2) $C_{1-6}$ alk-$C_{6-10}$ aryl, (f2) amino-$C_{1-20}$ alkyl, (g2) polyethylene glycol of —$(CH_2)_{s2}(OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2) amino-polyethylene glycol of —$NR^{N1}(CH_2)_{s2}(CH_2CH_2O)_{s1}(CH_2)_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (20) —$NR^{J'}C(O)OR^{K'}$, wherein $R^{J'}$ is selected from the group consisting of (a1) hydrogen and (b1) $C_{1-6}$ alkyl, and $R^{K'}$ is selected from the group consisting of (a2) $C_{1-20}$ alkyl (e.g., $C_{1-6}$ alkyl), (b2) $C_{2-20}$ alkenyl (e.g., $C_{2-6}$ alkenyl), (c2) $C_{6-10}$ aryl, (d2) hydrogen, (e2) $C_{1-6}$ alk-$C_{6-10}$ aryl, (f2) amino-$C_{1-20}$ alkyl, (g2) polyethylene glycol of —$(CH_2)_{s2}(OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2) amino-polyethylene glycol of —$NR^{N1}(CH_2)_{s2}(CH_2CH_2O)_{s1}(CH_2)_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (21) amidine; and (22) silyl groups such as trimethylsilyl, t-butyldimethylsilyl, and tri-isopropylsilyl. In some embodiments, each of these groups can be further substituted as described herein. For example, the alkylene group of a $C_1$-alkaryl can be further substituted with an oxo group to afford the respective aryloyl substituent.

The term "alkylene" and the prefix "alk-," as used herein, represent a saturated divalent hydrocarbon group derived from a straight or branched chain saturated hydrocarbon by the removal of two hydrogen atoms, and is exemplified by methylene, ethylene, isopropylene, and the like. The term "$C_{x-y}$ alkylene" and the prefix "$C_{x-y}$ alk-" represent alkylene groups having between x and y carbons. Exemplary values for x are 1, 2, 3, 4, 5, and 6, and exemplary values for y are 2, 3, 4, 5, 6, 7, 8, 9, 10, 12, 14, 16, 18, or 20 (e.g., $C_{1-6}$, $C_{1-10}$, $C_{2-20}$, $C_{2-6}$, $C_{2-10}$, or $C_{2-20}$ alkylene). In some embodiments, the alkylene can be further substituted with 1, 2, 3, or 4 substituent groups as defined herein for an alkyl group.

The term "alkenyl," as used herein, represents monovalent straight or branched chain groups of, unless otherwise specified, from 2 to 20 carbons (e.g., from 2 to 6 or from 2 to 10 carbons) containing one or more carbon-carbon double bonds and is exemplified by ethenyl, 1-propenyl, 2-propenyl, 2-methyl-1-propenyl, 1-butenyl, 2-butenyl, and the like. Alkenyls include both cis and trans isomers. Alkenyl groups may be optionally substituted with 1, 2, 3, or 4 substituent groups that are selected, independently, from amino, aryl, cycloalkyl, or heterocyclyl (e.g., heteroaryl), as defined herein, or any of the exemplary alkyl substituent groups described herein.

The term "alkynyl," as used herein, represents monovalent straight or branched chain groups from 2 to 20 carbon atoms (e.g., from 2 to 4, from 2 to 6, or from 2 to 10 carbons) containing a carbon-carbon triple bond and is exemplified by ethynyl, 1-propynyl, and the like. Alkynyl groups may be optionally substituted with 1, 2, 3, or 4 substituent groups that are selected, independently, from aryl, cycloalkyl, or heterocyclyl (e.g., heteroaryl), as defined herein, or any of the exemplary alkyl substituent groups described herein.

The term "amino," as used herein, represents —N($R^{N1}$)$_2$, wherein each $R^{N1}$ is, independently, H, OH, NO$_2$, N($R^{N2}$)$_2$, SO$_2$O$R^{N2}$, SO$_2R^{N2}$, SO$R^{N2}$, an N-protecting group, alkyl, alkenyl, alkynyl, alkoxy, aryl, alkaryl, cycloalkyl, alkcycloalkyl, carboxyalkyl (e.g., optionally substituted with an O-protecting group, such as optionally substituted arylalkoxycarbonyl groups or any described herein), sulfoalkyl, acyl (e.g., acetyl, trifluoroacetyl, or others described herein), alkoxycarbonylalkyl (e.g., optionally substituted with an O-protecting group, such as optionally substituted arylalkoxycarbonyl groups or any described herein), heterocyclyl (e.g., heteroaryl), or alkheterocyclyl (e.g., alkheteroaryl), wherein each of these recited $R^{N1}$ groups can be optionally substituted, as defined herein for each group; or two $R^{N1}$ combine to form a heterocyclyl or an N-protecting group, and wherein each $R^{N2}$ is, independently, H, alkyl, or aryl. The amino groups of the invention can be an unsubstituted amino (i.e., —NH$_2$) or a substituted amino (i.e., —N($R^{N1}$)$_2$). In a preferred embodiment, amino is —NH$_2$ or —NH$R^{N1}$, wherein $R^{N1}$ is, independently, OH, NO$_2$, NH$_2$, N$R^{N2}_2$, SO$_2$O$R^{N2}$, SO$_2R^{N2}$, SO$R^{N2}$, alkyl, carboxyalkyl, sulfoalkyl, acyl (e.g., acetyl, trifluoroacetyl, or others described herein), alkoxycarbonylalkyl (e.g., t-butoxycarbonylalkyl) or aryl, and each $R^{N2}$ can be H, C$_{1-20}$ alkyl (e.g., C$_{1-6}$ alkyl), or C$_{6-10}$ aryl.

The term "amino acid," as described herein, refers to a molecule having a side chain, an amino group, and an acid group (e.g., a carboxy group of —CO$_2$H or a sulfo group of —SO$_3$H), wherein the amino acid is attached to the parent molecular group by the side chain, amino group, or acid group (e.g., the side chain). As used herein, the term "amino acid" in its broadest sense, refers to any compound and/or substance that can be incorporated into a polypeptide chain, e.g., through formation of one or more peptide bonds. In some embodiments, an amino acid has the general structure H$_2$N—C(H)(R)—COOH. In some embodiments, an amino acid is a naturally-occurring amino acid. In some embodiments, an amino acid is a synthetic amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. In some embodiments, an amino acid, including a carboxy- and/or amino-terminal amino acid in a polypeptide, can contain a structural modification as compared with the general structure above. For example, in some embodiments, an amino acid may be modified by methylation, amidation, acetylation, and/or substitution as compared with the general structure. In some embodiments, such modification may, for example, alter the circulating half life of a polypeptide containing the modified amino acid as compared with one containing an otherwise identical unmodified amino acid. In some embodiments, such modification does not significantly alter a relevant activity of a polypeptide containing the modified amino acid, as compared with one containing an otherwise identical unmodified amino acid. As will be clear from context, in some embodiments, the term "amino acid" is used to refer to a free amino acid; in some embodiments it is used to refer to an amino acid residue of a polypeptide. In some embodiments, the amino acid is attached to the parent molecular group by a carbonyl group, where the side chain or amino group is attached to the carbonyl group. In some embodiments, the amino acid is an α-amino acid. In certain embodiments, the amino acid is a β-amino acid. In some embodiments, the amino acid is a γ-amino acid. Exemplary side chains include an optionally substituted alkyl, aryl, heterocyclyl, alkaryl, alkheterocyclyl, aminoalkyl, carbamoylalkyl, and carboxyalkyl. Exemplary amino acids include alanine, arginine, asparagine, aspartic acid, cysteine, glutamic acid, glutamine, glycine, histidine, hydroxynorvaline, isoleucine, leucine, lysine, methionine, norvaline, ornithine, phenylalanine, proline, pyrrolysine, selenocysteine, serine, taurine, threonine, tryptophan, tyrosine, and valine. Amino acid groups may be optionally substituted with one, two, three, or, in the case of amino acid groups of two carbons or more, four substituents independently selected from the group consisting of: (1) C$_{1-6}$ alkoxy; (2) C$_{1-6}$ alkylsulfinyl; (3) amino, as defined herein (e.g., unsubstituted amino (i.e., —NH$_2$) or a substituted amino (i.e., —N($R^{N1}$)$_2$, where $R^{N1}$ is as defined for amino); (4) C$_{6-10}$ aryl-C$_{1-6}$ alkoxy; (5) azido; (6) halo; (7) (C$_{2-9}$ heterocyclyl)oxy; (8) hydroxyl; (9) nitro; (10) oxo (e.g., carboxyaldehyde or acyl); (11) C$_{1-7}$ spirocyclyl; (12) thioalkoxy; (13) thiol; (14) —CO$_2R^{A'}$, where $R^{A'}$ is selected from the group consisting of (a) C$_{1-20}$ alkyl (e.g., C$_{1-6}$ alkyl), (b) C$_{2-20}$ alkenyl (e.g., C$_{2-6}$ alkenyl), (c) C$_{6-10}$ aryl, (d) hydrogen, (e) C$_{1-6}$ alk-C$_{6-10}$ aryl, (f) amino-C$_{1-20}$ alkyl, (g) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or C$_{1-20}$ alkyl, and (h) amino-polyethylene glycol of —N$R^{N1}$(CH$_2$)$_{s2}$(CH$_2$CH$_2$O)$_{s1}$(CH$_2$)$_{s3}$N$R^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted C$_1$-6 alkyl; (15) —C(O)N$R^{B'}R^{C'}$, where each of $R^{B'}$ and $R^{C'}$ is, independently, selected from the group consisting of (a) hydrogen, (b) C$_{1-6}$ alkyl, (c) C$_{6-10}$ aryl, and (d) C$_{1-6}$ alk-C$_{6-10}$ aryl; (16) —SO$_2R^{D'}$, where $R^{D'}$ is selected from the group consisting of (a) C$_{1-6}$ alkyl, (b) C$_{6-10}$ aryl, (c) C$_{1-6}$ alk-C$_{6-10}$ aryl, and (d) hydroxyl; (17) —SO$_2$N$R^{E'}R^{F'}$, where each of $R^{E'}$ and $R^{F'}$ is, independently, selected from the group consisting of (a) hydrogen, (b) C$_{1-6}$ alkyl, (c) C$_{6-10}$ aryl and (d) C$_{1-6}$ alk-C$_{6-10}$ aryl; (18) —C(O)$R^{G'}$, where $R^{G'}$ is selected from the group consisting of (a) C$_{1-20}$ alkyl (e.g., C$_{1-6}$ alkyl), (b) C$_{2-20}$ alkenyl (e.g., C$_{2-6}$ alkenyl), (c) C$_{6-10}$ aryl, (d) hydrogen, (e) C$_{1-6}$ alk-C$_{6-10}$ aryl, (f) amino-C$_{1-20}$ alkyl, (g) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h) amino-polyethylene glycol of $—NR^{N1}(CH_2)_{s2}(CH_2CH_2O)_{s1}(CH_2)_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (19) $—NR^{H'}C(O)R^{I'}$, wherein $R^{H'}$ is selected from the group consisting of (a1) hydrogen and (b1) $C_1$-6 alkyl, and $R^{I'}$ is selected from the group consisting of (a2) $C_{1-20}$ alkyl (e.g., $C_{1-6}$ alkyl), (b2) $C_{2-20}$ alkenyl (e.g., $C_{2-6}$ alkenyl), (c2) $C_{6-10}$ aryl, (d2) hydrogen, (e2) $C_{1-6}$ alk-$C_{6-10}$ aryl, (f2) amino-$C_{1-20}$ alkyl, (g2) polyethylene glycol of $—(CH_2)_{s2}(OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2) amino-polyethylene glycol of $—NR^{N1}(CH_2)_{s2}(CH_2CH_2O)_{s1}(CH_2)_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (20) $—NR^{J'}C(O)OR^{K'}$, wherein $R^{J'}$ is selected from the group consisting of (a1) hydrogen and (b1) $C_{1-6}$ alkyl, and $R^{K'}$ is selected from the group consisting of (a2) $C_{1-20}$ alkyl (e.g., $C_{1-6}$ alkyl), (b2) $C_{2-20}$ alkenyl (e.g., $C_{2-6}$ alkenyl), (c2) $C_{6-10}$ aryl, (d2) hydrogen, (e2) $C_{1-6}$ alk-$C_{6-10}$ aryl, (f2) amino-$C_{1-20}$ alkyl, (g2) polyethylene glycol of $—(CH_2)_{s2}(OCH_2CH_2)_{s1}(CH_2)_{s3}OR'$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2) amino-polyethylene glycol of $—NR^{N1}(CH_2)_{s2}(CH_2CH_2O)_{s1}(CH_2)_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; and (21) amidine. In some embodiments, each of these groups can be further substituted as described herein.

The term "N-alkylated amino acids" as used herein, refers to amino acids containing an optionally substituted $C_1$ to $C_6$ alkyl on the nitrogen of the amino acid that forms the peptidic bond. N-alkylated amino acids include, but are not limited to, N-methyl amino acids, such as N-methyl-alanine, N-methyl-threonine, N-methyl-phenylalanine, N-methyl-aspartic acid, N-methyl-valine, N-methyl-leucine, N-methyl-glycine, N-methyl-isoleucine, N(α)-methyl-lysine, N(α)-methyl-asparagine, and N(α)-methyl-glutamine.

The term "aryl," as used herein, represents a mono-, bicyclic, or multicyclic carbocyclic ring system having one or two aromatic rings and is exemplified by phenyl, naphthyl, 1,2-dihydronaphthyl, 1,2,3,4-tetrahydronaphthyl, anthracenyl, phenanthrenyl, fluorenyl, indanyl, indenyl, and the like, and may be optionally substituted with 1, 2, 3, 4, or 5 substituents independently selected from the group consisting of: (1) $C_{1-7}$ acyl (e.g., carboxyaldehyde); (2) $C_{1-20}$ alkyl (e.g., $C_{1-6}$ alkyl, $C_{1-6}$ alkoxy-$C_{1-6}$ alkyl, $C_{1-6}$ alkylsulfinyl-$C_{1-6}$ alkyl, amino-$C_{1-6}$ alkyl, azido-$C_{1-6}$ alkyl, (carboxyaldehyde)-$C_{1-6}$ alkyl, halo-$C_{1-6}$ alkyl (e.g., perfluoroalkyl), hydroxy-$C_{1-6}$ alkyl, nitro-$C_{1-6}$ alkyl, or $C_{1-6}$ thioalkoxy-$C_{1-6}$ alkyl); (3) $C_{1-20}$ alkoxy (e.g., $C_{1-6}$ alkoxy, such as perfluoroalkoxy); (4) $C_{1-6}$ alkylsulfinyl; (5) $C_{6-10}$ aryl; (6) amino; (7) $C_{1-6}$ alk-$C_{6-10}$ aryl; (8) azido; (9) $C_{3-8}$ cycloalkyl; (10) $C_{1-6}$ alk-$C_{3-8}$ cycloalkyl; (11) halo; (12) $C_{1-12}$ heterocyclyl (e.g., $C_{1-12}$ heteroaryl); (13) ($C_{1-12}$ heterocyclyl)oxy; (14) hydroxyl; (15) nitro; (16) $C_{1-20}$ thioalkoxy (e.g., $C_{1-6}$ thioalkoxy); (17) $—(CH_2)_qCO_2R^{A'}$, where q is an integer from zero to four, and $R^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl; (18) $—(CH_2)_qCONR^{B'}R^{C'}$, where q is an integer from zero to four and where $R^{B'}$ and $R^{C'}$ are independently selected from the group consisting of (a) hydrogen, (b) $C_{1-6}$ alkyl, (c) $C_{6-10}$ aryl, and (d) $C_{1-6}$ alk-$C_{6-10}$ aryl; (19) $—(CH_2)_qSO_2R^{D'}$, where q is an integer from zero to four and where $R^{D'}$ is selected from the group consisting of (a) alkyl, (b) $C_{6-10}$ aryl, and (c) alk-$C_{6-10}$ aryl; (20) $—(CH_2)_qSO_2NR^{E'}R^{F'}$, where q is an integer from zero to four and where each of $R^{E'}$ and $R^{F'}$ is, independently, selected from the group consisting of (a) hydrogen, (b) $C_{1-6}$ alkyl, (c) $C_{6-10}$ aryl, and (d) $C_{1-6}$ alk-$C_{6-10}$ aryl; (21) thiol; (22) $C_{6-10}$ aryloxy; (23) $C_{3-8}$ cycloalkoxy; (24) $C_{6-10}$ aryl-$C_{1-6}$ alkoxy; (25) $C_{1-6}$ alk-$C_{1-12}$ heterocyclyl (e.g., $C_{1-6}$ alk-$C_{1-12}$ heteroaryl); (26) $C_{2-20}$ alkenyl; and (27) $C_{2-20}$ alkynyl. In some embodiments, each of these groups can be further substituted as described herein. For example, the alkylene group of a $C_1$-alkaryl or a $C_1$-alkheterocyclyl can be further substituted with an oxo group to afford the respective aryloyl and (heterocyclyl)oyl substituent group.

The "arylalkyl" group, which as used herein, represents an aryl group, as defined herein, attached to the parent molecular group through an alkylene group, as defined herein. Exemplary unsubstituted arylalkyl groups are from 7 to 30 carbons (e.g., from 7 to 16 or from 7 to 20 carbons, such as $C_{1-6}$ alk-$C_{6-10}$ aryl, $C_{1-10}$ alk-$C_{6-10}$ aryl, or $C_{1-20}$ alk-$C_{6-10}$ aryl). In some embodiments, the alkylene and the aryl each can be further substituted with 1, 2, 3, or 4 substituent groups as defined herein for the respective groups. Other groups preceded by the prefix "alk-" are defined in the same manner, where "alk" refers to a $C_{1-6}$ alkylene, unless otherwise noted, and the attached chemical structure is as defined herein.

The term "azido" represents an $—N_3$ group, which can also be represented as $—N{=}N{=}N$.

The terms "carbocyclic" and "carbocyclyl," as used herein, refer to an optionally substituted $C_{3-12}$ monocyclic, bicyclic, or tricyclic non-aromatic ring structure in which the rings are formed by carbon atoms. Carbocyclic structures include cycloalkyl, cycloalkenyl, and cycloalkynyl groups.

The "carbocyclylalkyl" group, which as used herein, represents a carbocyclic group, as defined herein, attached to the parent molecular group through an alkylene group, as defined herein. Exemplary unsubstituted carbocyclylalkyl groups are from 7 to 30 carbons (e.g., from 7 to 16 or from 7 to 20 carbons, such as $C_{1-6}$ alk-$C_{6-10}$ carbocyclyl, $C_{1-10}$ alk-$C_{6-10}$ carbocyclyl, or $C_{1-20}$ alk-$C_{6-10}$ carbocyclyl). In some embodiments, the alkylene and the carbocyclyl each can be further substituted with 1, 2, 3, or 4 substituent groups as defined herein for the respective groups. Other groups preceded by the prefix "alk-" are defined in the same manner, where "alk" refers to a $C_{1-6}$ alkylene, unless otherwise noted, and the attached chemical structure is as defined herein.

The term "carbonyl," as used herein, represents a C(O) group, which can also be represented as C=O.

The term "carboxy," as used herein, means $—CO_2H$.

The term "cyano," as used herein, represents an $—CN$ group.

The term "cycloalkyl," as used herein represents a monovalent saturated or unsaturated non-aromatic cyclic hydrocarbon group from three to eight carbons, unless otherwise specified, and is exemplified by cyclopropyl, cyclobutyl, cyclopentyl, cyclohexyl, cycloheptyl, bicycle heptyl, and the like. When the cycloalkyl group includes one carbon-carbon double bond, the cycloalkyl group can be referred to as a "cycloalkenyl" group. Exemplary cycloalkenyl groups include cyclopentenyl, cyclohexenyl, and the like. The cycloalkyl groups of this invention can be optionally substituted with: (1) $C_{1-7}$ acyl (e.g., carboxyaldehyde); (2) $C_{1-20}$ alkyl (e.g., $C_{1-6}$ alkyl, $C_{1-6}$ alkoxy-$C_{1-6}$ alkyl, $C_{1-6}$ alkylsulfinyl-$C_{1-6}$ alkyl, amino-$C_{1-6}$ alkyl, azido-$C_{1-6}$ alkyl, (carboxyaldehyde)-$C_{1-6}$ alkyl, halo-$C_{1-6}$ alkyl (e.g., perfluoroalkyl), hydroxy-$C_{1-6}$ alkyl, nitro-$C_{1-6}$ alkyl, or $C_{1-6}$ thioalkoxy-$C_{1-6}$ alkyl); (3) $C_{1-20}$ alkoxy (e.g., $C_{1-6}$ alkoxy, such as perfluoroalkoxy); (4) $C_{1-6}$ alkylsulfinyl; (5) $C_{6-10}$ aryl; (6) amino; (7) $C_{1-6}$ alk-$C_{6-10}$ aryl; (8) azido; (9) $C_{3-8}$ cycloalkyl; (10) $C_{1-6}$ alk-$C_{3-8}$ cycloalkyl; (11) halo; (12) $C_{1-12}$ heterocyclyl (e.g., $C_{1-12}$ heteroaryl); (13) ($C_{1-12}$ heterocyclyl)oxy; (14) hydroxyl; (15) nitro; (16) $C_{1-20}$ thioalkoxy (e.g., $C_{1-6}$ thioalkoxy); (17) —$(CH_2)_qCO_2R^{A'}$, where q is an integer from zero to four, and $R^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl; (18) —$(CH_2)_qCONR^{B'}R^{C'}$, where q is an integer from zero to four and where $R^{B'}$ and $R^{C'}$ are independently selected from the group consisting of (a) hydrogen, (b) $C_{6-10}$ alkyl, (c) $C_{6-10}$ aryl, and (d) $C_{1-6}$ alk-$C_{6-10}$ aryl; (19) —$(CH_2)_qSO_2R^{D'}$, where q is an integer from zero to four and where $R^{D'}$ is selected from the group consisting of (a) $C_{6-10}$ alkyl, (b) $C_{6-10}$ aryl, and (c) $C_{1-6}$ alk-$C_{6-10}$ aryl; (20) —$(CH_2)_qSO_2NR^{E'}R^{F'}$, where q is an integer from zero to four and where each of $R^{E'}$ and $R^{F'}$ is, independently, selected from the group consisting of (a) hydrogen, (b) $C_{6-10}$ alkyl, (c) $C_{6-10}$ aryl, and (d) $C_{1-6}$ alk-$C_{6-10}$ aryl; (21) thiol; (22) $C_{6-10}$ aryloxy; (23) $C_{3-8}$ cycloalkoxy; (24) $C_{6-10}$ aryl-$C_{1-6}$ alkoxy; (25) $C_{1-6}$ alk-$C_{1-12}$ heterocyclyl (e.g., $C_{1-6}$ alk-$C_{1-12}$ heteroaryl); (26) oxo; (27) $C_{2-20}$ alkenyl; and (28) $C_{2-20}$ alkynyl. In some embodiments, each of these groups can be further substituted as described herein. For example, the alkylene group of a $C_1$-alkaryl or a $C_1$-alkheterocyclyl can be further substituted with an oxo group to afford the respective aryloyl and (heterocyclyl)oyl substituent group.

The "cycloalkylalkyl" group, which as used herein, represents a cycloalkyl group, as defined herein, attached to the parent molecular group through an alkylene group, as defined herein (e.g., an alkylene group of from 1 to 4, from 1 to 6, from 1 to 10, or form 1 to 20 carbons). In some embodiments, the alkylene and the cycloalkyl each can be further substituted with 1, 2, 3, or 4 substituent groups as defined herein for the respective group.

The term "diastereomer," as used herein means stereoisomers that are not mirror images of one another and are non-superimposable on one another.

The term "enantiomer," as used herein, means each individual optically active form of a compound of the invention, having an optical purity or enantiomeric excess (as determined by methods standard in the art) of at least 80% (i.e., at least 90% of one enantiomer and at most 10% of the other enantiomer), preferably at least 90% and more preferably at least 98%.

The term "halo," as used herein, represents a halogen selected from bromine, chlorine, iodine, or fluorine.

The term "heteroalkyl," as used herein, refers to an alkyl group, as defined herein, in which one or two of the constituent carbon atoms have each been replaced by nitrogen, oxygen, or sulfur. In some embodiments, the heteroalkyl group can be further substituted with 1, 2, 3, or 4 substituent groups as described herein for alkyl groups. The terms "heteroalkenyl" and heteroalkynyl," as used herein refer to alkenyl and alkynyl groups, as defined herein, respectively, in which one or two of the constituent carbon atoms have each been replaced by nitrogen, oxygen, or sulfur. In some embodiments, the heteroalkenyl and heteroalkynyl groups can be further substituted with 1, 2, 3, or 4 substituent groups as described herein for alkyl groups.

The term "heteroaryl," as used herein, represents that subset of heterocyclyls, as defined herein, which are aromatic: i.e., they contain 4n+2 pi electrons within the mono- or multicyclic ring system. Exemplary unsubstituted heteroaryl groups are of 1 to 12 (e.g., 1 to 11, 1 to 10, 1 to 9, 2 to 12, 2 to 11, 2 to 10, or 2 to 9) carbons. In some embodiment, the heteroaryl is substituted with 1, 2, 3, or 4 substituents groups as defined for a heterocyclyl group.

The term "heteroarylalkyl" refers to a heteroaryl group, as defined herein, attached to the parent molecular group through an alkylene group, as defined herein. Exemplary unsubstituted heteroarylalkyl groups are from 2 to 32 carbons (e.g., from 2 to 22, from 2 to 18, from 2 to 17, from 2 to 16, from 3 to 15, from 2 to 14, from 2 to 13, or from 2 to 12 carbons, such as $C_{1-6}$ alk-$C_{1-12}$ heteroaryl, $C_{1-10}$ alk-$C_{1-12}$ heteroaryl, or $C_{1-20}$ alk-$C_{1-12}$ heteroaryl). In some embodiments, the alkylene and the heteroaryl each can be further substituted with 1, 2, 3, or 4 substituent groups as defined herein for the respective group. Heteroarylalkyl groups are a subset of heterocyclylalkyl groups.

The term "heterocyclyl," as used herein represents a 5-, 6- or 7-membered ring, unless otherwise specified, containing one, two, three, or four heteroatoms independently selected from the group consisting of nitrogen, oxygen, and sulfur. The 5-membered ring has zero to two double bonds, and the 6- and 7-membered rings have zero to three double bonds. Exemplary unsubstituted heterocyclyl groups are of 1 to 12 (e.g., 1 to 11, 1 to 10, 1 to 9, 2 to 12, 2 to 11, 2 to 10, or 2 to 9) carbons. The term "heterocyclyl" also represents a heterocyclic compound having a bridged multicyclic structure in which one or more carbons and/or heteroatoms bridges two non-adjacent members of a monocyclic ring, e.g., a quinuclidinyl group. The term "heterocyclyl" includes bicyclic, tricyclic, and tetracyclic groups in which any of the above heterocyclic rings is fused to one, two, or three carbocyclic rings, e.g., an aryl ring, a cyclohexane ring, a cyclohexene ring, a cyclopentane ring, a cyclopentene ring, or another monocyclic heterocyclic ring, such as indolyl, quinolyl, isoquinolyl, tetrahydroquinolyl, benzofuryl, benzothienyl and the like. Examples of fused heterocyclyls include tropanes and 1,2,3,5,8,8a-hexahydroindolizine. Heterocyclics include pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidiniyl, morpholinyl, thiomorpholinyl, thiazolyl, thiazolidinyl, isothiazolyl, isothiazolidinyl, indolyl, indazolyl, quinolyl, isoquinolyl, quinoxalinyl, dihydroquinoxalinyl, quinazolinyl, cinnolinyl, phthalazinyl, benzimidazolyl, benzothiazolyl, benzoxazolyl, benzothiadiazolyl, furyl, thienyl, thiazolidinyl, isothiazolyl, triazolyl, tetrazolyl, oxadiazolyl (e.g., 1,2,3-oxadiazolyl), purinyl, thiadiazolyl (e.g., 1,2,3-thiadiazolyl), tetrahydrofuranyl, dihydrofuranyl, tetrahydrothienyl, dihydrothienyl, dihydroindolyl, dihydroquinolyl, tetrahydroquinolyl, tetrahydroisoquinolyl, dihydroisoquinolyl, pyranyl, dihydropyranyl, dithiazolyl, benzofuranyl, isobenzofuranyl, benzothienyl, and the like, including dihydro and tetrahydro forms thereof, where one or more double bonds are reduced and replaced with hydrogens. Still other exemplary heterocyclyls include: 2,3,4,5-tetrahydro-2-oxo-oxazolyl; 2,3-dihydro-2-oxo-1H-imidazolyl; 2,3,4,5-tetrahydro-5-oxo-1H-pyrazolyl (e.g., 2,3,4,5-tetrahydro-2-phenyl-5-oxo-1H-pyrazolyl); 2,3,4,5-tetrahydro-2,4-dioxo-1H-imidazolyl (e.g., 2,3,4,5-tetrahydro-2,4-dioxo-5-methyl-5-phenyl-1H-imidazolyl); 2,3-dihydro-2-thioxo-1,3,4-oxadiazolyl(e.g., 2,3-dihydro-2-thioxo-5-phenyl-1,3,4-oxadiazolyl); 4,5-dihydro-5-oxo-1H-triazolyl (e.g., 4,5-dihydro-3-methyl-4-amino 5-oxo-1H-triazolyl); 1,2,3,4-tetrahydro-2,4-dioxopyridinyl (e.g., 1,2,3,4-tetrahydro-2,4-dioxo-3,3-diethylpyridinyl); 2,6-dioxo-piperidinyl (e.g., 2,6-dioxo-3-ethyl-3-phenylpiperidinyl); 1,6-dihydro-6-oxopyridiminyl; 1,6-dihydro-4-oxopyrimidinyl (e.g., 2-(methylthio)-1,6-dihydro-4-oxo-5-methylpyrimidin-1-yl); 1,2,3,4-tetrahydro-2, 4-dioxopyrimidinyl (e.g., 1,2,3,4-tetrahydro-2,4-dioxo-3-ethylpyrimidinyl); 1,6-dihydro-6-oxo-pyridazinyl (e.g., 1,6-dihydro-6-oxo-3-ethylpyridazinyl); 1,6-dihydro-6-oxo-1,2, 4-triazinyl (e.g., 1,6-dihydro-5-isopropyl-6-oxo-1,2,4-triazinyl); 2,3-dihydro-2-oxo-1H-indolyl (e.g., 3,3-dimethyl-2,3-dihydro-2-oxo-1H-indolyl and 2,3-dihydro-2-oxo-3,3'-spiropropane-1H-indol-1-yl); 1,3-dihydro-1-oxo-2H-iso-indolyl; 1,3-dihydro-1,3-dioxo-2H-iso-indolyl; 1H-benzopyrazolyl (e.g., 1-(ethoxycarbonyl)-1H-benzopyrazolyl); 2,3-dihydro-2-oxo-1H-benzimidazolyl (e.g., 3-ethyl-2,3-dihydro-2-oxo-1H-benzimidazolyl); 2,3-dihydro-2-oxo-benzoxazolyl (e.g., 5-chloro-2,3-dihydro-2-oxo-benzoxazolyl); 2,3-dihydro-2-oxo-benzoxazolyl; 2-oxo-2H-benzopyranyl; 1,4-benzodioxanyl; 1,3-benzodioxanyl; 2,3-dihydro-3-oxo,4H-1,3-benzothiazinyl; 3,4-dihydro-4-oxo-3H-quinazolinyl (e.g., 2-methyl-3,4-dihydro-4-oxo-3H-quinazolinyl); 1,2,3,4-tetrahydro-2,4-dioxo-3H-quinazolyl (e.g., 1-ethyl-1,2,3,4-tetrahydro-2,4-dioxo-3H-quinazolyl); 1,2,3,6-tetrahydro-2,6-dioxo-7H-purinyl (e.g., 1,2,3,6-tetrahydro-1,3-dimethyl-2,6-dioxo-7H-purinyl); 1,2, 3,6-tetrahydro-2,6-dioxo-1H-purinyl (e.g., 1,2,3,6-tetrahydro-3,7-dimethyl-2,6-dioxo-1H-purinyl); 2-oxobenz[c,d] indolyl; 1,1-dioxo-2H-naphth[1,8-c,d]isothiazolyl; and 1,8-naphthylenedicarboxamido. Additional heterocyclics include 3,3a,4,5,6,6a-hexahydro-pyrrolo[3,4-b]pyrrol-(2H)-yl, and 2,5-diazabicyclo[2.2.1]heptan-2-yl, homopiperazinyl (or diazepanyl), tetrahydropyranyl, dithiazolyl, benzofuranyl, benzothienyl, oxepanyl, thiepanyl, azocanyl, oxecanyl, and thiocanyl. Heterocyclic groups also include groups of the formula

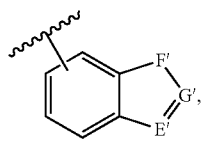

where

E' is selected from the group consisting of —N— and —CH—; F' is selected from the group consisting of —N=CH—, —NH—CH$_2$—, —NH—C(O)—, —NH—, —CH=N—, —CH$_2$—NH—, —C(O)—NH—, —CH=CH—, —CH$_2$—, —CH$_2$CH$_2$—, —CH$_2$O—, —OCH$_2$—, —O—, and —S—; and G' is selected from the group consisting of —CH— and —N—. Any of the heterocyclyl groups mentioned herein may be optionally substituted with one, two, three, four or five substituents independently selected from the group consisting of: (1) $C_{1-7}$ acyl (e.g., carboxyaldehyde); (2) $C_{1-20}$ alkyl (e.g., $C_{1-6}$ alkyl, $C_{1-6}$ alkoxy-$C_{1-6}$ alkyl, $C_{1-6}$ alkylsulfinyl-$C_{1-6}$ alkyl, amino-$C_{1-6}$ alkyl, azido-$C_{1-6}$ alkyl, (carboxyaldehyde)-$C_{1-6}$ alkyl, halo-$C_{1-6}$ alkyl (e.g., perfluoroalkyl), hydroxy-$C_{1-6}$ alkyl, nitro-$C_{1-6}$ alkyl, or $C_{1-6}$ thioalkoxy-$C_{1-6}$ alkyl); (3) $C_{1-20}$ alkoxy (e.g., $C_{1-6}$ alkoxy, such as perfluoroalkoxy); (4) $C_{1-6}$ alkylsulfinyl; (5) $C_{6-10}$ aryl; (6) amino; (7) $C_{1-6}$ alk-$C_{6-10}$ aryl; (8) azido; (9) $C_{3-8}$ cycloalkyl; (10) $C_{1-6}$ alk-$C_{3-8}$ cycloalkyl; (11) halo; (12) $C_{1-12}$ heterocyclyl (e.g., $C_{2-12}$ heteroaryl); (13) ($C_{1-12}$ heterocyclyl)oxy; (14) hydroxyl; (15) nitro; (16) $C_{1-20}$ thioalkoxy (e.g., $C_{1-6}$ thioalkoxy); (17) —(CH$_2$)$_q$CO$_2$R$^{A'}$, where q is an integer from zero to four, and R$^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl; (18) —(CH$_2$)$_q$CONR$^{B'}$R$^{C'}$, where q is an integer from zero to four and where R$^{B'}$ and R$^{C'}$ are independently selected from the group consisting of (a) hydrogen, (b) $C_{1-6}$ alkyl, (c) $C_{6-10}$ aryl, and (d) $C_{1-6}$ alk-$C_{6-10}$ aryl; (19) —(CH$_2$)$_q$SO$_2$R$^{D'}$, where q is an integer from zero to four and where R$^{D'}$ is selected from the group consisting of (a) $C_{1-6}$ alkyl, (b) $C_{6-10}$ aryl, and (c) $C_{1-6}$ alk-$C_{6-10}$ aryl; (20) —(CH$_2$)$_q$SO$_2$NR$^{E'}$R$^{F'}$, where q is an integer from zero to four and where each of R$^{E'}$ and R$^{F'}$ is, independently, selected from the group consisting of (a) hydrogen, (b) $C_{1-6}$ alkyl, (c) $C_{6-10}$ aryl, and (d) $C_{1-6}$ alk-$C_{6-10}$ aryl; (21) thiol; (22) $C_{6-10}$ aryloxy; (23) $C_{3-8}$ cycloalkoxy; (24) arylalkoxy; (25) $C_{1-6}$ alk-$C_{1-12}$ heterocyclyl (e.g., $C_{1-6}$ alk-$C_{1-12}$ heteroaryl); (26) oxo; (27) ($C_{1-12}$ heterocyclyl)imino; (28) $C_{2-20}$ alkenyl; and (29) $C_{2-20}$ alkynyl. In some embodiments, each of these groups can be further substituted as described herein. For example, the alkylene group of a $C_1$-alkaryl or a $C_1$-alkheterocyclyl can be further substituted with an oxo group to afford the respective aryloyl and (heterocyclyl)oyl substituent group.

The "heterocyclylalkyl" group, which as used herein, represents a heterocyclyl group, as defined herein, attached to the parent molecular group through an alkylene group, as defined herein. Exemplary unsubstituted heterocyclylalkyl groups are from 2 to 32 carbons (e.g., from 2 to 22, from 2 to 18, from 2 to 17, from 2 to 16, from 3 to 15, from 2 to 14, from 2 to 13, or from 2 to 12 carbons, such as $C_{1-6}$ alk-$C_{1-12}$ heterocyclyl, $C_{1-10}$ alk-$C_{1-12}$ heterocyclyl, or $C_{1-20}$ alk-$C_{1-12}$ heterocyclyl). In some embodiments, the alkylene and the heterocyclyl each can be further substituted with 1, 2, 3, or 4 substituent groups as defined herein for the respective group.

The term "hydrocarbon," as used herein, represents a group consisting only of carbon and hydrogen atoms.

The term "hydroxyl," as used herein, represents an —OH group. In some embodiments, the hydroxyl group can be substituted with 1, 2, 3, or 4 substituent groups (e.g., O-protecting groups) as defined herein for an alkyl.

The term "isomer," as used herein, means any tautomer, stereoisomer, enantiomer, or diastereomer of any compound of the invention. It is recognized that the compounds of the invention can have one or more chiral centers and/or double bonds and, therefore, exist as stereoisomers, such as double-bond isomers (i.e., geometric E/Z isomers) or diastereomers (e.g., enantiomers (i.e., (+) or (−)) or cis/trans isomers). According to the invention, the chemical structures depicted herein, and therefore the compounds of the invention, encompass all of the corresponding stereoisomers, that is, both the stereomerically pure form (e.g., geometrically pure, enantiomerically pure, or diastereomerically pure) and enantiomeric and stereoisomeric mixtures, e.g., racemates. Enantiomeric and stereoisomeric mixtures of compounds of the invention can typically be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically or enantiomerically pure intermediates, reagents, and catalysts by well-known asymmetric synthetic methods.

The term "N-protected amino," as used herein, refers to an amino group, as defined herein, to which is attached one or two N-protecting groups, as defined herein.

The term "N-protecting group," as used herein, represents those groups intended to protect an amino group against undesirable reactions during synthetic procedures. Commonly used N-protecting groups are disclosed in Greene, "Protective Groups in Organic Synthesis," 3$^{rd}$ Edition (John Wiley & Sons, New York, 1999), which is incorporated herein by reference. N-protecting groups include acyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries such as protected or unprotected D, L or D, L-amino acids such as alanine, leucine, phenylalanine, and the like; sulfonyl-containing groups such as benzenesulfonyl, p-toluenesulfonyl, and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl, and the like, alkaryl groups such as benzyl, triphenylmethyl, benzyloxymethyl, and the like and silyl groups, such as trimethylsilyl, and the like. Preferred N-protecting groups are formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "nitro," as used herein, represents an —NO$_2$ group.

The term "O-protecting group," as used herein, represents those groups intended to protect an oxygen containing (e.g., phenol, hydroxyl, or carbonyl) group against undesirable reactions during synthetic procedures. Commonly used O-protecting groups are disclosed in Greene, "Protective Groups in Organic Synthesis," 3$^{rd}$ Edition (John Wiley & Sons, New York, 1999), which is incorporated herein by reference. Exemplary O-protecting groups include acyl, aryloyl, or carbamyl groups, such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, t-butyldimethylsilyl, tri-iso-propylsilyloxymethyl, 4,4'-dimethoxytrityl, isobutyryl, phenoxyacetyl, 4-isopropylpehenoxyacetyl, dimethylformamidino, and 4-nitrobenzoyl; alkylcarbonyl groups, such as acyl, acetyl, propionyl, pivaloyl, and the like; optionally substituted arylcarbonyl groups, such as benzoyl; silyl groups, such as trimethylsilyl (TMS), tert-butyldimethylsilyl (TBDMS), tri-iso-propylsilyloxymethyl (TOM), triisopropylsilyl (TIPS), and the like; ether-forming groups with the hydroxyl, such methyl, methoxymethyl, tetrahydropyranyl, benzyl, p-methoxybenzyl, trityl, and the like; alkoxycarbonyls, such as methoxycarbonyl, ethoxycarbonyl, isopropoxycarbonyl, n-isopropoxycarbonyl, n-butyloxycarbonyl, isobutyloxycarbonyl, sec-butyloxycarbonyl, t-butyloxycarbonyl, 2-ethylhexyloxycarbonyl, cyclohexyloxycarbonyl, methyloxycarbonyl, and the like; alkoxyalkoxycarbonyl groups, such as methoxymethoxycarbonyl, ethoxymethoxycarbonyl, 2-methoxyethoxycarbonyl, 2-ethoxyethoxycarbonyl, 2-butoxyethoxycarbonyl, 2-methoxyethoxymethoxycarbonyl, allyloxycarbonyl, propargyloxycarbonyl, 2-butenoxycarbonyl, 3-methyl-2-butenoxycarbonyl, and the like; haloalkoxycarbonyls, such as 2-chloroethoxycarbonyl, 2-chloroethoxycarbonyl, 2,2,2-trichloroethoxycarbonyl, and the like; optionally substituted arylalkoxycarbonyl groups, such as benzyloxycarbonyl, p-methylbenzyloxycarbonyl, p-methoxybenzyloxycarbonyl, p-nitrobenzyloxycarbonyl, 2,4-dinitrobenzyloxycarbonyl, 3,5-dimethylbenzyloxycarbonyl, p-chlorobenzyloxycarbonyl, p-bromobenzyloxy-carbonyl, fluorenylmethyloxycarbonyl, and the like; and optionally substituted aryloxycarbonyl groups, such as phenoxycarbonyl, p-nitrophenoxycarbonyl, o-nitrophenoxycarbonyl, 2,4-dinitrophenoxycarbonyl, p-methyl-phenoxycarbonyl, m-methylphenoxycarbonyl, o-bromophenoxycarbonyl, 3,5-dimethylphenoxycarbonyl, p-chlorophenoxycarbonyl, 2-chloro-4-nitrophenoxy-carbonyl, and the like); substituted alkyl, aryl, and alkaryl ethers (e.g., trityl; methylthiomethyl; methoxymethyl; benzyloxymethyl; siloxymethyl; 2,2,2,-trichloroethoxymethyl; tetrahydropyranyl; tetrahydrofuranyl; ethoxyethyl; 1-[2-(trimethylsilyl)ethoxy]ethyl; 2-trimethylsilylethyl; t-butyl ether; p-chlorophenyl, p-methoxyphenyl, p-nitrophenyl, benzyl, p-methoxybenzyl, and nitrobenzyl); silyl ethers (e.g., trimethylsilyl; triethylsilyl; triisopropylsilyl; dimethylisopropylsilyl; t-butyldimethylsilyl; t-butyldiphenylsilyl; tribenzylsilyl; triphenylsilyl; and diphenymethylsilyl); carbonates (e.g., methyl, methoxymethyl, 9-fluorenylmethyl; ethyl; 2,2,2-trichloroethyl; 2-(trimethylsilyl)ethyl; vinyl, allyl, nitrophenyl; benzyl; methoxybenzyl; 3,4-dimethoxybenzyl; and nitrobenzyl); carbonyl-protecting groups (e.g., acetal and ketal groups, such as dimethyl acetal, 1,3-dioxolane, and the like; acylal groups; and dithiane groups, such as 1,3-dithianes, 1,3-dithiolane, and the like); carboxylic acid-protecting groups (e.g., ester groups, such as methyl ester, benzyl ester, t-butyl ester, orthoesters, and the like; and oxazoline groups.

The term "oxo" as used herein, represents =O.

The prefix "perfluoro," as used herein, represents anyl group, as defined herein, where each hydrogen radical bound to the alkyl group has been replaced by a fluoride radical. For example, perfluoroalkyl groups are exemplified by trifluoromethyl, pentafluoroethyl, and the like.

The term "protected hydroxyl," as used herein, refers to an oxygen atom bound to an O-protecting group.

The term "spirocyclyl," as used herein, represents a $C_{2-7}$ alkylene diradical, both ends of which are bonded to the same carbon atom of the parent group to form a spirocyclic group, and also a $C_{1-6}$ heteroalkylene diradical, both ends of which are bonded to the same atom. The heteroalkylene radical forming the spirocyclyl group can containing one, two, three, or four heteroatoms independently selected from the group consisting of nitrogen, oxygen, and sulfur. In some embodiments, the spirocyclyl group includes one to seven carbons, excluding the carbon atom to which the diradical is attached. The spirocyclyl groups of the invention may be optionally substituted with 1, 2, 3, or 4 substituents provided herein as optional substituents for cycloalkyl and/or heterocyclyl groups.

The term "stereoisomer," as used herein, refers to all possible different isomeric as well as conformational forms which a compound may possess (e.g., a compound of any formula described herein), in particular all possible stereochemically and conformationally isomeric forms, all diastereomers, enantiomers and/or conformers of the basic molecular structure. Some compounds of the present invention may exist in different tautomeric forms, all of the latter being included within the scope of the present invention.

The term "sulfonyl," as used herein, represents an —S(O)$_2$— group.

The term "thiol," as used herein. represents an —SH group.

Definitions

In this application, unless otherwise clear from context, (i) the term "a" may be understood to mean "at least one"; (ii) the term "or" may be understood to mean "and/or"; (iii) the terms "comprising" and "including" may be understood to encompass itemized components or steps whether presented by themselves or together with one or more additional components or steps; and (iv) the terms "about" and "approximately" may be understood to permit standard variation as would be understood by those of ordinary skill in the art; and (v) where ranges are provided, endpoints are included.

As used herein, the term "π-effect interaction" refers to attractive, non-covalent interactions between aromatic rings.

As used herein, the term "active site" refers to the location on a protein (e.g., an enzyme) where substrate molecules bind and undergo a chemical reaction. By "does not bind at the active site" is meant that no atoms of a compound or complex substantially participate in binding with residues within the active site (e.g., residues that participate in binding to a natural substrate molecule).

As used herein, the term "administration" refers to the administration of a composition (e.g., a compound, a complex or a preparation that includes a compound or complex as described herein) to a subject or system. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal and vitreal.

As is known in the art, "affinity" is a measure of the tightness with which a particular ligand binds to its partner. Affinities can be measured in different ways. In some embodiments, affinity is measured by a quantitative assay. In some such embodiments, binding partner concentration may be fixed to be in excess of ligand concentration so as to mimic physiological conditions. Alternatively or additionally, in some embodiments, binding partner concentration and/or ligand concentration may be varied. In some such embodiments, affinity may be compared to a reference under comparable conditions (e.g., concentrations).

As used herein, the term "analog" refers to a substance that shares one or more particular structural features, elements, components, or moieties with a reference substance. Typically, an "analog" shows significant structural similarity with the reference substance, for example sharing a core or consensus structure, but also differs in certain discrete ways. In some embodiments, an analog is a substance that can be generated from the reference substance by chemical manipulation of the reference substance. In some embodiments, an analog is a substance that can be generated through performance of a synthetic process substantially similar to (e.g., sharing a plurality of steps with) one that generates the reference substance. In some embodiments, an analog is or can be generated through performance of a synthetic process different from that used to generate the reference substance.

As used herein, the term "animal" refers to any member of the animal kingdom. In some embodiments, "animal" refers to humans, at any stage of development. In some embodiments, "animal" refers to non-human animals, at any stage of development. In some embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, and/or worms. In some embodiments, an animal may be a transgenic animal, genetically-engineered animal, and/or a clone.

As used herein, the term "antagonist" refers to a compound that i) inhibits, decreases or reduces the effects of a target protein (e.g., a eukaryotic target protein such as a mammalian target protein or a fungal target protein or a prokaryotic target protein such as a bacterial target protein); and/or ii) inhibits, decreases, reduces, or delays one or more biological events. An antagonist may be direct (in which case it exerts its influence directly upon its target) or indirect (in which case it exerts its influence by other than binding to its target; e.g., by interacting with a regulator of the target protein (e.g., a eukaryotic target protein such as a mammalian target protein or a fungal target protein or a prokaryotic target protein such as a bacterial target protein), for example so that level or activity of the target protein is altered).

As used herein, the terms "approximately" and "about" are each intended to encompass normal statistical variation as would be understood by those of ordinary skill in the art as appropriate to the relevant context. In certain embodiments, the terms "approximately" or "about" each refer to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1% or less in either direction (greater than or less than) of a stated value, unless otherwise stated or otherwise evident from the context (e.g., where such number would exceed 100% of a possible value).

Two events or entities are "associated" with one another, as that term is used herein, if the presence, level and/or form of one is correlated with that of the other. For example, a particular entity (e.g., polypeptide) is considered to be associated with a particular disease, disorder, or condition, if its presence, level and/or form correlates with incidence of and/or susceptibility of the disease, disorder, or condition (e.g., across a relevant population). In some embodiments, two or more entities are physically "associated" with one another if they interact, directly or indirectly, so that they are and remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

It will be understood that the term "binding" as used herein, typically refers to association (e.g., non-covalent or covalent) between or among two or more entities. "Direct" binding involves physical contact between entities or moieties; indirect binding involves physical interaction by way of physical contact with one or more intermediate entities. Binding between two or more entities can typically be assessed in any of a variety of contexts—including where interacting entities or moieties are studied in isolation or in the context of more complex systems (e.g., while covalently or otherwise associated with a carrier entity and/or in a biological system or cell).

The affinity of a molecule X for its partner Y can generally be represented by the dissociation constant ($K_D$). Affinity can be measured by common methods known in the art, including those described herein. Specific illustrative and exemplary embodiments for measuring binding affinity are described below. The term "$K_D$," as used herein, is intended to refer to the dissociation equilibrium constant of a particular compound-protein or complex-protein interaction. Typically, the compounds of the invention bind to presenter proteins with a dissociation equilibrium constant ($K_D$) of less than about $10^{-6}$ M, such as less than approximately $10^{-7}$ M, $10^{-8}$ M, $10^{-9}$ M, or $10^{-10}$ M or even lower, e.g., when determined by surface plasmon resonance (SPR) technology using the presenter protein as the analyte and the compound as the ligand. The presenter protein/compound complexes of the invention bind to target proteins (e.g., a eukaryotic target protein such as a mammalian target protein or a fungal target protein or a prokaryotic target protein such as a bacterial target protein) with a dissociation equilibrium constant ($K_D$) of less than about $10^{-6}$ M, such as less than approximately $10^{-7}$ M, $10^{-8}$ M, $10^{-9}$ M, or $10^{-10}$ M or even lower, e.g., when determined by surface plasmon resonance (SPR) technology using the target protein as the analyte and the complex as the ligand.

As used herein, the term "binding free energy" refers to the difference in energy between bound and unbound states of a complex. Binding free energy may be determined by methods known in the art including using the equation $\Delta G = -RT\ln K$ using an experimentally derived dissociation constant, Kd. Binding free energy can be calculated using a computational algorithm known in the art, e.g., molecular dynamic simulations, free-energy perturbations or Monte Carlo protocols, as implemented in commercial software such as AMBER (Cornell et al. J. Am. Chem. Soc. 1995, 117, 5179) CHARMM (Brooks et al. J. Comp. Chem. 1983, 4, 187), or Desmond (Boowers et al. Proc. ACM/IEEE Conf. Supercomputing, 2006, SCO6).

As used herein, the term "buried surface area" refers to the surface area of a protein or a complex that is not exposed to solvent. Buried surface area may be determined by methods known in the art including by calculating inaccessibility to solvent. Inaccessibility to solvent may be calculated computationally with a rolling probe of 1.4 A, using a program such as PDBePISA release version 1.48 (http://www.ebi.ac.uk/pdbe/pisa/).

As used herein, the term "cell penetrant" refers to compounds that when added to a cell's environment can enter the intracellular domain without killing the cell. Whether a compound is cell penetrant may be determined using any method known in the art, e.g., the biosensor method described herein As used herein, the term "characteristic portion" is used, in the broadest sense, to refer to a portion of a substance whose presence (or absence) correlates with presence (or absence) of a particular feature, attribute, or activity of the substance. In some embodiments, a characteristic portion of a substance is a portion that is found in the substance and in related substances that share the particular feature, attribute or activity, but not in those that do not share the particular feature, attribute or activity. In certain embodiments, a characteristic portion shares at least one functional characteristic with the intact substance. For example, in some embodiments, a "characteristic portion" of a protein or polypeptide is one that contains a continuous stretch of amino acids, or a collection of continuous stretches of amino acids, that together are characteristic of a protein or polypeptide. In some embodiments, each such continuous stretch generally contains at least 2, 5, 10, 15, 20, 50, or more amino acids. In general, a characteristic portion of a substance (e.g., of a protein, antibody, etc.) is one that, in addition to the sequence and/or structural identity specified above, shares at least one functional characteristic with the relevant intact substance. In some embodiments, a characteristic portion may be biologically active.

As used herein, the phrase "characteristic sequence element" refers to a sequence element found in a polymer (e.g., in a polypeptide or nucleic acid) that represents a characteristic portion of that polymer. In some embodiments, presence of a characteristic sequence element correlates with presence or level of a particular activity or property of the polymer. In some embodiments, presence (or absence) of a characteristic sequence element defines a particular polymer as a member (or not a member) of a particular family or group of such polymers. A characteristic sequence element typically comprises at least two monomers (e.g., amino acids or nucleotides). In some embodiments, a characteristic sequence element includes at least 2, 3, 4, 5, 6, 7, 8, 9, 10, 11, 12, 13, 14, 15, 20, 25, 30, 35, 40, 45, 50, or more monomers (e.g., contiguously linked monomers). In some embodiments, a characteristic sequence element includes at least first and second stretches of contiguous monomers spaced apart by one or more spacer regions whose length may or may not vary across polymers that share the sequence element. In certain embodiments, particular characteristic sequence elements may be referred to as "motifs".

As used herein, the term "clogP" refers to the calculated partition coefficient of a molecule or portion of a molecule. The partition coefficient is the ratio of concentrations of a compound in a mixture of two immiscible phases at equilibrium (e.g., octanol and water) and measures the hydrophobicity or hydrophilicity of a compound. A variety of methods are available in the art for determining clogP For example, in some embodiments, clogP can be determined using quantitative structure-property relationship algorithms known in the art (e.g., using fragment based prediction methods that predict the log P of a compound by determining the sum of its non-overlapping molecular fragments). Several algorithms for calculating clogP are known in the art including those used by molecular editing software such as CHEMDRAW® Pro, Version 12.0.2.1092 (Camrbridgesoft, Cambridge, Mass.) and MARVINSKETCH® (ChemAxon, Budapest, Hungary). A compound is considered to have met a threshold cLogP if it meets the threshold in at least one of the above methods.

As used herein, the term "collection" refers to a group of 2, 5, 10, $10^2$, $10^3$, $10^4$, $10^5$, $10^6$, $10^7$, $10^8$, $10^9$, or more different molecules. In some embodiments, at least 10% (e.g., at least 20%, at least 30%, at least 40%, at least 50%, at least 60%, at least 70%, at least 80%, at least 90%, at least 95%, at least 99% or 100%) of the compounds in the collection are compounds (e.g., macrocyclic compounds)s described herein.

As used herein, the term "combination therapy" refers to those situations in which a subject is simultaneously exposed to two or more therapeutic regimens (e.g., two or more compounds such as macrocyclic compounds). In some embodiments, two or more compounds may be administered simultaneously; in some embodiments, such compounds may be administered sequentially; in some embodiments, such compounds are administered in overlapping dosing regimens.

The term "comparable," as used herein, refers to two or more compounds, entities, situations, sets of conditions, etc that may not be identical to one another but that are sufficiently similar to permit comparison therebetween so that conclusions may reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such compounds, entities, situations, sets of conditions, etc to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

As used herein, the term "complex" refers to a group of two or more compounds and/or proteins which are bound together through a binding interaction (e.g., a non-covalent interaction, such as a hydrophobic effect interaction, an electrostatic interaction, a van der Waals interaction, or π-effect interaction). Examples of complexes are "presenter protein/compound complex" which include a compound of the invention bound to a presenter protein.

As used herein, the term "corresponding to" is often used to designate a structural element or moiety in an compound of interest that shares a position (e.g., in three-dimensional space or relative to another element or moiety) with one present in an appropriate reference compound. For example, in some embodiments, the term is used to refer to position/identity of a residue in a polymer, such as an amino acid residue in a polypeptide or a nucleotide residue in a nucleic acid. Those of ordinary skill will appreciate that, for purposes of simplicity, residues in such a polymer are often designated using a canonical numbering system based on a reference related polymer, so that a residue in a first polymer "corresponding to" a residue at position 190 in the reference polymer, for example, need not actually be the $190^{th}$ residue in the first polymer but rather corresponds to the residue found at the $190^{th}$ position in the reference polymer; those of ordinary skill in the art readily appreciate how to identify "corresponding" amino acids, including through use of one or more commercially-available algorithms specifically designed for polymer sequence comparisons.

As used herein, the term "designed" refers to a compound (i) whose structure is or was selected by the hand of man; (ii) that is produced by a process requiring the hand of man; and/or (iii) that is distinct from natural substances and other known compounds.

Many methodologies described herein include a step of "determining." Those of ordinary skill in the art, reading the present specification, will appreciate that such "determining" can utilize or be accomplished through use of any of a variety of techniques available to those skilled in the art, including for example specific techniques explicitly referred to herein. In some embodiments, determining involves manipulation of a physical sample. In some embodiments, determining involves consideration and/or manipulation of data or information, for example utilizing a computer or other processing unit adapted to perform a relevant analysis. In some embodiments, determining involves receiving relevant information and/or materials from a source. In some embodiments, determining involves comparing one or more features of a sample or entity to a comparable reference.

As used herein, the term "depsi-linkage" refers to the replacement of an amide bond with an ester bond.

As used herein, the term "dosage form" refers to a physically discrete unit of an active compound (e.g., a therapeutic or diagnostic agent) for administration to a subject. Each unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total amount of a therapeutic composition or compound administered to a particular subject is determined by one or more attending physicians and may involve administration of multiple dosage forms.

As used herein, the term "dosing regimen" refers to a set of unit doses (typically more than one) that are administered individually to a subject, typically separated by periods of time. In some embodiments, a given therapeutic compound has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount In some embodiments, a dosing regimen is correlated with a desired or beneficial outcome when administered across a relevant population (i.e., is a therapeutic dosing regimen).

As used herein, the term "engineered" is used to describe a compound whose design and/or production involves action of the hand of man. For example, in some embodiments, an "engineered" compound is prepared by in vitro chemical synthesis. In some embodiments, an "engineered" compound is produced by a cell that has been genetically manipulated relative to a reference wild type cell. In some embodiments, an "engineered" compound is produced by a cell in culture. In some embodiments, an "engineered" compound is produced by a cell in culture conditions specifically modified to enhance production of the compound. In some embodiments, an "engineered" compound has a structure designed or selected by in silico modeling.

As used herein, the term "flat surface site," as is understood in the art, refers to a site on a surface of a protein structure that has a relatively flat character, (e.g., a site that does not include a well-defined pocket or cavity with an area of greater than 500 Å$^2$, a volume of greater than 400 Å$^3$, and a depth greater than 13 Å). In some embodiments, a site may be determined to be flat by utilizing a commercial algorithm known in the art e.g., a site may be determined to be flat if it does not include a well-defined pocket or cavity with an area of greater than 500 Å$^2$, a volume of greater than 400 Å$^3$, and a depth greater than 13 Å as determined by CAST (Liang et al. Prot. Sci. 1998, 7:1884) or Sitemap (Halgren J. Chem. Inf. Model. 2009, 49:377). Those of ordinary skill in the art are familiar with the concept of flatness and, moreover are aware of its relationship to "druggability." In some embodiments, a protein is considered to have a flat surface site if it is undruggable as defined herein, e.g., is determined to be undruggable using the program DOGSITESCORER®.

As used herein, the term "hydrophobic residue" refers to an amino acid that has a hydropathy index value equal to or greater than proline. Examples of hydrophobic residues are valine, isoleucine, leucine, methionine, phenylalanine, tryptophan, alanine, glycine, and cysteine.

As used herein, the term "hydrophobic surface site" refers to site on a surface of a protein structure comprising at least 30% hydrophobic residues).

As used herein, the term "identity" refers to the overall relatedness between polymeric molecules, e.g., between nucleic acid molecules (e.g., DNA molecules and/or RNA molecules) and/or between polypeptide molecules. Calculation of the percent identity of two nucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix.

As used herein, the term "isolated" refers to a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated compounds are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. In some embodiments, isolation involves or requires disruption of covalent bonds (e.g., to isolate a polypeptide domain from a longer polypeptide and/or to isolate a nucleotide sequence element from a longer oligonucleotide or nucleic acid).

The term "macrocyclic compound," as used herein, refers to a small molecule compound containing a ring with nine or more ring atoms. Macrocyclic compounds include macrolides, a group of small molecules containing a macrocyclic lactone, such as erythromycin, rapamycin, and FK506. In some embodiments, a macrocyclic compound is a small molecule in which greater than 25% (e.g., greater than 30%, greater than 35%, greater than 40%, greater than 45%) of the non-hydrogen atoms in the small molecule are included in a single or fused ring structure. In some embodiments, the macrocyclic compound is not a compound described in Benjamin et al. Nat. Rev. Drug. Discov. 2011, 10(11), 868-880 or Sweeney, Z. K. et al. J. Med. Chem. 2014, epub ahead of print, the structures of which are incorporated by reference.

The term "target protein interacting moiety" as used herein, refers to a group of ring atoms and the moieties attached thereto (e.g., atoms within 20 atoms of a ring atom such as, atoms within 15 atoms of a ring atom, atoms within 10 atoms of a ring atom, atoms within 5 atoms of a ring atom) that, when the compound is in a complex with a presenter protein, specifically bind to a target protein (e.g., a eukaryotic target protein such as a mammalian target protein or a fungal target protein or a prokaryotic target protein such as a bacterial target protein).

The term "modulator" is used to refer to an entity whose presence or level in a system in which an activity of interest is observed correlates with a change in level and/or nature of that activity as compared with that observed under otherwise comparable conditions when the modulator is absent. In some embodiments, a modulator is an activator, in that activity is increased in its presence as compared with that observed under otherwise comparable conditions when the modulator is absent. In some embodiments, a modulator is an antagonist or inhibitor, in that activity is reduced in its presence as compared with otherwise comparable conditions when the modulator is absent. In some embodiments, a modulator interacts directly with a target entity whose activity is of interest. In some embodiments, a modulator interacts indirectly (i.e., directly with an intermediate compound that interacts with the target entity) with a target entity whose activity is of interest. In some embodiments, a modulator affects level of a target entity of interest; alternatively or additionally, in some embodiments, a modulator affects activity of a target entity of interest without affecting level of the target entity. In some embodiments, a modulator affects both level and activity of a target entity of interest, so that an observed difference in activity is not entirely explained by or commensurate with an observed difference in level. In some embodiments, a modulator is an allosteric modulator such as an allosteric agonist.

As used herein, an atom that "participates in binding" is within 4 Å of the entity to which they bind or connects to an atom that is with 4 Å of the entity to which they bind.

As used herein, the term "pharmaceutical composition" refers to an active compound, formulated together with one or more pharmaceutically acceptable carriers. In some embodiments, active compound is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

A "pharmaceutically acceptable excipient," as used herein, refers any inactive ingredient (for example, a vehicle capable of suspending or dissolving the active compound) having the properties of being nontoxic and non-inflammatory in a subject. Typical excipients include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol. Those of ordinary skill in the art are familiar with a variety of agents and materials useful as excipients.

The term "pharmaceutically acceptable salt," as use herein, refers to those salts of the compounds described here that are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, pharmaceutically acceptable salts are described in: Berge et al., J. *Pharmaceutical Sciences* 66:1-19, 1977 and in *Pharmaceutical Salts: Properties, Selection, and Use*, (Eds. P. H. Stahl and C. G. Wermuth), Wiley-VCH, 2008. The salts can be prepared in situ during the final isolation and purification of the compounds described herein or separately by reacting the free base group with a suitable organic acid.

The compounds of the invention may have ionizable groups so as to be capable of preparation as pharmaceutically acceptable salts. These salts may be acid addition salts involving inorganic or organic acids or the salts may, in the case of acidic forms of the compounds of the invention be prepared from inorganic or organic bases. Frequently, the compounds are prepared or used as pharmaceutically acceptable salts prepared as addition products of pharmaceutically acceptable acids or bases. Suitable pharmaceutically acceptable acids and bases are well-known in the art, such as hydrochloric, sulphuric, hydrobromic, acetic, lactic, citric, or tartaric acids for forming acid addition salts, and potassium hydroxide, sodium hydroxide, ammonium hydroxide, caffeine, various amines, and the like for forming basic salts. Methods for preparation of the appropriate salts are well-established in the art.

Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like. Representative alkali or alkaline earth metal salts include sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine and the like.

The term "polar surface area" refers to the surface sum over all polar atoms of a molecule or portion of a molecule, including their attached hydrogens. Polar surface area is determined computationally using a program such as CHEMDRAW® Pro, Version 12.0.2.1092 (Cambridgesoft, Cambridge, Mass.).

The term "presenter protein" refers to a protein that binds to a small molecule to form a complex that binds to and modulates the activity of a target protein (e.g., a eukaryotic target protein such as a mammalian target protein or a fungal target protein or a prokaryotic target protein such as a bacterial target protein). In some embodiments, the presenter protein is a relatively abundant protein (e.g., the presenter protein is sufficiently abundant that participation in a tripartite complex does not substantially impact the biological role of the presenter protein in a cell and/or viability or other attributes of the cell). In certain embodiments, the presenter protein is a protein that has chaperone activity within a cell. In some embodiments, the presenter protein is a protein that has multiple natural interaction partners within a cell. In certain embodiments, the presenter protein is one which is known to bind a small molecule to form a binary complex that is known to or suspected of binding to and modulating the biological activity of a target protein.

The term "presenter protein binding moiety" refers to a group of ring atoms and the moieties attached thereto (e.g., atoms within 20 atoms of a ring atom such as, atoms within 15 atoms of a ring atom, atoms within 10 atoms of a ring atom, atoms within 5 atoms of a ring atom) that participate in binding to a presenter protein such that the compound specifically binds to said presenter protein, for example, with a $K_D$ of less than 10 µM (e.g., less than 5 µM, less than 1 µM, less than 500 nM, less than 200 nM, less than 100 nM, less than 75 nM, less than 50 nM, less than 25 nM, less than 10 nM) or inhibits the peptidyl-prolyl isomerase activity of the presenter protein, for example, with an $IC_{50}$ of less than 1 µM (e.g., less than 0.5 µM, less than 0.1 µM, less than 0.05 µM, less than 0.01 µM). It will be understood that the presenter protein binding moiety does not necessarily encompass the entirety of atoms in the compound that interact with the presenter protein. It will also be understood that one or more atoms of the presenter protein binding moiety may be within the target protein interaction moiety (e.g., eukaryotic target protein interacting moiety such as mammalian target protein interacting moiety or fungal target protein interacting moiety or prokaryotic target protein interacting moiety such as a bacterial target protein interacting moiety).

The term "pure" means substantially pure or free of unwanted components (e.g., other compounds and/or other components of a cell lysate), material defilement, admixture or imperfection.

The term "reference" is often used herein to describe a standard or control compound, individual, population, sample, sequence or value against which a compound, individual, population, sample, sequence or value of interest is compared. In some embodiments, a reference compound, individual, population, sample, sequence or value is tested and/or determined substantially simultaneously with the testing or determination of the compound, individual, population, sample, sequence or value of interest. In some embodiments, a reference compound, individual, population, sample, sequence or value is a historical reference, optionally embodied in a tangible medium. Typically, as would be understood by those skilled in the art, a reference compound, individual, population, sample, sequence or value is determined or characterized under conditions comparable to those utilized to determine or characterize the compound, individual, population, sample, sequence or value of interest.

The term "ring atoms" refers to the atoms of a cyclic compound that comprise the innermost portion of the ring. For example, using this method FK506 has 21 ring atoms and rapamycin has 29 ring atoms.

The term "site of a naturally occurring protein-protein interaction" refers to a location on the surface of the structure of a protein that includes atoms which participate in binding between the protein and another protein in the proteins natural environment.

The term "small molecule" means a low molecular weight organic and/or inorganic compound. In general, a "small molecule" is a molecule that is less than about 5 kilodaltons (kD) in size. In some embodiments, a small molecule is less than about 4 kD, 3 kD, about 2 kD, or about 1 kD. In some embodiments, the small molecule is less than about 800 daltons (D), about 600 D, about 500 D, about 400 D, about 300 D, about 200 D, or about 100 D. In some embodiments, a small molecule is less than about 2000 g/mol, less than about 1500 g/mol, less than about 1000 g/mol, less than about 800 g/mol, or less than about 500 g/mol. In some embodiments, a small molecule is not a polymer. In some embodiments, a small molecule does not include a polymeric moiety. In some embodiments, a small molecule is not a protein or polypeptide (e.g., is not an oligopeptide or peptide). In some embodiments, a small molecule is not a polynucleotide (e.g., is not an oligonucleotide). In some embodiments, a small molecule is not a polysaccharide. In some embodiments, a small molecule does not comprise a polysaccharide (e.g., is not a glycoprotein, proteoglycan, glycolipid, etc.). In some embodiments, a small molecule is not a lipid. In some embodiments, a small molecule is a modulating compound. In some embodiments, a small molecule is biologically active. In some embodiments, a small molecule is detectable (e.g., comprises at least one detectable moiety). In some embodiments, a small molecule is a therapeutic.

Those of ordinary skill in the art, reading the present disclosure, will appreciate that certain small molecule compounds described herein may be provided and/or utilized in any of a variety of forms such as, for example, salt forms, protected forms, pro-drug forms, ester forms, isomeric forms (e.g., optical and/or structural isomers), isotopic forms, etc. In some embodiments, reference to a particular compound may relate to a specific form of that compound. In some embodiments, reference to a particular compound may relate to that compound in any form. In some embodiments, where a compound is one that exists or is found in nature, that compound may be provided and/or utilized in accordance in the present invention in a form different from that in which it exists or is found in nature. Those of ordinary skill in the art will appreciate that a compound preparation including a different level, amount, or ratio of one or more individual forms than a reference preparation or source (e.g., a natural source) of the compound may be considered to be a different form of the compound as described herein. Thus, in some embodiments, for example, a preparation of a single stereoisomer of a compound may be considered to be a different form of the compound than a racemic mixture of the compound; a particular salt of a compound may be considered to be a different form from another salt form of the compound; a preparation containing one conformational isomer ((Z) or (E)) of a double bond may be considered to be a different form from one containing the other conformational isomer ((E) or (Z)) of the double bond; a preparation in which one or more atoms is a different isotope than is present in a reference preparation may be considered to be a different form; etc.

As used herein, the terms "specific binding" or "specific for" or "specific to" refer to an interaction between a binding agent and a target entity. As will be understood by those of ordinary skill, an interaction is considered to be "specific" if it is favored in the presence of alternative interactions, for example, binding with a $K_D$ of less than 10 µM (e.g., less than 5 µM, less than 1 µM, less than 500 nM, less than 200 nM, less than 100 nM, less than 75 nM, less than 50 nM, less than 25 nM, less than 10 nM). In many embodiments, specific interaction is dependent upon the presence of a particular structural feature of the target entity (e.g., an epitope, a cleft, a binding site). It is to be understood that specificity need not be absolute. In some embodiments, specificity may be evaluated relative to that of the binding agent for one or more other potential target entities (e.g., competitors). In some embodiments, specificity is evaluated relative to that of a reference specific binding agent. In some embodiments specificity is evaluated relative to that of a reference non-specific binding agent.

The term "specific" when used with reference to a compound having an activity, is understood by those skilled in the art to mean that the compound discriminates between potential target entities or states. For example, in some embodiments, a compound is said to bind "specifically" to its target if it binds preferentially with that target in the presence of one or more competing alternative targets. In many embodiments, specific interaction is dependent upon the presence of a particular structural feature of the target entity (e.g., an epitope, a cleft, a binding site). It is to be understood that specificity need not be absolute. In some embodiments, specificity may be evaluated relative to that of the binding agent for one or more other potential target entities (e.g., competitors). In some embodiments, specificity is evaluated relative to that of a reference specific binding agent. In some embodiments specificity is evaluated relative to that of a reference non-specific binding agent. In some embodiments, the agent or entity does not detectably bind to the competing alternative target under conditions of binding to its target entity. In some embodiments, binding agent binds with higher on-rate, lower off-rate, increased affinity, decreased dissociation, and/or increased stability to its target entity as compared with the competing alternative target(s).

The term "structural organization" refers to the average three dimensional configuration of the atoms and bonds of molecule. By "substantially unchanged structural organization" is meant that the root mean squared deviation (RMSD) of two aligned structures is less than 1. The RMSD can be calculated, e.g., by using the align command in PyMOL version 1.7rc1 (Schrödinger LLC). Alternatively, RMSD can be calculated using the ExecutiveRMS parameter from the algorithm LigAlign (J. Mol. Graphics and Modelling 2010, 29, 93-101).

The term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

The term "does not substantially bind" to a particular protein as used herein can be exhibited, for example, by a molecule or portion of a molecule having a $K_D$ for the target of $10^{-4}$ M or greater, alternatively $10^{-5}$ M or greater, alternatively $10^{-6}$ M or greater, alternatively $10^{-7}$ M or greater, alternatively $10^{-8}$ M or greater, alternatively $10^{-9}$ M or greater, alternatively $10^{-10}$ M or greater, alternatively $10^{-11}$ M or greater, alternatively $10^{-12}$ M or greater, or a $K_D$ in the range of $10^{-4}$ M to $10^{-12}$ M or $10^{-6}$ M to $10^{-10}$ M or $10^{-7}$ M to $10^{-9}$ M.

The term "substantial structural similarity" refers to presence of shared structural features such as presence and/or identity of particular amino acids at particular positions (see definitions of "shared sequence homology" and "shared sequence identity"). In some embodiments the term "substantial structural similarity" refers to presence and/or identity of structural elements (for example: loops, sheets, helices, H-bond donors, H-bond acceptors, glycosylation patterns, salt bridges, and disulfide bonds). In some embodiments, the term "substantial structural similarity" refers to three dimensional arrangement and/or orientation of atoms or moieties relative to one another (for example: distance and/or angles between or among them between an agent of interest and a reference agent).

The term "target protein" refers to a protein that is not mTOR or calcineurin that binds with a small molecule/presenter protein/compound complex as described herein, but that does not substantially bind with either the small molecule or the presenter protein alone. In some embodiments, the small molecule/presenter protein/compound complex does not substantially bind to mTOR or calcineurin. In some embodiments, the target protein participates in a biological pathway associated with a disease, disorder or condition. In some embodiments, a target protein is a naturally-occurring protein; in some such embodiments, a target protein is naturally found in certain mammalian cells (e.g., a mammalian target protein), fungal cells (e.g., a fungal target protein), bacterial cells (e.g., a bacterial target protein) or plant cells (e.g., a plant target protein). In some embodiments, a target protein is characterized by natural interaction with one or more natural presenter protein/natural small molecule complexes. In some embodiments, a target protein is characterized by natural interactions with a plurality of different natural presenter protein/natural small molecule complexes; in some such embodiments some or all of the complexes utilize the same presenter protein (and different small molecules). In some embodiments, a target protein does not substantially bind to a complex of cyclosporin, rapamycin, or FK506 and a presenter protein (e.g., FKBP). Target proteins can be naturally occurring, e.g., wild type. Alternatively, the target protein can vary from the wild type protein but still retain biological function, e.g., as an allelic variant, a splice mutant or a biologically active fragment. Exemplary mammalian target proteins are GTPases, GTPase activating protein, Guanine nucleotide-exchange factor, heat shock proteins, ion channels, coiled-coil proteins, kinases, phosphatases, ubiquitin ligases, transcription factors, chromatin modifier/remodelers, proteins with classical protein-protein interaction domains and motifs, or any other proteins that participate in a biological pathway associated with a disease, disorder or condition.

The term "target protein interacting moiety" refers to a group of ring atoms and the moieties attached thereto (e.g., atoms within 20 atoms of a ring atom such as, atoms within 15 atoms of a ring atom, atoms within 10 atoms of a ring atom, atoms within 5 atoms of a ring atom) that participate in binding to a target protein (e.g., a eukaryotic target protein such as a mammalian target protein or a fungal target protein or a prokaryotic target protein such as a bacterial target protein) when the compound is in a complex with a presenter protein. It will be understood that the target protein interacting moiety does not necessarily encompass the entirety of atoms in the compound that interact with the target protein. It will also be understood that one or more atoms of the presenter protein binding moiety may also be present in the target protein interacting moiety.

A "therapeutic regimen" refers to a dosing regimen whose administration across a relevant population is correlated with a desired or beneficial therapeutic outcome.

The term "therapeutically effective amount" means an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. It is specifically understood that particular subjects may, in fact, be "refractory" to a "therapeutically effective amount." To give but one example, a refractory subject may have a low bioavailability such that clinical efficacy is not obtainable. In some embodiments, reference to a therapeutically effective amount may be a reference to an amount as measured in one or more specific tissues (e.g., a tissue affected by the disease, disorder or condition) or fluids (e.g., blood, saliva, serum, sweart, tears, urine, etc). Those of ordinary skill in the art will appreciate that, in some embodiments, a therapeutically effective amount may be formulated and/or administered in a single dose. In some embodiments, a therapeutically effective amount may be formulated and/or administered in a plurality of doses, for example, as part of a dosing regimen.

The term "traditional binding pocket" refers to cavities or pockets on a protein structure with physiochemical and/or geometric properties comparable to proteins whose activity has been modulated by one or more small molecules. In some embodiments, a traditional binding pocket is a well-defined pocket with a volume greater than 1000 $A^3$. Those of ordinary skill in the art are familiar with the concept of a traditional binding pocket and, moreover are aware of its relationship to "druggability". In certain embodiments, a protein is considered to not have a traditional binding pocket if it is undruggable, as defined herein.

The term "treatment" (also "treat" or "treating"), in its broadest sense, refers to any administration of a substance (e.g., provided compositions) that partially or completely alleviates, ameliorates, relives, inhibits, delays onset of, reduces severity of, and/or reduces incidence of one or more symptoms, features, and/or causes of a particular disease, disorder, and/or condition. In some embodiments, such treatment may be administered to a subject who does not exhibit signs of the relevant disease, disorder and/or condition and/or of a subject who exhibits only early signs of the disease, disorder, and/or condition. Alternatively or additionally, in some embodiments, treatment may be administered to a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

The term "undruggable target" refers to proteins that are not members of a protein family which is known to be targeted by drugs and/or does not possess a binding site that is suitable for high-affinity binding to a small molecule. Methods for determining whether a target protein is undruggable are known in the art. For example, whether a target protein is undruggable may be determined using an structure-based algorithm, such as those used by the program DOGSITESCORER® (Universitat Hamburg, Hamburg, Germany) that assesses druggability based on parameters computed for binding pockets on a protein including volume, surface area, lipophilic surface area, depth, and/or hydrophobic ratio.

As used herein, the term "van der Waals interaction" refers to the attractive or repulsive forces between atoms that are not due to covalent bonds, electrostatic interactions, or hydrogen bonding.

The term "variant" refers to an entity that shows significant structural identity with a reference entity but differs structurally from the reference entity in the presence or level of one or more chemical moieties as compared with the reference entity. In many embodiments, a variant also differs functionally from its reference entity. In general, whether a particular entity is properly considered to be a "variant" of a reference entity is based on its degree of structural identity with the reference entity. As will be appreciated by those skilled in the art, any biological or chemical reference entity has certain characteristic structural elements. A variant, by definition, is a distinct chemical entity that shares one or more such characteristic structural elements. To give but a few examples, a small molecule may have a characteristic core structural element (e.g., a macrocycle core) and/or one or more characteristic pendent moieties so that a variant of the small molecule is one that shares the core structural element and the characteristic pendent moieties but differs in other pendent moieties and/or in types of bonds present (single vs double, E vs Z, etc) within the core, a polypeptide may have a characteristic sequence element comprised of a plurality of amino acids having designated positions relative to one another in linear or three-dimensional space and/or contributing to a particular biological function, a nucleic acid may have a characteristic sequence element comprised of a plurality of nucleotide residues having designated positions relative to on another in linear or three-dimensional space. For example, a variant polypeptide may differ from a reference polypeptide as a result of one or more differences in amino acid sequence and/or one or more differences in chemical moieties (e.g., carbohydrates, lipids, etc) covalently attached to the polypeptide backbone. In some embodiments, a variant polypeptide shows an overall sequence identity with a reference polypeptide that is at least 85%, 86%, 87%, 88%, 89%, 90%, 91%, 92%, 93%, 94%, 95%, 96%, 97%, or 99%. Alternatively or additionally, in some embodiments, a variant polypeptide does not share at least one characteristic sequence element with a reference polypeptide. In some embodiments, the reference polypeptide has one or more biological activities. In some embodiments, a variant polypeptide shares one or more of the biological activities of the reference polypeptide. In some embodiments, a variant polypeptide lacks one or more of the biological activities of the reference polypeptide. In some embodiments, a variant polypeptide shows a reduced level of one or more biological activities as compared with the reference polypeptide. In many embodiments, a polypeptide of interest is considered to be a "variant" of a parent or reference polypeptide if the polypeptide of interest has an amino acid sequence that is identical to that of the parent but for a small number of sequence alterations at particular positions. Typically, fewer than 20%, 15%, 10%, 9%, 8%, 7%, 6%, 5%, 4%, 3%, 2% of the residues in the variant are substituted as compared with the parent. In some embodiments, a variant has 10, 9, 8, 7, 6, 5, 4, 3, 2, or 1 substituted residue as compared with a parent. Often, a variant has a very small number (e.g., fewer than 5, 4, 3, 2, or 1) number of substituted functional residues (i.e., residues that participate in a particular biological activity). Furthermore, a variant typically has not more than 5, 4, 3, 2, or 1 additions or deletions, and often has no additions or deletions, as compared with the parent. Moreover, any additions or deletions are typically fewer than about 25, about 20, about 19, about 18, about 17, about 16, about 15, about 14, about 13, about 10, about 9, about 8, about 7, about 6, and commonly are fewer than about 5, about 4, about 3, or about 2 residues. In some embodiments, the parent or reference polypeptide is one found in nature. As will be understood by those of ordinary skill in the art, a plurality of variants of a particular polypeptide of interest may commonly be found in nature.

The term "wild-type" refers to an entity having a structure and/or activity as found in nature in a "normal" (as contrasted with mutant, diseased, altered, etc) state or context.

Those of ordinary skill in the art will appreciate that wild-type genes and polypeptides often exist in multiple different forms (e.g., alleles).

DETAILED DESCRIPTION OF CERTAIN EMBODIMENTS

Figure 1:
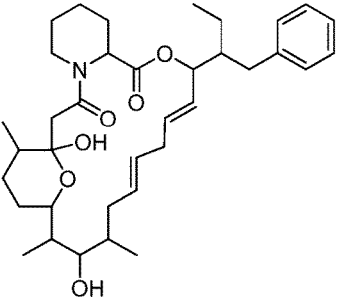
FIG. 1 is a table of exemplary compounds of the invention.
Figure 1:
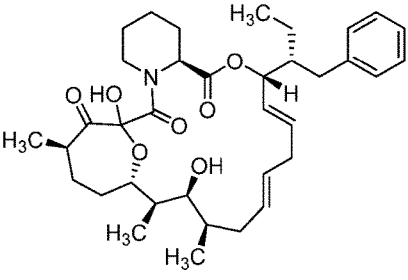
Figure 1:
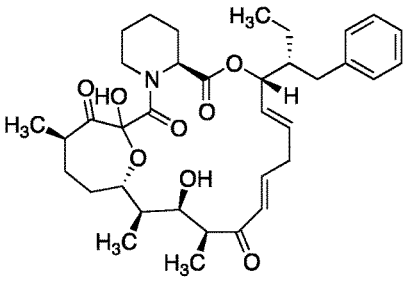
Figure 1:
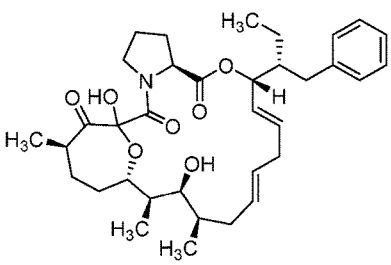
Figure 1:
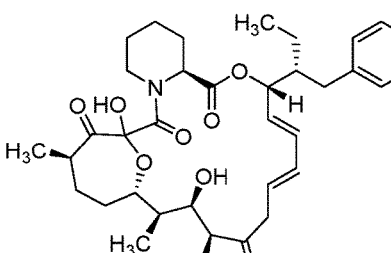
Figure 1:
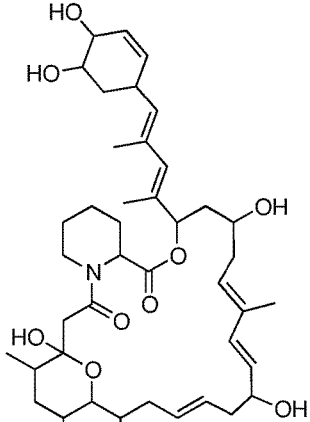
Figure 1:
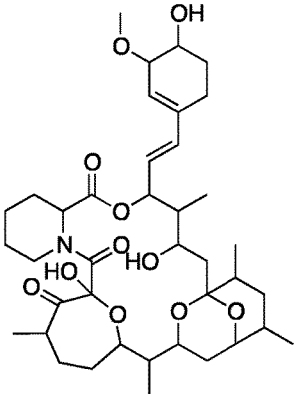
Figure 1:
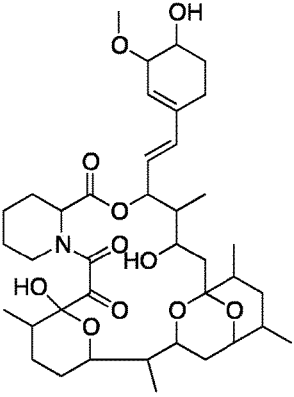
Figure 1:
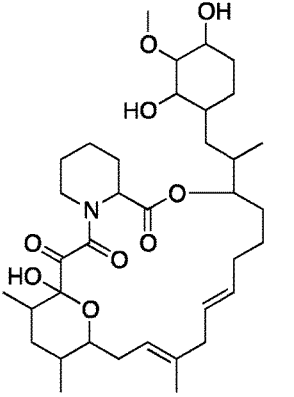
Figure 1:
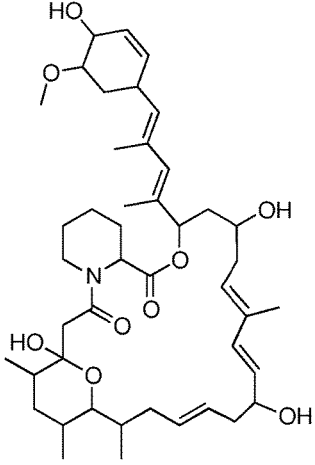
Figure 1:
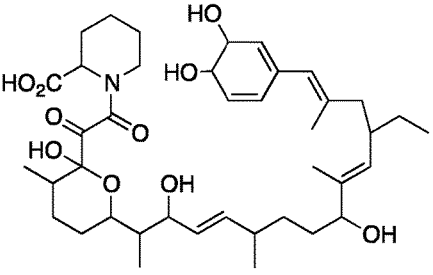
Figure 1:
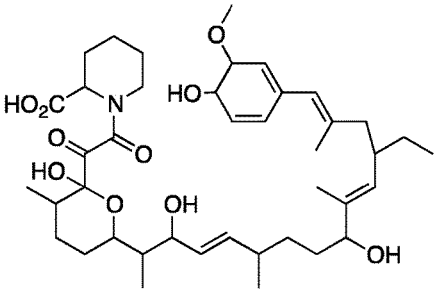
Figure 1:
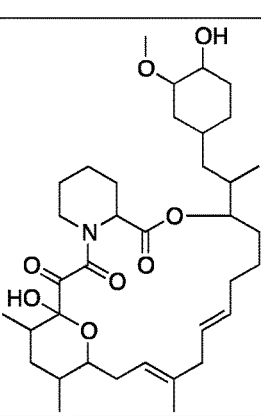
Figure 1:
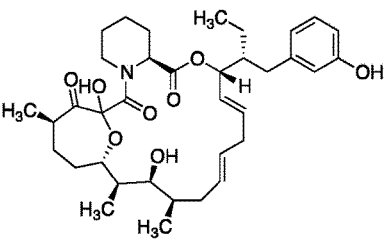
Figure 1:
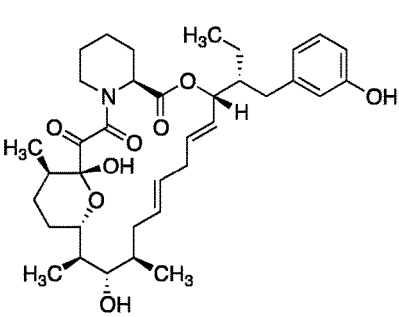

Small molecules are limited in their targeting ability because their interactions with the target are driven by adhesive forces, the strength of which is roughly proportional to contact surface area. Because of their small size, the only way for a small molecule to build up enough intermolecular contact surface area to effectively interact with a target protein is to be literally engulfed by that protein. Indeed, a large body of both experimental and computational data supports the view that only those proteins having a hydrophobic "pocket" on their surface are capable of binding small molecules. In those cases, binding is enabled by engulfment.

Nature has evolved a strategy that allows a small molecule to interact with target proteins at sites other than hydrophobic pockets. This strategy is exemplified by naturally occurring immunosuppressive drugs cyclosporine A, rapamycin, and FK506. The biological activity of these drugs involves the formation of a high-affinity complex of the small molecule with a small presenting protein. The composite surface of the small molecule and the presenting protein engages the target. Thus, for example, the binary complex formed between cyclosporin A and cyclophilin A targets calcineurin with high affinity and specificity, but neither cyclosporin A or cyclophilin A alone binds calcineurin with measurable affinity.

Many important therapeutic targets exert their function by complexation with other proteins. The protein/protein interaction surfaces in many of these systems contain an inner core of hydrophobic side chains surrounded by a wide ring of polar residues. The hydrophobic residues contribute nearly all of the energetically favorable contacts, and hence this cluster has been designated as a "hotspot" for engagement in protein-protein interactions. Importantly, in the aforementioned complexes of naturally occurring small molecules with small presenting proteins, the small molecule provides a cluster of hydrophobic functionality akin to a hotspot, and the protein provides the ring of mostly polar residues. In other words, presented small molecule systems mimic the surface architecture employed widely in natural protein/protein interaction systems.

Nature has demonstrated the ability to reprogram the target specificity of presented small molecules—portable hotspots—through evolutionary diversification. In the best characterized example, the complex formed between FK506 binding protein (FKBP) and FK506 targets calcineurin. However, FKBP can also form a complex with the related molecule rapamycin, and that complex interacts with a completely different target, TorC1. To date, no methodology has been developed to reprogram the binding and modulating ability of presenter protein/ligand interfaces so that they can interact with and modulate other target proteins that have previously been considered undruggable.

In addition, it is well established that some drug candidates fail because they modulate the activity of both the intended target and other non-intended proteins as well. The problem is particularly daunting when the drug binding site of the target protein is similar to binding sites in non-target proteins. The insulin like growth factor receptor (IGF-1R), whose ATP binding pocket is structurally similar to the binding pocket of the non-target insulin receptor (IR), is one such example. Small molecule development candidates that were designed to target IGF-1R typically have the unacceptable side effect of also modulating the insulin receptor. However, structural dissimilarities do exist between these two proteins in the regions surrounding the ATP binding pocket. Despite such knowledge, no methodology exists to date to take advantage of those differences and develop drugs that are specific to IGF-1R over IR.

The present invention features compounds (e.g., macrocyclic compounds) capable of modulating biological processes, for example through binding to a presenter protein (e.g., a member of the FKBP family, a member of the cyclophilin family, or PIN1) and a target protein. In some embodiments, the target and/or presenter proteins are intracellular proteins. In some embodiments, the target and/or presenter proteins are mammalian proteins. In some embodiments, provided compounds participate in tripartite presenter protein/compound/target protein complexes inside cells, e.g., mammalian cells. In some embodiments, provided compounds may be useful in the treatment of diseases and disorders such as cancer, inflammation, or infections.

Compounds

The invention features compounds (e.g., macrocyclic compounds) capable of modulating biological processes, for example through binding to a presenter protein (e.g., a member of the FKBP family, a member of the cyclophilin family, or PIN1) and a target protein (e.g., a eukaryotic target protein such as a mammalian target protein or a fungal target protein or a prokaryotic target protein such as a bacterial target protein). In brief, these compounds bind endogenous intracellular presenter proteins, such as the FKBPs and the resulting binary complexes selectively bind and modulate the activity of intracellular target proteins. Without wishing to be bound by any particular theory, we proposed that formation of a tripartite complex among the presenter protein, the compound, and the target protein is driven by both protein-compound and protein-protein interactions, and both are required for modulation (e.g., positive or negative modulation) of the targeted protein's activity. In some embodiments, the compounds of the invention "re-program" the binding of the presenter proteins to protein targets that either do not normally bind to the presenter protein or have binding that is greatly enhanced in the presence of the compound thereby resulting in the ability to modulate (e.g., positively or negatively modulate) the activity of these new targets.

As described herein, compounds of the invention include a presenter protein binding moiety and a target protein interacting moiety. In some embodiments, the presenter protein binding moiety and target protein interacting moiety are separate portions of the ring structure, e.g., they do not overlap. In some embodiments, the presenter protein binding moiety and target protein interacting moiety are connected to one another by linkers on one or both sides.

In some embodiments, compounds of the invention do not substantially bind to the target protein in the absence of forming a complex, as described herein. In some embodiments, a complex of a compound of the invention and a presenter protein binds to the target protein with at least 5-fold (at least 10-fold, at least 20-fold, at least 30-fold, at least 40-fold, at least 50-fold, at least 100-fold) greater affinity than the affinity of the compound to the target protein in the absence of forming a complex, as described herein. In certain embodiments, compounds of the invention do not substantially modulate the activity of the target protein in the absence forming a complex with a presenter protein. For example, in some embodiments, the compounds of the invention inhibit the activity of the target protein with an $IC_{50}$ of greater than 10 µM (e.g., greater than 20 µM, greater than 50 µM, greater than 100 µM, greater than 500 µM). Alternatively, compounds of the invention enhance the activity of the target protein with an $AC_{50}$ of greater than 10 µM (e.g., greater than 20 µM, greater than 50 µM, greater than 100 µM, greater than 500 µM). In certain embodiments, a complex of the compound and a presenter protein is at least 5-fold active (i.e., has a 5-fold lower $IC_{50}$ or $AC_{50}$) than the compound alone.

Compounds (e.g., macrocyclic compounds) of the invention generally bind strongly to the presenter protein. For example, in some embodiments, the compounds (e.g., macrocyclic compounds) of the invention bind to the presenter protein with a $K_D$ of less than 10 µM (e.g., less than 5 µM, less than 1 µM, less than 500 nM, less than 200 nM, less than 100 nM, less than 75 nM, less than 50 nM, less than 25 nM, less than 10 nM) or inhibit the peptidyl-prolyl isomerase activity of the presenter protein, for example, with an $IC_{50}$ of less than 1 µM (e.g., less than 0.5 µM, less than 0.1 µM, less than 0.05 µM, less than 0.01 µM).

In some embodiments, the invention includes compounds having a structure according to formulae XIV to XVIII as described herein:

Formula XIV
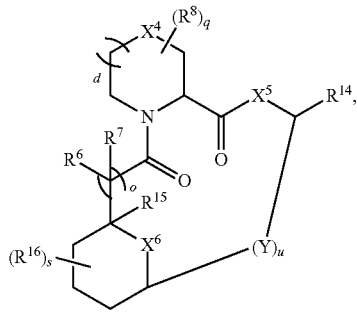

Formula XV
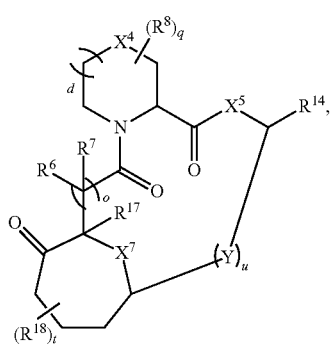

Formula XVI
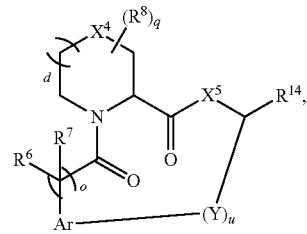

Formula XVII
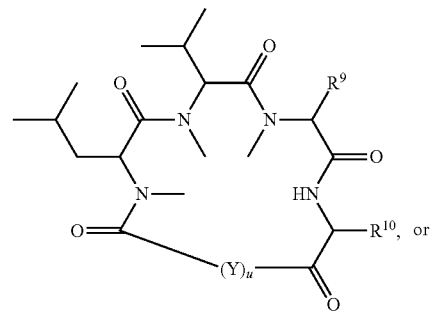

Formula XVIII
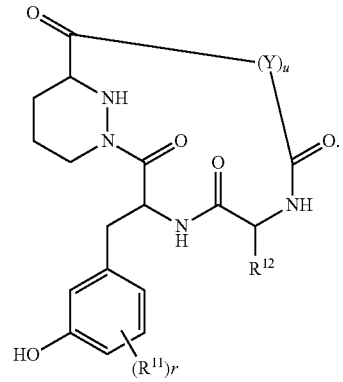

Figure 2:
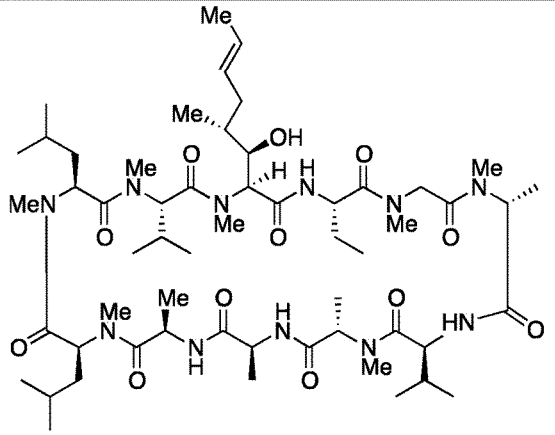
FIG. 2 is a table of exemplary compounds of the invention.
Figure 2:
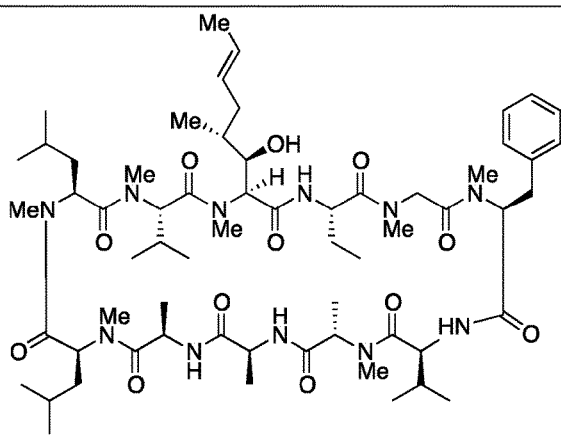
Figure 2:
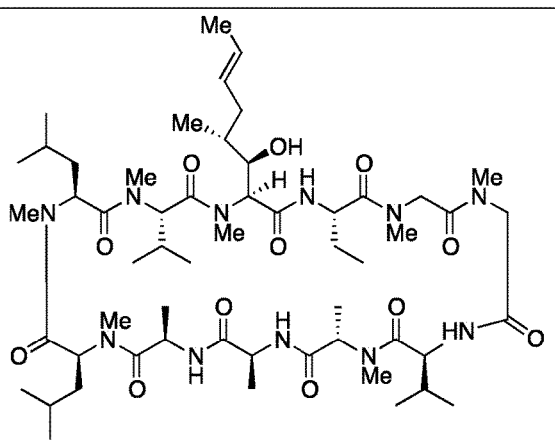
Figure 2:
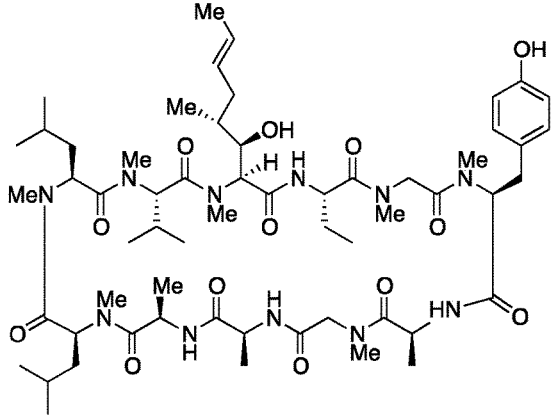
Figure 2:
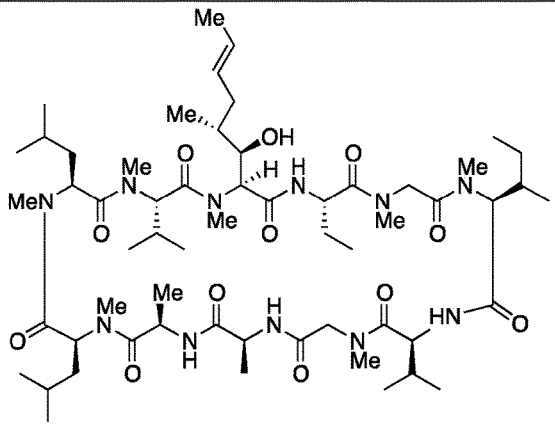
Figure 2:
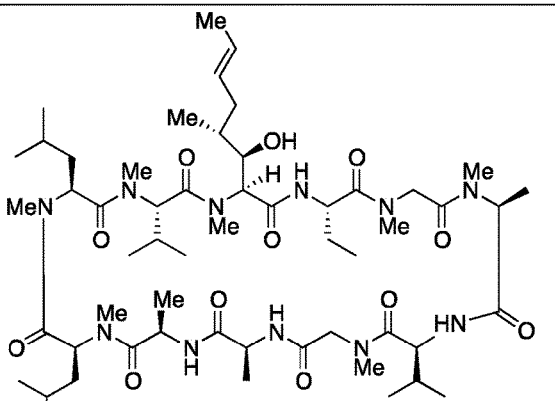
Figure 2:
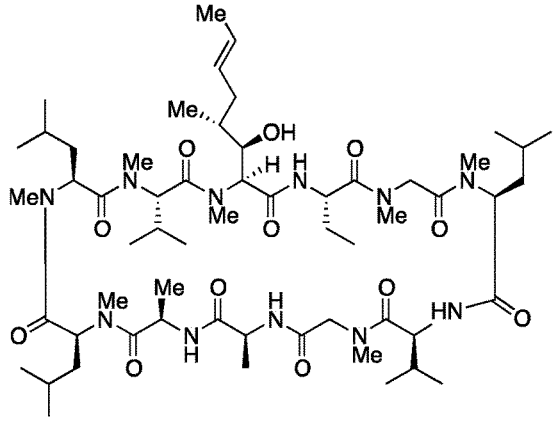
Figure 2:
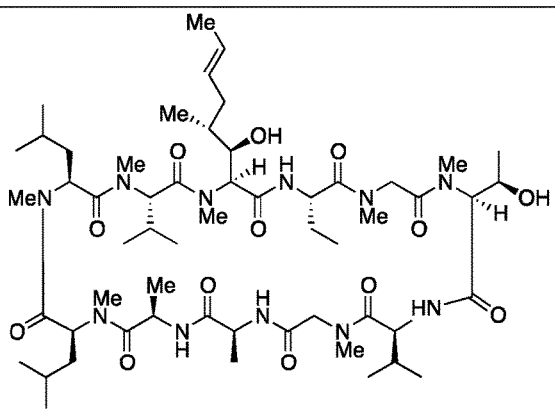
Figure 2:
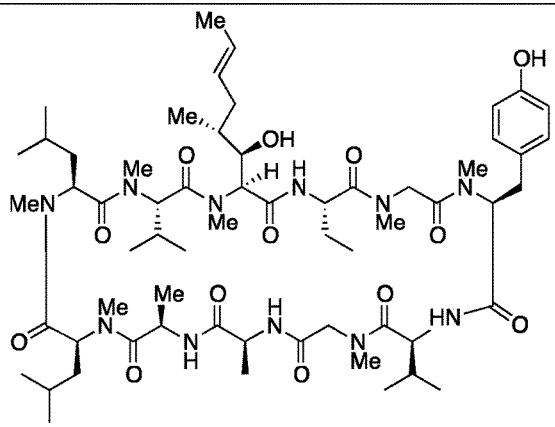
Figure 2:
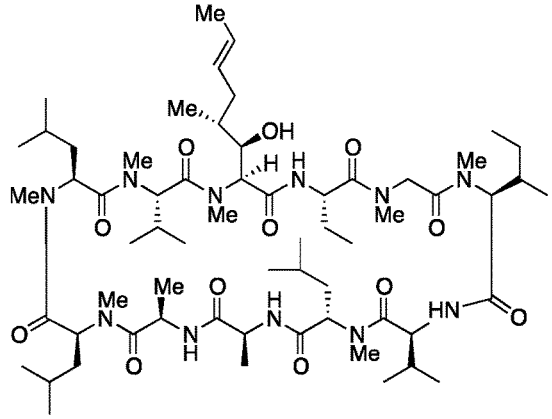
Figure 2:
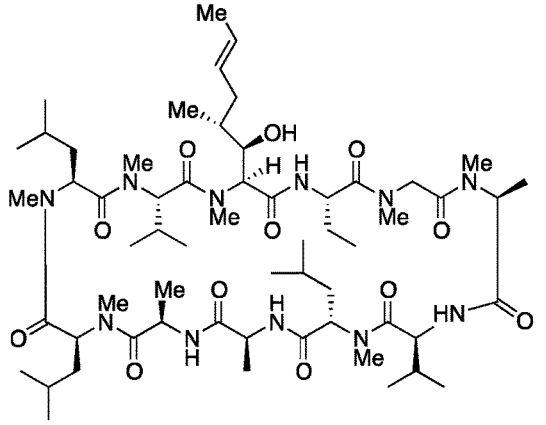
Figure 2:
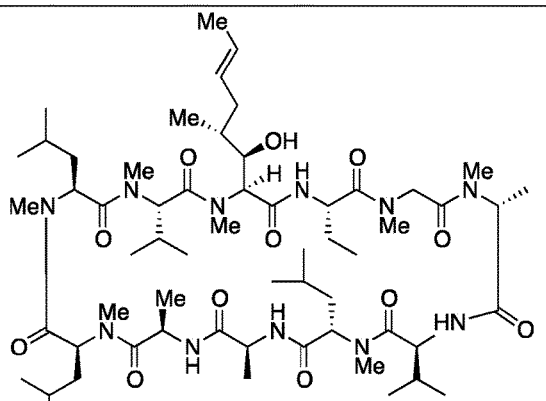
Figure 2:
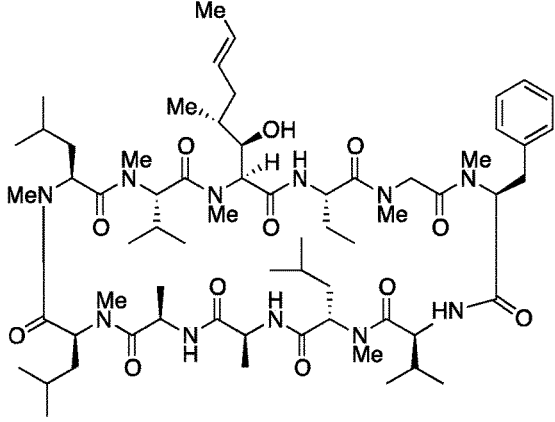
Figure 2:
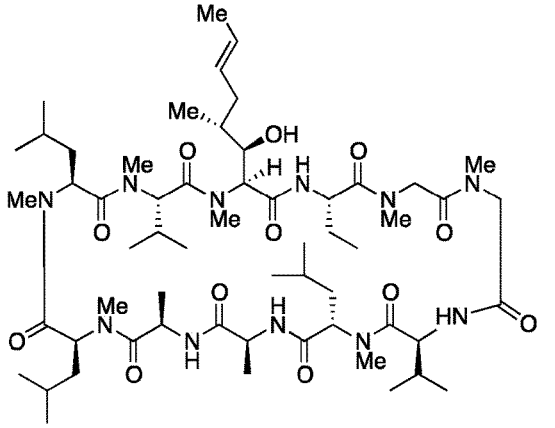
Figure 2:
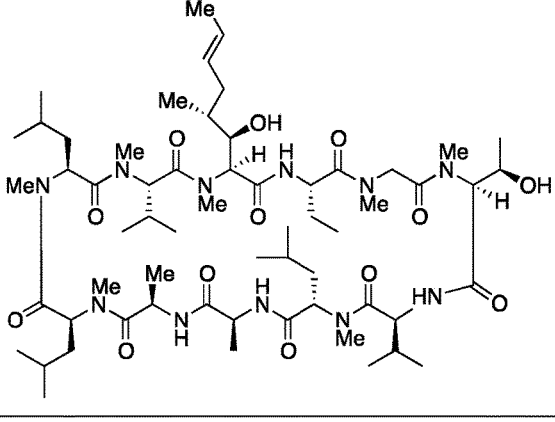
Figure 2:
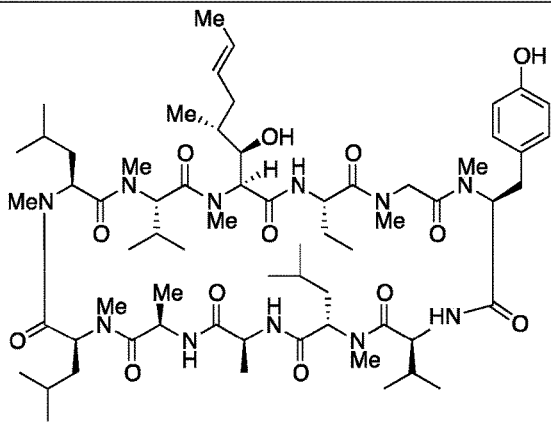
Figure 2:
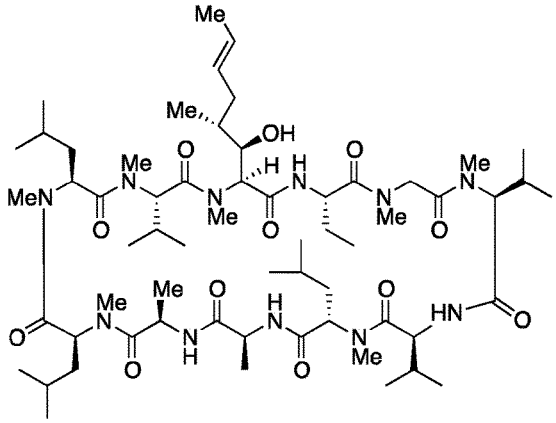
Figure 2:
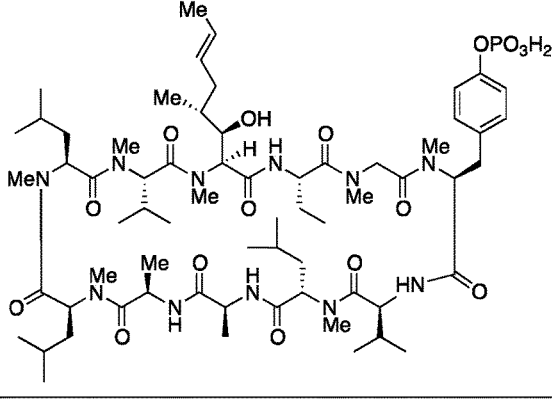
Figure 2:
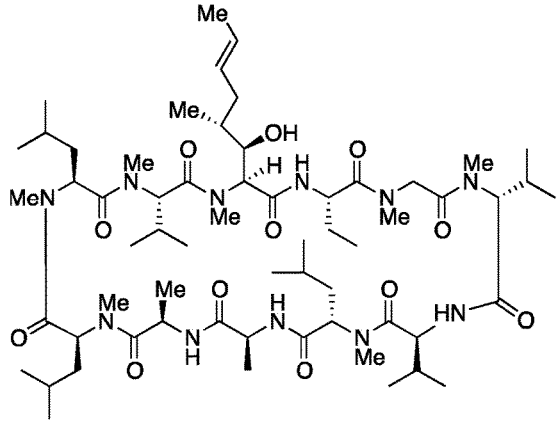
Figure 2:
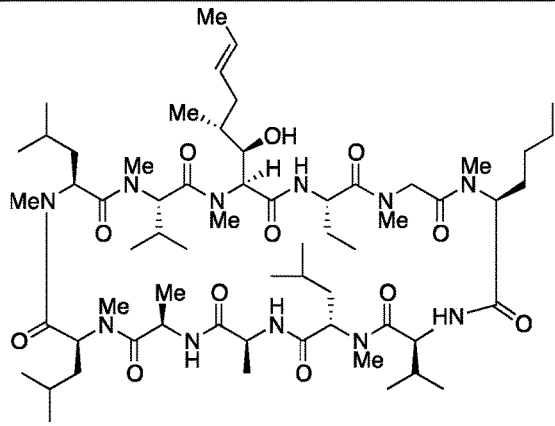
Figure 2:
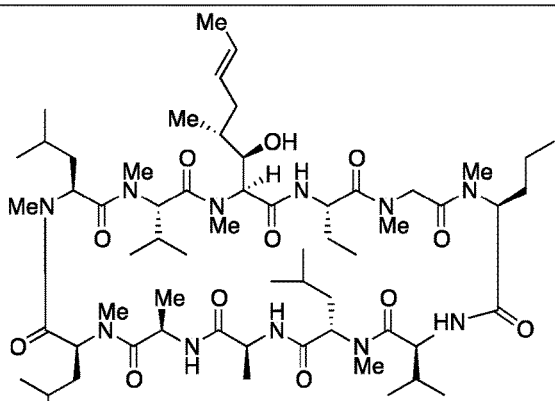
Figure 2:
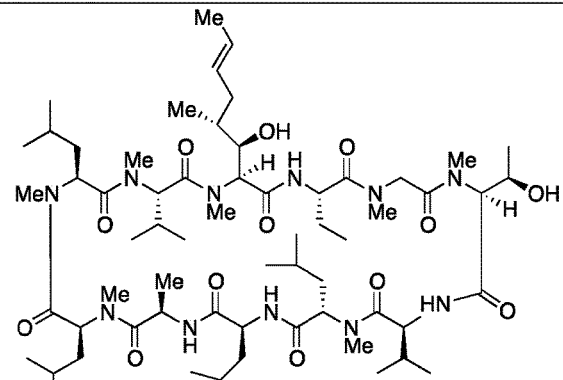
Figure 2:
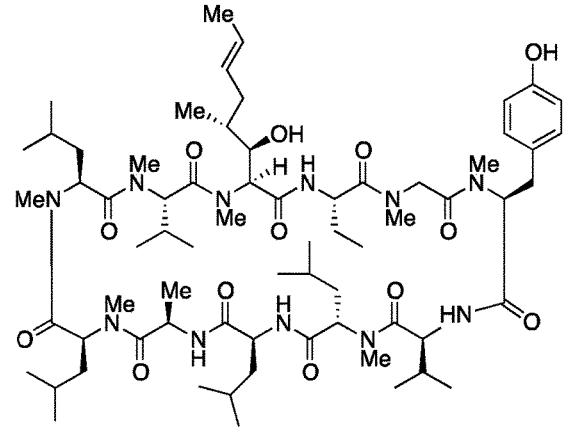
Figure 2:
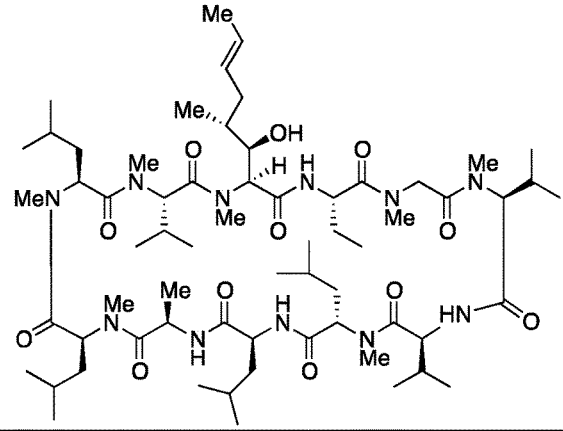
Figure 2:
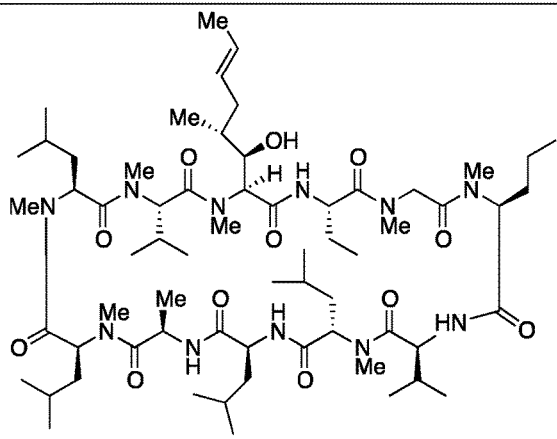
Figure 2:
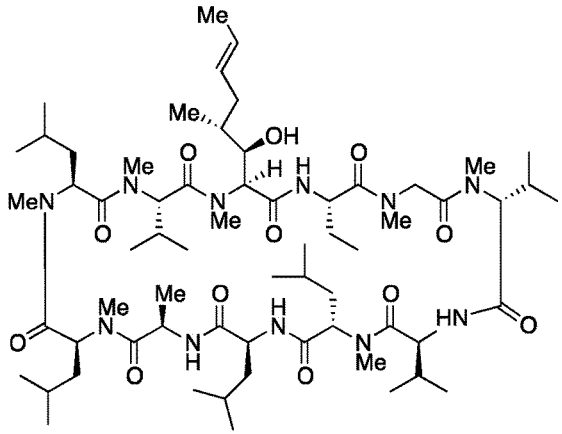
Figure 2:
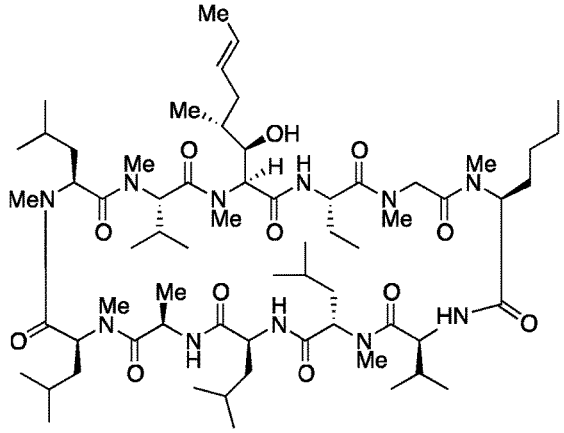
Figure 2:
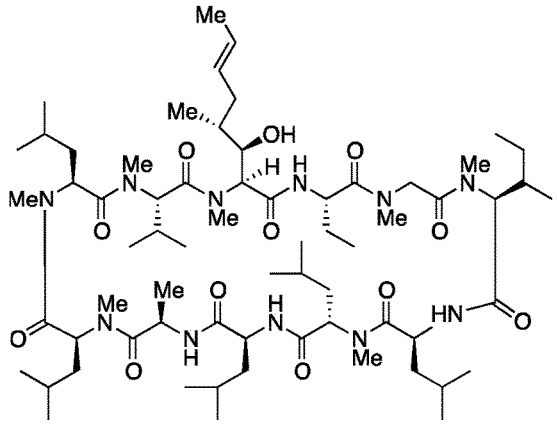
Figure 2:
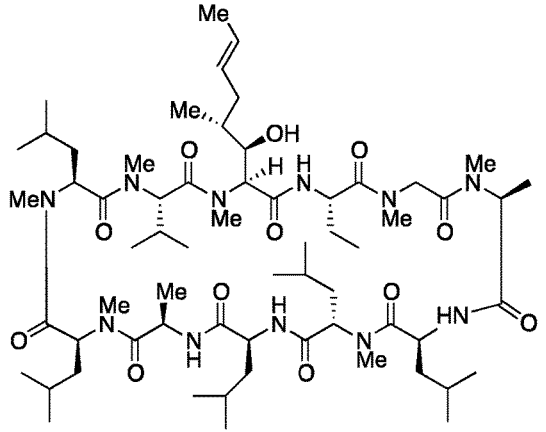
Figure 2:
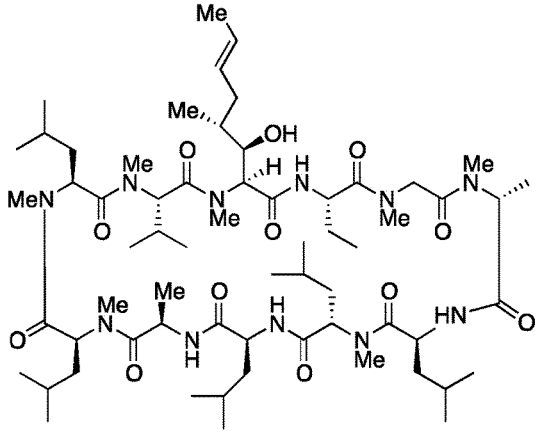
Figure 2:
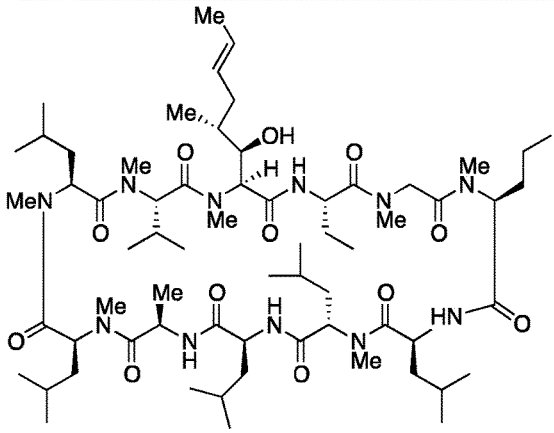
Figure 2:
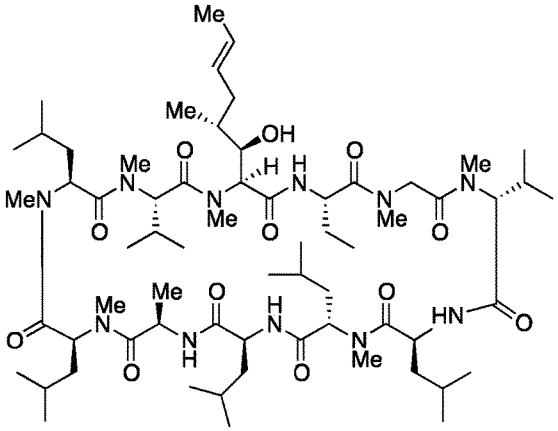
Figure 2:
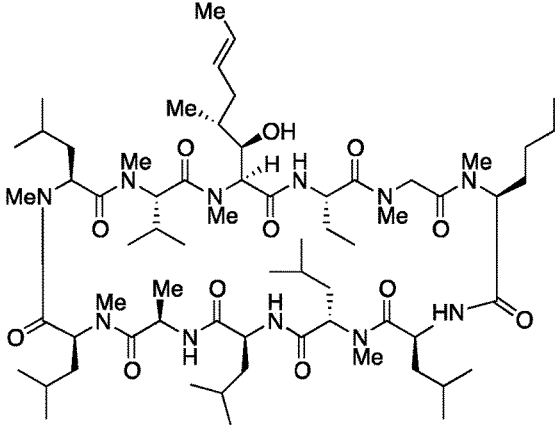
Figure 2:
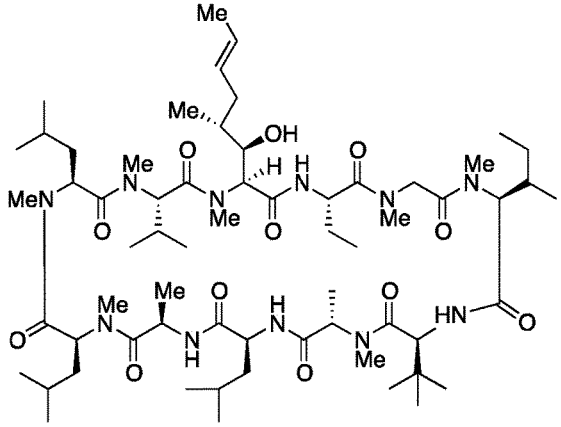
Figure 2:
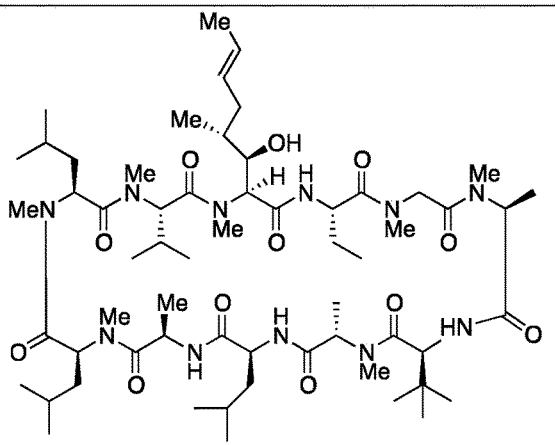
Figure 2:
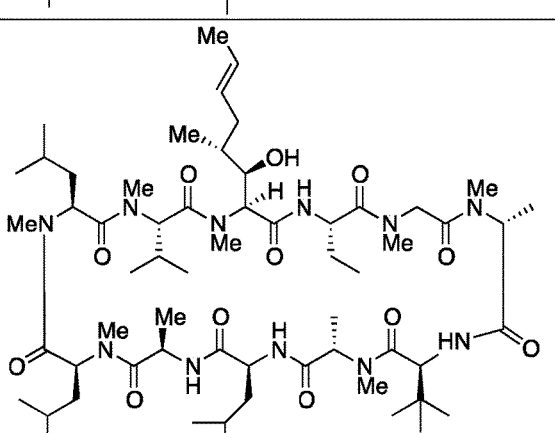
Figure 2:
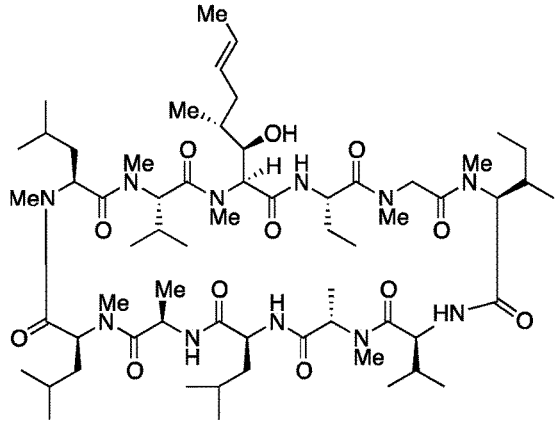
Figure 2:
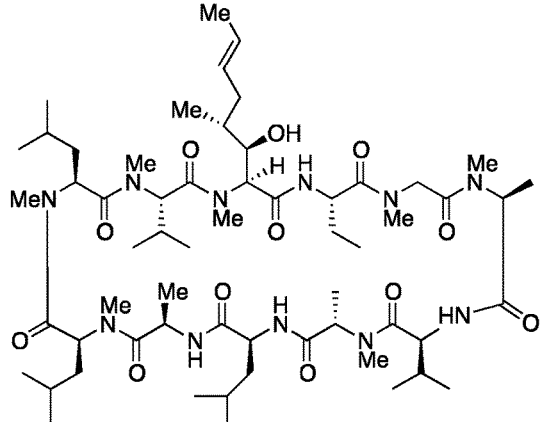
Figure 2:
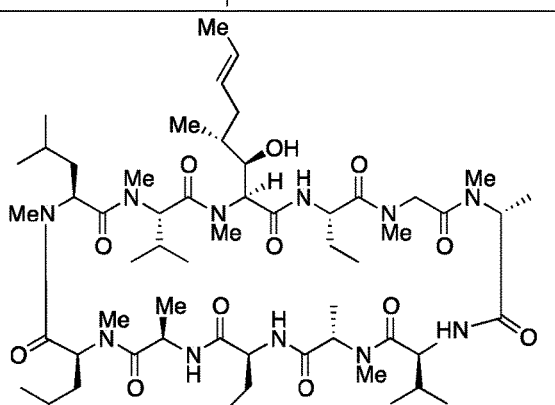
Figure 2:
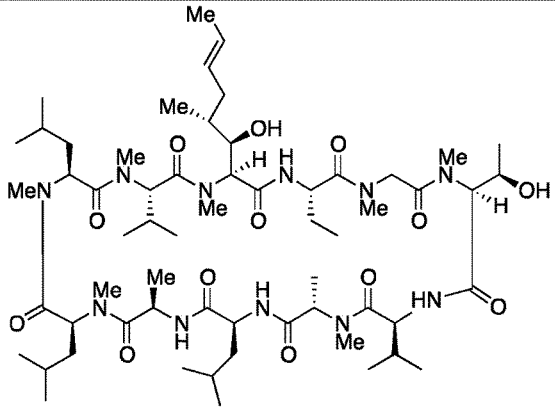
Figure 2:
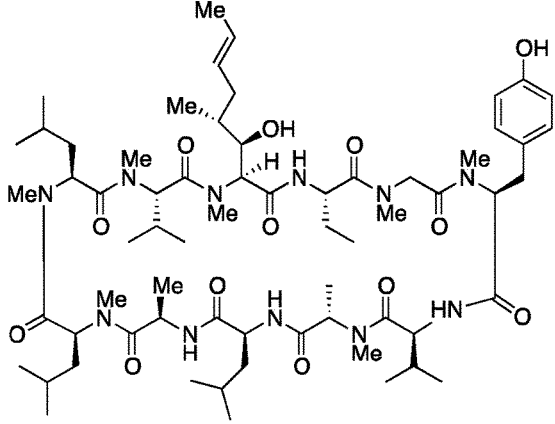
Figure 2:
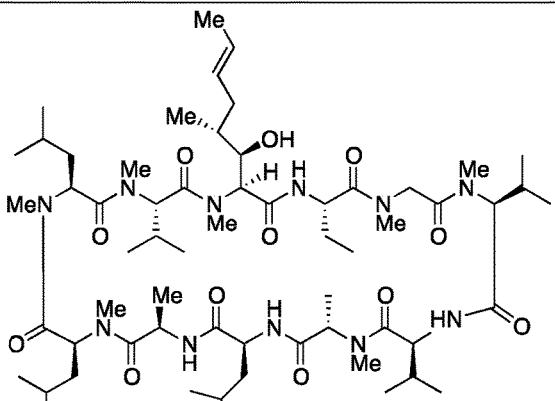
Figure 2:
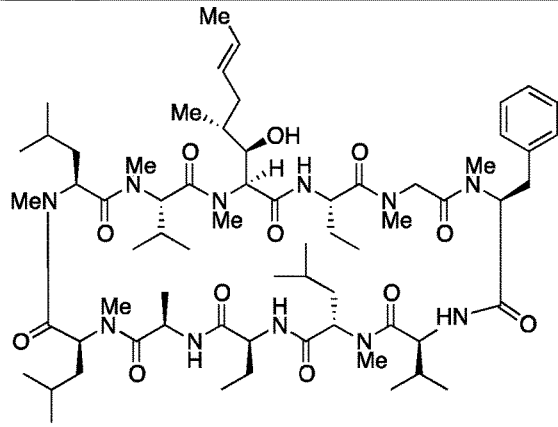
Figure 2:
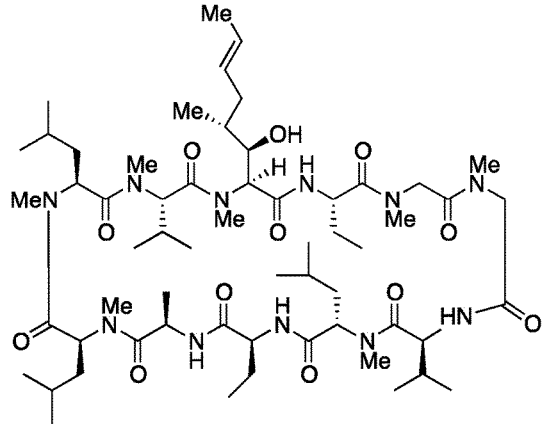
Figure 2:
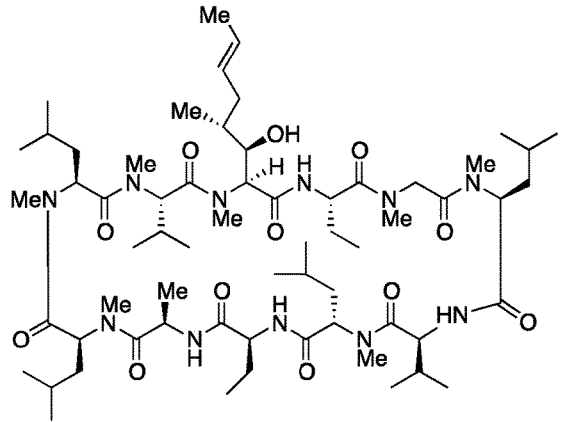

In certain embodiments, a compound has the structure of any of the compounds in FIG. 1 or FIG. 2.

In some embodiments, a compound is a natural compound (e.g., synthesized by an genetically unmodified bacterial strain). In some embodiments, a compound is a variant of a natural compound (e.g., a semi-synthetic compound). In some embodiments, a variant shares ring size with the reference natural compound. In some embodiments, a variant differs from the reference natural compound only by identity of one or more substituents (e.g., for at least one position, the variant has a different substituent or set of substituents than is found at the corresponding position in an appropriate reference compound).

In some embodiments, compounds of the invention (e.g., macrocyclic compounds of the invention) include 12 to 40 ring atoms (e.g., 12 to 20 ring atoms, 14 to 20 ring atoms, 17 to 25 ring atom, 21 to 26 ring atoms, 20 to 30 ring atoms, 25 to 35 ring atoms, 30 to 40 ring atoms). In some embodiments, such compounds include 19 ring atoms. In some embodiments, such compounds have an even number of ring atoms. In certain embodiments, at least 25% (e.g., at least 30%, at least 35%, at least 40%, at least 45%) of the atoms in the compound are included in a single or fused ring system.

In some embodiments, compounds of the invention include a ring (e.g., a macrocycle) whose ring atoms are selected from the group consisting of carbon atoms, hydrogen atoms, nitrogen atoms, oxygen atoms, sulfur atoms, phosphorous atoms, silicon atoms and combinations thereof; in some embodiments all ring atoms in the compound are selected from this group. In some embodiments, compounds of the invention include a ring (e.g., a macrocycle) whose ring atoms are selected only from the group consisting carbon atoms, hydrogen atoms, nitrogen atoms, oxygen atoms and combinations thereof; in some embodiments, all ring atoms in the compound are selected only from the group consisting carbon atoms, hydrogen atoms, nitrogen atoms, oxygen atoms and combinations thereof.

In certain embodiments, ring linkage in provided compounds (e.g., macrocyclic compounds) of the invention includes a ketone, an ester, an amide, an ether, a thioester, a urea, an amidine, or a hydrocarbon.

In some embodiments, a provided compound is non-peptidal. In certain embodiments, a provided compound includes one or more amino acid residues. In some embodiments, a provided compound includes only amino acid residues.

In some embodiments, the molecular weight of compounds of the invention is between 400 and 2000 daltons (e.g., 400 to 600 daltons, 500 to 700 daltons, 600 to 800 daltons, 700 to 900 daltons, 800 to 1000 daltons, 900 to 1100 daltons, 1000 to 1200 daltons, 1100 to 1300 daltons, 1200 to 1400 daltons, 1300 to 1500 daltons, 1400 to 1600 daltons, 1500 to 1700 daltons, 1600 to 1800 daltons, 1700 to 1900 daltons, 1800 to 2000 daltons, 400 to 1000 daltons, 1000-2000 daltons). In some embodiments, the molecular weight of compounds of the invention is less than 2000 daltons (e.g., less than 500 daltons, less than 600 daltons, less than 700 daltons, less than 800 daltons, less than 900 daltons, less than 1000 daltons, less than 1100 daltons, less than 1200 daltons, less than 1300 daltons, less than 1400 daltons, less than 1500 daltons, less than 1600 daltons, less than 1700 daltons, less than 1800 daltons, less than 1900 daltons).

In certain embodiments, molecule provided compound is hydrophobic. For example, in some embodiments, compounds have a cLogP of equal to or greater than 2 (e.g., equal to or greater than 2.5, equal to or greater than 3.0, equal to or greater than 3.5, equal to or greater than 4, equal to or greater than 4.5, equal to or greater than 5, equal to or greater than 5.5, equal to or greater than 6, equal to or greater than 6.5, equal to or greater than 7). Alternatively, in some embodiments, compounds have a cLogP of between 2 and 7 (e.g., between 2 and 4, between 3.5 and 4.5, between 4 and 5, between 4.5 and 5.5, between 5 and 6, between 5.5 and 6.5, between 6 and 7, between 4 and 7, between 4 and 6, between 4 and 5.5). A provided compound may also be characterized as hydrophobic by having low solubility in water. For example, in some embodiments, compounds have a solubility of greater than 1 µM in water (e.g., greater than 1 µM, greater than 2 µM, greater than 5 µM, greater than 10 µM, greater than 20 µM, greater than 30 µM, greater than 40 µM, greater than 50 µM, greater than 75 µM, greater than 100 µM). Alternatively, in some embodiments, compounds have a solubility in water of between 1-100 µM (e.g., 1-10 µM, 5-10 µM, 5-20 µM, 10-50 µM, 5-50 µM, 20-100 µM).

In some embodiments, compounds of the invention are cell penetrant (e.g., they are able to enter the intracellular domain of a cell without killing the cell and/or are capable of entering the intercellular domain when contacted with extracellular environs).

Compounds of the invention may or may not be naturally occurring. In some embodiments, compounds of the invention are not naturally occurring. In certain embodiments, compounds of the invention are engineered. An engineered compound is a compound whose design and/or production involves action of the hand of man (e.g., a compound prepared by chemical synthesis, a compound prepared by a cell that has been genetically manipulated relative to a reference wild type cell, a compound produced by a cell in culture conditions modified to enhance production of the compound).

In certain embodiments, a provided compound (e.g., macrocyclic compound) is not a compound described in Benjamin et al. Nat. Rev. Drug. Discov. 2011, 10(11), 868-880 or Sweeney, Z. K. et al. J. Med. Chem. 2014, epub ahead of print, the structures of which are incorporated by reference and/or a compound having the structure:

Presenter Protein Binding Moiety

Compounds of the invention include a presenter protein binding moiety. This moiety includes the group of ring atoms (e.g., 5 to 20 ring atoms, 5 to 10 ring atoms, 10 to 20 ring atoms) and the moieties attached thereto (e.g., atoms within 20 atoms of a ring atom such as, atoms within 15 atoms of a ring atom, atoms within 10 atoms of a ring atom, atoms within 5 atoms of a ring atom) that participate in binding to a presenter protein such that a provided compound specifically binds to said presenter protein, for example, with a $K_D$ of less than 10 µM (e.g., less than 5 µM, less than 1 µM, less than 500 nM, less than 200 nM, less than 100 nM, less than 75 nM, less than 50 nM, less than 25 nM, less than 10 nM) or inhibits the peptidyl-prolyl isomerase activity of the presenter protein, for example, with an $IC_{50}$ of less than 1 µM (e.g., less than 0.5 µM, less than 0.1 µM, less than 0.05 µM, less than 0.01 µM). In some embodiments, the presenter protein binding moiety does not encompass the entirety of atoms in a provided compound that interact with the presenter protein. In some embodiments, one or more atoms of the presenter protein binding moiety may be within the target protein interaction moiety (e.g., eukaryotic target protein interacting moiety such as a mammalian target protein interacting moiety or a fungal target protein interacting moiety or prokaryotic target protein interacting moiety such as a bacterial target protein interacting moiety). In certain embodiments, one or more atoms of the presenter protein binding moiety do not interact with the presenter protein.

In some embodiments, a presenter protein binding moiety includes a N-acyl proline moiety, a N-acyl-pipecolic acid moiety, a N-acyl 3-morpholino-carboxylic acid moiety, and/or a N-acyl piperzic acid moiety (e.g., with acylation on either nitrogen atom. In certain embodiments, a presenter protein binding moiety includes a N-acyl-pipecolic acid moiety. In some embodiments, a presenter protein binding moiety includes a N-acyl proline moiety. In certain embodiments, a presenter protein binding moiety includes a N-acyl 3-morpholino-carboxylic acid moiety. In some embodiments, a presenter protein binding moiety includes a N-acyl piperzic acid moiety.

In some embodiments, at least one atom of a presenter protein binding moiety participates in binding with one or more (e.g., two, three, four, five, six, seven, eight, nine, ten, eleven, twelve, thirteen, fourteen, or fifteen) of Tyr 27, Phe 37, Asp 38, Arg 41, Phe 47, Gln 54, Glu 55, Val 56, Ile 57, Trp 60, Ala 82, Try 83, His 88, Ile 92, and/or Phe 100 of FKBP12. In some embodiments, at least one at of a presenter protein binding moiety participates in binding with at least one (e.g., two, three, or four) of Arg 41, Gln 54, Glu 55, and/or Ala 82 of FKBP12.

In some embodiments, a presenter protein binding moiety has a structure according to Formula I-VIII:

Formula I, Formula II, Formula III, Formula IV, Formula V, Formula VI, Formula VII, Formula VIII In some embodiments, a presenter protein binding moiety has a structure according to Formula Ia-IVa:

Formula Ia, Formula IIa

Formula IIIa
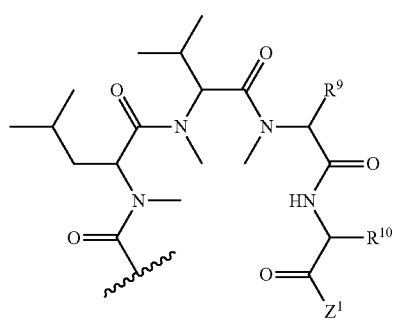
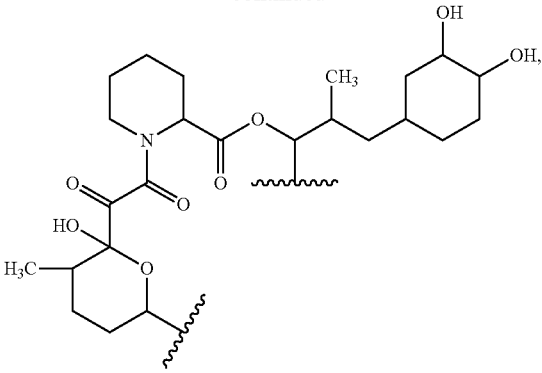
Formula IVa
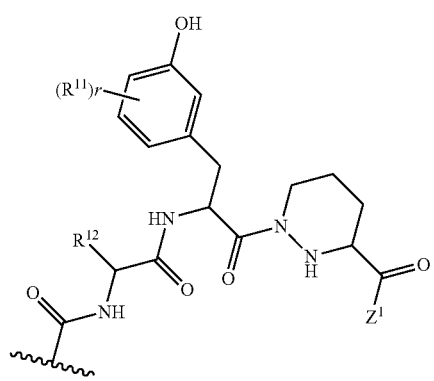
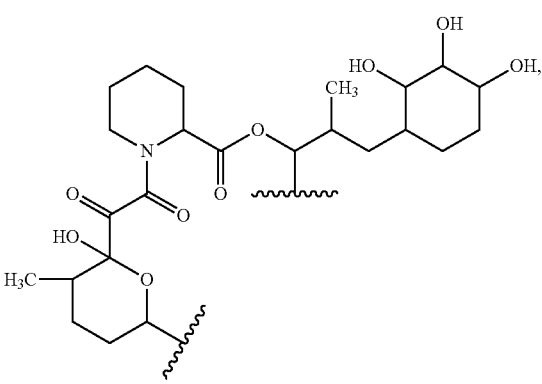
In some embodiments, a presenter protein binding moiety includes or consists of the structure:
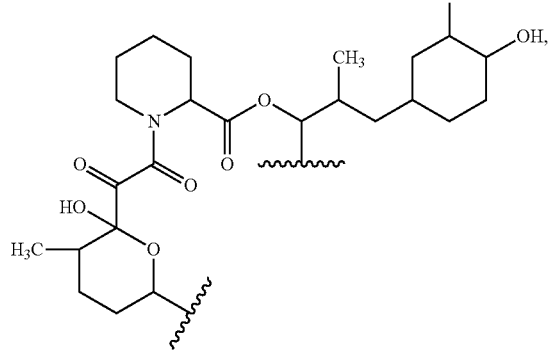
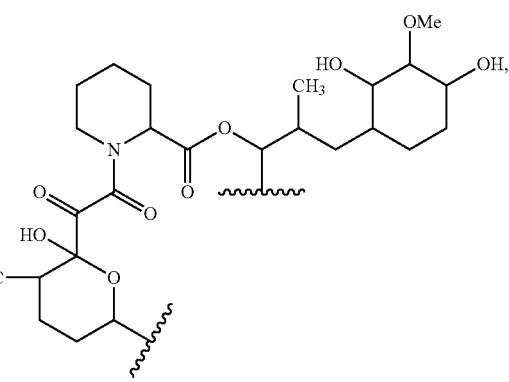
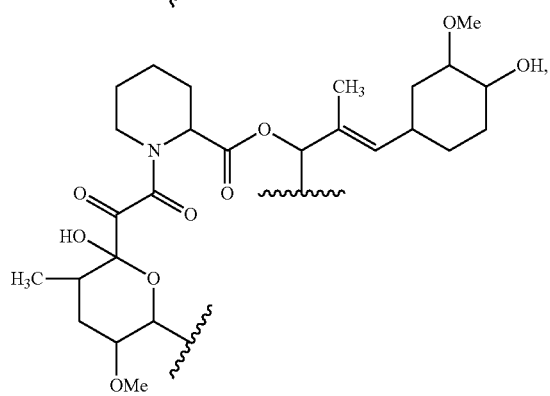
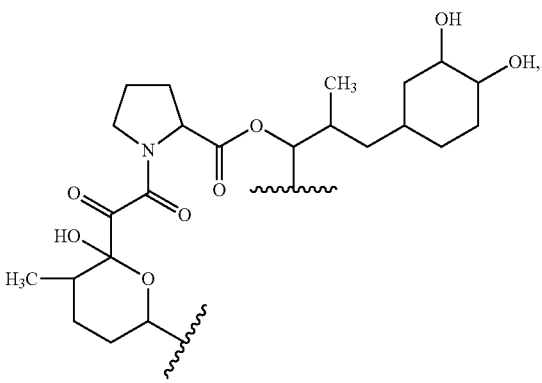

73
-continued
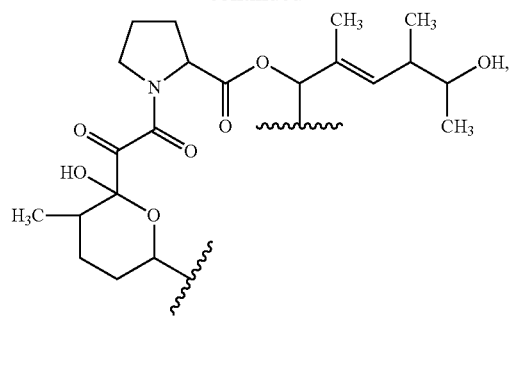
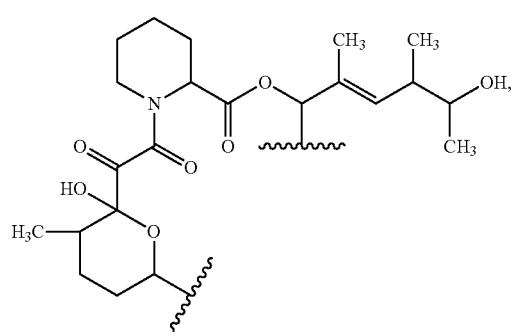
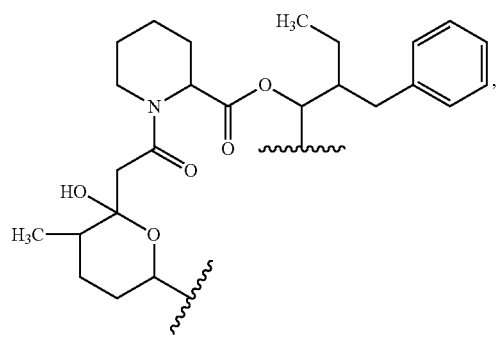
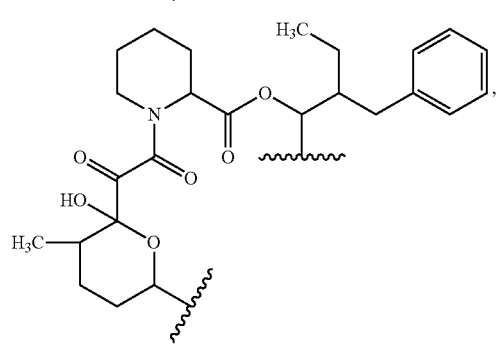
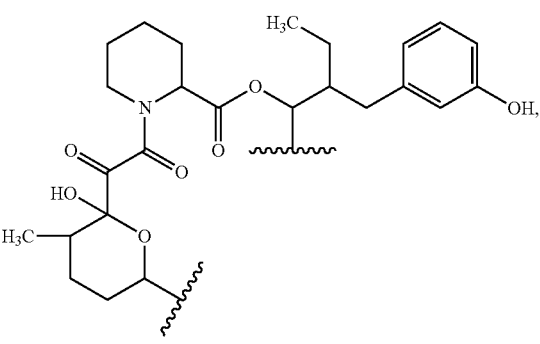
74
-continued
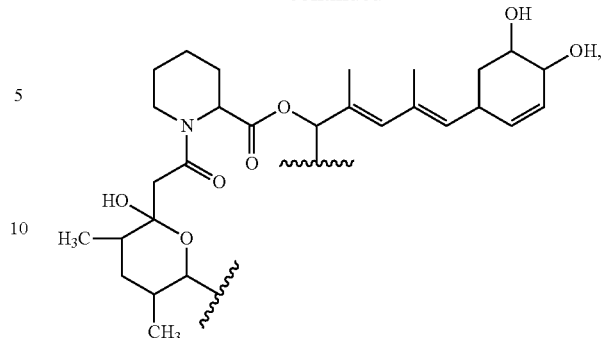
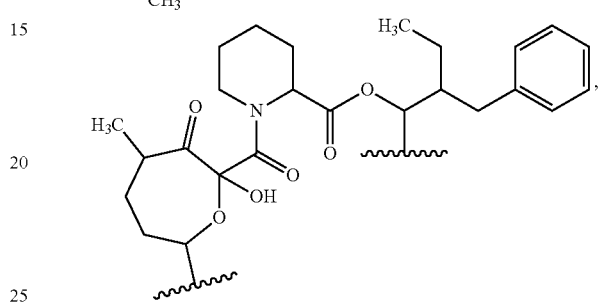
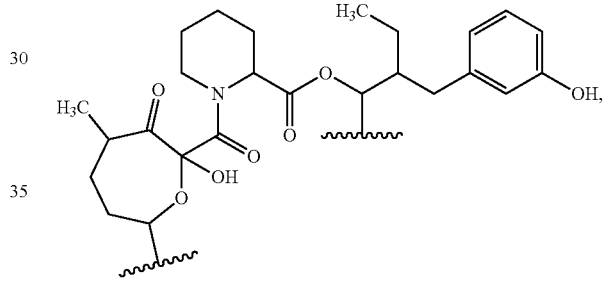
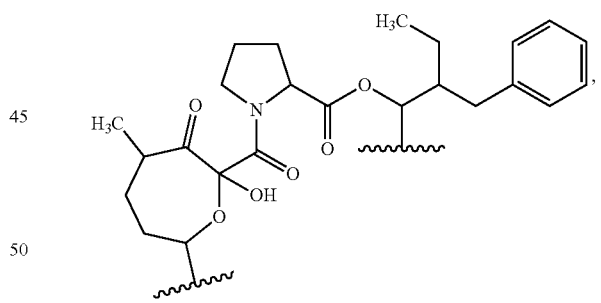
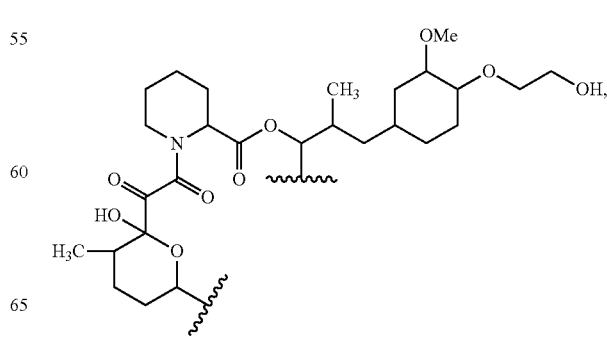

-continued
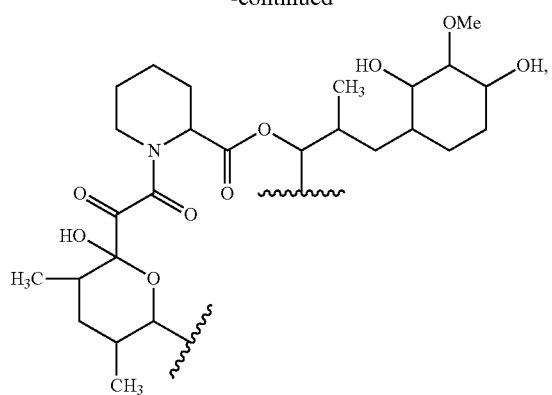
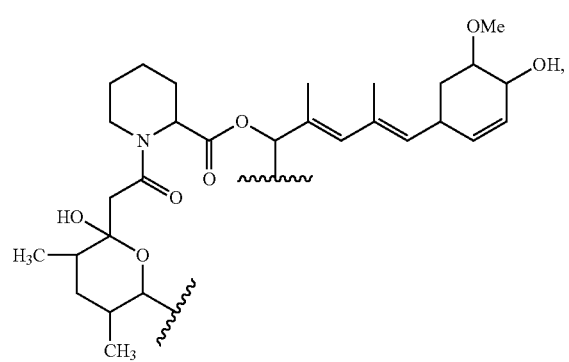
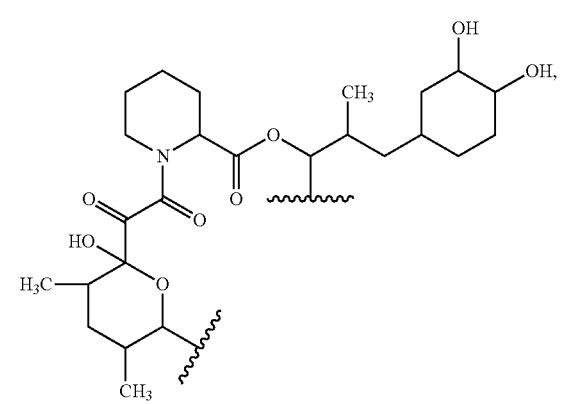
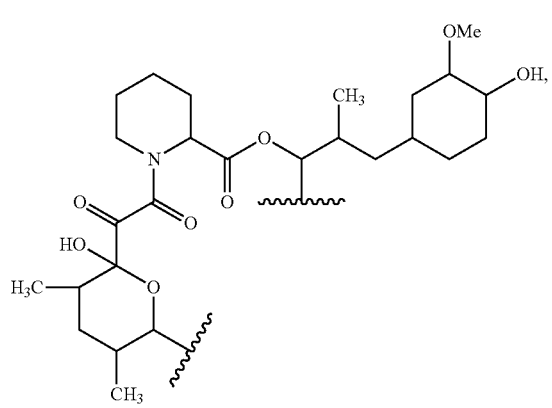
-continued
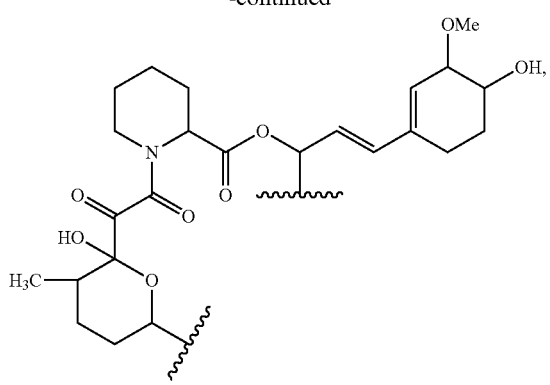
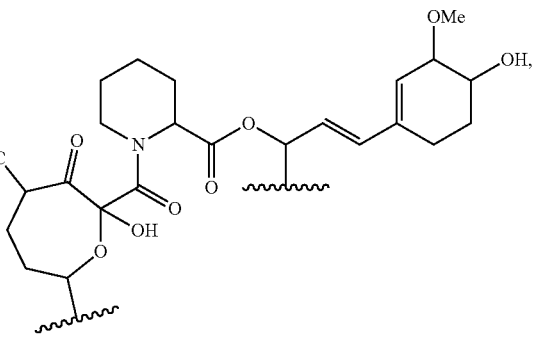
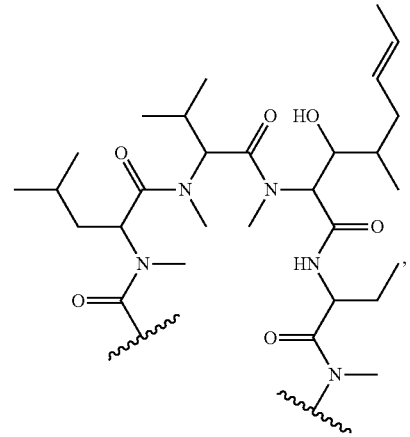
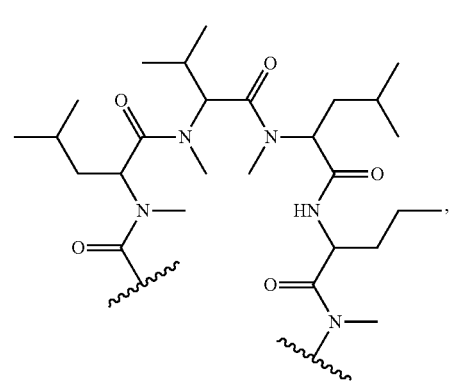

-continued
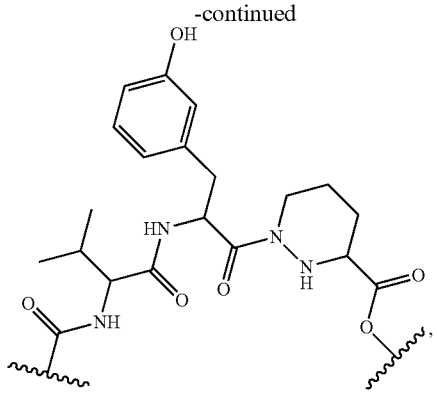
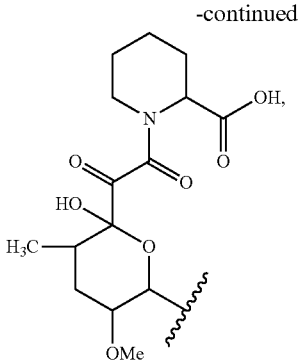
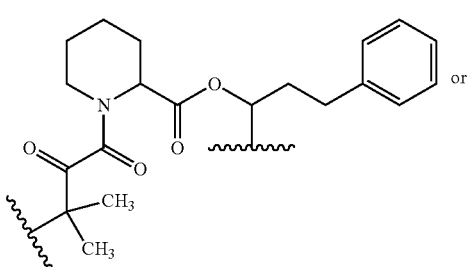 or
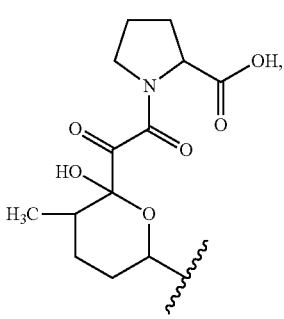
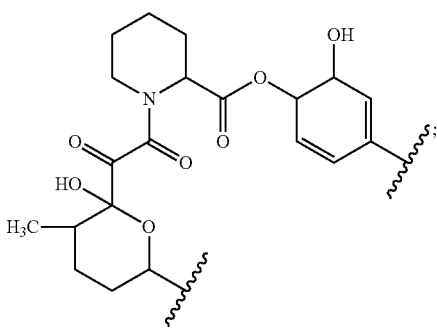
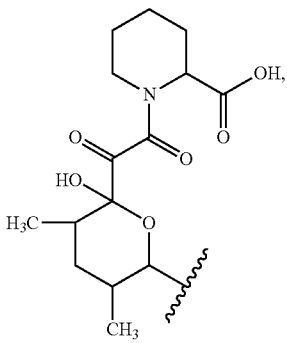
or a stereoisomer thereof.
In certain embodiments, the presenter protein binding moiety is or includes the structure:
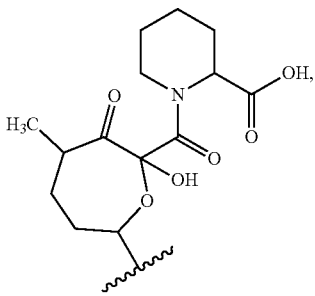
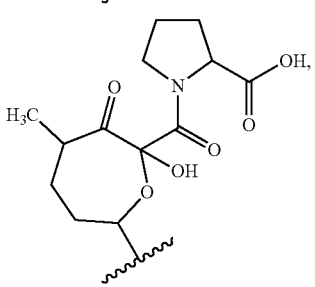

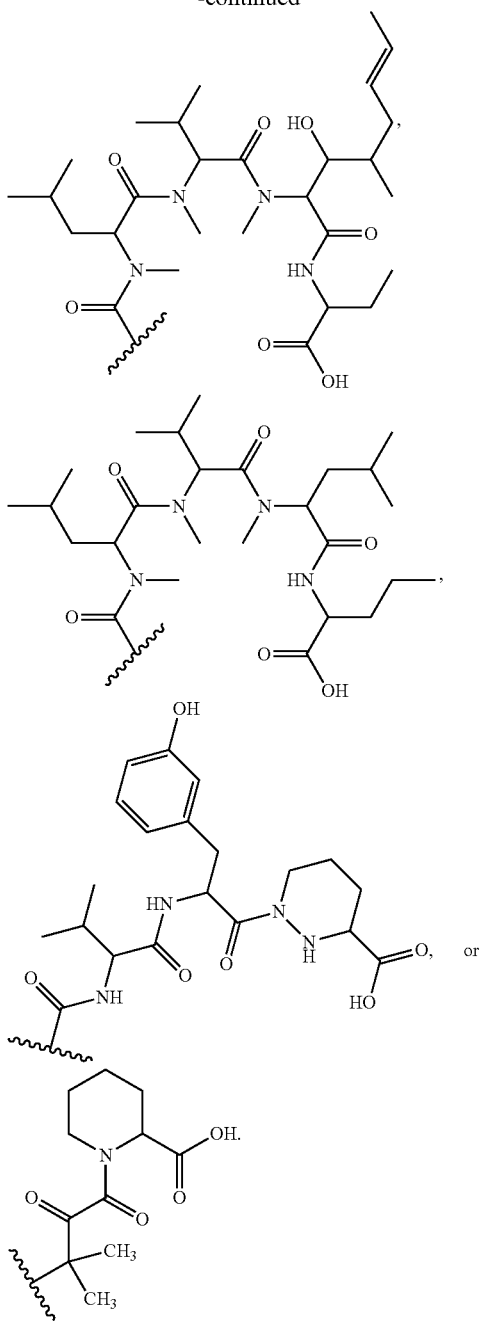

Target Protein Interacting Moiety

Compounds of the invention include a target protein interacting moiety (e.g., a eukaryotic target protein interacting moiety such as a mammalian target protein interacting moiety or a fungal target protein interacting moiety or a prokaryotic target protein interacting moiety such as a bacterial target protein interacting moiety). This moiety includes the group of ring atoms (e.g., 5 to 20 ring atoms, 5 to 10 ring atoms, 10 to 20 ring atoms) and the moieties attached thereto (e.g., atoms within 20 atoms of a ring atom such as, atoms within 15 atoms of a ring atom, atoms within 10 atoms of a ring atom, atoms within 5 atoms of a ring atom) that when the compound is in a complex with a presenter protein, specifically bind to a target protein. In some embodiments, a target protein interacting moiety comprises a plurality of the atoms in the compound that interact with the target protein. In some embodiments, one or more atoms of a target protein interacting moiety may be within the presenter protein binding moiety. In certain embodiments, one or more atoms of a target protein interacting moiety do not interact with the target protein.

A target protein can bind to a ring atom in a target protein interacting moiety. Alternatively, a target protein can bind to two or more ring atoms in a target protein interacting moiety. In another alternative, a target protein bind can to a substituent attached to one or more ring atoms in a target protein interacting moiety. In another alternative, a target protein can bind to a ring atom in a target protein interacting moiety and to a substituent attached to one or more ring atoms in a target protein interacting moiety. In another alternative, a target protein binds to a group that mimics a natural ligand of a target protein and wherein the group that mimics a natural ligand of a target protein is attached to a target protein interacting moiety. In yet another alternative, a target protein binds to a presenter protein and the affinity of a target protein for a presenter protein in the binary complex is increased relative to the affinity of a target protein for a presenter protein in the absence of the complex. Binding in these examples is typically through, but not limited to non-covalent interactions of a target protein to a target protein interacting moiety.

In some embodiments, a target protein interacting moiety is hydrophobic. For example, in some embodiments, a target protein interacting moiety has a cLogP of equal to or greater than 2 (e.g., equal to or greater than 2.5, equal to or greater than 3, equal to or greater than 3.5, equal to or greater than 4, equal to or greater than 4.5, equal to or greater than 5, equal to or greater than 5.5, equal to or greater than 6, equal to or greater than 6.5, equal to or greater than 7). Alternatively, in some embodiments, a target protein interacting moiety has a cLogP of between 2 and 7 (e.g., between 2 and 4, between 2.5 and 4.5, between 3 and 5, between 3.5 and 5.5, between 4 and 6, between 4.5 and 6.5, between 5 and 7, between 3 and 6, between 3 and 5, between 3 and 5.5). A target protein interacting moiety may also be characterized as hydrophobic by having low polar surface area. For example, in some embodiments, a target protein interacting moiety has a polar surface area of less than 350 Å$^2$ (e.g., less than 300 Å$^2$, less than 250 Å$^2$, less than 200 Å$^2$, less than 150 Å$^2$, less than 125 Å$^2$).

In some embodiments, a target protein interacting moiety comprises one or more hydrophobic pendant groups (e.g., one or more methyl, ethyl, isopropyl, phenyl, benzyl, and/or phenethyl groups). In some embodiments, the pendant groups comprise fewer than 30 total atoms (e.g., fewer than 25 total atoms, fewer than 20 total atoms, fewer than 15 total atoms, fewer than 10 total atoms.) Alternatively, in some embodiments, the pendant groups comprise between 10 and 30 total atoms (e.g., 10 to 20 total atoms, 15 to 25 total atoms, 20 to 30 total atoms). In certain embodiments the pendant groups have a molecular weight less than 200 daltons (e.g., less than 150 daltons, less than 100 daltons, less than 75 daltons, less than 50 daltons). Alternatively, in some embodiments, the pendant groups have a molecular weight between 50 to 200 daltons (e.g., 50 to 100 daltons, 75 to 150 daltons, 100 to 200 daltons).

In some embodiments, a target protein interacting moiety is hydrocarbon based (e.g., the moiety comprises mostly carbon-carbon bonds). In some embodiments, a target protein interacting moiety is hydrocarbon based and includes a linear bivalent $C_4$-$C_{30}$ (e.g., $C_6$-$C_{20}$, $C_6$-$C_{15}$) aliphatic group consisting predominantly of carbon and hydrogen, optionally including one or more double bonds. In some embodiments, the bivalent aliphatic group can also be substituted with a group that mimics a natural ligand that binds to a target protein. Examples include phosphotyrosine mimics and ATP mimetics.

In some embodiments, a target protein interacting moiety is peptide based (e.g., the moiety comprises peptide bonds). In some embodiments, a target protein interacting moiety is peptide based and includes one or more (e.g., two, three, four, five, six, seven, or eight) alanine residues, one or more (e.g., two, three, four, five, six, seven, or eight) valine residues, one or more isoleucine (e.g., two, three, four, five, six, seven, or eight) residues, one or more leucine (e.g., two, three, four, five, six, seven, or eight) residues, one or more methionine (e.g., two, three, four, five, six, seven, or eight) residues, one or more phenylalanine (e.g., two, three, four, five, six, seven, or eight) residues, one or more (e.g., two, three, four, five, six, seven, or eight) tyrosine residues, one or more (e.g., two, three, four, five, six, seven, or eight) tryptophan residues, one or more (e.g., two, three, four, five, six, seven, or eight) glycine residues, and/or one or more (e.g., two, three, four, five, six, seven, or eight) proline residues. In some embodiments, a target protein interacting moiety is peptide based an includes one or more (e.g., two, three, four, five, six, seven, or eight) arginine residues or one or more (e.g., two, three, four, five, six, seven, or eight) lysine residues. In some embodiments, a target protein interacting moiety is peptide based and includes one or more (e.g., two, three, four, five, six, seven, or eight) non-natural amino acids, one or more (e.g., two, three, four, five, six, seven, or eight) D-amino acids, and/or one or more (e.g., two, three, four, five, six, seven, or eight) N-alkylated amino acids. In some embodiments, a target protein interacting moiety is peptide based and includes predominantly D-amino acids (e.g., at least 50% of the amino acids are D-amino acids, at least 75% of the amino acids are D-amino acids, 100% of the amino acids are D-amino acids). In certain embodiments, a target protein interacting moiety is peptide based and includes predominantly N-alkylated amino acids (e.g., at least 50% of the amino acids are N-alkylated amino acids, at least 75% of the amino acids are N-alkylated amino acids, 100% of the amino acids are N-alkylated amino acids). In certain embodiments, a target protein interacting moiety is peptide based and includes one or more (e.g., two, three, four, five, six, seven, or eight) depsi-linkages.

In some embodiments, a target protein interacting moiety (e.g., a eukaryotic target protein interacting moiety such as a mammalian target protein interacting moiety or a fungal target protein interacting moiety or a prokaryotic target protein interacting moiety such as a bacterial target protein interacting moiety) has a structure according to Formula IX:

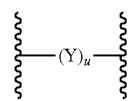

Formula IX wherein u is an integer from 1 to 20; and each Y is, independently, any amino acid, O, $NR^{20}$, S, S(O), $SO_2$, or has the structure of any one of Formulae X-XIII:

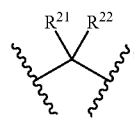

Formula X

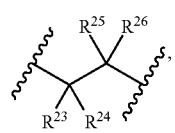

Formula XI

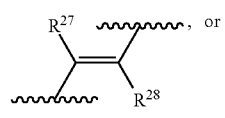

Formula XII

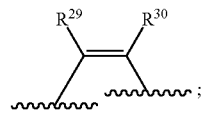

Formula XIII wherein each $R^{20}$ is, independently, hydrogen, optionally substituted $C_1$-$C_6$ alkyl, optionally substituted $C_2$-$C_6$ alkenyl, optionally substituted $C_2$-$C_6$ alkynyl, optionally substituted aryl, $C_3$-$C_7$ carbocyclyl, optionally substituted $C_6$-$C_{10}$ aryl $C_1$-$C_6$ alkyl, and optionally substituted $C_3$-$C_7$ carbocyclyl $C_1$-$C_6$ alkyl or $R^{19}$ combines with any $R^{20}$, $R^{21}$, $R^{22}$, $R^{23}$, $R^{24}$, $R^{25}$, $R^{26}$, $R^{27}$, $R^{28}$, $R^{29}$, or $R^{30}$ to form an optionally substituted $C_3$-$C_{10}$ carbocyclyl, optionally substituted $C_6$-$C_{10}$ aryl, or optionally substituted $C_2$-$C_9$ heteroaryl;

each $R^{21}$ and $R^{22}$ is, independently, hydrogen, halogen, optionally substituted hydroxyl, optionally substituted amino, or $R^{20}$ and $R^{21}$ combine to form =O, optionally substituted $C_1$-$C_6$ alkyl, optionally substituted $C_2$-$C_6$ alkenyl, optionally substituted $C_2$-$C_6$ alkynyl, optionally substituted $C_3$-$C_{10}$ carbocyclyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl, or $R^{21}$ or $R^{22}$ combines with any $R^{20}$, $R^{21}$, $R^{22}$, $R^{23}$, $R^{24}$, $R^{25}$, $R^{26}$, $R^{27}$, $R^{28}$, $R^{29}$, or $R^{30}$ to form an optionally substituted $C_3$-$C_{10}$ carbocyclyl, optionally substituted $C_6$-$C_{10}$ aryl, or optionally substituted $C_2$-$C_9$ heteroaryl;

each $R^{23}$, $R^{24}$, $R^{25}$, and $R^{26}$ is, independently, hydrogen, hydroxyl, or $R^{23}$ and $R^{24}$ combine to form =O, or $R^{23}$, $R^{24}$, $R^{25}$, or $R^{26}$ combines with any $R^{20}$, $R^{21}$, $R^{22}$, $R^{23}$, $R^{24}$, $R^{25}$, $R^{26}$, $R^{27}$, $R^{28}$, $R^{29}$, or $R^{30}$ to form an optionally substituted $C_3$-$C_{10}$ carbocyclyl, optionally substituted $C_6$-$C_{10}$ aryl, or optionally substituted $C_2$-$C_9$ heteroaryl; and each $R^{27}$, $R^{28}$, $R^{29}$, and $R^{30}$ is, independently, hydrogen, optionally substituted $C_1$-$C_6$ alkyl, optionally substituted $C_2$-$C_6$ alkenyl, optionally substituted $C_2$-$C_6$ alkynyl, optionally substituted $C_3$-$C_{10}$ carbocyclyl, optionally substituted $C_6$-$C_{10}$ aryl, optionally substituted $C_6$-$C_{10}$ aryl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocyclyl, or optionally substituted $C_2$-$C_9$ heterocyclyl $C_1$-$C_6$ alkyl, or $R^{27}$, $R^{28}$, $R^{29}$, or $R^{30}$ combines with any $R^{20}$, $R^{21}$, $R^{22}$, $R^{23}$, $R^{24}$, $R^{25}$, $R^{26}$, $R^{27}$, $R^{28}$, $R^{29}$, or $R^{30}$ to form an optionally substituted $C_3$-$C_{10}$ carbocyclyl, optionally substituted $C_6$-$C_{10}$ aryl, or optionally substituted $C_2$-$C_9$ heteroaryl.

In some embodiments, a target protein interacting moiety has a structure according to Formula IXa:

Formula IXa

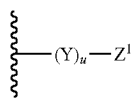

In certain embodiments, a target protein interacting moiety (e.g., a eukaryotic target protein interacting moiety such as a mammalian target protein interacting moiety or a fungal target protein interacting moiety or a prokaryotic target protein interacting moiety such as a bacterial target protein interacting moiety) does not include the structure:

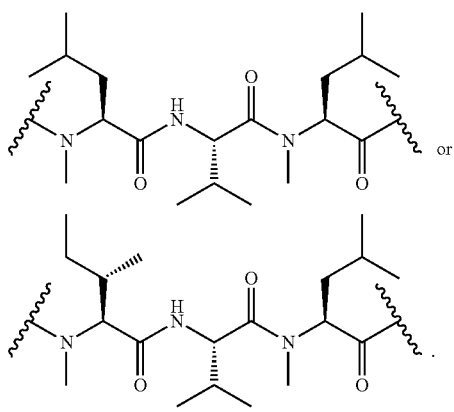

Linkers

The compounds of the invention include a linker (e.g., two linkers connecting the presenter protein binding moiety and target protein interacting moiety (e.g., a eukaryotic target protein interacting moiety such as a mammalian target protein interacting moiety or a fungal target protein interacting moiety or a prokaryotic target protein interacting moiety such as a bacterial target protein interacting moiety)). The linker component of the invention is, at its simplest, a bond, but may also provide a linear, cyclic, or branched molecular skeleton having pendant groups covalently linking two moieties.

In some embodiments, at least one atom of a linker participates in binding to the presenter protein and/or the target protein. In certain embodiments, at least one atom of a linker does not participate in binding to the presenter protein and/or the target protein.

Thus, linking of the two moieties is achieved by covalent means, involving bond formation with one or more functional groups located on either moiety. Examples of chemically reactive functional groups which may be employed for this purpose include, without limitation, amino, hydroxyl, sulfhydryl, carboxyl, carbonyl, carbohydrate groups, vicinal diols, thioethers, 2-aminoalcohols, 2-aminothiols, guanidinyl, imidazolyl, and phenolic groups.

The covalent linking of the two moieties may be effected using a linker that contains reactive moieties capable of reaction with such functional groups present in either moiety. For example, an amine group of a moiety may react with a carboxyl group of the linker, or an activated derivative thereof, resulting in the formation of an amide linking the two.

Examples of moieties capable of reaction with sulfhydryl groups include α-haloacetyl compounds of the type $XCH_2CO-$ (where X=Br, Cl, or I), which show particular reactivity for sulfhydryl groups, but which can also be used to modify imidazolyl, thioether, phenol, and amino groups as described by Gurd, *Methods Enzymol.* 11:532 (1967). N-Maleimide derivatives are also considered selective towards sulfhydryl groups, but may additionally be useful in coupling to amino groups under certain conditions. Reagents such as 2-iminothiolane (Traut et al., *Biochemistry* 12:3266 (1973)), which introduce a thiol group through conversion of an amino group, may be considered as sulfhydryl reagents if linking occurs through the formation of disulfide bridges.

Examples of reactive moieties capable of reaction with amino groups include, for example, alkylating and acylating agents. Representative alkylating agents include:

(i) α-haloacetyl compounds, which show specificity towards amino groups in the absence of reactive thiol groups and are of the type $XCH_2CO-$ (where X=Br, Cl, or I), for example, as described by Wong *Biochemistry* 24:5337 (1979);

(ii) N-maleimide derivatives, which may react with amino groups either through a Michael type reaction or through acylation by addition to the ring carbonyl group, for example, as described by Smyth et al., *J. Am. Chem. Soc.* 82:4600 (1960) and *Biochem. J.* 91:589 (1964);

(iii) aryl halides such as reactive nitrohaloaromatic compounds;

(iv) alkyl halides, as described, for example, by McKenzie et al., *J. Protein Chem.* 7:581 (1988);

(v) aldehydes and ketones capable of Schiff's base formation with amino groups, the adducts formed usually being stabilized through reduction to give a stable amine;

(vi) epoxide derivatives such as epichlorohydrin and bisoxiranes, which may react with amino, sulfhydryl, or phenolic hydroxyl groups;

(vii) chlorine-containing derivatives of s-triazines, which are very reactive towards nucleophiles such as amino, sulfhydryl, and hydroxyl groups;

(viii) aziridines based on s-triazine compounds detailed above, e.g., as described by Ross, *J. Adv. Cancer Res.* 2:1 (1954), which react with nucleophiles such as amino groups by ring opening;

(ix) squaric acid diethyl esters as described by Tietze, *Chem. Ber.* 124:1215 (1991); and (x) α-haloalkyl ethers, which are more reactive alkylating agents than normal alkyl halides because of the activation caused by the ether oxygen atom, as described by Benneche et al., *Eur. J. Med. Chem.* 28:463 (1993).

Representative amino-reactive acylating agents include:

(i) isocyanates and isothiocyanates, particularly aromatic derivatives, which form stable urea and thiourea derivatives respectively;

(ii) sulfonyl chlorides, which have been described by Herzig et al., *Biopolymers* 2:349 (1964);

(iii) acid halides;

(iv) active esters such as nitrophenylesters or N-hydroxysuccinimidyl esters;

(v) acid anhydrides such as mixed, symmetrical, or N-carboxyanhydrides;

(vi) other useful reagents for amide bond formation, for example, as described by M. Bodansky, *Principles of Peptide Synthesis*, Springer-Verlag, 1984;

(vii) acylazides, e.g., wherein the azide group is generated from a preformed hydrazide derivative using sodium nitrite, as described by Wetz et al., *Anal. Biochem.* 58:347 (1974);

(viii) imidoesters, which form stable amidines on reaction with amino groups, for example, as described by Hunter and Ludwig, *J. Am. Chem. Soc.* 84:3491 (1962); and (ix) haloheteroaryl groups such as halopyridine or halopyrimidine.

Aldehydes and ketones may be reacted with amines to form Schiff's bases, which may advantageously be stabilized through reductive amination. Alkoxylamino moieties readily react with ketones and aldehydes to produce stable alkoxamines, for example, as described by Webb et al., in *Bioconjugate Chem.* 1:96 (1990).

Examples of reactive moieties capable of reaction with carboxyl groups include diazo compounds such as diazoacetate esters and diazoacetamides, which react with high specificity to generate ester groups, for example, as described by Herriot, *Adv. Protein Chem.* 3:169 (1947). Carboxyl modifying reagents such as carbodiimides, which react through O-acylurea formation followed by amide bond formation, may also be employed.

It will be appreciated that functional groups in either moiety may, if desired, be converted to other functional groups prior to reaction, for example, to confer additional reactivity or selectivity. Examples of methods useful for this purpose include conversion of amines to carboxyls using reagents such as dicarboxylic anhydrides; conversion of amines to thiols using reagents such as N-acetylhomocysteine thiolactone, S-acetylmercaptosuccinic anhydride, 2-iminothiolane, or thiol-containing succinimidyl derivatives; conversion of thiols to carboxyls using reagents such as α-haloacetates; conversion of thiols to amines using reagents such as ethylenimine or 2-bromoethylamine; conversion of carboxyls to amines using reagents such as carbodiimides followed by diamines; and conversion of alcohols to thiols using reagents such as tosyl chloride followed by transesterification with thioacetate and hydrolysis to the thiol with sodium acetate.

So-called zero-length linkers, involving direct covalent joining of a reactive chemical group of one moiety with a reactive chemical group of the other without introducing additional linking material may, if desired, be used in accordance with the invention.

More commonly, however, the linker will include two or more reactive moieties, as described above, connected by a spacer element. The presence of such a spacer permits bifunctional linkers to react with specific functional groups within either moiety, resulting in a covalent linkage between the two. The reactive moieties in a linker may be the same (homobifunctional linker) or different (heterobifunctional linker, or, where several dissimilar reactive moieties are present, heteromultifunctional linker), providing a diversity of potential reagents that may bring about covalent attachment between the two moieties.

Spacer elements in the linker typically consist of linear or branched chains and may include a $C_{1-10}$ alkyl, $C_{2-10}$ alkenyl, $C_{2-10}$ alkynyl, $C_{2-6}$ heterocyclyl, $C_{6-12}$ aryl, $C_{7-14}$ alkaryl, $C_{3-10}$ alkheterocyclyl, $C_2$-$C_{100}$ polyethylene glycol, or $C_{1-10}$ heteroalkyl.

In some instances, the linker is described by Formula V.

Examples of homobifunctional linkers useful in the preparation of conjugates of the invention include, without limitation, diamines and diols selected from ethylenediamine, propylenediamine and hexamethylenediamine, ethylene glycol, diethylene glycol, propylene glycol, 1,4-butanediol, 1,6-hexanediol, cyclohexanediol, and polycaprolactone diol.

In some embodiments, the linker is a bond or a linear chain of up to 10 atoms, independently selected from carbon, nitrogen, oxygen, sulfur or phosphorous atoms, wherein each atom in the chain is optionally substituted with one or more substituents independently selected from alkyl, alkenyl, alkynyl, aryl, heteroaryl, chloro, iodo, bromo, fluoro, hydroxyl, alkoxy, aryloxy, carboxy, amino, alkylamino, dialkylamino, acylamino, carboxamido, cyano, oxo, thio, alkylthio, arylthio, acylthio, alkylsulfonate, arylsulfonate, phosphoryl, and sulfonyl, and wherein any two atoms in the chain may be taken together with the substituents bound thereto to form a ring, wherein the ring may be further substituted and/or fused to one or more optionally substituted carbocyclic, heterocyclic, aryl, or heteroaryl rings.

In some embodiments, the linker has the structure of Formula XIX:

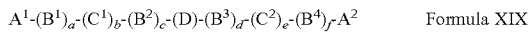

$$A^1\text{-}(B^1)_a\text{-}(C^1)_b\text{-}(B^2)_c\text{-}(D)\text{-}(B^3)_d\text{-}(C^2)_e\text{-}(B^4)_f\text{-}A^2 \qquad \text{Formula XIX}$$

where $A^1$ is a bond between the linker and presenter protein binding moiety; $A^2$ is a bond between the mammalian target interacting moiety and the linker; $B^1$, $B^2$, $B^3$, and $B^4$ each, independently, is selected from optionally substituted $C_1$-$C_2$ alkyl, optionally substituted $C_1$-$C_3$ heteroalkyl, O, S, and $NR^N$; $R^N$ is hydrogen, optionally substituted $C_{1-4}$ alkyl, optionally substituted $C_{3-4}$ alkenyl, optionally substituted $C_{2-4}$ alkynyl, optionally substituted $C_{2-6}$ heterocyclyl, optionally substituted $C_{6-12}$ aryl, or optionally substituted $C_{1-7}$ heteroalkyl; $C^1$ and $C^2$ are each, independently, selected from carbonyl, thiocarbonyl, sulphonyl, or phosphoryl; a, b, c, d, e, and f are each, independently, 0 or 1; and D is optionally substituted $C_{1-10}$ alkyl, optionally substituted $C_{2-10}$ alkenyl, optionally substituted $C_{2-10}$ alkynyl, optionally substituted $C_{2-6}$ heterocyclyl, optionally substituted $C_{6-12}$ aryl, optionally substituted $C_2$-$C_{10}$ polyethylene glycol, or optionally substituted $C_{1-10}$ heteroalkyl, or a chemical bond linking $A^1\text{-}(B^1)_a\text{-}(C^1)_b\text{-}(B)_c\text{-}$ to $\text{-}(B)_d\text{-}(C^2)_e\text{-}(B^4)_f\text{-}A^2$.

Compound Characteristics

Pharmacokinetic Parameters

Preliminary exposure characteristics of the compounds can be evaluated using, e.g., an in vivo Rat Early Pharmacokinetic (EPK) study design to show bioavailability. For example, Male Sprague-Dawley rats can be dosed via oral (PO) gavage in a particular formulation. Blood samples can then be collected from the animals at 6 timepoints out to 4 hours post-dose. Pharmacokinetic analysis can then performed on the LC-MS/MS measured concentrations for each timepoint of each compound.

Cell Permeability

In some embodiments, the compound is cell penetrant. To determine permeability of a compound any method known in the art may be employed such as a Biosensor assay as described herein.

Proteins

Presenter Proteins

Presenter proteins can bind a small molecule to form a complex, which can bind to and modulate the activity of a target protein (e.g., a eukaryotic target protein such as a mammalian target protein or a fungal target protein or a prokaryotic target protein such as a bacterial target protein). In some embodiments, the presenter protein is a mammalian presenter protein (e.g., a human presenter protein). In some embodiments, the presenter protein is a fungal presenter protein. In certain embodiments, the presenter protein is a bacterial presenter protein. In some embodiments, the presenter protein is a plant presenter protein. In some embodiments, the presenter protein is a relatively abundant protein (e.g., the presenter protein is sufficiently abundant that participation in a tripartite complex does not materially negatively impact the biological role of the presenter protein in a cell and/or viability or other attributes of the cell). In some embodiments, the presenter protein is more abundant than the target protein. In certain embodiments, the presenter protein is a protein that has chaperone activity within a cell. In some embodiments, the presenter protein has multiple natural interaction partners within a cell. In certain embodiments, the presenter protein is one which is known to bind a small molecule to form a binary complex that is known to or suspected of binding to and modulating the biological activity of a target protein. Immunophilins are a class of presenter proteins which are known to have these functions and include FKBPs and cyclophilins. In some embodiments, a reference presenter protein exhibits peptidyl prolyl isomerase activity; in some embodiments, a presenter protein shows comparable activity to the reference presenter protein. In certain embodiments, the presenter protein is a member of the FKBP family (e.g., FKBP12, FKBP12.6, FKBP13, FKBP19, FKBP22, FKBP23, FKBP25, FKBP36, FKBP38, FKBP51, FKBP52, FKBP60, FKBP65, and FKBP133), a member of the cyclophilin family (e.g., PP1A, CYPB, CYPC, CYP40, CYPE, CYPD, NKTR, SRCyp, CYPH, CWC27, CYPL1, CYP60, CYPJ, PPIL4, PPIL6, RANBP2, PPWD1, PPIAL4A, PPIAL4B, PPIAL4C, PPIAL4D, or PPIAL4G), or PIN1. The "FKBP family" is a family of proteins that have prolyl isomerase activity and function as protein folding chaperones for proteins containing proline residues. Genes that encode proteins in this family include AIP, AIPL1, FKBP1A, FKBP1B, FKBP2, FKBP3, FKBP4, FKBP5, FKBP6, FKBP7, FKBP8, FKBP9, FKBP9L, FKBP10, FKBP11, FKBP14, FKBP15, and LOC541473.

The "cyclophilin family" is a family of proteins that bind to cyclosporine. Genes that encode proteins in this family include PPIA, PPIB, PPIC, PPID, PPIE, PPIF, PPIG, PPIH, SDCCAG-10, PPIL1, PPIL2, PPIL3, PPIL4, P270, PPWD1, and COAS-2. Exemplary cyclophilins include PP1A, CYPB, CYPC, CYP40, CYPE, CYPD, NKTR, SRCyp, CYPH, CWC27, CYPL1, CYP60, CYPJ, PPIL4, PPIL6, RANBP2, PPWD1, PPIAL4A, PPIAL4B, PPIAL4C, PPIAL4D, and PPIAL4G.

In some embodiments, a presenter protein is a chaperone protein such as GRP78/BiP, GRP94, GRP170, calnexin, calreticulin, HSP47, ERp29, Protein disulfide isomerase (PDI), and ERp57.

In some embodiments, a presenter protein is an allelic variant or splice variant of a FKBP or cyclophilin disclosed herein.

In some embodiments, a presenter protein is a polypeptide whose amino acid sequence i) shows significant identity with that of a reference presenter protein; ii) includes a portion that shows significant identity with a corresponding portion of a reference presenter protein; and/or iii) includes at least one characteristic sequence found in presenter protein. In many embodiments, identity is considered "significant" for the purposes of defining an presenter protein if it is above 80%, 81%, 82%, 83%, 84%, 85%, 86%, 87%, 89%, 90%, 91%, 92%, 93%, 94%, 95%, 96%, 97%, 98%, 99%, or higher. In some embodiments, the portion showing significant identity has a length of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 210, 220, 230, 240, 250, 300, 350, 450, 500, 550, 600 amino acids or more.

Representative presenter proteins are encoded by the genes or homologs thereof listed in Table 1; in some embodiments, a reference presenter protein is encoded by a gene set forth in Table 1. Also, those of ordinary skill in the art, referring to Table 3, can readily identify sequences that are characteristic of presenter proteins generally, and/or of particular subsets of presenter proteins.

TABLE 1

Genes that Encode Selected Presenter Proteins

| Gene Name | Uniprot Accession Number |
|---|---|
| AIP | O00170 |
| AIPL1 | Q9NZN9 |
| FKBP1A | P62942 |
| FKBP1B | P68106 |
| FKBP2 | P26885 |
| FKBP3 | Q00688 |
| FKBP4 | Q02790 |
| FKBP5 | Q13451 |
| FKBP6 | O75344 |
| FKBP7 | Q9Y680 |
| FKBP8 | Q14318 |
| FKBP9 | O95302 |
| FKBP9L | Q75LS8 |
| FKBP10 | Q96AY3 |
| FKBP11 | Q9NYL4 |
| FKBP14 | Q9NWM8 |
| FKBP15 | Q5T1M5 |
| LOC541473 | — |
| PPIA | Q567Q0 |
| PPIB | P23284 |
| PPIC | P45877 |
| PPID | Q08752 |
| PPIE | Q9UNP9 |
| PPIG | Q13427 |
| PPIH | O43447 |
| PPIL1 | Q9Y3C6 |
| PPIL2 | Q13356 |
| PPIL3 | Q9H2H8 |
| PPIL4 | Q8WUA2 |
| PPIL5 | Q32Q17 |
| PPIL6 | Q8IXY8 |
| PPWD1 | Q96BP3 |

Target Proteins

A target protein (e.g., a eukaryotic target protein such as a mammalian target protein or a fungal target protein or a prokaryotic target protein such as a bacterial target protein) is a protein which mediates a disease condition or a symptom of a disease condition. As such, a desirable therapeutic effect can be achieved by modulating (inhibiting or increasing) its activity. Target proteins useful in the complexes and methods of the invention include those which do not naturally associate with a presenter protein, e.g., those which have an affinity for a presenter protein in the absence of a binary complex with a compound of the invention of greater than 1 µM, preferably greater than 5 µM, and more preferably greater than 10 µM. Alternatively, target proteins which do not naturally associate with a presenter protein are those which have an affinity for a compound of the invention in the absence of a binary complex greater than 1 µM, preferably greater than 5 µM, and more preferably greater than 10 µM. In another alternative, target proteins which do not naturally associate with a presenter protein are those which have an affinity for a binary complex of cyclosporine, rapamycin, or FK506 and a presenter protein (e.g., FKBP) of greater than 1 µM, preferably greater than 5 µM, and more preferably greater than 10 µM. In yet another alternative, target proteins which do not naturally associate with a presenter protein are those which are other than calcineurin or mTOR. The selection of suitable target proteins for the complexes and methods of the invention may depend on the presenter protein. For example, target proteins that have low affinity for a cyclophilin may have high affinity for an FKBP and would not be used together with the latter.

Target proteins can be naturally occurring, e.g., wild type. Alternatively, a target protein can vary from the wild type protein but still retain biological function, e.g., as an allelic variant, a splice mutant or a biologically active fragment.

In some embodiments, a target protein is a transmembrane protein. In some embodiments, a target protein has a coiled coil structure. In certain embodiments, a target protein is one protein of a dimeric complex.

In some embodiments, a target protein of the invention includes one or more surface sites (e.g., a flat surface site) characterized in that, in the absence of forming a presenter protein/compound complex, small molecules typically demonstrate low or undetectable binding to the site(s). In some embodiments, a target protein includes one or more surface sites (e.g., a flat surface site) to which, in the absence of forming a presenter protein/compound complex, a particular small molecule (e.g., the compound) shows low or undetectable binding (e.g., binding at least 2, 3, 4, 5, 6, 7, 8, 9, 10, 20, 30, 40, 50, 100 fold or more lower than that observed with a presenter protein/compound complex involving the same compound). In some embodiments, a target protein has a surface characterized by one or more sites (and, in some embodiments, an entire surface) that lack(s) any a traditional binding pocket, for example, a cavity or pocket on the protein structure with physiochemical and/or geometric properties comparable to proteins whose activity has been modulated by one or more small molecules. In certain embodiments, a target protein has a traditional binding pocket and a site for a protein-protein interaction. In some embodiments, a target protein is an undruggable target, for example, a target protein is not a member of a protein family which is known to be targeted by drugs and/or does not possess a binding site that is expected (e.g., according to art-accepted understanding, as discussed herein) to be suitable for binding to a small molecule.

In some embodiments, the target protein is a GTPase such as DIRAS1, DIRAS2, DIRAS3, ERAS, GEM, HRAS, KRAS, MRAS, NKIRAS1, NKIRAS2, NRAS, RALA, RALB, RAP1A, RAP1B, RAP2A, RAP2B, RAP2C, RASD1, RASD2, RASL10A, RASL10B, RASL11A, RASL11B, RASL12, REM1, REM2, RERG, RERGL, RRAD, RRAS, RRAS2, RHOA, RHOB, RHOBTB1, RHOBTB2, RHOBTB3, RHOC, RHOD, RHOF, RHOG, RHOH, RHOJ, RHOQ, RHOU, RHOV, RND1, RND2, RND3, RAC1, RAC2, RAC3, CDC42, RAB1A, RAB1B, RAB2, RAB3A, RAB3B, RAB3C, RAB3D, RAB4A, RAB4B, RAB5A, RAB5B, RAB5C, RAB6A, RAB6B, RAB6C, RAB7A, RAB7B, RAB7L1, RAB8A, RAB8B, RAB9, RAB9B, RABL2A, RABL2B, RABL4, RAB10, RAB11A, RAB11B, RAB12, RAB13, RAB14, RAB15, RAB17, RAB18, RAB19, RAB20, RAB21, RAB22A, RAB23, RAB24, RAB25, RAB26, RAB27A, RAB27B, RAB28, RAB2B, RAB30, RAB31, RAB32, RAB33A, RAB33B, RAB34, RAB35, RAB36, RAB37, RAB38, RAB39, RAB39B, RAB40A, RAB40AL, RAB40B, RAB40C, RAB41, RAB42, RAB43, RAP1A, RAP1B, RAP2A, RAP2B, RAP2C, ARF1, ARF3, ARF4, ARF5, ARF6, ARL1, ARL2, ARL3, ARL4, ARL5, ARL5C, ARL6, ARL7, ARL8, ARL9, ARL10A, ARL10B, ARL10C, ARL11, ARL13A, ARL13B, ARL14, ARL15, ARL16, ARL17, TRIM23, ARL4D, ARFRP1, ARL13B, RAN, RHEB, RHEBL1, RRAD, GEM, REM, REM2, RIT1, RIT2, RHOT1, or RHOT2. In some embodiments, the target protein is a GTPas activating protein such as NF1, IQGAP1, PLEXIN-B1, RASAL1, RASAL2, ARHGAP5, ARHGAP8, ARHGAP12, ARHGAP22, ARHGAP25, BCR, DLC1, DLC2, DLC3, GRAF, RALBP1, RAP1GAP, SIPA1, TSC2, AGAP2, ASAP1, or ASAP3. In some embodiments, the target protein is a Guanine nucleotide-exchange factor such as CNRASGEF, RASGEF1A, RASGRF2, RASGRP1, RASGRP4, SOS1, RALGDS, RGL1, RGL2, RGR, ARHGEF10, ASEF/ARHGEF4, ASEF2, DBS, ECT2, GEF-H1, LARG, NET1, OBSCURIN, P-REX1, P-REX2, PDZ-RHOGEF, TEM4, TIAM1, TRIO, VAV1, VAV2, VAV3, DOCK1, DOCK2, DOCK3, DOCK4, DOCK8, DOCK10, C3G, BIG2/ARFGEF2, EFA6, FBX8, or GEP100. In certain embodiments, the target protein is a protein with a protein-protein interaction domain such as ARM; BAR; BEACH; BH; BIR; BRCT; BROMO; BTB; C1; C2; CARD; CC; CALM; CH; CHROMO; CUE; DEATH; DED; DEP; DH; EF-hand; EH; ENTH; EVH1; F-box; FERM; FF; FH2; FHA; FYVE; GAT; GEL; GLUE; GRAM; GRIP; GYF; HEAT; HECT; IQ; LRR; MBT; MH1; MH2; MIU; NZF; PAS; PB1; PDZ; PH; POLO-Box; PTB; PUF; PWWP; PX; RGS; RING; SAM; SC; SH2; SH3; SOCS; SPRY; START; SWIRM; TIR; TPR; TRAF; SNARE; TUBBY; TUDOR; UBA; UEV; UIM; VHL; VHS; WD40; WW; SH2; SH3; TRAF; Bromodomain; or TPR. In some embodiments, the target protein is a heat shock protein such as Hsp20, Hsp27, Hsp70, Hsp84, alpha B crystalline, TRAP-1, hsf1, or Hsp90. In certain embodiments, the target protein is an ion channel such as Cav2.2, Cav3.2, IKACh, Kv1.5, TRPA1, NAv1.7, Nav1.8, Nav1.9, P2X3, or P2X4. In some embodiments, the target protein is a coiled-coil protein such as geminin, SPAG4, VAV1, MAD1, ROCK1, RNF31, NEDP1, HCCM, EEA1, Vimentin, ATF4, Nemo, SNAP25, Syntaxin 1a, FYCO1, or CEP250. In certain embodiments, the target protein is a kinase such as ABL, ALK, AXL, BTK, EGFR, FMS, FAK, FGFR1, 2, 3, 4, FLT3, HER2/ErbB2, HER3/ErbB3, HER4/ErbB4, IGF1R, INSR, JAK1, JAK2, JAK3, KIT, MET, PDGFRA, PDGFRB, RET RON, ROR1, ROR2, ROS, SRC, SYK, TIE1, TIE2, TRKA, TRKB, KDR, AKT1, AKT2, AKT3, PDK1, PKC, RHO, ROCK1, RSK1, RKS2, RKS3, ATM, ATR, CDK1, CDK2, CDK3, CDK4, CDK5, CDK6, CDK7, CDK8, CDK9, CDK10, ERK1, ERK2, ERK3, ERK4, GSK3A, GSK3B, JNK1, JNK2, JNK3, AurA, ARuB, PLK1, PLK2, PLK3, PLK4, IKK, KIN1, cRaf, PKN3, c-Src, Fak, PyK2, or AMPK. In some embodiments, the target protein is a phosphatase such as WIP1, SHP2, SHP1, PRL-3, PTP1B, or STEP. In certain embodiments the target protein is a ubiquitin ligase such as BMI-1, MDM2, NEDD4-1, Beta-TRCP, SKP2, E6AP, or APC/C. In some embodiments, the target protein is a chromatin modifier/remodeler such as a chromatin modifier/remodeler encoded by the gene BRG1, BRM, ATRX, PRDM3, ASH1L, CBP, KAT6A, KAT6B, MLL, NSD1, SETD2, EP300, KAT2A, or CREBBP. In some embodiments, the target protein is a transcription factor such as a transcription factor encoded by the gene EHF, ELF1, ELF3, ELF4, ELF5, ELK1, ELK3, ELK4, ERF, ERG, ETS1, ETV1, ETV2, ETV3, ETV4, ETV5, ETV6, FEV, FLI1, GAVPA, SPDEF, SPI1, SPIC, SPIB, E2F1, E2F2, E2F3, E2F4, E2F7, E2F8, ARNTL, BHLHA15, BHLHB2, BHLBHB3, BHLHE22, BHLHE23, BHLHE41, CLOCK, FIGLA, HAS5, HES7, HEY1, HEY2, ID4, MAX, MESP1, MLX, MLXIPL, MNT, MSC, MYF6, NEUROD2, NEUROG2, NHLH1, OLIG1, OLIG2, OLIG3, SREBF2, TCF3, TCF4, TFAP4, TFE3, TFEB, TFEC, USF1, ARF4, ATF7, BATF3, CEBPB, CEBPD, CEBPG, CREB3, CREB3L1, DBP, HLF, JDP2, MAFF, MAFG, MAFK, NRL, NFE2, NFIL3, TEF, XBP1, PROX1, TEAD1, TEAD3, TEAD4, ONECUT3, ALX3, ALX4, ARX, BARHL2, BARX, BSX, CART1, CDX1, CDX2, DLX1, DLX2, DLX3, DLX4, DLX5, DLX6, DMBX1, DPRX, DRGX, DUXA, EMX1, EMX2, EN1, EN2, ESX1, EVX1, EVX2, GBX1, GBX2, GSC, GSC2, GSX1, GSX2, HESX1, HMX1, HMX2, HMX3, HNF1A, HNF1B, HOMEZ, HOXA1, HOXA10, HOXA13, HOXA2, HOXAB13, HOXB2, HOXB3, HOXB5, HOXC10, HOXC11, HOXC12, HOXC13, HOXD11, HOXD12, HOXD13, HOXD8, IRX2, IRX5, ISL2, ISX, LBX2, LHX2, LHX6, LHX9, LMX1A, LMX1B, MEIS1, MEIS2, MEIS3, MEOX1, MEOX2, MIXL1, MNX1, MSX1, MSX2, NKX2-3, NKX2-8, NKX3-1, NKX3-2, NKX6-1, NKX6-2, NOTO, ONECUT1, ONECUT2, OTX1, OTX2, PDX1, PHOX2A, PHOX2B, PITX1, PITX3, PKNOX1, PROP1, PRRX1, PRRX2, RAX, RAXL1, RHOXF1, SHOX, SHOX2, TGIF1, TGIF2, TGIF2LX, UNCX, VAX1, VAX2, VENTX, VSX1, VSX2, CUX1, CUX2, POU1F1, POU2F1, POU2F2, POU2F3, POU3F1, POU3F2, POU3F3, POU3F4, POU4F1, POU4F2, POU4F3, POU5F1P1, POU6F2, RFX2, RFX3, RFX4, RFX5, TFAP2A, TFAP2B, TFAP2C, GRHL1, TFCP2, NFIA, NFIB, NFIX, GCM1, GCM2, HSF1, HSF2, HSF4, HSFY2, EBF1, IRF3, IRF4, IRF5, IRF7, IRF8, IRF9, MEF2A, MEF2B, MEF2D, SRF, NRF1, CPEB1, GMEB2, MYBL1, MYBL2, SMAD3, CENPB, PAX1, PAX2, PAX9, PAX3, PAX4, PAX5, PAX6, PAX7, BCL6B, EGR1, EGR2, EGR3, EGR4, GLIS1, GLIS2, GLI2, GLIS3, HIC2, HINFP1, KLF13, KLF14, KLF16, MTF1, PRDM1, PRDM4, SCRT1, SCRT2, SNAI2, SP1, SP3, SP4, SP8, YY1, YY2, ZBED1, ZBTB7A, ZBTB7B, ZBTB7C, ZIC1, ZIC3, ZIC4, ZNF143, ZNF232, ZNF238, ZNF282, ZNF306, ZNF410, ZNF435, ZBTB49, ZNF524, ZNF713, ZNF740, ZNF75A, ZNF784, ZSCAN4, CTCF, LEF1, SOX10, SOX14, SOX15, SOX18, SOX2, SOX21, SOX4, SOX7, SOX8, SOX9, SRY, TCF7L1, FOXO3, FOXB1, FOXC1, FOXC2, FOXD2, FOXD3, FOXG1, FOXI1, FOXJ2, FOXJ3, FOXK1, FOXL1, FOXO1, FOXO4, FOXO6, FOXP3, EOMES, MGA, NFAT5, NFATC1, NFKB1, NFKB2, TP63, RUNX2, RUNX3, T, TBR1, TBX1, TBX15, TBX19, TBX2, TBX20, TBX21, TBX4, TBX5, AR, ESR1, ESRRA, ESRRB, ESRRG, HNF4A, NR2C2, NR2E1, NR2F1, NR2F6, NR3C1, NR3C2, NR4A2, RARA, RARB, RARG, RORA, RXRA, RXRB, RXRG, THRA, THRB, VDR, GATA3, GATA4, or GATA5; or C-myc, Max, Stat3, androgen receptor, C-Jun, C-Fox, N-Myc, L-Myc, MITF, Hif-1alpha, Hif-2alpha, Bcl6, E2F1, NF-kappaB, Stat5, or ER(coact). In certain embodiments, the target protein is TrkA, P2Y14, mPEGS, ASK1, ALK, Bcl-2, BCL-XL, mSIN1, RORγt, IL17RA, eIF4E, TLR7 R, PCSK9, IgE R, CD40, CD40L, Shn-3, TNFR1, TNFR2, IL31RA, OSMR, IL12beta1,2, Tau, FASN, KCTD 6, KCTD 9, Raptor, Rictor, RALGAPA, RALGAPB, Annexin family members, BCOR, NCOR, beta catenin, AAC 11, PLD1, PLD2, Frizzled7, RaLP, MLL-1, Myb, Ezh2, RhoGD12, EGFR, CTLA4R, GCGC (coact), Adiponectin R2, GPR 81, IMPDH2, IL-4R, IL-13R, IL-1R, IL2-R, IL-6R, IL-22R, TNF-R, TLR4, Nrlp3, or OTR.

Complexes

Presenter Protein/Compound Complexes

In naturally occurring protein-protein interactions, the binding event is driven largely by hydrophobic residues on flat surface sites of the two proteins, in contrast to many small molecule-protein interactions which are driven by interactions between the small molecule in a cavity or pocket on the protein. The hydrophobic residues on the flat surface site form hydrophobic hot spots on the two interacting proteins wherein most of the binding interactions between the two proteins are van der Waals interactions. Small molecules may be used as portable hotspots for proteins which are lacking one (e.g., presenter proteins) through the formation of complexes (e.g., a presenter protein/compound complex) to participate in pseudo protein-protein interactions (e.g., forming a tripartite complex with a target protein).

Many mammalian proteins are able to bind to any of a plurality of different partners; in some cases, such alternative binding interactions contribute to biological activity of the proteins. Many of these proteins adapt the inherent variability of the hot spot protein regions to present the same residues in different structural contexts. More specifically, the protein-protein interactions can be mediated by a class of natural products produced by a select group of fungal and bacterial species. These molecules exhibit both a common structural organization and resultant functionality that provides the ability to modulate protein-protein interaction. These molecules contain a presenter protein binding moiety that is highly conserved and a target protein interacting moiety that exhibits a high degree of variability among the different natural products. The presenter protein binding moiety confers specificity for the presenter protein and allows the molecule to bind to the presenter protein to form a binary complex; the mammalian target protein interacting moiety confers specificity for the target protein and allows the binary complex to bind to the target protein, typically modulating (e.g., positively or negatively modulating) its activity.

These natural products are presented by presenter proteins, such as FKBPs and cyclophilins and act as diffusible, cell-penetrant, orally bio-available adaptors for protein-protein interactions. Examples include well known and clinically relevant molecules such as Rapamycin (Sirolimus), FK506 (Tacrolimus), and Cyclosporin. In brief, these molecules bind endogenous intracellular presenter proteins, the FKBPs e.g. rapamycin and FK506 or cyclophilins e.g. diluents, and the resulting binary complexes of presenter protein-bound molecules selectively bind and inhibit the activity of intracellular target proteins. Formation of a tripartite complex between the presenter protein, the molecule, and the target protein is driven by both protein-molecule and protein-protein interactions and both are required for inhibition of the target protein. In the example of the FKBP-rapamycin complex, the intracellular target is the serine-threonine kinase mTOR, whereas for FKBP-FK506 complex, the intracellular target is the phosphatase calcineurin. Of particular interest in the preceding two examples, FKBP12 is utilized as a partner presentation protein by both the rapamycin and FK506 presentation ligands. Moreover, the sub-structure components of rapamycin and FK506 responsible for binding to FKBP12 are closely related structurally, i.e. the so-called "Conserved Region," but it is the dramatic structural differences between rapamycin and FK506 in the non FKBP12-binding regions, i.e. the "Variable Region," that results in the specific targeting of two distinct intracellular proteins, mTOR and calcineurin, respectively. In this fashion, the Variable Regions of rapamycin and FK506 are serving as contributors to the binding energy necessary for enabling presenter protein-target protein interaction.

In some embodiments, a presenter protein/compound complexes of the invention bind to a target protein with at least 5-fold (e.g., at least 10-fold, at least 20-fold, at least 30-fold, at least 40-fold, at least 50-fold, at least 100-fold) greater affinity than the complex binds to each of mTOR and/or calcineurin.

In some embodiments, a presenter protein/compound complexes of the invention bind to a target protein with at least 5-fold (e.g., at least 10-fold, at least 20-fold, at least 30-fold, at least 40-fold, at least 50-fold, at least 100-fold) greater affinity than the affinity of the compound to a target protein when the compound is not bound in a complex with a presenter protein.

In certain embodiments, a presenter protein/compound complexes of the invention bind to a target protein with at least 5-fold (e.g., at least 10-fold, at least 20-fold, at least 30-fold, at least 40-fold, at least 50-fold, at least 100-fold) greater affinity than the affinity of the presenter protein to a target protein when the presenter protein is not bound in a complex with a compound.

In some embodiments, a presenter protein/compound complexes of the invention inhibit a naturally occurring interaction between a target protein and a ligand, such as a protein or a small molecule that specifically binds to the target protein.

In certain embodiments, when the presenter protein is a prolyl isomerase, the prolyl isomerase activity is inhibited by formation of the presenter protein/compound complex. In some embodiments of the presenter protein/compound complexes of the invention, the compound specifically binds to said presenter protein with a $K_D$ of less than 10 µM (e.g., less than 5 µM, less than 1 µM, less than 500 nM, less than 200 nM, less than 100 nM, less than 75 nM, less than 50 nM, less than 25 nM, less than 10 nM) or inhibits the peptidyl-prolyl isomerase activity of the presenter protein, for example, with an $IC_{50}$ of less than 1 µM (e.g., less than 0.5 µM, less than 0.1 µM, less than 0.05 µM, less than 0.01 µM).

Tripartite Complexes

The vast majority of small molecule drugs act by binding a functionally important site on a target protein, thereby modulating (e.g., positively or negatively modulating) the activity of that protein. For example, the cholesterol-lowering drugs statins bind the enzyme active site of HMG-CoA reductase, thus preventing the enzyme from engaging with its substrates. The fact that many such drug/target interacting pairs are known may have misled some into believing that a small molecule modulator could be discovered for most, if not all, proteins provided a reasonable amount of time, effort, and resources. This is far from the case. Current estimates hold that only about 10% of all human proteins are targetable by small molecules. The other 90% are currently considered refractory or intractable toward small molecule drug discovery. Such targets are commonly referred to as "undruggable." These undruggable targets include a vast and largely untapped reservoir of medically important human proteins. Thus, there exists a great deal of interest in discovering new molecular modalities capable of modulating the function of such undruggable targets.

The present invention encompasses the recognition that small molecules are typically limited in their targeting ability because their interactions with the target are driven by adhesive forces, the strength of which is roughly proportional to contact surface area. Because of their small size, the only way for a small molecule to build up enough intermolecular contact surface area to effectively interact with a target protein is to be literally engulfed by that protein. Indeed, a large body of both experimental and computational data supports the view that only those proteins having a hydrophobic "pocket" on their surface are capable of binding small molecules. In those cases, binding is enabled by engulfment. Not a single example exists of a small molecule binding with high-affinity to a protein outside of a hydrophobic pocket.

Nature has evolved a strategy that allows a small molecule to interact with target proteins at sites other than hydrophobic pockets. This strategy is exemplified by the naturally occurring immunosuppressive drugs cyclosporine A, rapamycin, and FK506. The activity of these drugs involves the formation of a high-affinity complex of the small molecule with a small presenting protein. The composite surface of the small molecule and the presenting protein then engages the target. Thus, for example, the binary complex formed between cyclosporine A and cyclophilin A targets calcineurin with high affinity and specificity, but neither cyclosporine A or cyclophilin A alone binds calcineurin with measurable affinity.

Many important therapeutic targets exert their function by complexation with other proteins. The protein/protein interaction surfaces in many of these systems contain an inner core of hydrophobic side chains surrounded by a wide ring of polar residues. The hydrophobic residues contribute nearly all of the energetically favorable contacts, and hence this cluster has been designated as a "hotspot" for engagement in protein-protein interactions. Importantly, in the aforementioned complexes of naturally occurring small molecules with small presenting proteins, the small molecule provides a cluster of hydrophobic functionality akin to a hotspot, and the protein provides the ring of mostly polar residues. In other words, presented small molecule systems mimic the surface architecture employed widely in natural protein/protein interaction systems.

Compounds (e.g., macrocyclic compounds) of the invention are capable of modulating biological processes, for example through binding to a presenter protein (e.g., a member of the FKBP family, a member of the cyclophilin family, or PIN1) to form a presenter protein/compound complex as described above which binds to a target protein to form a tripartite complex. The formation of these tripartite complexes allow for modulation of proteins that do not have traditional binding pockets and/or are considered undruggable. The presenter protein/compound complexes are able to modulate biological processes through cooperative binding between the compound and the presenter protein. Both the compound and presenter protein have low affinity for the target protein alone, but the presenter protein/compound complex has high affinity for the target protein. Cooperative binding can be determined by measurement of the buried surface area of the target protein that includes atoms from the compound and/or presenter protein and/or by measurement of the free binding energy contribution of the compound and/or presenter protein. Binding is considered cooperative if at least one atom from each of the compound and presenter protein participates in binding with the target protein.

The binding of a presenter protein/compound complex and a target protein is achieved through formation of a combined binding site including residues from both the presenter protein and compound that allow for increased affinity that would not be possible with either the presenter protein or compound alone. For example at least 20% (e.g., at least 25%, at least 30%, at least 35%, at least 40%, at least 45%, at least 50%) of the total buried surface area of the target protein in the tripartite complex includes one or more atoms that participate in binding to the compound and/or at least 20% (e.g., at least 25%, at least 30%, at least 35%, at least 40%, at least 45%, at least 50%) of the total buried surface area of the target protein in the tripartite complex includes one or more atoms that participate in binding to the presenter protein. Alternatively, the compound contributes at least 10% (e.g., at least 20%, at least 25%, at least 30%, at least 35%, at least 40%, at least 45%, at least 50%, at least 60%, at least 70%, at least 80%, at least 90%) of the total binding free energy of the tripartite complex and/or the presenter protein contributes at least 10% (e.g., at least 20% at least 25%, at least 30%, at least 35%, at least 40%, at least 45%, at least 50%, at least 60%, at least 70%, at least 80%, at least 90%) of the total binding free energy of the tripartite complex.

In some embodiments, a presenter protein/compound complex binds at a flat surface site on a target protein. In some embodiments, a compound (e.g., macrocyclic compound) in a presenter protein/compound complex binds at a hydrophobic surface site on a target protein, e.g., a site that includes at least 50% hydrophobic residues. In some embodiments, at least 70% of the binding interactions between one or more of the atoms of a compound and one or more atoms of a target protein are van der Waals and/or π-effect interactions. In certain embodiments, a presenter protein/compound complex binds to a target protein at a site of a naturally occurring protein-protein interaction between a target protein and a protein that specifically binds the target protein. In some embodiments, a presenter protein/compound complex does not bind at an active site of a target protein. In some embodiments, a presenter protein/compound complex binds at an active site of a target protein.

A characteristic of compounds of the invention that form tripartite complexes with a presenter protein and a target protein is a lack of major structural reorganization in the presenter protein/compound complex compared to the tripartite complex. This lack of major structural reorganization results in a low entropic cost to reorganize into a configuration favorable for the formation of the tripartite complex once the presenter protein/compound complex has been formed. For example, threshold quantification of RMSD can be measured using the align command in PyMOL version 1.7rc1 (Schrödinger LLC). Alternatively, RMSD can be calculated using the ExecutiveRMS parameter from the algorithm LigAlign (J. Mol. Graphics and Modelling 2010, 29, 93-101). In some embodiments, the structural organization of the compound (i.e., the average three dimensional configuration of the atoms and bonds of the molecule) is substantially unchanged in the tripartite complex compared to the compound when in the presenter protein/compound complex before binding to the target protein. For example, the root mean squared deviation (RMSD) of the two aligned structures is less than 1.

Utility and Administration

Compounds and presenter protein/compound complexes described herein are useful in the methods of the invention and, while not bound by theory, are believed to exert their desirable effects through their ability to modulate (e.g., positively or negatively modulate) the activity of a target protein (e.g., a eukaryotic target protein such as a mammalian target protein or a fungal target protein or a prokaryotic target protein such as a bacterial target protein), through interaction with presenter proteins and the target protein.

Kits

In some embodiments, the present invention relates to a kit for conveniently and effectively carrying out the methods in accordance with the present invention. In general, the pharmaceutical pack or kit comprises one or more containers filled with one or more of the ingredients of the pharmaceutical compositions of the invention. Such kits are especially suited for the delivery of solid oral forms such as tablets or capsules. Such a kit preferably includes a number of unit dosages, and may also include a card having the dosages oriented in the order of their intended use. If desired, for instance if the subject suffers from Alzheimer's disease, a memory aid can be provided, for example in the form of numbers, letters, or other markings or with a calendar insert, designating the days in the treatment schedule in which the dosages can be administered. Alternatively, placebo dosages, or calcium dietary supplements, either in a form similar to or distinct from the dosages of the pharmaceutical compositions, can be included to provide a kit in which a dosage is taken every day. Optionally associated with such container(s) can be a notice in the form prescribed by a governmental agency regulating the manufacture, use or sale of pharmaceutical products, which notice reflects approval by the agency of manufacture, use or sale for human administration.

Pharmaceutical Compositions

For use as treatment of human and animal subjects, the compounds of the invention can be formulated as pharmaceutical or veterinary compositions. Depending on the subject to be treated, the mode of administration, and the type of treatment desired—e.g., prevention, prophylaxis, or therapy—the compounds are formulated in ways consonant with these parameters. A summary of such techniques is found in *Remington: The Science and Practice of Pharmacy*, 21$^{st}$ Edition, Lippincott Williams & Wilkins, (2005); and *Encyclopedia of Pharmaceutical Technology*, eds. J. Swarbrick and J. C. Boylan, 1988-1999, Marcel Dekker, New York, each of which is incorporated herein by reference.

Compounds described herein may be present in amounts totaling 1-95% by weight of the total weight of the composition. The composition may be provided in a dosage form that is suitable for intraarticular, oral, parenteral (e.g., intravenous, intramuscular), rectal, cutaneous, subcutaneous, topical, transdermal, sublingual, nasal, vaginal, intravesicular, intraurethral, intrathecal, epidural, aural, or ocular administration, or by injection, inhalation, or direct contact with the nasal, genitourinary, reproductive or oral mucosa. Thus, the pharmaceutical composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, preparations suitable for iontophoretic delivery, or aerosols. The compositions may be formulated according to conventional pharmaceutical practice.

In general, for use in treatment, compounds described herein may be used alone, or in combination with one or more other active agents. An example of other pharmaceuticals to combine with the compounds described herein would include pharmaceuticals for the treatment of the same indication. Another example of a potential pharmaceutical to combine with compounds described herein would include pharmaceuticals for the treatment of different yet associated or related symptoms or indications. Depending on the mode of administration, compounds will be formulated into suitable compositions to permit facile delivery. Each compound of a combination therapy may be formulated in a variety of ways that are known in the art. For example, the first and second agents of the combination therapy may be formulated together or separately. Desirably, the first and second agents are formulated together for the simultaneous or near simultaneous administration of the agents.

Compounds of the invention may be prepared and used as pharmaceutical compositions comprising an effective amount of a compound described herein and a pharmaceutically acceptable carrier or excipient, as is well known in the art. In some embodiments, a composition includes at least two different pharmaceutically acceptable excipients or carriers.

Formulations may be prepared in a manner suitable for systemic administration or topical or local administration. Systemic formulations include those designed for injection (e.g., intramuscular, intravenous or subcutaneous injection) or may be prepared for transdermal, transmucosal, or oral administration. A formulation will generally include a diluents as well as, in some cases, adjuvants, buffers, preservatives and the like. Compounds can be administered also in liposomal compositions or as microemulsions.

For injection, formulations can be prepared in conventional forms as liquid solutions or suspensions or as solid forms suitable for solution or suspension in liquid prior to injection or as emulsions. Suitable excipients include, for example, water, saline, dextrose, glycerol and the like. Such compositions may also contain amounts of nontoxic auxiliary substances such as wetting or emulsifying agents, pH buffering agents and the like, such as, for example, sodium acetate, sorbitan monolaurate, and so forth.

Various sustained release systems for drugs have also been devised. See, for example, U.S. Pat. No. 5,624,677, which is herein incorporated by reference.

Systemic administration may also include relatively non-invasive methods such as the use of suppositories, transdermal patches, transmucosal delivery and intranasal administration. Oral administration is also suitable for compounds of the invention. Suitable forms include syrups, capsules, and tablets, as is understood in the art.

Each compound of a combination therapy, as described herein, may be formulated in a variety of ways that are known in the art. For example, the first and second agents of the combination therapy may be formulated together or separately.

The individually or separately formulated agents can be packaged together as a kit. Non-limiting examples include, but are not limited to, kits that contain, e.g., two pills, a pill and a powder, a suppository and a liquid in a vial, two topical creams, etc. The kit can include optional components that aid in the administration of the unit dose to subjects, such as vials for reconstituting powder forms, syringes for injection, customized IV delivery systems, inhalers, etc. Additionally, the unit dose kit can contain instructions for preparation and administration of the compositions. The kit may be manufactured as a single use unit dose for one subject, multiple uses for a particular subject (at a constant dose or in which the individual compounds may vary in potency as therapy progresses); or the kit may contain multiple doses suitable for administration to multiple subjects ("bulk packaging"). The kit components may be assembled in cartons, blister packs, bottles, tubes, and the like.

Formulations for oral use include tablets containing the active ingredient(s) in a mixture with nontoxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

Two or more compounds may be mixed together in a tablet, capsule, or other vehicle, or may be partitioned. In one example, the first compound is contained on the inside of the tablet, and the second compound is on the outside, such that a substantial portion of the second compound is released prior to the release of the first compound.

Formulations for oral use may also be provided as chewable tablets, or as hard gelatin capsules wherein the active ingredient is mixed with an inert solid diluents (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

The liquid forms in which the compounds and compositions of the present invention can be incorporated for administration orally include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Generally, when administered to a human, the oral dosage of any of the compounds of the combination of the invention will depend on the nature of the compound, and can readily be determined by one skilled in the art. Typically, such dosage is normally about 0.001 mg to 2000 mg per day, desirably about 1 mg to 1000 mg per day, and more desirably about 5 mg to 500 mg per day. Dosages up to 200 mg per day may be necessary.

Administration of each drug in a combination therapy, as described herein, can, independently, be one to four times daily for one day to one year, and may even be for the life of the subject. Chronic, long-term administration may be indicated.

The following Examples are intended to illustrate the synthesis of a representative number of compounds and the use of these compounds for the induction of chemotaxis and antifungal activity. Accordingly, the Examples are intended to illustrate but not to limit the invention. Additional compounds not specifically exemplified may be synthesized using conventional methods in combination with the methods described herein.

EXAMPLES

Example 1. General Fermentation and Isolation Protocols

Compounds synthesized by bacterial strains may be fermented and isolated using the following general protocol:

General Fermentation Protocol

Strains: Bacterial strains such as *Streptomyces malaysiensis* DSM41697, other producing species or genetically modified derivatives producing FKBP ligands (Example: F1, F2, F3 or structurally similar compounds and their analogs) were propagated aseptically on a solid medium (Example: ISP4).

Working cell bank: Spores or mycelia derived from the cultures grown on a solid medium plate at 30° C. for 3-14 d were used to inoculate a liquid culture (Example: 40 ml ATCC172 liquid medium in an 250 ml Erlenmeyer flask). The culture was incubated with shaking at 30° C. for 2-3 d. The resulting cell suspension was mixed with sterile 50% glycerol giving a mixture containing a final concentration of 15-25% glycerol. Aliquots (about 1 ml) of glycerol-mycelia mixture were stored at −80° C. in sterile cryovials until further use.

Primary seed culture: Primary seed cultures (Example: 40 mL ATCC172 medium in a 250 mL Erlenmeyer flask) were inoculated with 1 mL working cell bank suspension. Cultures were incubated on a shaker with a 2-inch throw at 200-220 rpm for 2-3 d at 30° C.

Secondary seed culture: Secondary seed cultures (Example: 100-200 mL ATCC172 in an 500 mL Erlenmeyer flask) were inoculated with the primary seed cultures (5% v/v) and incubated as described above with various incubation periods of time (Example: 18-48 h).

Production fermentation in flasks: Production fermentation was done in a 1.8 L Fernbach or Erlenmeyer flask containing 0.5 L production medium supporting biosynthesis of these compounds (Example: Medium 8430 or its derivatives). The culture was inoculated with a seed culture prepared as described above at 2-5% (v/v), and incubated as described above conditions for 3-7 d.

Production fermentation in bioreactors: Production fermentation was done in a bioreactor (7.5 L capacity, New Brunswick Scientific, NJ, USA) controlled by a BioFlo 300 module. The bioreactor containing 5 L of sterilized medium (Example: 8430 and its derivatives) was inoculated with a seed culture (2-5%, v/v) and incubated for 3-7 d with or without controlled parameters such as dissolved oxygen amounts (Example: 10-50%), propeller speed (Example 200-500 rpm), pH (Example: pH 4.5-7.0), temperature (Example: 25-35° C.), and nutrient feeding when appropriate.

| ISP4 (per liter) | |
|---|---|
| Soluble Starch | 10.0 g |
| Dipotassium Phosphate | 1.0 g |
| Magnesium Sulfate USP | 1.0 g |
| Sodium Chloride | 1.0 g |
| Ammonium Sulfate | 2.0 g |
| Calcium Carbonate | 2.0 g |
| Ferrous Sulfate | 1.0 mg |

| ISP4 (per liter) | |
|---|---|
| Manganous Chloride | 1.0 mg |
| Zinc Sulfate | 1.0 mg |
| Agar | 20.0 g |

TABLE 2

| ATCC #172 media (per liter) | |
|---|---|
| Yeast extract | 5 g |
| Difco Soluble Starch | 20 g |
| Dextrose | 10 g |
| NZ Amine A | 5 g |
| Calcium Carbonate | 3 g |

Add distilled water to 1000 mL, no pH adjustment.

TABLE 3

| 8430 Medium | |
|---|---|
| Component | Amount |
| Pharmamedia or Proflo powder (ADM) | 10 g |
| D-Mannitol | 20 g |
| Yeast extract | 1.0 g |
| $KH_2PO_4$ | 0.10 g |
| MES buffer, hemi-Na+ salt (100 mM final) | 20.67 g (adjust media to pH 6.5 final with 5N NaOH) |
| $MgSO_4$—$7H_2O$ (Anh.) | 0.05 g/L |
| $CaCl_2$—$2H_2O$ | 0.02 g/L |
| R2 trace elements solution* | 2 mL |

Add distilled water to 1000 mL.

Proflo oil containing dominantly oleate and palmitate was added (4 mL/L) as an antifoam agent.

TABLE 4

| *R2 trace element solution. | |
|---|---|
| Element | Amount (mg/L) |
| $ZnSO_4$—$7H_2O$ | 40 |
| $FeCl_3$—$6H_2O$ | 200 |
| $CuCl_2$—$2H_2O$ | 10 |
| $MnCl2$—$2H_2O$ | 10 |
| $Na_2B_4O_7$—$10H_2O$ | 10 |
| $(NH_4)_6Mo_7O_{24}$—$4H_2O$ | 10 |

General Isolation Protocol

Fermentation broth of a strain producing specific compounds was separated to supernatant and microbial pellets by centrifugation. Target compounds in the supernatant can be extracted either with partition extraction using water-immiscible solvents such as dichloromethane (DCM), ethyl acetate (EtOAc), etc or with solid phase extraction by mixing with non-polar resins such as HP20, HP20ss, etc. The target compounds in the pellets can be extracted repeatedly (4×) using ethyl EtOAc-methanol (9:1, v/v). The microbial extracts are pooled in preparation for concentrating in vacuo. To this extract can be added the material eluted from the HP20 beads (using organic solvents such as methanol (MeOH), DCM, acetonitrile, isopropanol (IPA), etc) and/or the organic phase of the liquid/liquid extraction of the original supernatant.

The combined extracts are filtered through Celite and dried in vacuo yielding a primary crude and this material is weighed. The primary crude is dissolved in minimal 100% MeOH or a mixture of DCM and tetrahydrofuran (THF). To this a binding medium such as silica gel powder is added to the flask and re-dried in vacuo for normal-phase silica gel column chromatography. The ratio of crude to silica gel in the column bed is preferably ca. 1:5 (wt/wt). The crude material can be fractionated over a RediSep® Normal-phase Silica Flash Column using step gradients, linear gradients or isocratic elution conditions. Elution solvents can include hexane, heptane, ethyl acetate, ethanol, acetone, isopropanol, or other organic solvents, or combination. Fractions with enriched target compound(s) are pooled and dried for further purification after LC/MS analysis and/or Thin Layer Chromatography (TLC) analysis.

Further purification could be achieved via normal-phase or specific prep-HPLC columns such as Waters Spherisorb CN, Waters Prep Silica, or Kromacil 60-5DIOL. Elution solvents can also include hexane, heptane, ethyl acetate, ethanol, acetone, isopropanol, or other organic solvents, or combination. Fractions with enriched or pure target compound(s) are pooled and dried for further workup after LC/MS analysis and/or Thin Layer Chromatography (TLC) analysis.

Additional purification could be achieved various reverse-phase prep-HPLC depending on the complexity of the enriched material and target compounds' properties such as polarity, solubility, etc. Reverse-phase Prep-HPLC columns employed for separation include Waters Sunfire Prep C18 OBD, Waters Xbridge Prep C18 OBD, Kromacil C4, Thermo Acclaim Polar Advantage 2, and Phenomenex Luna C18. Common solvent systems are a mixture of water and acetonitrile or methanol without or with 0.1% formic acid or 0.01% trifluoroacetic acid modifiers or 25 mM ammonium formate buffer. The elution mode can be either linear gradient or isocratic. Fractions with pure target compound(s) are pooled and dried for further workup after LC/MS analysis and/or Thin Layer Chromatography (TLC) analysis.

Fractions containing pure compounds are subjected to workup and drying process to obtain pure solid material. Certain target compounds can be extracted with ethyl acetate or dichloromethane from aqueous matrix after reverse-phase column chromatographic purification. Solvent removal and drying techniques include rotavap, speedvac, and lyophilization. Purity and chemical structure of purified target compounds are determined by LC-MS(/MS) and NMR techniques.

Example 2. Isolation of F2 and F3

10 L fermentation broth of *Streptomyces malaysiensis* (NRRL B-24313; ATCC BAA-13; DSM 41697; JCM 10672; KCTC 9934; NBRC 16446; CGMCC 4.1900; IFO 16448) producing F1 (target mass 595), F2 (target mass 609) and Compound 3 (target mass 623) was separated by centrifugation. F1 and F2 are present in both the clarified broth and microbial pellets. Target compounds in the supernatant were extracted once with EtOAc at a ratio of volume (1:1, v/v). The pellets were extracted 3 times with 1.5 L of EtOAc-MeOH (9:1, v/v) stirring with an overhead stirrer for 1 h-1.5 h for each extraction. The organic extracts were filtered through Celite. The combined filtrates were evaporated at 35° C. until dryness to afford ca. 30 g of crude extract. The residue was then dissolved in 90 mL of DCM-THF (80:20, v/v), and to this 60 g of silica gel were added and dried in vacuo at 35° C. The dried residue/silica mixture was loaded onto a 120 g RediSep silica gold cartridge. Compounds were eluted with 100% heptane to heptane-EtOAc (6:4, v/v) with a linear gradient over 30 min at 85 mL/min and collected with 50 mL per fraction on a Teledyne ISCO Combiflash Rf instrument.

By TLC, F2 enriched fractions were eluted at 20% to 30% EtOAc in heptane. The pooled fraction was then concentrated at 35° C. to provide 900 mg of enriched F2 material which was further re-purified on a silica gel cartridge. Ca. 1 mL of DCM was used to dissolve the fraction and 1.8 g of silica gel was added. The dried mixture was loaded onto a 80 g RediSep silica gold cartridge. Compounds were eluted with 100% heptane to heptane-EtOAc (6:4, v/v) with a linear gradient over 30 min at 60 mL/min and collected with 50 mL per fraction. By TLC, pure fractions 25-28 were combined for solvent removal in vacuo at 35° C. to obtain 300 mg of pure F2 (beta-form) for structure elucidation and biological tests.

F2: $^1$H NMR (500 MHz, Benzene-$d_6$) δ 7.20-7.13 (m, 4H), 7.0-7.05 (m, 1H), 5.82 (s, 1H), 5.79-5.69 (m, 2H), 5.51 (m, 1H), 5.46-5.35 (m, 3H), 4.60 (d, J=12 Hz, 1H), 3.98-3.90 (m, 1H), 3.63 (dqd, J=13, 6.5, 3.0 Hz, 1H), 3.22 (d, J=3.6 Hz, 1H), 3.07 (td, J=12, 2.8 Hz, 1H), 3.00 (t, J=9.9 Hz, 1H), 2.93 (dd, J=13, 4.4 Hz, 1H), 2.63-2.54 (m, 3H), 2.20 (d, J=13 Hz, 1H), 2.11-2.03 (m, 1H), 1.99-1.86 (m, 2H), 1.79-1.71 (m, 1H), 1.68-1.60 (m, 1H), 1.51-1.47 (m, 1H), 1.45 (d, J=6.6 Hz, 3H), 1.37 (m, 4H), 1.31 (m, 1H), 1.30 (d, J=6.6 Hz, 3H), 1.29-1.22 (m, 2H), 1.16-1.08 (m, 1H), 1.04-0.94 (m, 1H), 0.82 (t, J=7.4 Hz, 3H), 0.69 (d, J=6.7 Hz, 3H). $^{13}$C NMR (125 MHz, Benzene-$d_6$) δ 209.9, 169.7, 167.5, 141.3, 132.2, 129.6, 129.4, 128.7, 128.0, 127.7, 126.4, 98.2, 79.7, 75.5, 71.1, 51.9, 46.9, 44.2, 44.0, 40.4, 36.2, 35.3, 35.3, 35.2, 34.0, 33.3, 25.4, 25.3, 22.5, 21.1, 17.4, 17.1, 11.6, 9.7. HR-MS [M+Na]$^+$: calc [$C_{36}H_{51}NO_7$+Na]$^+$ 632.3563, obs 632.3569.

By TLC and LC-MS analysis, Compound 3 enriched fractions were eluted at 30% to 40% EtOAc in heptane. The pooled fraction was then concentrated at 35° C. to provide 500 mg of enriched Compound 3 material which was further re-purified by reverse-phase prep-HPLC on a Thermo Polar Advantage II column (5 μm, 250×21.2 mm). Prep-HPLC conditions included 70% acetonitrile in water plus 0.1% formic acid, isocratic elution mode at 15 mL/min, 254 nm. The enriched Compound 3 sample was dissolved in 10 mL methanol for repeatable 10 injections. Target Compound 3 peak at 23.5 minute was collected. After extraction with EtOAc from prep-HPLC pooled fractions and organic solvent removal in vacuo, 250 mg of pure Compound 3 were obtained. Its chemical structure was subsequently determined by various LC-MS and NMR techniques.

F3: $^1$H NMR (500 MHz, Benzene-$d_6$, 1:1 mixture of rotamers) δ 7.30 (m, 1H), 7.20-7.10 (m, 6H), 7.10-7.06 (m, 3H), 7.00 (m, 2H), 5.65-5.55 (m, 2H), 5.45 (m, 1H), 5.25-5.15 (m, 2H), 4.98 (dd, J=15, 7.3 Hz, 1H), 4.89 (dd, J=8.9, 5.0 Hz, 1H), 4.67 (dd, J=15, 8.8 Hz, 1H), 4.45 (m, 2H), 4.20 (m, 2H), 4.13 (m, 1H), 3.87 (m, 1H), 3.57 (m, 2H), 3.35-3.05 (m, 3H), 2.72 (m, 2H), 2.65-2.50 (m, 2H), 2.50-2.30 (m, 6H), 2.08 (m, 1H), 1.93 (m, 1H), 1.80-0.90 (m, 50H) [1.71 (d, J=6.8 Hz, 3H), 1.54 (d, J=6.8 Hz, 3H)], 1.24 (d, J=6.5 Hz, 3H), 1.18 (d, J=6.6 Hz, 3H), 1.08 (d, J=6.8 Hz, 3H), 1.01 (m, J=6.7 Hz, 3H)], 0.73 (t, J=7.5 Hz, 3H), 0.69 (t, J=7.5 Hz, 3H). $^{13}$C NMR (125 MHz, Benzene-$d_6$) δ 201.5, 199.9, 197.8, 191.6, 170.4, 169.5, 166.8, 166.6, 145.4, 144.8, 140.6, 140.5, 133.9, 131.3, 129.7, 129.4, 129.3, 128.8, 128.8, 128.4, 128.3, 126.6, 126.5, 126.0, 100.0, 99.3, 80.6, 78.2, 73.1, 72.4, 71.7, 70.6, 57.1, 52.6, 51.9, 51.1, 45.8, 45.4, 44.2, 42.5, 42.2, 39.8, 35.8, 35.7, 35.6, 34.1, 33.6, 33.4, 29.9, 29.9, 29.3, 28.2, 27.4, 27.1, 25.1, 25.1, 22.3, 22.2, 21.3, 21.2, 16.6, 16.2, 14.6, 13.7, 11.2, 11.1, 10.6, 9.5. HR-MS [M+H]$^+$: calc [$C_{36}H_{49}NO_8$+H]$^+$ 624.3536, obs 624.3547.

Example 3. Isolation of F22

10 L of fermentation broth produced from a recombinant strain S1806 were centrifuged to obtain the pellets and supernatant. The pellets were extracted 3 times with 1.5 L of EtOAc-MeOH (9:1, v/v). The organic solvents were combined and concentrated in vacuo to obtain 1.8 g of crude extract. To this, 2 mL of Heptane-THF (4:1, v/v) was added to dissolve and 2 g of Celite were then added to obtain the dried mixture after removal of solvents on a rotavapor at 30° C. The dried residue/celite mixture was loaded onto a 40 g RediSep silica gold cartridge for column chromatography. Compounds were fractionated with a linear gradient elution from 100% n-heptane to 40% EtOAc in heptane (v/v) over 25 min at 20 mL/min collected with 50 mL per fraction. F22 (target mass 607) was primarily enriched in Fraction 14 identified by LC-MS analysis. Fraction 14 was then dried in vacuo at 30° C. to afford 17.8 mg solid material which was further purified by prep-HPLC on a Thermo Polar Advantage II column (5 μm, 250×21.2 mm). Prep-HPLC conditions included 90% acetonitrile in water plus 0.1% formic acid, isocratic elution mode at 15 mL/min, 254 nm. The sample was dissolved in 1.78 mL methanol for repeatable 5 injections. Target F22 peak at 11.5 minute was collected. After solvent removal in vacuo, 3.64 mg of pure F22 was obtained. Its chemical structure was subsequently determined by various LC-MS/MS and NMR techniques.

Example 4. Synthesis of Selected Compounds

Instrumentation:
Purification was performed on HPLC preparative using Agilent SD-1 system.
Electrospray LC/MS analysis was performed using an Agilent 1260 Infinity system equipped with an Agilent 1260 series LC pump. The methods used were:
Analytical HPLC Method 1:
Agilent Zorbax Extend C-18 reverse phase column (2.1×50 mm), 1.8 μm:
Solvent A: Water+0.1% Formic Acid
Solvent B: Acetonitrile+0.1% Formic Acid
Flow rate: 0.5 mL/min
Injection volume: 5 μL
Column temperature: 40° C.
Gradient:

| Time, min | % A | % B |
|---|---|---|
| 0 | 95 | 5 |
| 3 | 30 | 70 |
| 10 | 0 | 100 |
| 13 | 0 | 100 |
| 14 | 95 | 5 |
| 16 | 95 | 5 |

Analytical HPLC Method 2:
ThermoScientific Acclaim, Polar Advantage II, 4.6×150 mm, 5 μm
Solvent A: Water+0.1% Formic Acid
Solvent B: Acetonitrile+0.1% Formic Acid
Flow rate: 0.8 mL/min
Injection volume: 5 μL
Column temperature: 40° C.
Isocratic:

| Time, min | % A | % B |
|---|---|---|
| 0 | 20 | 80 |
| 6 | 20 | 80 |
| 7 | 5 | 95 |
| 9 | 5 | 95 |
| 10 | 20 | 80 |
| 12 | 20 | 80 |

Electrospray UHPLC/MS was performed using an Agilent 1290 Infinity system equipped with an Agilent 1290 series LC pump. The columns used were the same.
Analytical UHPLC Method 1:
Agilent Zorbax Extend C-18 reverse phase column (2.1×50 mm), 1.8 μm:
Solvent A: Water+0.1% Formic Acid
Solvent B: Acetonitrile+0.1% Formic Acid
Flow rate: 0.5 mL/min
Injection volume: 5 μL
Column temperature: 40° C.
Gradient:

| Time, min | % A | % B |
|---|---|---|
| 0 | 95.24 | 4.76 |
| 5.21 | 30.19 | 69.81 |
| 9.66 | 9.04 | 90.96 |
| 10.5 | 0 | 100 |
| 11.5 | 0 | 100 |
| 12 | 95.24 | 4.76 |
| 13 | 95.24 | 4.76 |

Purification Method A:
Performed using an ACCLAIM Polar Advantage II (21.2× 250 mm) column. Flow rate 17 mL/min, isocratic 70% B. Solvent A was 0.1% aqueous formic acid, solvent B was 100% acetonitrile containing 0.1% formic acid.

105
Synthesis of F11

Synthesis of (2S)-1-((4R,7S)-7-((2R,3S,4R,11S, 12R)-12-benzyl-3,11-dihydroxy-4-methyltetradecan-2-yl)-2-hydroxy-4-methyl-3-oxooxepane-2-carbonyl)piperidine-2-carboxylic acid C-11 lactone. F11

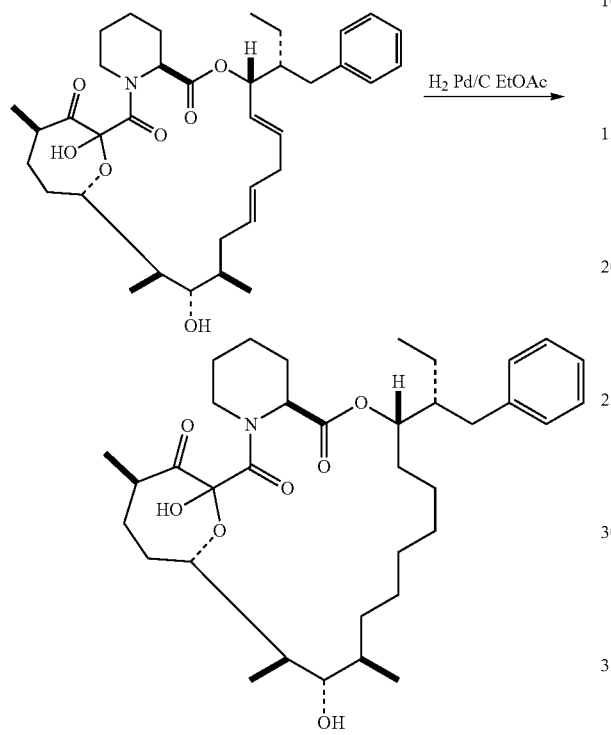

To a mixture of (2S)-1-((4R,7S)-7-((2R,3S,4R,6E,9E, 11R,12R)-12-benzyl-3,11-dihydroxy-4-methyltetradeca-6,9-dien-2-yl)-2-hydroxy-4-methyl-3-oxooxepane-2-carbonyl)piperidine-2-carboxylic acid C-11 lactone (5 mg, 8.2 umol) and 10% palladium on carbon (2 mg) and a stirrer bead under nitrogen was added ethyl acetate (1 mL). The flask was charged with hydrogen and stirred vigorously for 1.5 hr. The atmosphere of hydrogen was replaced with nitrogen and the reaction filtered through celite. The celite pad was washed with more ethyl acetate and the solvent evaporated in vacuo. The residue was purified by chromatography on silica gel, gradient elution ethyl acetate:hexanes 40:60 to 100:0 to afford the title compound.

1H NMR (CDCl3, 500 MHz): δ 7.28 (m, 2H), 7.19 (m, 1H), 7.13 (d, J=6.98 Hz, 2H), 5.65 (s, 1H), 5.26 (d, J=4.92 Hz, 1H), 5.11 (m, 1H), 4.67 (d, J=13.02 Hz, 1H), 4.02 (dd, J=10.67, 1.13 Hz, 1H), 3.35 (m, 1H), 3.23-3.10 (m, 2H), 2.72 (dd, J=13.85, 5.50 Hz, 1H), 2.50 (dd, J=13.93, 9.25 Hz, 1H), 2.39 (m, 1H), 1.95-1.73 (m, 5H), 1.71-1.15 (m, 25H), 1.03 (d, J=6.71 Hz, 3H), 0.85 (t, J=7.42 Hz, 3H), 0.79 (d, J=6.82 Hz, 3H) ppm.

13C NMR (CDCl3, 500 MHz): δ 210.5, 170.3, 167.4, 140.5, 129.0, 128.3, 126.0, 97.8, 79.1, 76.9, 71.1, 52.0, 45.9, 43.9, 43.5, 39.9, 36.3, 35.1, 33.1, 32.3, 31.9, 29.1, 27.9, 27.1, 25.8, 25.1, 23.4, 22.1, 21.1, 20.0, 17.0, 16.6, 11.5, 8.9 ppm.

MS (ESI): calculated for (C36H55NO7+H)+ 614.4057. found 614.4066.

106
Synthesis of F24

Synthesis of (S)-1-(2-((2R,3R,6S)-6-((2R,3R,4S,6E, 9E,11R,12R)-12-benzyl-3,11-dihydroxy-4-methyl-5-oxotetradeca-6,9-dien-2-yl)-2-hydroxy-3-methyltetrahydro-2H-pyran-2-yl)-2-oxoacetyl)piperidine-2-carboxylic acid C-11 lactone

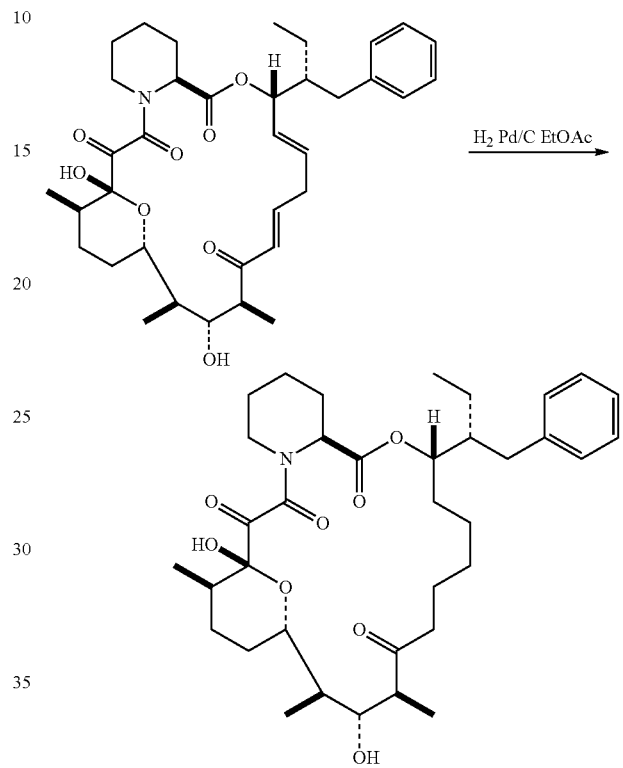

To a solution of F3 (24.2 mg, 36.7 μmol) in ethyl acetate (1 mL) under nitrogen was added 10% Pd/C (12 mg, 50% w/w). The flask was charged with hydrogen and the suspension was stirred at room temperature for 30 min. The hydrogen was replaced with nitrogen and the reaction mixture was then filtered through celite. The filtrate was concentrated under vacuum to give 24 mg of crude product, of which, a portion was purified using Method A to afford the tetrahydro WDB-003 as a white solid (11 mg, 47.8%). TLC: (50/50 heptane/ethyl acetate) Rf=0.45.

1H NMR (400 MHz, C6D6, 1:0.3 mixture of rotamers, asterisk (*) denotes peaks associated with the minor isomer) δ 7.25-7.0 (m, 5H), 6.18* (s, 1H), 5.33-5.28 (m, 2H), 5.11* (d, J=12 Hz, 1H), 4.92* (m, 1H), 4.45* (d, J=12 Hz, 1H), 4.24 (m, 1H), 4.06* (td, J=8 Hz, 1H), 3.40 (dd, J=4 Hz, 1H), 3.88 (t, J=8 Hz, 1H), 3.65 (d, J=12 Hz, 1H), 3.30 (td, J=12 Hz, 1H), 3.02* (td, J=12, 4 Hz, 1H), 2.84* (m, 1H), 2.74 (dd, 16, 8 Hz, 1H), 2.65 (q, 8 Hz, 1H), 2.61-2.48 (m, 2H), 2.38-2.09 (m, 5H), 1.73-1.54 (m, 6H), 1.47-1.02 (m, 28H), 0.90 (m, 4H), 0.80 (t, J=8 Hz, 3H), 0.73* (t, J=8 Hz, 3H) ppm.

13C NMR (400 MHz, C6D6) δ: 212.59, 197.51, 170.64, 166.70, 140.93, 129.39, 128.77, 128.17, 127.94, 126.43, 99.30, 76.54, 72.64, 71.61, 52.46, 51.24, 46.46, 45.30, 41.62, 40.82, 36.20, 35.31, 32.09, 29.96, 29.47, 27.67, 26.17, 25.71, 24.92, 22.57, 21.78, 21.59, 16.59, 13.68, 11.49, 10.37 ppm. MS (ESI): calculated for (C36H53NO8+Na)+ 650.37. found 650.3.

Synthesis of F25

Synthesis of (2S)-1-((4R,7S)-7-((2R,3R,4S,11S,12R)-12-benzyl-3,11-dihydroxy-4-methyl-5-oxotetradecan-2-yl)-2-hydroxy-4-methyl-3-oxooxepane-2-carbonyl)piperidine-2-carboxylic acid C-11 lactone

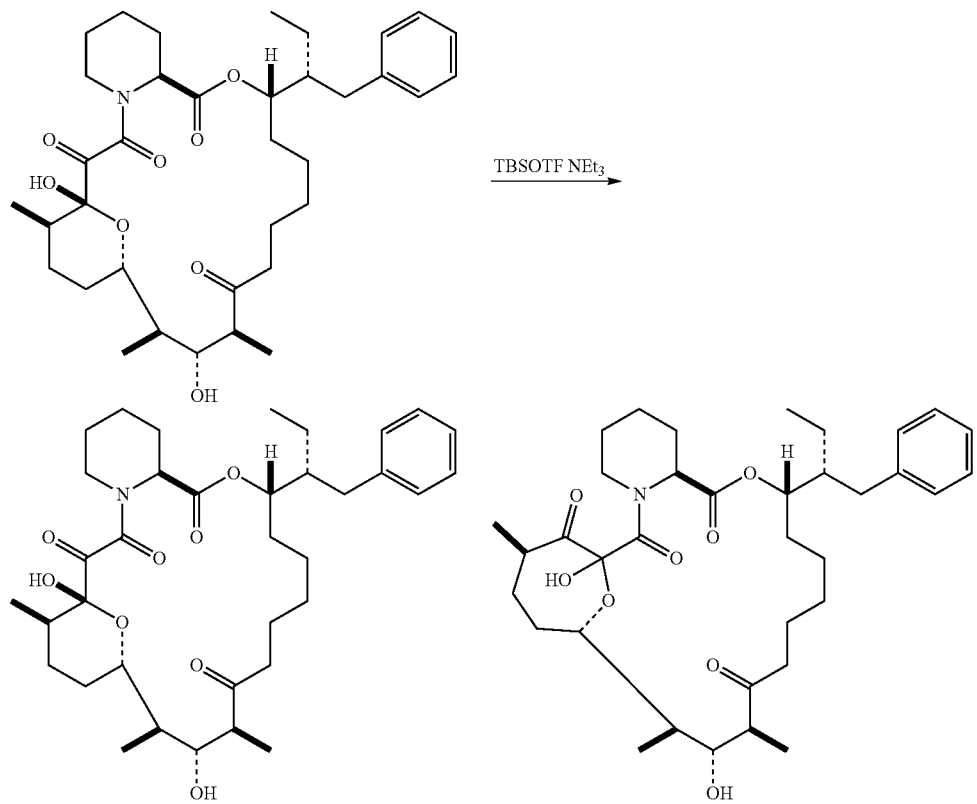

tert-Butyldimethylsilyl trifluoromethanesulfonate (6.9 μL, 30.1 μmol) was added by syringe to an ice-cooled solution of (S)-1-(2-((2R,3R,6S)-6-((2R,3R,4S,6E,9E,11R,12R)-12-benzyl-3,11-dihydroxy-4-methyl-5-oxotetradeca-6,9-dien-2-yl)-2-hydroxy-3-methyltetrahydro-2H-pyran-2-yl)-2-oxoacetyl)piperidine-2-carboxylic acid C-11 lactone-F24 (18.8 mg, 30.1 μL) and triethylamine (4.0 μL, 30.1 μL) in dichoromethane (2 mL) under nitrogen. The resulting solution was stirred at 0° C. for 15 min and was then allowed to warm to room temperature for 2 h. The reaction was cooled to 0° C. and a second portion of triethylamine (4.0 μL, 30.1 μL) and tert-butyldimethylsilyl trifluoromethanesulfonate (6.9 μL, 30.1 μmol) was added. The reaction was again allowed to warm to room temperature and stirred under nitrogen 16 h. Dichloromethane (10 mL) and 0.5 M aqueous sodium bicarbonate solution (10 mL) were added and the organic layer was separated and washed with 5% brine solution (10 mL), dried over anhydrous sodium sulfate, filtered, and the filtrate concentrated in vacuo. The crude product was purified using method A to afford the starting material as a white solid (2.52 mg) and the title compound (4.51 mg) as a white solid.

$^1$H NMR (400 MHz, C$_6$D$_6$) δ 7.26-7.16 (m, 4H), 7.07 (tt, J=6.4, 2 Hz, 1H), 5.58 (s, 1H), 5.39 (d, J=4.8 Hz, 1H), 5.17 (m, 1H), 4.67 (d, J=12.4 Hz, 1H), 4.29 (d, J=10.8 Hz, 1H), 3.42 (m, 1H), 3.06 (td, J=11.2, 2.8 Hz, 1H), 2.92 (t, J=10 Hz, 1H), 2.85 (m, 1H), 2.75 (s, 1H), 2.66 (dd, J=14, 5.6 Hz, 1H), 2.52 (dd, J=14, 9.2 Hz, 1H), 2.35 (m, 1H), 2.28 (m, 1H), 1.84 (m, 2H), 1.68-1.59 (m, 2H), 1.46-1.06 (m, 23H), 0.88 (m, 4H), 0.82 (t, 3H, J=7.2 Hz) ppm.

$^{13}$C NMR (400 MHz, C$_6$D$_6$) δ: 226.15, 210.53, 209.8, 179.03, 167.59, 140.84, 129.40, 128.77, 128.18, 127.9, 126.45, 98.16, 79.21, 76.85, 70.48, 52.20, 46.07, 44.46, 43.88, 42.76, 36.67, 35.30, 35.14, 32.88, 30.53, 27.94, 25.49, 25.32, 24.57, 22.39, 21.36, 20.72, 16.98, 15.16, 11.68, 9.08 ppm.

MS (ESI): calculated for (C$_{36}$H$_{53}$NO$_8$+Na)$^+$ 650.37. found 650.3.

Example 5. Synthesis of Cyclosporine Analogs

General Protocol

Over 2,000 analogs of cyclosporine have been made using solution-phase peptide synthesis, for example according to the method of Li et al. *J. Org. Chem* 2000(65), 2951. In the amino acid sequence of cyclosporine: cyclo-(D-Ala$^8$-MeLeu$^9$-MeLeu$^{10}$-MeVal$^{11}$-MeLeu$^1$-Nva$^2$-Sar$^3$-MeLeu$^4$-Val$^5$-MeLeu$^6$-Ala$^7$), the polypeptide stretch from D-Ala$^8$ to Sar$^a$ can be considered the "constant" region responsible for the majority of binding with cyclophilin A. Therefore cyclosporine analogues that preserve cyclophilin binding can be made by synthesis of a tetrapeptide surrogate for the MeLeu$^4$-Val$^5$-MeLeu$^6$-Ala$^7$ fragment, then elongation and cyclization.

In a specific example for the synthesis of cyclo-(D-Ala$^8$-MeLeu$^9$-MeLeu$^{10}$-MeVal$^{11}$-MeLeu$^1$-Nva$^2$-Sar$^3$-Gly$^4$-Gly$^5$-Gly$^6$-Gly$^7$), Fmoc-Gly-OH and Ala-OBzl are coupled in the presence of 2,6-lutidine and BDMP (5-(1H-benzotriazol-1-yloxy)-3,4-dihydro-1-methyl 2H-pyrrolium hexachloroantimonate) to yield Fmoc-Gly-Gly-OBzl. Removal of the Fmoc group with diethylamine followed by coupling with Fmoc-Gly-OH (promoted by BDMP) yields Fmoc-Gly-Gly-Gly-OBzl. Another iteration of Fmoc removal and Fmoc-Gly-OH coupling yields Fmoc-Gly-Gly-Gly-Gly-OBzl. This suitably protected tetrapeptide can be elaborated to the cyclosporine analog cyclo-(D-Ala$^8$-MeLeu$^9$-MeLeu$^{10}$-MeVal$^{11}$-MeLeu$^1$-Nva$^2$-Sar$^3$-Gly$^4$-Gly$^5$-Gly$^6$-Gly$^7$) in accordance with the methods provided by Li et al.

Example 6. Synthesis of Cyclic Peptide Compounds of the Invention

General Protocol

The general method described by Ishizawa et al. J. Am. Chem. Soc. 2013(135), 5433 can be used. A synthetic constant region is prepared wherein the ends terminate in a carboxylic acid, and a (2-chloroacetamido)-acylated amine (in either orientation). Subsequently, a peptidic variable region is prepared using standard Fmoc solid phase peptide synthesis (SPPS), starting from Fmoc-Gly-Wang resin. A cysteine residue is incorporated at an internal position so as to effect later macrocyclization. The linear polypeptide is coupled with the synthetic constant region, then cleaved from the resin using trifluoroacetic acid. To promote macrocyclization, the peptide is treated with triethylamine in DMSO.

Example 7. Binding of Compounds to Cyclophilin A

The binding of compounds of the invention to Cyclophilin A can be determined using the following protocol.

General Protocol

This protocol utilizes Perkin Elmers AlphaLISA technology platform to detect cyclosporine analogues by measuring the inhibition of binding of biotinylated Cyclosporin A to FLAG tagged Cyclophilin A.

Reagents:

10×TBST Buffer (Boston BioProducts IBB-181), Biotinylated Cyclosporin A (in-house), FLAG tagged Cyclophilin A (in-house); anti-FLAG Donor beads (PerkinElmer AS103) and Streptavidin Acceptor beads (PerkinElmer AL125); Compounds in DMSO (in-house), Cyclosporin A (LC Labs Cat# C-6000).

Equipment:

Biotek Synergy2, Janus MTD Head pipettor, Eppendorf Repeat Pipettor

Supplies:

White 96-well Corning ½ area plates (Cat #3642), 96-well polypropylene full skirt (180 ul) PCR plates, 96-well Viaflow P20 tips for Janus MTD Head pipettor.

Experimental Protocol/Description of Assay:

Add 20 uL of 6 nM Biotinylated CsA working stock to each well of the 96-well plate. Add 1 uL of test compound (100% DMSO) to each well of the plate using the Janus MTD head and P20 tips (except control wells). Add 1 uL of DMSO to negative control wells and 1 uL of 500 uM Cyclosporin A solution to positive control wells. In the dark, add 20 uL of combined Donor/Acceptor beads to each well. Incubate in the dark for 30 minutes at room temperature. In the dark, add 10 uL of 25 nM Flag tagged CypA working stock to each well. Incubate in the dark for 60 minutes at room temperature. Protect plate from light until reading on Biotek Synergy2 Plate Reader; Alphalisa 96-well protocol (680 excitation/615 emission).

Results:

The binding affinity of 104 cyclosporine analogs for cyclophilin A was determined as shown in Table 5.

TABLE 5

Cyclophilin A Binding of Cyclosporine Analogs

| # | % signal | % inhibition of CsA binding to Cyclophilin A | IC50 value of CsA binding to Cyclophilin A |
|---|---|---|---|
| C1 | 0.56 | 99.44 | <2 uM |
| C2 | 5.25 | 94.75 | <2 uM |
| C3 | 13.43 | 86.57 | <2 uM |
| C4 | 4.12 | 95.88 | <2 uM |
| C5 | 9.09 | 90.91 | <2 uM |
| C6 | 7.29 | 92.71 | <2 uM |
| C7 | 2.65 | 97.35 | <2 uM |
| C8 | 9.44 | 90.56 | <2 uM |
| C9 | 0.11 | 99.89 | <2 uM |
| C10 | 0.56 | 99.44 | <2 uM |
| C11 | 6.27 | 93.73 | <2 uM |
| C12 | 3.22 | 96.78 | <2 uM |
| C13 | 2.70 | 97.30 | <2 uM |
| C14 | 9.36 | 90.64 | <2 uM |
| C15 | 2.93 | 97.07 | <2 uM |
| C16 | 2.56 | 97.44 | <2 uM |
| C17 | 17.17 | 82.83 | <2 uM |
| C18 | 2.12 | 97.88 | <2 uM |
| C19 | 16.79 | 83.21 | <2 uM |
| C20 | 2.77 | 97.23 | <2 uM |
| C21 | 31.08 | 68.92 | <2 uM |
| C22 | 5.97 | 94.03 | <2 uM |
| C23 | 1.28 | 98.72 | <2 uM |
| C24 | 6.65 | 93.35 | <2 uM |
| C25 | 0.37 | 99.63 | <2 uM |
| C26 | 3.92 | 96.08 | <2 uM |
| C27 | 5.27 | 94.73 | <2 uM |
| C28 | 1.06 | 98.94 | <2 uM |
| C29 | 1.23 | 98.77 | <2 uM |
| C30 | 0.06 | 99.94 | <2 uM |
| C31 | −0.03 | 100.03 | <2 uM |
| C32 | 0.14 | 99.86 | <2 uM |
| C33 | −0.08 | 100.08 | <2 uM |
| C34 | −0.01 | 100.01 | <2 uM |
| C35 | 0.89 | 99.11 | <2 uM |
| C36 | 2.08 | 97.92 | <2 uM |
| C37 | 1.56 | 98.44 | <2 uM |
| C38 | 1.57 | 98.43 | <2 uM |
| C39 | 3.78 | 96.22 | <2 uM |
| C40 | 0.40 | 99.60 | <2 uM |
| C41 | 0.73 | 99.27 | <2 uM |
| C42 | 1.26 | 98.74 | <2 uM |
| C43 | 0.29 | 99.71 | <2 uM |
| C44 | −0.07 | 100.07 | <2 uM |
| C45 | −0.03 | 100.03 | <2 uM |
| C46 | 1.04 | 98.96 | <2 uM |
| C47 | 4.29 | 95.71 | <2 uM |
| C48 | 15.72 | 84.28 | <2 uM |
| C49 | 19.41 | 80.59 | <2 uM |
| C50 | 6.06 | 93.94 | <2 uM |
| C51 | 3.38 | 96.62 | <2 uM |
| C52 | 7.40 | 92.60 | <2 uM |
| C53 | −0.01 | 100.01 | <2 uM |
| C54 | 0.90 | 99.10 | <2 uM |
| C55 | 32.88 | 67.12 | <2 uM |
| C56 | 2.44 | 97.56 | <2 uM |
| C57 | 0.15 | 99.85 | <2 uM |
| C58 | 3.28 | 96.72 | <2 uM |
| C59 | 11.76 | 88.24 | <2 uM |
| C60 | 52.68 | 47.32 | <2 uM |
| C61 | 14.38 | 85.62 | <2 uM |
| C62 | 27.12 | 72.88 | <2 uM |
| C63 | 4.64 | 95.36 | <2 uM |
| C64 | 28.50 | 71.50 | <2 uM |
| C65 | 0.27 | 99.73 | <2 uM |
| C66 | 10.95 | 89.05 | <2 uM |
| C67 | 40.86 | 59.14 | <2 uM |
| C68 | 20.46 | 79.54 | <2 uM |
| C69 | 0.03 | 99.97 | <2 uM |

TABLE 5-continued

Cyclophilin A Binding of Cyclosporine Analogs

| # | % signal | % inhibition of CsA binding to Cyclophilin A | IC50 value of CsA binding to Cyclophilin A |
|---|---|---|---|
| C70 | 0.05 | 99.95 | <2 uM |
| C71 | −0.05 | 100.05 | <2 uM |
| C72 | 2.78 | 97.22 | <2 uM |
| C73 | 0.01 | 99.99 | <2 uM |
| C74 | 4.92 | 95.08 | <2 uM |
| C75 | 3.88 | 96.12 | <2 uM |
| C76 | 5.09 | 94.91 | <2 uM |
| C77 | 0.44 | 99.56 | <2 uM |
| C78 | 1.42 | 98.58 | <2 uM |
| C79 | 3.24 | 96.76 | <2 uM |
| C80 | 3.35 | 96.65 | <2 uM |
| C81 | 0.76 | 99.24 | <2 uM |
| C82 | 0.77 | 99.23 | <2 uM |
| C83 | 0.65 | 99.35 | <2 uM |
| C84 | 6.81 | 93.19 | <2 uM |
| C85 | 0.87 | 99.13 | <2 uM |
| C86 | 17.23 | 82.77 | <2 uM |
| C87 | 4.53 | 95.47 | <2 uM |
| C88 | 5.94 | 94.06 | <2 uM |
| C89 | 3.10 | 96.90 | <2 uM |
| C90 | 6.46 | 93.54 | <2 uM |
| C91 | 5.17 | 94.83 | <2 uM |
| C92 | 9.00 | 91.00 | <2 uM |
| C93 | 1.28 | 98.72 | <2 uM |
| C94 | 3.71 | 96.29 | <2 uM |
| C95 | 6.90 | 93.10 | <2 uM |
| C96 | 5.00 | 95.00 | <2 uM |
| C97 | 6.42 | 93.58 | <2 uM |
| C98 | 4.70 | 95.30 | <2 uM |
| C99 | 2.59 | 97.41 | <2 uM |
| C100 | 4.28 | 95.72 | <2 uM |
| C101 | 0.15 | 99.85 | <2 uM |
| C102 | 0.70 | 99.30 | <2 uM |
| C103 | 13.65 | 86.35 | <2 uM |
| C104 | 0.99 | 99.01 | <2 uM |

Example 8. Binding of Compounds to FKBP12

The binding of compounds of the invention to FKBP12 can be determined using the following protocol.

General Protocol

This protocol utilizes Perkin Elmers AlphaLISA technology platform to detect FKBP binders by measuring the inhibition of binding of biotinylated FK506 to FLAG tagged FKBP12.

Reagents:

10×TBST Buffer (Boston BioProducts IBB-181), Biotinylated FK506 (in-house), FLAG tagged FKBP (in-house); anti-FLAG Donor beads (Perkin Elmer AS103) and Streptavidin Acceptor beads (PerkinElmer AL125); Compounds in DMSO (in-house), FK506.

Equipment:

Biotek Synergy2, Janus MTD Head pipettor, Eppendorf Repeat Pipettor

Supplies:

White 96-well Corning ½ area plates (Cat #3642), 96-well polypropylene full skirt (180 ul) PCR plates, 96-well Viaflow P20 tips for Janus MTD Head pipettor.

Experimental Protocol/Description of Assay:

Add 20 uL of 12.5 nM FKBP-FLAG working stock to each well of the 96-well plate. Add 1 uL of test compound (100% DMSO) to each well of the plate using the Janus MTD head and P20 tips (except control wells). Add 1 uL of DMSO to negative control wells and 1 uL of 50 uM FK506 solution to positive control wells. In the dark, add 20 uL of combined Donor/Acceptor beads to each well. Incubate in the dark for 30 minutes at room temperature. In the dark, add 10 uL of 5 nM biotinylated FK506 working stock to each well. Incubate in the dark for 60 minutes at room temperature. Protect plate from light until reading on Biotek Synergy2 Plate Reader; Alphalisa 96-well protocol (680 excitation/615 emission).

Results:

The FKBP12 binding for selected compounds was determined as shown in Table 6.

TABLE 6

FKBP12 Binding

| # | Binding affinity to FKBP12 (by displacement of FK506) |
|---|---|
| F1 | 355 nM |
| F2 | 1.5 nM |
| F3 | 0.34 nM |
| F4 | 4.8 nM |
| F5 | 18.8 nM |
| F6 | 60 nM |
| F7 | 26 nM |
| F8 | 10.6 |
| F9 | 0.3 nM |
| F10 | 21.1 nM |
| F11 | 0.51 nM |
| F12 | 36.3 nM |
| F13 | 33.6 nM |
| F14 | 1800 nM |
| F15 | 1930 nM |
| F16 | 67.5 nM |
| F17 | 0.26 nM |
| F18 | 229 nM |
| F19 | 0.22 nM |
| F20 | 0.95 nM |
| F21 | 1.1 nM |
| F22 | 785 nM |
| F23 | 4690 nM |
| F24 | 0.21 nM |

Example 9. SPR Protocol to Measure Binding of a Compound to FKBP12

This protocol utilizes Surface Plasmon Resonance (SPR) as a method to determine kinetics ($K_D$, $K_a$, $K_d$) for the binding of compound (analyte) to immobilized FKBP12 (ligand).

Reagents:

Compound in 100% DMSO (in-house), 10×HBS-P+ buffer (GE Healthcare BR-1006-71), Assay buffer (1×HBS-P+ buffer, 1% DMSO), 12×HIS tagged FKBP12 (in-house).

Equipment:

BIACORE™ X100 (GE Healthcare)

Supplies:

NTA Sensor chip (GE Healthcare BR-1000-34)

Experimental Protocol:

Experiments are performed at 25° C. Stock solution of 12×HIS tagged FKBP12 is diluted to 100 nM in assay buffer (1% DMSO final). Approximately 500-600 RU of FKBP12 is immobilized on one of two flow cells of an activated NTA chip. The second flow cell is not activated as a reference for non-specific interaction of the analyte to the sensor chip. Various concentrations of compound (1 nM-1 μM range), serially diluted into the same assay buffer (1% DMSO final), are injected onto the FKBP12 surface and reference surface at a flow rate of 10 μl/min. The surface is regenerated between analyte injections with 350 mM EDTA.

Data Fitting:

The BiaEvaluation software program is used for data fitting. All data is reference subtracted against both the reference flow cell and a buffer injection. For kinetic analyses, data is locally fit to a 1:1 interaction model.

TABLE 7

FKBP12 Binding Data

| # | SPR affinity to FKBP12: $K_D$ |
|---|---|
| F1 | 71.5 nM |
| F2 | 12.6 nM |
| F3 | 1.3 nM |
| F4 | 23.1 nM |
| F5 | 7 nM |
| F6 | 141.2 nM |
| F7 | 120 nM |
| F8 | 66 nM |
| F9 | 0.23 nM |
| F10 | 17.2 nM |
| F11 | 21.5 nM |
| F12 | 21.2 nM |
| F13 | 105.7 nM |
| F16 | 290 nM |
| F17 | 0.2 nM |

Example 10. Determination of Binding of F2 and F11 to FKBP12 by SPR

This protocol utilizes Surface Plasmon Resonance (SPR) as a method to determine kinetics ($K_D$, $K_a$, $K_d$) for the binding of F2 and F11 (analyte) to immobilized FKBP12 (ligand).

Reagents:
F2 and F11 in 100% DMSO (in-house), 10×HBS-P+ buffer (GE Healthcare BR-1006-71), Assay buffer (1×HBS-P+ buffer, 1% DMSO), 12×HIS tagged FKBP12 (in-house).

Equipment:
BIACORE™ X100 (GE Healthcare)

Supplies:
NTA Sensor chip (GE Healthcare BR-1000-34)

Experimental Protocol:
Experiments are performed at 25° C. Stock solution of 12×HIS tagged FKBP12 is diluted to 100 nM in assay buffer (1% DMSO final). Approximately 500-600 RU of FKBP12 is immobilized on one of two flow cells of an activated NTA chip. The second flow cell is not activated as a reference for non-specific interaction of the analyte to the sensor chip. Various concentrations of F2 or F11 (1 nM-1 µM range), serially diluted into the same assay buffer (1% DMSO final), are injected onto the FKBP12 surface and reference surface at a flow rate of 10 µl/min. The surface is regenerated between analyte injections with 350 mM EDTA.

Data Fitting:
The BiaEvaluation software program is used for data fitting. All data is reference subtracted against both the reference flow cell and a buffer injection. For kinetic analyses, data is locally fit to a 1:1 interaction model.

Results:
The values for binding of F2 to FKBP 12 are: $K_a$ (1/Ms): 4.50×10$^4$; $K_d$ (1/s): 5.94×10$^4$; and $K_D$: 13.2 nM.

The values for binding of F11 to FKBP12 are: $K_a$ (1/Ms): 5.67×10$^5$; $K_d$ (1/s): 8.8×10$^{-3}$; and $K_D$: 15.6 nM.

Example 11. Determination of Cell Permeability of Compounds

Cell permeability of compounds can be determined using the following protocol.

General Protocol

This protocol utilizes a modified FKBP or cyclophilin destabilizing mutant to determine the bioactivity of FKBP binding compounds or cyclophilin binding compounds in whole cell assay.

Reagents:
DMEM, DMEM without Phenol Red, 10% FBS, 1× Sodium Pyruvate, 1× Glutamax. Add 125 ul of media with compound per well.

Equipment:
Biotek Synergy2, Janus MTD Head pipettor, Eppendorf Repeat Pipettor

Supplies:
White 96-well Corning ½ area plates (Cat #3642), 96-well polypropylene full skirt (180 ul) PCR plates, 96-well Viaflow P20 tips for Janus MTD Head pipettor.

Experimental Protocol/Description of Assay:
Plate HeLa-FKBP12 cells (for FKBP binding compounds) or HeLa-Cyclophilin A cells (for cyclophilin binding compounds) and seed overnight at 5 k/well (approximately ~18 hrs.). Using a multi-channel pipet, take out the old media and add ~125 ul of new media with compounds. Compounds are diluted using DMEM without Phenol Red, 10% FBS, 1× Sodium Pyruvate, 1× Glutamax. Add 125 ul of media with compound per well. Cells are treated with compounds at concentration: 30, 10, 3.33, 1.11, 0.37, 0.12, 0.04 and 0.013 uM. Time points are taken at 72 hrs and plate read using plate reader with excitation/emission: 575/620.

Calculation:
Cell binding/permeability is calculated in fold-change (Total RFU of treated samples/total RFU of DMSO treated samples or total RFU above background (Total RFU minus total RFU of DMSO treated samples).

Results:
Cell permeability data was gathered for selected compounds as shown in Table 8.

TABLE 8

Biosensor Permeability

| # | Biosensor Permeability IC50 value |
|---|---|
| C33 | <3 uM |
| C34 | <3 uM |
| C35 | >3 uM |
| C36 | <3 uM |
| C37 | >3 uM |
| C38 | <3 uM |
| C39 | <3 uM |
| C40 | <3 uM |
| C41 | >3 uM |
| C42 | >3 uM |
| C43 | <3 uM |
| C44 | <3 uM |
| F2 | <1 uM |
| F4 | <1 uM |
| F6 | <1 uM |
| F9 | <1 uM |
| F10 | >1 uM |
| F12 | >1 uM |
| F13 | >1 uM |
| F14 | >1 uM |
| F16 | >1 uM |
| F17 | <1 uM |
| F18 | <1 uM |
| F19 | <1 uM |
| F20 | <1 uM |
| F21 | <1 uM |
| F22 | >1 uM |
| F23 | >1 uM |

Example 12. Binding of a Presenter Protein/Compound Complex to a Target Protein The binding of a presenter protein/compound complex of the invention to a target protein can be determined using the following protocol.

General Protocol for Cyclophilin A Complexes

This protocol utilizes Perkin Elmers AlphaLISA technology platform to detect cyclosporine analogues by measuring the binding of 6×HIS tagged target protein+FLAG tagged Cyclophilin A and cyclosporine compound.

Reagents:
10×TBST Buffer (Boston BioProducts IBB-181), MgCl$_2$ (Sigman), 6×HIS tagged target protein (in-house), FLAG tagged Cyclophilin A (in-house); anti-FLAG Donor beads (PerkinElmer AS103) and Streptavidin Acceptor beads (PerkinElmer AL125); Compounds in DMSO (in-house), Cyclosporin A (LC Labs Cat# C-6000).

Equipment:
Biotek Synergy2, Janus MTD Head pipettor, Eppendorf Repeat Pipettor.

Supplies:
White 96-well Corning ½ area plates (Cat #3642), 96-well polypropylene full skirt (180 ul) PCR plates, 96-well Viaflow P20 tips for Janus MTD Head pipettor.

Experimental Protocol/Description of Assay:
Add 20 uL of 250 nM 6×HIS tagged target protein working stock to each well of the 96-well plate. Add 1 uL of test compound (100% DMSO) to each well of the plate using the Janus MTD head and P20 tips (except control wells). Add 1 uL of DMSO to control wells. In the dark, add 20 uL of combined Donor/Acceptor beads to each well. Incubate in the dark for 30 minutes at room temperature. In the dark, add 10 uL of 10 uM Flag tagged CypA working stock to each well. Incubate in the dark for 60 minutes at room temperature. Protect plate from light until reading on Biotek Synergy2 Plate Reader; Alphalisa 96-well protocol (680 excitation/615 emission).

General Protocol for FKBP12 Complexes

This protocol utilizes Perkin Elmers AlphaLISA technology platform to detect compounds by measuring the binding of 6×HIS tagged target protein+FLAG tagged FKBP12 and FKBP binding compound.

Reagents:
10×TBST Buffer (Boston BioProducts IBB-181), MgCl$_2$ (Sigman), 6×HIS tagged target protein (in-house), FLAG tagged FKBP12 (in-house); anti-FLAG Donor beads (PerkinElmer AS103) and Streptavidin Acceptor beads (PerkinElmer AL125); Compounds in DMSO (in-house), FK506.

Equipment:
Biotek Synergy2, Janus MTD Head pipettor, Eppendorf Repeat Pipettor.

Supplies:
White 96-well Corning ½ area plates (Cat #3642), 96-well polypropylene full skirt (180 ul) PCR plates, 96-well Viaflow P20 tips for Janus MTD Head pipettor.

Experimental Protocol/Description of Assay:
Add 20 uL of 250 nM 6×HIS tagged target protein working stock to each well of the 96-well plate. Add 1 uL of test compound (100% DMSO) to each well of the plate using the Janus MTD head and P20 tips (except control wells). Add 1 uL of DMSO to control wells. In the dark, add 20 uL of combined Donor/Acceptor beads to each well. Incubate in the dark for 30 minutes at room temperature. In the dark, add 10 uL of 10 uM Flag tagged FKBP12 working stock to each well. Incubate in the dark for 60 minutes at room temperature. Protect plate from light until reading on Biotek Synergy2 Plate Reader; Alphalisa 96-well protocol (680 excitation/615 emission).

Example 13. Determination of Binding of Presenter Protein/Compound Complexes to Target Proteins by SPR This protocol utilizes Surface Plasmon Resonance (SPR) as a method to determine kinetics ($K_D$, $K_a$, $K_d$) for the binding of mammalian target protein (analyte) to immobilized FKBP12-compound binary complex (ligand).

Reagents:
Compound in 100% DMSO (in-house), 10×HBS-P+buffer (GE Healthcare BR-1006-71), Assay buffer (1×HBS-P+ buffer, 1% DMSO, 1 μM F2), 12×HIS tagged FKBP12 (in-house), mammalian target protein (in-house).

Equipment:
BIACORE™ X100 (GE Healthcare)

Supplies:
NTA Sensor chip (GE Healthcare BR-1000-34)

Experimental Protocol:
Experiments are performed at 25° C. Stock solution of 12×HIS tagged FKBP12 is diluted to 100 nM in assay buffer containing 1 μM compound (1% DMSO final). Approximately 200-400 RU of FKBP12 is immobilized on one of two flow cells of an activated NTA chip. The second flow cell is not activated as a reference for non-specific interaction of the analyte to the sensor chip. Various concentrations of target protein (1 nM-1 μM range), serially diluted into the same assay buffer containing 1 μM compound (1% DMSO final), are injected onto the FKBP12 surface and reference surface at a flow rate of 10 μl/min. The surface is regenerated between analyte injections with 350 mM EDTA.

Data Fitting:
The BiaEvaluation software program is used for data fitting. All data is reference subtracted against both the reference flow cell and a buffer injection. For kinetic analyses, data is locally fit to a 1:1 interaction model.

Example 14. Determination of Binding of FKBP12/F2 Complex to CEP250 by SPR

This protocol utilizes Surface Plasmon Resonance (SPR) as a method to determine kinetics ($K_D$, $K_a$, $K_d$) for the binding of CEP250 (analyte) to immobilized FKBP12-F2 binary complex (ligand).

Reagents:
F2 in 100% DMSO (in-house), 10×HBS-P+buffer (GE Healthcare BR-1006-71), Assay buffer (1×HBS-P+buffer, 1% DMSO, 1 μM F2), 12×HIS tagged FKBP12 (in-house), CEP250$_{29.2}$ (residues 1982-2231) and CEP250$_{11.4}$ (residues 2134-2231) (in-house).

Equipment:
BIACORE™ X100 (GE Healthcare)

Supplies:
NTA Sensor chip (GE Healthcare BR-1000-34)

Experimental Protocol:
Experiments are performed at 25° C. Stock solution of 12λHIS tagged FKBP12 is diluted to 100 nM in assay buffer containing 1 μM F2 (1% DMSO final). Approximately 200-400 RU of FKBP12 is immobilized on one of two flow cells of an activated NTA chip. The second flow cell is not activated as a reference for non-specific interaction of the analyte to the sensor chip. Various concentrations of CEP250 (1 nM-1 μM range), serially diluted into the same assay buffer containing 1 μM F2 (1% DMSO final), are injected onto the FKBP12 surface and reference surface at a flow rate of 10 μl/min. The surface is regenerated between analyte injections with 350 mM EDTA.

Data Fitting:

The BiaEvaluation software program is used for data fitting. All data is reference subtracted against both the reference flow cell and a buffer injection. For kinetic analyses, data is locally fit to a 1:1 interaction model.

Results:

The k values for the binding of the FKBP12/F2 complex to $CEP250_{11.4}$ and $CEP250_{29.2}$ are: $K_a$ (1/Ms): $5.71 \times 10^5$; $K_d$ (1/S): $3.09 \times 10^{-3}$; and $K_D$: 5.4 nM and $K_a$ (1/Ms): $3.11 \times 10^5$; $K_d$ (1/S): $9.25 \times 10^{-5}$; and $K_D$: 0.29 nM, respectively.

Example 15. Determination of Binding of Presenter Protein/Compound Complexes to Target Proteins by ITC General Protocol This protocol utilizes Isothermal Titration calorimetry (ITC) to directly measure the heat change associated with binding of presenter protein (e.g. FKBP, cyclophilin)-compound binary complexes to target proteins. Measurement of the heat change allows accurate determination of association constants ($K_a$), reaction stoichiometry (N), and the change in binding enthalpy (ΔH).

Reagents:

Compounds in 100% DMSO (in-house), Protein Buffer (10 mM HEPES, pH 7.5, 75 mM NaCl, 0.5 mM TCEP), assay buffer (protein buffer+1% DMSO), presenter protein (e.g. FKBP, cyclophilin) (in-house), target protein (in-house).

Equipment:

MicroCal™ $ITC_{200}$ (GE Healthcare)

Experimental Protocol:

presenter protein (e.g. FKBP, cyclophilin) stock solution is diluted to 10 μM in assay buffer (1% DMSO final). Compound is added to presenter protein to 20 μM (1% DMSO final), and binary complex is filled into the reaction cell of the ITC device after 5-10 min pre-incubation time. Target protein stocks are diluted to 50 μM in assay buffer and supplemented with 20 μM compound (1% DMSO final) before being filled into the injection syringe. A control experiment in the absence of compound is also run to determine the heat associated with operational artifacts and the dilution of titrant as it is injected from the syringe into the reaction cell. Data collection and analysis are as described for binding of FKBP12-F2 and FKBP12-F11 binary complexes to CEP250.

Example 16. Determination of Binding of FKBP12/F2 and FKBP12/F2 Complexes to CEP250 by ITC This protocol utilizes Isothermal Titration calorimetry (ITC) to directly measure the heat change associated with binding of FKBP12-F2 and FKBP12-F11 binary complexes to CEP250. Measurement of the heat change allows accurate determination of association constants ($K_a$), reaction stoichiometry (N), and the change in binding enthalpy (ΔH).

Reagents:

F2 and F11 in 100% DMSO (in-house), Protein Buffer (10 mM HEPES, pH 7.5, 75 mM NaCl, 0.5 mM TCEP), assay buffer (protein buffer+1% DMSO), FKBP12 (in-house), $CEP250_{29.4}$ (residues 1982-2231) and $CEP250_{11.4}$ (residues 2134-2231) (in-house).

Equipment:

MicroCal™ $ITC_{200}$ (GE Healthcare)

Experimental Protocol:

FKBP12 stock solution is diluted to 10 μM in assay buffer (1% DMSO final). Compound is added to FKBP12 to 20 μM (1% DMSO final), and binary complex is filled into the reaction cell of the ITC device after 5-10 min pre-incubation time. CEP250 protein stocks are diluted to 50 μM in assay buffer and supplemented with 20 μM compound (1% DMSO final) before being filled into the injection syringe. A control experiment in the absence of compound is also run to determine the heat associated with operational artifacts and the dilution of titrant as it is injected from the syringe into the reaction cell. More detailed experimental parameters are shown in Tables 11 and 12, below:

TABLE 9

| ITC Experimental Parameters | |
| --- | --- |
| Experimental device: MicroCal™ $iT_{200}$ (GE Healthcare) | |
| sample cell volume [μl] | 270 |
| injector volume [μl] | 40 |
| Experimental parameters | |
| Total # of Injections | 19 |
| Cell Temperature [° C.] | 25 |
| Reference Power [pCal/s] | 5 |
| Initial Delay [s] | 200 |
| Stirring Speed [rpm] | 750 |
| Injection parameters | |
| Volume [μl] | 2 |
| Duration [s] | 4 |
| Spacing [s] | 170-200 |
| Filter Period [s] | 5 |
| Feedback Mode/Gain | high |

TABLE 10

Protein and Ligand Concentrations for ITC
Final protein and ligand concentrations

| cell content | syringe content | ligand | DMSO assay conc. [%] |
| --- | --- | --- | --- |
| FKBP12, 10 μM | $CEP250_{29.4}$, 50 μM | none | 1.0 |
| FKBP12, 10 μM | $CEP250_{11.4}$, 50 μM | none | 1.0 |
| FKBP12, 10 μM | $CEP250_{29.4}$, 118 μM | F2, 20 μM | 1.0 |
| FKBP12, 10 μM | $CEP250_{29.4}$, 118 μM | F11, 20 μM | 1.0 |
| FKBP12, 10 μM | $CEP250_{11.4}$, 68 μM | F2, 20 μM | 1.0 |
| FKBP12, 10 μM | $CEP250_{11.4}$, 68 μM | F11, 20 μM | 1.0 |

Data Fitting:

Data were fitted with the Origin ITC200 software according to the following procedure:

1) Read raw data
2) In "mRawITC": adjust integration peaks and baseline, integrate all peaks
3) In "Delta H"—data control: remove bad data (injection #1 and other artifacts), subtract straight line (background subtraction)
4) In "Delta H"—model fitting: select one set of sites model, perform fitting with Levenberg-Marquardt algorithm until Chi Square is not reduced further, finish with "done" (parameters N, $K_a$ and ΔH are calculated based on fitting)

ITC measurements for the binding of FKBP12-F2 and FKBP12-F11 binary complexes to CEP250 are summarized in Table 11 below.

TABLE 11

| | | | | | | ΔH | −T*ΔS | ΔG |
| Experiment | cell content | syringe content | ligand | T [K] | N | Kd [μM]* | [kJ*mol−mol−1]** | [kJ*mol−mol−1]*** | [kJ*mol−mol−1]**** |
|---|---|---|---|---|---|---|---|---|---|
| 3 | FKBP12, 10 μM | CEP25029.4, 118 μM | none | 298 | ND | ND | ND | ND | ND |
| 4 | FKBP12, 10 μM | CEP25011.4, 68 μM | none | 298 | ND | ND | ND | ND | ND |
| 5 | FKBP12, 10 μM | CEP25029.4, 118 μM | F2, 20 μM | 298 | 0.50 | 0.19 | −52.21 | 13.80 | −38.41 |
| 6 | FKBP12, 10 μM | CEP25029.4, 118 μM | F11, 20 μM | 298 | 0.57 | 0.36 | −58.48 | 21.73 | −36.74 |
| 7 | FKBP12, 10 μM | CEP25011.4, 68 μM | F2, 20 μM | 298 | 0.56 | 0.07 | −49.37 | 8.62 | −40.75 |
| 8 | FKBP12, 10 μM | CEP25011.4, 68 μM | F11, 20 μM | 298 | 0.54 | 0.08 | −47.78 | 7.41 | −40.36 |

*$K_d$ (calculated from $K_a = 1/K_d$)
**ΔH
***T*ΔS (calculated from equation (−TΔS = ΔG − ΔH)
****ΔG = −RT ln $K_a$ = RT ln $K_d$ Results:

Overall, the data for FKBP12-F2 and FKBP12-F11 binary complexes binding to CEP250$_{11.4}$ and CEP250$_{29.4}$ show similar interaction parameters. $K_d$ values were similar for all combinations. All interactions show an almost identical thermodynamic profile in which binding is characterized by a purely enthalpic binding mode (−T*ΔS term is positive and does not contribute to the Gibbs free energy). Binding stoichiometries for all interactions were N=0.5-0.6 and support a 1:2 binding ratio for 1 CEP250 homodimer binding to 2 FKBP12 molecules, as evidenced in the crystal structure of CEP250$_{11.4}$/F2/FKBP12.

Example 17. Crystallographic Structural Determination of Tertiary Complexes

General Protocol

This protocol describes the crystallization and structure determination method for structures of specific FKBP12-compound-target protein ternary complexes.

Reagents:

Compound in 100% DMSO (in-house), FKBP12 (in-house), and mammalian target protein (in-house).

Equipment:

Superdex 200 (GE Healthcare)

Experimental Protocol:

A 3:1 molar excess of compound is added to FKBP12 in 12.5 mM HEPES pH 7.4, 75 mM NaCl buffer, and incubated overnight at 4° C. A 3:1 molar excess of FKBP12-compound binary complex is added to target protein and incubated at 4° C. overnight to complete ternary complex formation. Pure ternary complex is isolated by gel filtration purification on a Superdex 200 column in 12.5 mM HEPES pH 7.4, 75 mM NaCl. Purified complex (at 10-20 mg/ml) is subjected to crystallization at 22° C. using sitting drop vapor diffusion using various buffers, surfactants and salt solutions. For data collection, crystals are transferred to a solution containing mother liquor supplemented with 20-25% glycerol, and then frozen in liquid nitrogen. Diffraction datasets are collected at the Advanced Photon Source (APS) and processed with the HKL program. Molecular replacement solutions are obtained using the program PHASER in the CCP4 suite, using the published structure of FKBP12 (PDB-ID 1FKD) as a search model. Subsequent model building and refinement are performed according to standard protocols with the software packages CCP4 and COOT.

Example 18. Crystallographic Structural Determination of Tertiary Complexes of FKBP12/F2 and FKBP12/F11 Complexes with CEP250

This protocol describes the crystallization and structure determination method for structures of FKBP12-Compound 2-CEP250 and FKBP12-F11-CEP250 ternary complexes.

Reagents:

F2 and F11 in 100% DMSO (in-house), FKBP12 (in-house), and CEP250$_{11.4}$ (residues 2134-2231) (in-house).

Equipment:

Superdex 200 (GE Healthcare)

Experimental Protocol:

A 3:1 molar excess of F2 or F11 is added to FKBP12 in 12.5 mM HEPES pH 7.4, 75 mM NaCl buffer, and incubated overnight at 4° C. A 3:1 molar excess of FKBP12-F2 or FKBP12-F11 binary complex is added to CEP250$_{11.4}$ and incubated at 4° C. overnight to complete ternary complex formation. Pure ternary complex is isolated by gel filtration purification on a Superdex 200 column in 12.5 mM HEPES pH 7.4, 75 mM NaCl. Purified complex (at 10-20 mg/ml) is subjected to crystallization at 22° C. using sitting drop vapor diffusion. FKBP12-F2-CEP250 crystals grow in a well solution containing 0.2 M sodium malonate, 0.1 M HEPES 7.0, 21% PEG 3350. FKBP12-F11-CEP250 crystals grow in a well solution containing 0.1 M Tris pH 8.5, 0.2 M trimethylamine N-oxide, 22-24% PEG2000 MME. For data collection crystals are transferred to a solution containing mother liquor supplemented with 20-25% glycerol, and then frozen in liquid nitrogen. Diffraction datasets are collected at the Advanced Photon Source (APS) and processed with the HKL program. Molecular replacement solutions are obtained using the program PHASER in the CCP4 suite, using the published structure of FKBP12 (PDB-ID 1FKD) as a search model. Subsequent model building and refinement are performed according to standard protocols with the software packages CCP4 and COOT.

Results:

Overall structure of FKBP12-F2-CEP250: In the structure of FKBP12 with CEP250 in complex with F2, two FKBP12 monomers are bound to a homodimer of CEP250. The two CEP250 monomers form a coiled-coil structure. There are four hetero dimers on the asymmetric unit with basically the same overall conformation. The model comprises residues Met1 to Glu108 of FKBP12 and Asp2142 to His2228 of CEP250. The electron density shows an unambiguous binding mode for the ligand F2, including the orientation and conformation of the ligand.

The CEP250 residues involved in binding F2 are L2190, Q2191, V2193, A2194, M2195, F2196, L2197, and Q2198. The CEP250 residues involved in binding to FKBP12 are A2185, S2186, S2189, Q2191, M2195, Q2198, V2201, L2202, R2204, D2205, S2206, Q2208, Q2209, and Q2212.

The total buried surface area of the ternary complex is 1759 Å². The total buried surface area of CEP250 is 865 Å² of which 663 Å² is contributed by FKBP12 and 232 Å² is contributed by F2.

100% of the binding interactions in the ternary complex between F2 and CEP250 are van der Waals or pi-pi interactions. By comparison, 100% of the binding interactions between rapamycin and mTOR are van der Waals or pi-pi interactions, and 89% of the binding interactions between FK506 and calcineurin are van der Waals or pi-pi interactions while 11% are hydrogen bonds (two H-bonds from C13 and C15 OMe to Trp 352 N—H).

Overall structure of FKBP12-F11-CEP250: In the structure of FKBP12 with CEP250 in complex with F11, one FKBP12 monomer is bound to a homodimer of CEP250. The two CEP250 monomers form a coiled-coil structure. The crystals contain a heterotrimer (one FKBP12 and two CEP250) in the asymmetric unit. The model comprises residues Met1 to Glu108 of FKBP12 and Ser2143 to His2228 of CEP250. One short loop region of FKBP12 (18-19) is not fully defined by electron density and is not included in the model. The electron density shows an unambiguous binding mode for the ligand F11, including the orientation and conformation of the ligand.

The CEP250 residues involved in binding F2 are L2190, Q2191, V2193, A2194, M2195, F2196, L2197, and Q2198. The CEP250 residues involved in binding to FKBP12 are Q2182, A2185, S2186, S2189, Q2191, M2195, Q2198, V2201, L2202, R2204, D2205, S2206, Q2208, Q2209, and Q2212.

The total buried surface area of the ternary complex is 1648 Å². The total buried surface area of CEP250 is 831 Å² of which 590 Å² is contributed by FKBP12 and 241 Å² is contributed by F2.

Statistics of the final structures are listed in Table 12 and 13 below.

TABLE 12

| FKBP12-F2-CEP250 | |
| --- | --- |
| Ligand | F2 |
| Resolution [Å] | 136.05-2.20 |
| Number of reflections (working/test) | 50564/2723 |
| $R_{cryst}$ [%] | 20.8 |
| $R_{free}$[%]² | 25.6 |
| Total number of atoms: | |
| Protein | 6146 |
| Water | 226 |
| Ligan | 176 |
| PEG | 273 |
| Magnesium | 1 |
| Maltose | 7 |

TABLE 12-continued

| FKBP12-F2-CEP250 | |
| --- | --- |
| Ligand | F2 |
| Deviation from ideal geometry: ³ | |
| Bond lengths [Å] | 0.007 |
| Bond angles [°] | 1.17 |
| Bonded B's [Å²]⁴ | 5.4 |
| Ramachandran plot: ⁵ | |
| Most favoured regions [%] | 94.6 |
| Additional allowed regions [%] | 4.8 |
| Generously allowed regions [%] | 0.6 |
| Disallowed region [%] | 0.0 |

¹Values as defined in REFMAC5, without sigma cut-off
²Test-set contains 2.4% of measured reflections
³ Root mean square deviations from geometric target values
⁴Calculated with MOLEMAN
⁵ Calculated with PROCHECK

TABLE 13

| FKBP12-F11-CEP250 | |
| --- | --- |
| Ligand | F11 |
| Resolution [Å] | 72.84-2.10 |
| Number of reflections (working/test) | 16398/877 |
| $R_{cryst}$ [%] | 24.2 |
| $R_{free}$[%]² | 29.9 |
| Total number of atoms: | |
| Protein | 2224 |
| Water | 31 |
| Ligand | 44 |
| PEG | 14 |
| Deviation from ideal geometry: ³ | |
| Bond lengths [Å] | 0.008 |
| Bond angles [°] | 1.07 |
| Bonded B's [Å²]⁴ | 3.0 |
| Ramachandran plot: ⁵ | |
| Most favoured regions [%] | 93.5 |
| Additional allowed regions [%] | 4.9 |
| Generously allowed regions [%] | 1.6 |
| Disallowed region [%] | 0.0 |

¹Values as defined in REFMAC5, without sigma cut-off
²Test-set contains 5.1% of measured reflections
³ Root mean square deviations from geometric target values
⁴Calculated with MOLEMAN
⁵ Calculated with PROCHECK While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

All publications, patents and patent applications are herein incorporated by reference in their entirety to the same extent as if each individual publication, patent or patent application was specifically and individually indicated to be incorporated by reference in its entirety.

What is claimed is:
1. A compound represented by the structure:
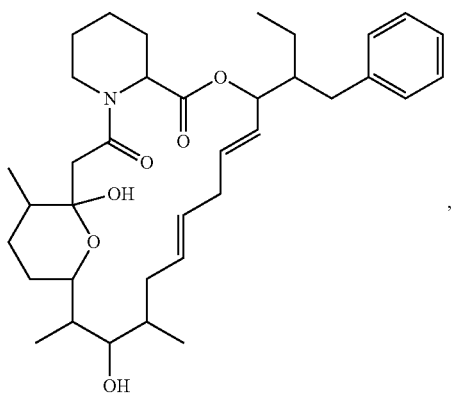
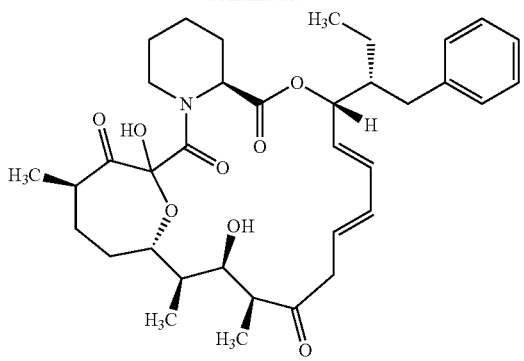
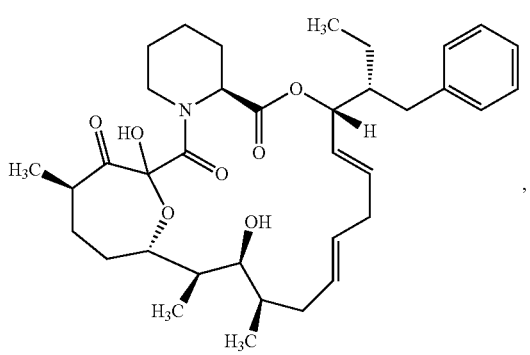
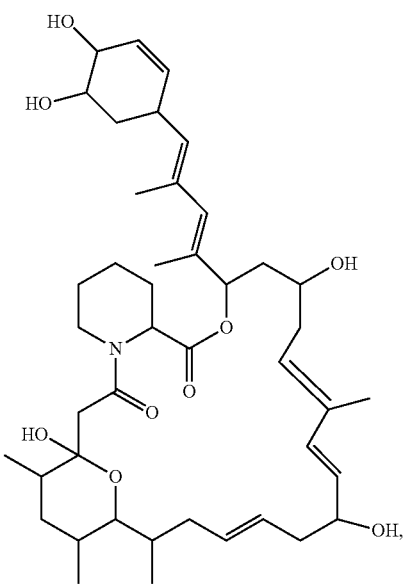
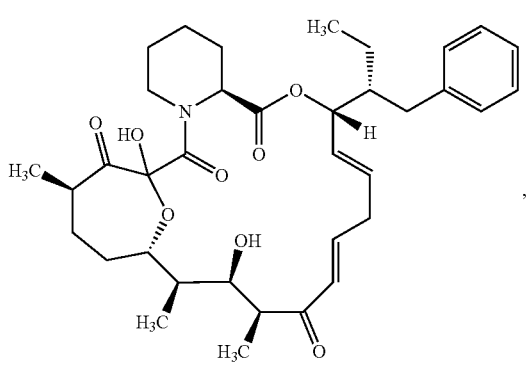
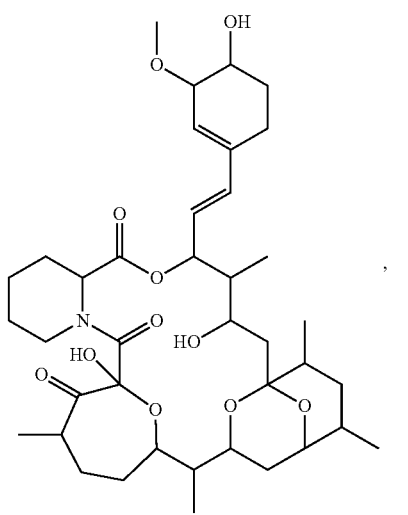

125
-continued
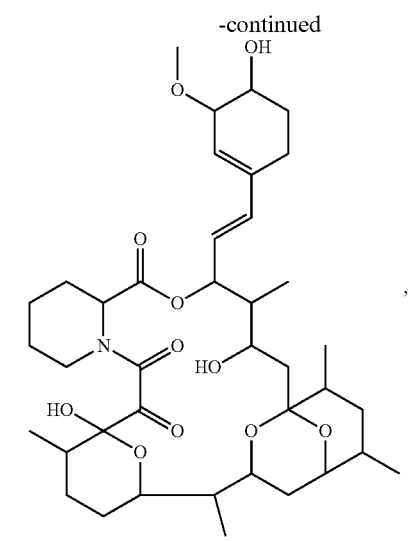
,
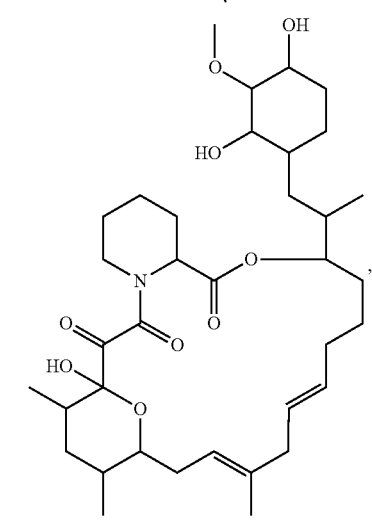
,
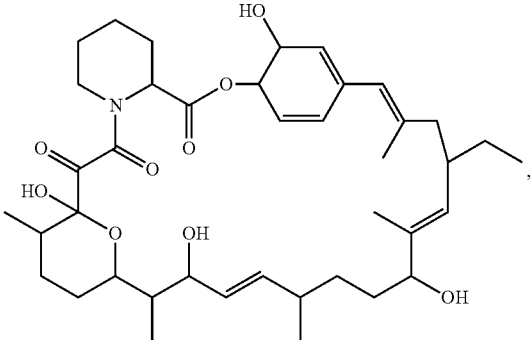
,
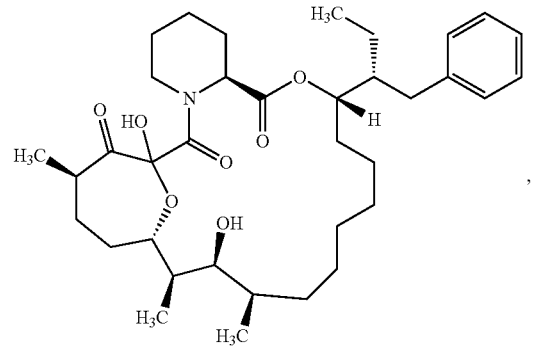
,
126
-continued
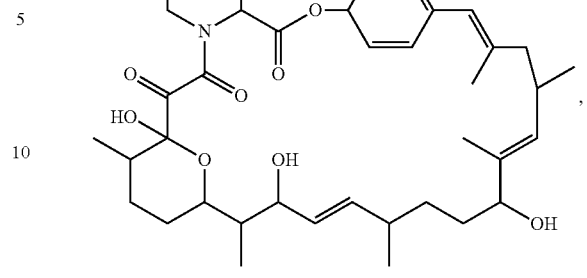
,
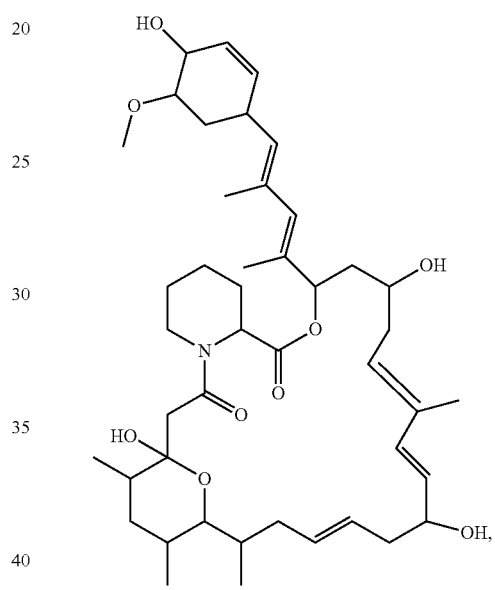
,
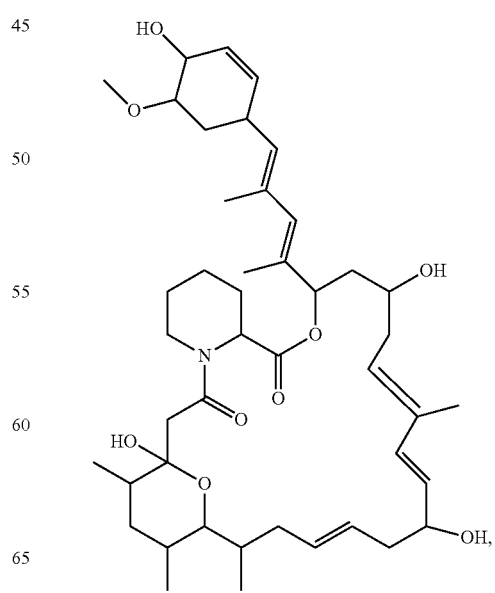
, 127
-continued
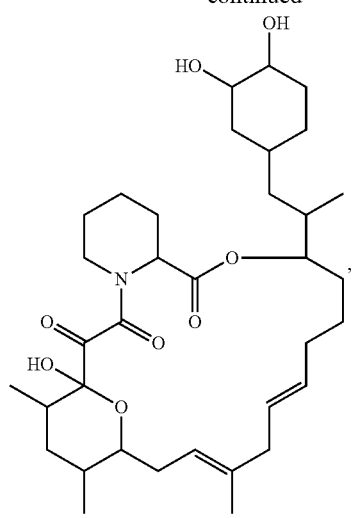
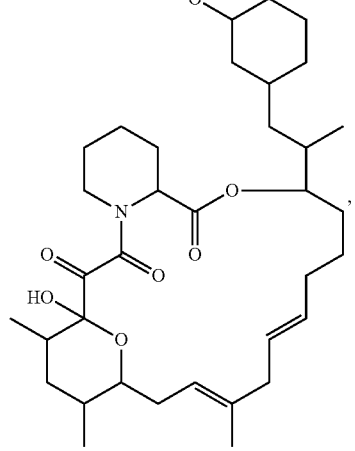
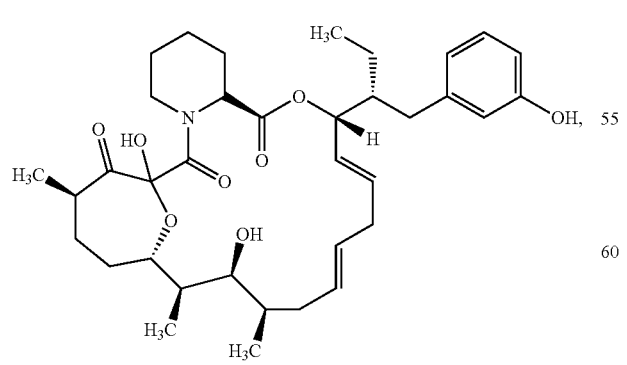
128
-continued
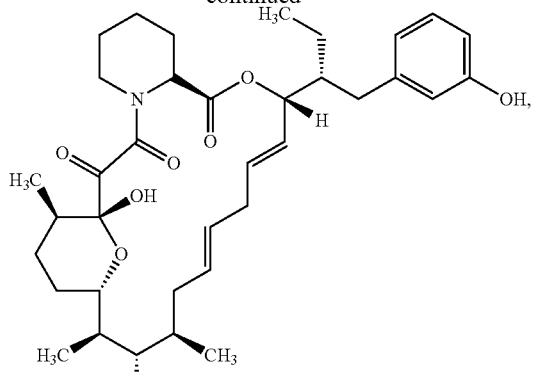
or a pharmaceutically acceptable salt thereof.
2. A pharmaceutical composition comprising a compound of claim 1 and a pharmaceutically acceptable excipient.
3. The pharmaceutical composition of claim 2 in unit dosage form.
* * * * *

UNITED STATES PATENT AND TRADEMARK OFFICE
CERTIFICATE OF CORRECTION

PATENT NO. : 10,039,839 B2  Page 1 of 1
APPLICATION NO. : 14/991403
DATED : August 7, 2018
INVENTOR(S) : Gregory Lawrence Verdine et al.

It is certified that error appears in the above-identified patent and that said Letters Patent is hereby corrected as shown below:

In the Claims

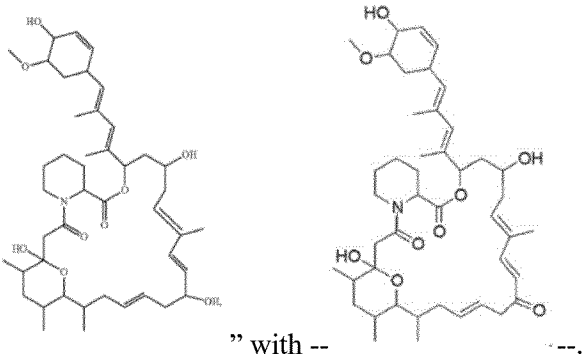

Column 126, Lines 45-65, replace "          " with --          --.

Signed and Sealed this
Twenty-sixth Day of October, 2021

Drew Hirshfeld
*Performing the Functions and Duties of the*
*Under Secretary of Commerce for Intellectual Property and*
*Director of the United States Patent and Trademark Office*